US012595269B2

(12) United States Patent
Borthwick et al.

(10) Patent No.: US 12,595,269 B2

(45) Date of Patent: Apr. 7, 2026

(54) MORPHOLINE-LIKE MONOAMINE RELEASERS

(71) Applicant: Solvonis Therapeutics Ireland Holdings Limited, Dublin (IE)

(72) Inventors: Alan Borthwick, London (GB); Fabrizio Micheli, Desenzano del Garda (IT); Alessandra Micoli, Verona (IT); Ferruccio Palazzesi, Verona (IT); Agostino Cianciulli, Verona (IT); Robin Tyacke, London (GB); David Nutt, London (GB)

(73) Assignee: Solvonis Therapeutics Ireland Holdings Limited, Dublin (IE)

( * ) Notice: Subject to any disclaimer, the term of this patent is extended or adjusted under 35 U.S.C. 154(b) by 0 days.

(21) Appl. No.: 18/838,986

(22) PCT Filed: Feb. 16, 2023

(86) PCT No.: PCT/EP2023/053973

§ 371 (c)(1),
(2) Date: Aug. 15, 2024

(87) PCT Pub. No.: WO2023/156565

PCT Pub. Date: Aug. 24, 2023

(65) Prior Publication Data

US 2025/0179089 A1 Jun. 5, 2025

Related U.S. Application Data

(60) Provisional application No. 63/310,982, filed on Feb. 16, 2022.

(51) Int. Cl.

*A61K 31/407* (2006.01)
*A61K 45/06* (2006.01)
*C07D 498/08* (2006.01)

(52) U.S. Cl.

CPC .......... *C07D 498/08* (2013.01); *A61K 31/407* (2013.01); *A61K 45/06* (2013.01)

(58) Field of Classification Search

CPC .................................................... A61K 31/407
USPC .......................................................... 514/412
See application file for complete search history.

(56) References Cited

U.S. PATENT DOCUMENTS

| | | | |
|---|---|---|---|
| 4,327,725 A | 5/1982 | Cortese et al. | |
| 4,624,848 A | 11/1986 | Lee | |
| 4,871,549 A | 10/1989 | Ueda et al. | |
| 4,968,509 A | 11/1990 | Radebaugh et al. | |
| 5,011,692 A | 4/1991 | Fujioka et al. | |
| 5,017,381 A | 5/1991 | Maruyama et al. | |
| 5,229,135 A | 7/1993 | Philippon et al. | |
| 5,260,068 A | 11/1993 | Chen | |
| 5,260,069 A | 11/1993 | Chen | |
| 5,456,923 A | 10/1995 | Nakamichi et al. | |
| 5,461,140 A | 10/1995 | Heller et al. | |
| 5,508,040 A | 4/1996 | Chen | |
| 5,516,527 A | 5/1996 | Curatolo | |
| 5,567,441 A | 10/1996 | Chen | |
| 5,686,105 A | 11/1997 | Kelm et al. | |
| 5,700,410 A | 12/1997 | Nakamichi et al. | |
| 5,837,284 A | 11/1998 | Mehta et al. | |
| 5,840,329 A | 11/1998 | Bai | |
| 5,977,175 A | 11/1999 | Lin | |
| 6,465,014 B1 | 10/2002 | Moroni et al. | |
| 6,875,751 B2 | 4/2005 | Imbach et al. | |
| 6,932,983 B1 | 8/2005 | Straub et al. | |
| 7,585,851 B2 | 9/2009 | Bryant et al. | |
| 7,964,580 B2 | 6/2011 | Sofia et al. | |
| 9,790,230 B2 * | 10/2017 | Cecere | A61P 25/24 |
| 2013/0203752 A1 | 8/2013 | Blough et al. | |
| 2020/0360311 A1 | 11/2020 | Golan et al. | |

FOREIGN PATENT DOCUMENTS

| | | | |
|---|---|---|---|
| WO | 2011146850 A1 | 11/2011 | |
| WO | 2015181061 A1 | 12/2015 | |
| WO | 2016015333 A1 | 2/2016 | |

OTHER PUBLICATIONS

PCT/EP2023/053973. International Search Report. Jun. 1, 2023.
PCT/EP2023/053973. Written Opinion of the International Searching Authority. Jun. 1, 2023.
Pinna et al. Behavioural addictions and the transition from DSM-IV-TR to DSM-5. Journal of Psychopathology, 2015; 21(4):380-389.
Rautio et al. Prodrugs: design and clinical applications. Rautio et al., Nat Rev Drug Discov. 2008;7(3):255-70.
Ray TS, Psychedelics and the Human Receptorome, PloS one, 2010; 5(2), e9019.
Rogers G, et al., The Harmful Effects of Recreational Ecstacy: A Systematic Review of Observational Evidence. Health Technology Assessment, 2009; 13(6): iii-iv, ix-xii, 1-315.
Sandtner et al. Binding Mode Selection Determines the Action of Ecstasy Homologs at Monoamine Transporters. Mol Pharmacol. 2016; 89(1):165-175.
Schenberg EE, Psychedelic-Assisted Psychotherapy: A Paradigm Shift in Psychiatric Research and Development. Frontiers in Pharmacology, 2018;9:733.
Schmid et al. Acute subjective effects in LSD- and MDMA-assisted psychotherapy. J Psychopharmacol. 2021;35(4):362-374.
Sessa B, et al. First study of safety and tolerability of 3,4-methylenedioxymethamphetamine-assisted psychotherapy in patients with alcohol use disorder. University of Bristol. 2021. 35(4);375-383.

(Continued)

*Primary Examiner* — Raymond J Henley, III

(74) *Attorney, Agent, or Firm* — CALYX LAW LLP; Graham Pechenik

(57) ABSTRACT

Disclosed herein are certain therapeutic substituted heterocyclic bridged ring compounds, including substituted morpholine, thiomorpholine, and piperidine compounds and their homologues, having various advantages over current compounds used in certain methods of drug-assisted therapy, such as MDMA, together with pharmaceutical compositions containing such compounds, and methods of their use to treat mental health disorders and CNS disorders.

20 Claims, 6 Drawing Sheets

(56) References Cited

OTHER PUBLICATIONS

Sessa B, Fischer FM. Underground MDMA-, LSD- and 2-CB-assisted individual and group psychotherapy in Zurich: Outcomes, implications and commentary. Drug Science, Policy and Law. 2015;2:2050324515578 08.
Simplício et al. Prodrugs for Amines, Molecules, 2008; 13(3):519-47.
Studerus et al. Psychometric Evaluation of the Altered States of Consciousness Rating Scale (OAV). PloS one, 2010; 5(8), e12412.
Thompson MR, et al. A role for oxytocin and 5-HT(1A) receptors in the prosocial effects of 3,4 methylenedioxymethamphetamine ("ecstasy"). Neuroscience; 2007. 146(2).
Tozzi et al. Gambling among youths in Switzerland and its association with other addictive behaviours. Swiss Medical Weekly, 2013; 143(w13768), 1-6.
Tsujikawa K, et al., Urinary excretion profiles of N-hydroxy-3,4-methylenedioxymethamphetamine in rats, Xenobiotica 2011;41(7):578-84.
Vig BS, et al., Amino Acids as Promoieties in Prodrug Design and Development. Advanced Drug Delivery Reviews, 2013;65(10):1370-85.
Walther et al. Systematic Structure-Activity Studies on Selected 2-, 3-, and 4-Monosubstituted Synthetic Methcathinone Analogs as Monoamine Transporter Releasing Agents. ACS Chem Neurosci. 2019;10(1):740-745.
Williams FM. Clinical Significance of Esterases in Man. Clin Pharmacokinet., 1985; 10(5):392-403.
Yamamoto et al. Metabolism of methamphetamine, amphetamine and p-hydroxymethamphetamine by rat-liver microsomal preparations in vitro. Xenobiotica, 1984;14(11)867-75.
Zhang JH, et al. A Simple Statistical Parameter for Use in Evaluation and Validation of High Throughput Screening Assays. Journal of Biomolecular Screening. 1999;4(2):62-73.
Arza et al. AAPA PharmaSciTech., 2009;10(1):220-6.
Baggott MJ, et al. Effects of 3,4-methylenedioxymethamphetamine on socioemotional feelings, authenticity, and autobiographical disclosure in healthy volunteers in a controlled setting. Journal of Psychopharmacology. 2016;30(4):378-87.
Baumann et al. Powerful cocaine-like actions of 3,4-methylenedioxypyrovalerone (MDPV), a principal constituent of psychoactive 'bath salts' products. Neuropsychopharmacology. 2013;38(4):552-562.
Bexis & Docherty. Role of alpha2A-adrenoceptors in the effects of MDMA on body temperature in the mouse. Br J Pharmacol. 2005;146(1):1-6.
Bhardwaj et al. Chemical delivery systems and soft drugs: Retrometabolic approaches of drug design. Saudi Pharm J. 2014;22(4):290-302.
Buchwald & Bodor. Recent advances in the design and development of soft drugs. Pharmazie. 2014;69(6):403-413.
Buchwald P. Soft drugs: design principles, success stories, and future perspectives. Expert Opin Drug Metab Toxicol. 2020;16(8):645-650.
Carleton NB, et al. Brief Fear of Negative Evaluation Scale-Revisited. Depression and Anxiety. 2006;23:297-303.
Chamberlain et al. Behavioural addiction—A rising tide?. Eur Neuropsychopharmacol. 2016;26(5):841-855.
De La Torre et al. Non-linear pharmacokinetics of MDMA ('ecstasy') in humans. Br J Clin Pharmacol. 2000;49(2): 104-109.
Di L. The Impact of Carboxylesterases in Drug Metabolism and Pharmacokinetics. Curr Drug Metab. 2019;20(2):91-102.
Dimitrov et al. Ketamine esters and amides as short-acting anaesthetics: Structure-activity relationships for the side-chain. Bioorg Med Chem. 2019;27(7):1226-1231.
Dimitrov et al. Structure-Activity Relationships for the Anaesthetic and Analgaesic Properties of Aromatic Ring-Substituted Ketamine Esters. Molecules. 2020;25(12):2950.
Domes G, et al. Oxytocin Improves "Mind Reading" in Humans. Biological Psychiatry. 2007;61:731-3.
Dunlap Le, et al. Dark Classics in Chemical Neuroscience: 3,4-Methylenedioxymethamphetamine (MDMA). ACS Chem Neurosci. 2018;9(10):2408-27.
Giovannitti JA, et al. Alpha-2 Adrenergic Receptor Agonists: A Review of Current Clinical Applications. American Dental Society of Anesthesiology. 2015;62:31-8.
Goldstein & Volkow. Dysfunction of the prefrontal cortex in addiction: neuroimaging findings and clinical implications. Nat Rev Neurosci. 2011;12(11):652-669.
Graeff et al. Role of 5-HT in Stress, Anxiety, and Depression. Pharmacology, Biochemistry, and Behavior. 1996; 54(1):129-41.
Greer GR & Tolbert R. A method of conducting therapeutic sessions with MDMA. J Psychoactive Drugs. 1998;30(4):371-379.
Grof S. LSD Psychotherapy. 1980.
Harris et al. Subjective and hormonal effects of 3,4-methylenedioxymethamphetamine (MDMA) in humans. Psychopharmacology (Berl). 2002; 162(4):396-405.
Harvey et al. Development of Rapidly Metabolized and Ultra-Short-Acting Ketamine Analogs. Anesth Analg. 2015;121(4):925-933.
Huang et al. Isobologram Analysis: A Comprehensive Review of Methodology and Current Research. Front Pharmacol. 2019;10:1222.
Hysek et al. MDMA enhances emotional empathy and prosocial behavior. Soc Cogn Affect Neurosci. 2014;9(11):1645-1652.
Jaiswal M, et al., Nanoemulsion: an advanced mode of drug delivery system. Biotech., 2015; 3(5):123-7.
Johnson et al. Human hallucinogen research: guidelines for safety. J Psychopharmacol. 2008;22(6):603-620.
Jose et al. Structure-activity relationships for ketamine esters as short-acting anaesthetics. Bioorg Med Chem. 2013;21(17):5098-5106.
Katz et al. Characterizing the psychological state produced by LSD. J Abnorm Psychol. 1968;73(1):1-14.
Kernis MH & Goldman BM. A Multicomponent Conceptualization of Authenticity: Theory and Research. Advances in Experimental Social Psychology. 2006;38.
Kirsch P, et al. Oxytocin Modulates Neural Circuitry for Social Cognition and Fear in Humans. Journal of Neuroscience. 2005;25(49):11489-93.
Konkoly et al. Natural course of behavioral addictions: a 5-year longitudinal study. BMC Psychiatry, 2015; 15:4.
Korfmacher et al. Utility of capillary microsampling for rat pharmacokinetic studies: Comparison of tail-vein bleed to jugular vein cannula sampling. J Pharmacol Toxicol Methods. 2015;76:7-14.
Laizure et al. The role of human carboxylesterases in drug metabolism: have we overlooked their importance?. Pharmacotherapy. 2013;33(2):210-222.
Leary MR. A Brief Version of the Fear of Negative Evaluation Scale. Personality and Social Psychology Bulletin. 1983;9(3):371-5.
Liechti ME et al, Gender Differences in the Subjective Effects of MDMA. Psychopharmacology (Berl) 2001; 154(2):161-8.
Luethi D & Liechti ME, Designer drugs: mechanism of action and adverse effects, Arch. Toxicol., 2020; 94, 1085-133.
Mas et al. Cardiovascular and neuroendocrine effects and pharmacokinetics of 3,4-methylenedioxymethamphetamine in humans. J Pharmacol Exp Ther. 1999;290(1):136-145.
McLaughlin et al. Synthesis, analytical characterization, and monoamine transporter activity of the new psychoactive substance 4-methylphenmetrazine (4-MPM), with differentiation from its ortho- and meta-positional isomers. Drug Test Anal. 2018;10(9):1404-1416.
Miller et al. Metabolic activation of the serotonergic neurotoxin para-chloroamphetamine to chemically reactive intermediates by hepatic and brain microsomal preparations. Biochem Pharmacol. 1986;35(10):1737-1742.
Mitchell et al. MDMA-assisted therapy for severe PTSD: a randomized, double-blind, placebo-controlled phase 3 study. Nat Med. 2021;27(6):1025-1033.
Mithoefer et al. A Manual for MDMA-Assisted Psychotherapy in the Treatment of Posttraumatic Stress Disorder.; 2015.

(56) References Cited

OTHER PUBLICATIONS

Mithoefer M, MDMA-Assisted Psychotherapy: How Different is it from Other Psychotherapy?. Manifesting minds: A review of psychedelics in science, medicine, sex, and spirituality. 2013; 125.
Mithoefer MC, et al., The safety and efficacy of ±3,4-methylenedioxymethamphetamine-assisted psychotherapy in subjects with chronic, treatment-resistant posttraumatic stress disorder: the first randomized controlled pilot study. J. of Psychopharmacology. 2010;25(4):439-452.
Mukker et al. A Pro-Soft Drug Approach for Mitigation of Side Effects of Inhaled Corticosteroids. J Pharm Sci. 2016;105(9):2509-2514.
Oehen P, et al., A Randomized Controlled Pilot Study of MDMA-Assisted Psychotherapy for Treatment of Resistant, chronic Post-Traumatic Strss Disorder (PTSD). Journal of Psychopharmacology. 2013:40-52.
Ortuno et al. Quantification of 3,4-methylenedioxymetamphetamine and its metabolites in plasma and urine by gas chromatography with nitrogen-phosphorus detection. J Chromatogr B Biomed Sci Appl. 1999;723(1-2):221-232.
Pacofsky et al. Relating the structure, activity, and physical properties of ultrashort-acting benzodiazepine receptor agonists. Bioorg Med Chem Lett. 2002;12(21):3219-3222.
Passie. Healing with Entactogens: Therapist and Patient Perspectives on MDMA-Assisted Group Psychotherapy, Torsten Passie. Multidisciplinary Association for Psychedelic Studies. 2012.
PCT/EP2023/053973. Information on Search Strategy. Jun. 1, 2023.
PCT/EP2023/053973. International Preliminary Report on Patentability. Aug. 20, 2024.

* cited by examiner

MORPHOLINE-LIKE MONOAMINE RELEASERS

CROSS-REFERENCE

This is a U.S. National Stage Entry under 35 U.S.C. § 371 of International Application No. PCT/EP2023/053973. filed Feb. 16, 2023, which claims priority under PCT Article 8(1) and Rule 4.10 to U.S. Provisional Application No. 63/310, 982, filed Feb. 16, 2022, and incorporated by reference for all purposes as if fully set forth herein.

TECHNICAL FIELD

Certain substituted heterocyclic bridged ring compounds, including substituted morpholine, thiomorpholine, and piperidine compounds and their homologues are disclosed, together with pharmaceutical compositions containing such compounds, and methods of their use to treat mental health disorders and CNS disorders.

BACKGROUND OF THE INVENTION

CNS disorders, of which mental health conditions are a part, are the leading cause of disability worldwide, and are estimated to lead to over a million lives lost to suicide. Additionally, they are estimated to cost the global economy over $1 trillion in lost productivity each year. They are also highly correlated with substance abuse, poor educational attainment, unemployment, homelessness, and incarceration, and are associated with a 40% higher risk of developing cardiovascular and metabolic diseases, as well as other comorbidities. Mental health disorders are estimated to affect 1 in 5 adults and 1 in 6 children aged 6-17 in the U.S., totaling nearly 50 million people. Moreover, their incidence has increased over recent decades in all age groups, and is expected to increase yet further as a result of the ongoing COVID-19 pandemic.

Despite the high prevalence and increasing incidence, only half of all people with a mental health condition receive treatment. Further, even for those who do receive treatment, the average delay between onset of symptoms and eventual treatment is 11 years. Myriad issues contribute to the failure of timely treatment; for example, half of U.S. counties do not have a single practicing psychiatrist, and a significant number of individuals lack insurance coverage. However, the primary reason why individuals fail to receive treatment is simply the absence of therapeutically effective treatment options available. Current treatment options for mental health conditions, specifically, consist generally of psychotherapy, pharmacotherapy (typically, SSRIs), and direct brain intervention, either provided alone or in combination (e.g., psychotherapy together with one or more daily medications). All however suffer serious drawbacks.

The enormous public health burden of CNS disorders necessitates the development of novel alternative compounds, especially those which minimize side effects, optimize efficacy, and allow for greater access. Provided herein are compounds, compositions, methods, uses, and pharmaceutical kits to meet these needs and others, and having such advantages and improvements as will become readily apparent through the disclosure below.

BRIEF SUMMARY OF THE INVENTION

The following presents a simplified summary of some embodiments of the invention in order to provide a basic understanding of the invention. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

In a first aspect, provided is a compound having the structure of Formula (1):

(1)

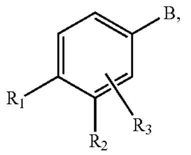

or a pharmaceutically acceptable salt, hydrate, or solvate thereof, wherein:

B is

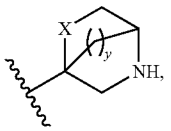

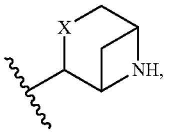

or

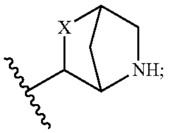

$R_1$, $R_2$, and $R_3$ are each independently hydrogen, —$CH_3$, —$OCH_3$, —$CF_3$, or halogen; or two of $R_1$, $R_2$ and $R_3$ are combined with the atoms to which they are each attached to form a $C_{4-8}$ cycloalkyl, $C_{4-10}$ heterocycloalkyl, or $C_{6-12}$ aryl; X is O, S, —O—$CH_2$, —O—C(O)—, or —S—$CH_2$; y is 1 or 2; and wherein at least one of $R_1$, $R_2$, and $R_3$ is not hydrogen.

In some embodiments, the compound has the structure of Formula (2):

(2)

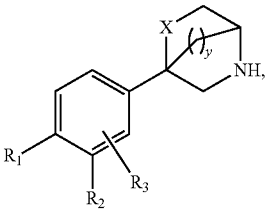

or a pharmaceutically acceptable salt, hydrate, or solvate thereof.

In some embodiments, X is O. In some embodiments, X is S. In some embodiments, X is —O—$CH_2$. In some embodiments, X is —O—C(O)—. In some embodiments, X is —S—$CH_2$.

In some embodiments, y is 1. In some embodiments, y is 2.

In some embodiments, $R_1$ is Cl. In some embodiments, $R_2$ is Cl. In some embodiments, $R_1$ and $R_2$ are both Cl. In some embodiments, $R_1$ is methyl. In some embodiments, $R_2$ is methyl. In some embodiments, $R_1$ and $R_2$ are both methyl. In some embodiments, $R_1$ and $R_2$ are taken together to form a methylenedioxy group.

In another aspect, provided is a compound selected from the group consisting of:
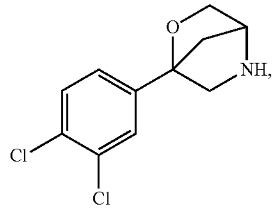
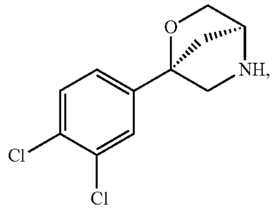
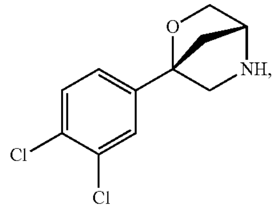
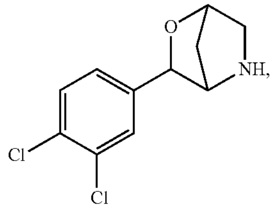
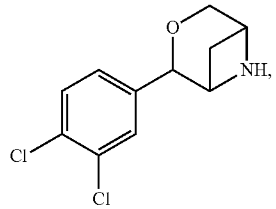
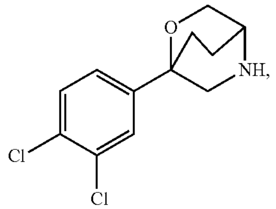
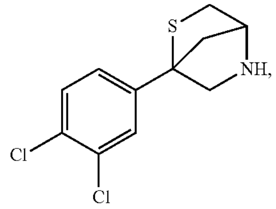
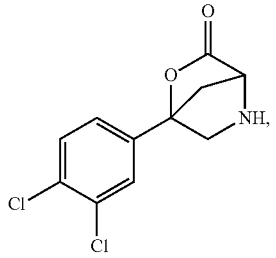
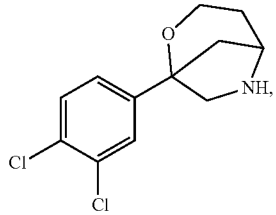
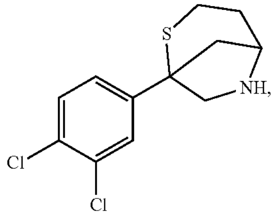
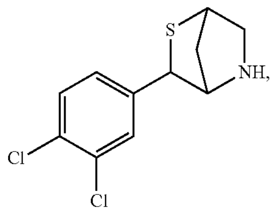
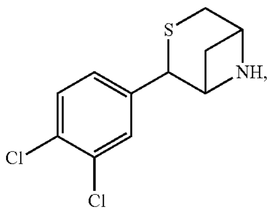
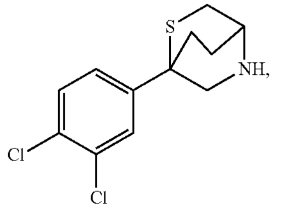
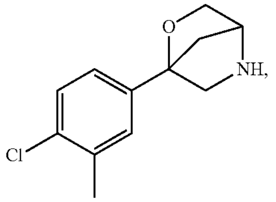
-continued
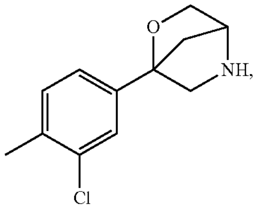
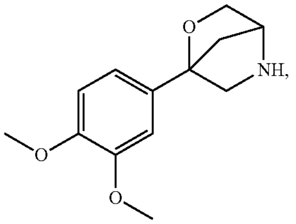
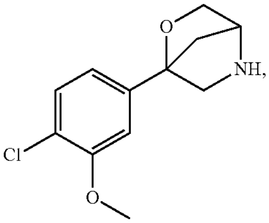
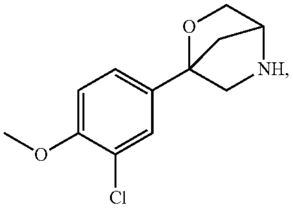
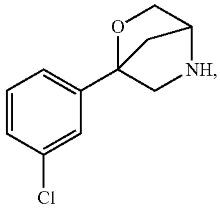
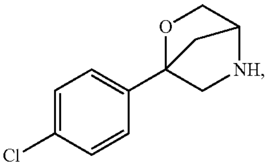
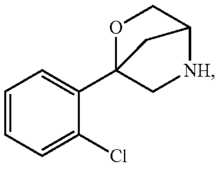
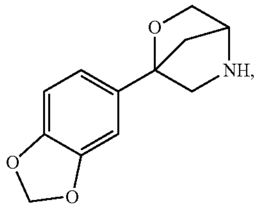
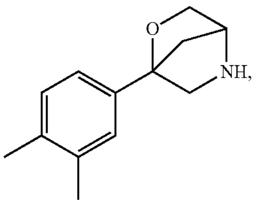
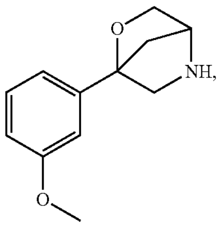
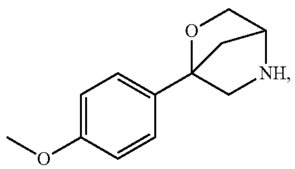
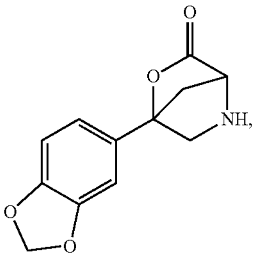
and
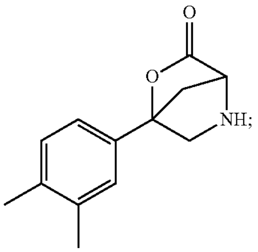
or a pharmaceutically acceptable salt, by, or solvate thereof.

In some embodiments, the compound is

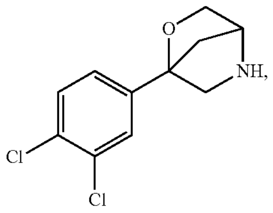

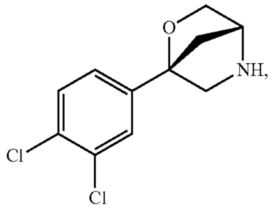

or

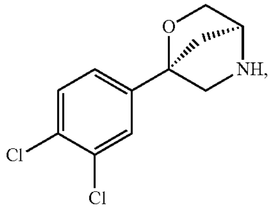

or a pharmaceutically acceptable salt, hydrate, or solvate thereof.

In some embodiments, the compound is

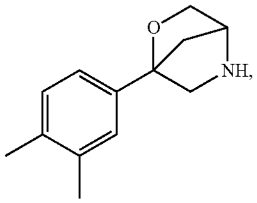

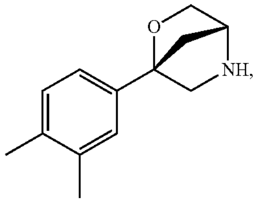

or

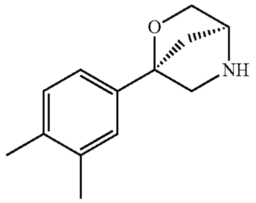

or a pharmaceutically acceptable salt, hydrate, or solvate thereof.

In some embodiments, the compound is

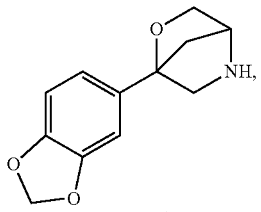

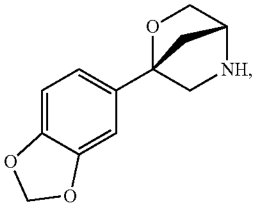

or

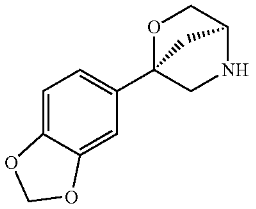

or a pharmaceutically acceptable salt, hydrate, or solvate thereof.

In some embodiments, the compound is a compound of Table 1.

Also provided is a single enantiomer of the compound of any of the preceding embodiments, or an enantiomerically enriched mixture of any proportions.

In another aspect, provided is a compound of any of the preceding embodiments, or a pharmaceutically acceptable salt thereof, wherein the compound stimulates release of a monoamine neurotransmitter and inhibits the function of a monoamine transporter. In another aspect, provided is a compound of any one of the preceding embodiments, or a pharmaceutically acceptable salt thereof, wherein the compound stimulates release of a monoamine neurotransmitter or inhibits the function of a monoamine transporter. In some embodiments, the monoamine neurotransmitter is any of serotonin (5-HT), dopamine (DA), and norepinephrine (NE), and/or the monoamine transporter is any of a serotonin transporter (SERT), a dopamine transporter (DAT), and a norepinephrine transporter (NET).

In another aspect, provided is a compound of any of the preceding embodiments, or a pharmaceutically acceptable salt thereof, for use in modulating neurotransmission. In some embodiments, modulating neurotransmission treats a substance use disorder, a behavioral addiction, or a mental health disorder.

In another aspect, provided is a compound of any of the preceding embodiments, or a pharmaceutically acceptable salt thereof, for use in the treatment of a substance use disorder, a behavioral addiction, or a mental health disorder.

In another aspect, provided is the use of a compound of any of the preceding embodiments, or a pharmaceutically acceptable salt thereof, for the manufacture of a medicament for use in treatment of substance use disorder, a behavioral addiction, or a mental health disorder.

In another aspect, provided is the use of a compound of any of the preceding embodiments, or a pharmaceutically acceptable salt thereof, for treating a substance use disorder, a behavioral addiction, or a mental health disorder.

In another aspect, provided is the use of a compound of any of the preceding embodiments, or a pharmaceutically acceptable salt thereof, for the manufacture of a medicament for use in treatment of substance use disorder, a behavioral addiction, or a mental health disorder.

In some embodiments, the substance use disorder, the behavioral addiction, or the mental health disorder is any of alcohol use disorder, opioid use disorder, nicotine dependence, stimulant use disorder, tobacco use disorder, gambling addiction, gambling disorder, sexual addiction, gaming addiction, shopping addiction, internet addiction, binge eating disorder, internet gaming addiction, an anxiety disorder, a depressive disorder, or a trauma or stressor related disorder.

In some aspects are disclosed pharmaceutical compositions comprising a therapeutically effective amount of a disclosed compound for use in treating a substance use disorder, a behavioral addiction, or a mental health disorder, and a pharmaceutically acceptable carrier, diluent, or excipient. In some embodiments, the composition is suitable for oral, buccal, sublingual, injectable, subcutaneous, intravenous, or transdermal administration. In some embodiments (sometimes, equivalently and simply as shorthand, "in embodiments"), the composition is suitable for oral administration. In embodiments, the composition is suitable for intravenous administration. In embodiments, the composition is in a unit dosage form.

In some embodiments, the composition further comprises a therapeutically effective amount of an additional active agent. In some embodiments, the additional active agent is selected from the group consisting of: amino acids, antioxidants, anti-inflammatory agents, analgesics, antineuropathic and antinociceptive agents, antimigraine agents, anxiolytics, antidepressants, antipsychotics, anti-PT SD agents, cannabinoids, immunostimulants, anti-cancer agents, antiemetics, orexigenics, antiulcer agents, antihistamines, antihypertensives, anticonvulsants, antiepileptics, bronchodilators, neuroprotectants, entactogens and empathogens, entheogens, psychedelics, tryptamines, terpenes, beta-carbolines, phenethylamines, monoamine oxidase inhibitors, sedatives, stimulants, serotonergic agents, nootropics, and vitamins. In some embodiments, the additional active agent acts to increase a therapeutic effect, provide an additional therapeutic effect, decrease an unwanted effect, increase stability or shelf-life, improve bioavailability, induce synergy, or alter pharmacokinetics or pharmacodynamics. In some embodiments, the additional therapeutic effect is an antioxidant, anti-inflammatory, analgesic, antineuropathic, antinociceptive, antimigraine, anxiolytic, antidepressant, antipsychotic, anti-PTSD, immunostimulant, anti-cancer, antiemetic, orexigenic, antiulcer, antihistamine, antihypertensive, anticonvulsant, antiepileptic, bronchodilator, neuroprotective, entactogenic, empathogenic, entheogenic, psychedelic, nootropic, sedative, or stimulant effect.

In some embodiments, the additional active agent is selected from the group consisting of: opioid antagonists (e.g., nalmefene, naltrexone), CB-1 antagonists (e.g., rimonabant), CRH1 antagonists (e.g., verucerfont, pexacerfont), NK1R antagonists (e.g., tradipitant), OTR agonists (e.g., oxytocin), GABA agents (e.g., topiramate, baclofen, benzodiazepines, such as alprazolam, diazepam or lorazepam), voltage-gated sodium channel inhibitors (e.g., oxacarbazepine, valproic acid, zonisamide), voltage-dependent calcium channel agonists (e.g., gabapentin, pregabalin), α7 nicotinic acetylcholine (ACh) receptor agonists (e.g., varenicline), 5-HT3 antagonists (e.g., ondansetron), 5-HT1A receptor partial agonists (e.g., aripiprazole), 5-HT2A receptor antagonists (e.g., quetiapine, olanzapine, mirtazapine), 5-HT reuptake inhibitors (e.g., trazodone), SERT inhibitors (e.g., duloxetine), α1 adrenoreceptor antagonists (e.g., doxazosin, prazosin), glucocorticoid receptor antagonists (e.g., mifepristone), α1 adrenoreceptor agonists (e.g., guanfacine), AChE inhibitors (e.g., citicoline), dopamine D2 receptor antagonists (e.g., tiapride), α2 adrenoreceptor agonists (e.g., clonidine), NMDA receptor antagonists (e.g., acamprosate), and aldehyde dehydrogenase inhibitors (e.g., disulfiram), including pharmaceutically acceptable salts. In some embodiments, the patient is also administered a therapeutically effective amount of an additional active agent, where the additional active agent is selected from the group above.

In some aspects are disclosed unit dosage forms comprising a therapeutically effective amount of a disclosed compound. In some embodiments, the unit dosage form is formulated for oral administration. In embodiments, the unit dosage form is formulated for immediate release, controlled release, sustained release, extended release, or modified release. In embodiments, the unit dosage form is formulated for intravenous administration. In embodiments, the unit dosage form comprises the compound in a total amount of between 1 and 100 mg. In embodiments, the unit dosage form comprises the compound in a total amount of between 5 and 50 mg.

In some aspects are disclosed methods for modulating neurotransmission in a mammal, comprising administering to the mammal a therapeutically effective amount of a disclosed compound, composition, or unit dosage form. In some embodiments, the neurotransmission is serotonergic neurotransmission. In some embodiments, the neurotransmission is dopaminergic neurotransmission. In some embodiments, modulating neurotransmission comprises one or more of: (a) stimulating release of serotonin, and/or reducing serotonin uptake, by inhibiting the function of a serotonin transporter (SERT); and (b) stimulating release of dopamine, and/or reducing dopamine uptake, by inhibiting the function of a dopamine transporter (DAT). In some embodiments, the neurotransmission comprises reduced peak norepinephrine levels relative to peak serotonin levels and/or peak dopamine levels. In some embodiments, the neurotransmission is noradrenergic neurotransmission. In some embodiments, noradrenaline levels are increased from baseline following administration of the compound in a microdialysis assay. In some embodiments, the increase in noradrenaline levels from baseline is reduced relative to an increase in noradrenaline levels produced by MDMA or MEAI in a microdialysis assay. In some embodiments, modulating neurotransmission treats a substance use disorder, a behavioral addiction, or a mental health disorder in the mammal.

In some embodiments, the compound or the composition is orally administered to a mammal or a subject. In some embodiments, the compound or the composition is intravenously administered to the mammal or the subject.

In some aspects are disclosed methods of treating a medical condition in a mammal in need of such treatment, comprising administering a disclosed compound, composition, or unit dosage form. In some embodiments, the medical condition is a disorder linked to dysregulation or inadequate functioning of neurotransmission. In some embodiments, the disorder is linked to dysregulation or inadequate functioning of neurotransmission is that of serotonergic neurotransmission. In embodiments, the medical condition is a substance abuse disorder, a behavioral addiction, or a mental health disorder. In embodiments, the mammal is a human.

In some aspects are disclosed methods of reducing the symptoms of a substance use disorder, a behavioral addiction, or a mental health disorder in a human, comprising identifying a human in need of said reducing, and administering to the human a disclosed compound, composition, or unit dosage form. In some aspects are disclosed methods of treating a substance use disorder patient, a behavioral addiction patient, or a mental health patient in need thereof, comprising administering to the patient a therapeutically effective amount of a disclosed compound, composition, or unit dosage form.

In some embodiments, the substance abuse disorder, behavioral addiction, or mental health disorder is selected from the group consisting of: alcohol use disorder, nicotine dependency, opioid use disorder, stimulant use disorder, sedative, hypnotic, or anxiolytic use disorder, tobacco use disorder, gambling disorder, compulsive sexual behavior, sexual addiction, gaming addiction, shopping addiction, internet addiction, kleptomania, pyromania, compulsive buying, pornography addiction, binge eating disorder, internet gaming addiction, exercise addiction or overtraining syndrome, love addiction, work addiction or workaholism, and technological addictions, post-traumatic stress disorder (PTSD), an anxiety disorder, a depressive disorder, adjustment disorder, affective disorder, depression, atypical depression, postpartum depression, catatonic depression, a depressive disorder due to a medical condition, premenstrual dysphoric disorder, seasonal affective disorder, dysthymia, anxiety, phobia disorders, binge disorders, body dysmorphic disorder, alcohol or drug abuse or dependence disorders, substance-related disorders, substance-induced mood disorder, a mood disorder related to another health condition, disruptive behavior disorders, eating disorders, impulse control disorders, obsessive compulsive disorder (OCD), attention deficit hyperactivity disorder (ADHD), personality disorders, attachment disorders, and dissociative disorders. In some embodiments, the substance abuse disorder is any of alcohol use disorder, nicotine dependence, sedative, hypnotic, or anxiolytic use disorder, opioid abuse disorder, stimulant use disorder, and tobacco use disorder. In some embodiments, the behavioral addiction is any of gambling disorder, compulsive sexual behavior, sexual addiction, gaming addiction, shopping addiction, internet addiction, kleptomania, pyromania, compulsive buying, pornography addiction, binge eating disorder, internet gaming addiction, exercise addiction or overtraining syndrome, love addiction, work addiction or workaholism, and technology addiction. In some embodiments, the mental health disorder is any of an anxiety disorder, a depressive disorder, OCD, or PTSD. In some embodiments, the anxiety disorder is generalized anxiety disorder (GAD). In embodiments, the depressive disorder is major depressive disorder (MDD) or treatment-resistant depression (TRD).

In some aspects are disclosed methods of improving psychological functioning in a human, comprising identifying a human in need of said improving, and administering to the human a disclosed compound, composition, or unit dosage form. In some embodiments, the improvement in psychological functioning is a reduction of neuroticism or psychological defensiveness, an increase in creativity or openness to experience, an increase in decision-making ability, an increase in feelings of wellness or satisfaction, or an increase in ability to fall or stay asleep.

In some embodiments, the compound is administered in combination with one or more psychotherapy sessions. In embodiments, the patient has successfully completed a group therapy preparation course prior to the one or more psychotherapy sessions. In embodiments, the patient has met all predefined inclusion criteria, and the patient has not met any predefined exclusion criteria, prior to the one or more psychotherapy sessions. In some embodiments, the one or more psychotherapy sessions is between 5 and 20 psychotherapy sessions, during which at least two of said psychotherapy sessions the patient is administered the compound. In some embodiments, the method of the invention results in one or more of: (a) a reduction of substance use, (b) a reduction of substance cravings, (c) a promotion of substance abstinence, (d) a prevention of relapse, or (e) an improvement of at least one symptom of the substance use disorder. In some embodiments, the method of the invention results in one or more of: (a) an increase in quality of life, (b) an increase in psychosocial functioning, (c) a decrease in use or frequency of a prescription medication, (d) a decrease in use or frequency of a recreational drug, (e) a decrease in obsessive compulsive thoughts, (f) a decrease in suicidality, (g) an increase in feelings of empathy, or (h) an increase in self-compassion. In some embodiments, the method of the invention results in an improvement of at least one symptom of a comorbid psychiatric disorder, such as antisocial personality disorder, borderline personality disorder, depression, anxiety, schizophrenia, attention deficit hyperactivity disorder, bipolar disorder, obsessive compulsive disorder, binge eating disorder, or PTSD. In some embodiments, the results are measured at least 1 month, at least 3 months, at least 6 months, at least 9 months, or at least 1 year from baseline, or from the first psychotherapy session.

In some embodiments, the patient has a genetic variation associated with a mental health disorder, SUP, AUD, trauma or stressor related disorder, depression, or anxiety, and including a genetic variation in mGluR5 or FKBP5. In some embodiments, the patient has a genetic variation associated with the metabolism of ester bonds, including metabolism in the plasma, gut, liver, or other tissues, such as a polymorphism relating to an endogenous esterase. In some embodiments, the patient has AUD, nicotine dependency, opioid use disorder, sedative, hypnotic, or anxiolytic use disorder, stimulant use disorder, or tobacco use disorder. In some embodiments, the patient has gambling disorder, compulsive sexual behavior, sexual addiction, gaming addiction, shopping addiction, internet addiction, kleptomania, pyromania, compulsive buying, pornography addiction, binge eating disorder, internet gaming addiction, exercise addiction or overtraining syndrome, love addiction, work addiction or workaholism, or technology addiction. In some embodiments, the patient has a depressive disorder or an anxiety disorder.

The foregoing has outlined broadly and in summary certain pertinent features of the disclosure so that the detailed description of the invention that follows may be better understood, and so that the present contribution to the art can be more fully appreciated. Hence, this summary is to be considered as a brief and general synopsis of only some of the objects and embodiments disclosed herein, is provided solely for the benefit and convenience of the reader, and is not intended to limit in any manner the scope, or range of equivalents, to which the claims are lawfully entitled. Additional features of the invention are described hereinafter. It should be appreciated by those in the art that all disclosed specific compositions and methods are only exemplary, and may be readily utilized as a basis for modifying or designing other compositions and methods for carrying out the same purposes. Such equivalent compositions and methods will be appreciated to be also within the scope and spirit of the invention as set forth in the claims. It also will be appreciated that headings within this document are being utilized only to expedite its review by a reader. They should not be construed as limiting the invention in any manner.

BRIEF SUMMARY OF THE DRAWINGS

To further clarify various aspects of the invention, a more particular description thereof is rendered by reference to certain exemplary embodiments illustrated in the figures. The figures depict only illustrated embodiments of the invention and are not limiting of its scope. They are simply provided as exemplary illustrations of embodiments of the invention. Certain aspects of the invention are therefore further described and explained with additional specificity and detail, but still by way of example only, with reference to the accompanying figures in which.

INCORPORATION BY REFERENCE

Figure 1:
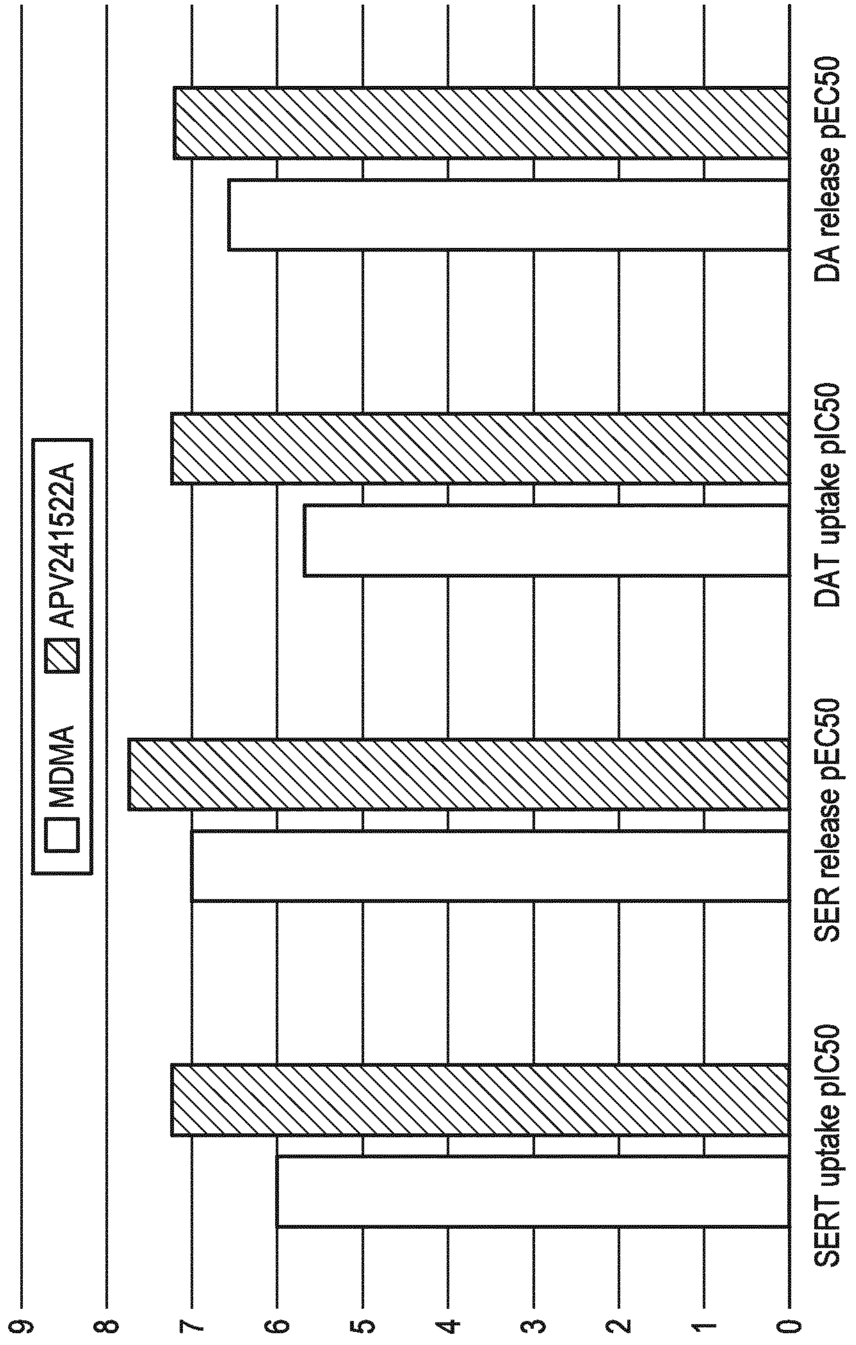
FIG. 1 depicts the inhibitory activity of exemplary compound APV241522A and reference compound MDMA on DAT and SERT, expressed as pIC50 or pEC50.

Each cited patent, publication, and non-patent literature is hereby incorporated by reference in its entirety, as if each was incorporated by reference individually, and as if each is fully set forth herein. However, where such reference is made, and whether to patents, publications, non-patent literature, or other sources of information, it is for the general purpose of providing context for discussing features of the invention. Accordingly, unless specifically stated otherwise, the reference is not to be construed as an admission that the document or underlying information, in any jurisdiction, is prior art or part of the common general knowledge in the art.

DETAILED DESCRIPTION OF THE INVENTION

While various aspects and features of certain embodiments are summarized above, the following detailed description illustrates several exemplary embodiments in further detail to enable one of skill in the art to practice such embodiments, and to make and use the full scope of the invention claimed. The described examples are for illustrative purposes and are not intended to limit the scope of the invention or its applications. It will be understood that many modifications, substitutions, changes, and variations in the described examples, embodiments, applications, and details illustrated herein can be made by those in the art without departing from the spirit of the invention, or the scope of the invention as described in the claims. It also will be appreciated that the headings within this document are being utilized only to expedite its review by a reader. They should not be construed as limiting the invention in any manner.

Among aspects of the invention are novel drug compounds that act as monoamine releasing agents. Among other aspects of the invention are novel drug compounds that act as monoamine uptake inhibitors. Among other aspects of the invention are novel drug compounds that act as receptor agents, such as receptor agonists or partial agonists, at monoamine receptors. Among yet other aspects are pharmaceutical compositions and methods for the treatment of CNS disorders relating to or affected by one or more monoamine neurotransmitter systems, such as mental health conditions and mental disorders, and psychiatric and neuropsychiatric disorders.

The scope of the invention includes all embodiments and formulations thereof, not only those expressly described below, and it will be understood that many modifications, substitutions, changes, and variations in the described embodiments, applications, and details of the invention illustrated herein can be made by those skilled in the art without departing from the spirit of the invention, or the scope of the invention as set forth in the appended claims.

As mentioned, there is a significant need for therapeutically effective CNS disorder treatment options. One such promising emerging therapeutic option is that of 3,4-methylenedioxymethamphetamine (MDMA) which, in human clinical studies currently underway, has started to accumulate evidence demonstrating that the Schedule I controlled drug has rapid and long-lasting therapeutic effects in treating mental health disorders following only limited doses when taken in combination with psychotherapy.

MDMA is a member of a pharmacological class called empathogens, or entactogens, that have demonstrated antidepressant, anxiolytic, and prosocial effects. These effects are believed to be produced or mediated, at least in part, by promoting raised levels of the monoamine neurotransmitters serotonin (5-HT), dopamine (DA), and norepinephrine (NE), by increasing activity at $5\text{-HT}_{1A}$ and $5\text{-HT}_{1B}$ receptors (Graeff et al., Pharmacol. Biochem. Behav., 54(1):129-41, 1996), and by acting at $5\text{-HT}_2$ receptors (Liechti and Vollenweider, Psychopharmacol., 2001; 154(2): 161-8; see also Bexis and Docherty, Br. J. Pharmacol., 146(1):1-6, 2005; Giovannitti et al., Anesth. Prog., 62(1):31-9, 2015; Thompson et al., Neurosci., 146(2):509-14, 2007; Kirsch et al., J. Neurosci., 25(49):11489-93, 2005; Domes et al., Biol. Psychiatry., 61(6):731-3, 2007; Ray, Plos One, 5(3):10, 2010; see Table 5 and accompanying text in Dunlap et al., ACS Chem Neurosci. 2018 Oct. 17; 9(10):2408-2427).

The term "empathogen" ("generating a state of empathy") was independently suggested in 1983-84 by the psychologist and psychopharmacologist Ralph Metzner and the Purdue University professor of pharmacology and medicinal chemistry David Nichols who in 1986 also coined the term "entactogen" ("to touch within") (Holland et al., Park Street Press, 2001 at 182 n.2). True to their names (used interchangeably herein), empathogens and entactogens such as MDMA can increase compassion for the self and others, reduce psychological defenses and fear of emotional injury, and enhance levels of trust and the capacity for introspection and communication. In part due to such effects, MDMA has been granted "breakthrough therapy" designation by the U.S. Food and Drug Administration (FDA).

In a recent randomized, double-blind, placebo-controlled, multi-site phase 3 clinical trial, as part of research sponsored by the Multidisciplinary Assoc. for Psychedelic Studies (MAPS), MDMA-assisted therapy was highly efficacious in individuals with severe PTSD, and treatment was safe and well-tolerated, even in those with comorbidities (Mitchell et al., Nat. Med., 27, 1025-1033, 2021). Studies have also demonstrated potential for MDMA to address other difficult-to-treat CNS disorders including, among others, substance abuse, obsessive compulsive disorder (OCD), phobias, eating disorders, depression, end-of-life anxiety, and social anxiety.

Although MDMA generally produces no long-lasting or serious adverse events, it is known to cause transient adverse events that are mild to moderate in severity, including increased anxiety, cardiovascular effects such as increased blood pressure and heart rate, hyperthermia, hyperhidrosis, jaw tightness and bruxism, muscle tightness, unpleasant stimulation, reduced appetite, nausea, poor concentration, and impaired balance (see, e.g., Harris et al., Psychopharmacol. (Berl), 162(4):396-405, 2002; Liechti et al., Psychopharmacol. (Berl), 154(2):161-8, 2001; Oehen et al., J. Psychopharmacol., 27(1): 40-52, 2013; Mas et al., J. Pharmacol. Exp. Ther., 290(1): 136-45, 1999; Mithoefer et al., J. of Psychopharmacol., 25(4): 439-452, 2010; Rogers et al., Health Technol. Assess., 2009; 13(6): iii-iv, ix-xii, 1-315). MDMA is expected to be approved only for drug-assisted psychotherapy, where it will be administered during one or more day-long drug-assisted sessions, generally with two trained psychotherapists or clinicians. This paradigm may restrict access to vulnerable and disadvantaged patient populations. Enhancing access to the therapeutic benefits of MDMA may be accomplished by providing compounds with comparable or superior efficacy and relatively diminished side effects, as well as other improvements such as optimized time course of drug action.

MAPS' MDMA-assisted treatment protocol for PTSD outlines six to eight hour long sessions and notes that peak effects may last from one to three hours (Mithoefer, A Manual for MDMA-Assisted Psychotherapy In the Treatment of Posttraumatic Stress Disorder, 2015; 7). Several factors, including conflicts in provider and subject schedules, as well as cost, may limit the practicality of implementing such protocols on a broad scale. Providing an alternative compound with a reduced duration of action relative to MDMA may enhance treatment feasibility and access. Accordingly, there is a need for improved therapeutic options.

Amphetamines and cathinones, which share structural similarities with MDMA, have been pursued for therapeutic purposes. Such compounds may be categorized as stimulants that interact with monoamine transporters and induce adverse effects related to the stimulation of sympathetic nerves, including anxiety, insomnia, and hyperthermia, among others. In particular, 3,4-dichloroamphetamine (DCA) and para-chloroamphetamine (PCA), which possess a chlorinated phenyl structural moiety, act as selective serotonin releasing agents but also exhibit neurotoxic activity. Metabolism of such compounds into reactive and toxic metabolites has been associated with long-term neurotoxicity (Miller et al., Biochemical Pharmacol., 1986; 35(10): 1737-1742). In structure-activity relationship studies of methcathinone analogs, monoamine release efficacy was determined to be weakest when the phenyl ring is substituted at the 2-position relative to compounds substituted at the 3- or 4-positions (Walther et al., ACS Chemical Neuroscience, 2018).

Substituted phenylmorpholines and substituted phenmetrazines have been shown to exhibit diverse effects in monoamine release and uptake assays, and phenyl ring substitution has been described to increase serotonin release (US20130203752). Pharmacological studies of phenmetrazine derivatives substituted with a methyl group at the 2- and 3-position indicate stimulant-like properties, whereas a methylphenmetrazine derivative substituted at the 4-position has been shown to have greater potency at SERT, which could be indicative of entactogen-like properties (McLaughlin et al., Drug Testing and Analysis, 2018). Such compounds are substrates at NET and DAT, but are also associated with sympathomimetic adverse events, which can result in serious complications (Luethi and Liechti, Archives of Toxicology, 2020).

There exists a need for compounds that display entactogenic pharmacological properties with improved safety profiles. In certain therapeutic contexts, there exists an additional need for such compounds to display a relatively abbreviated duration of action, for example, to provide short-acting entactogenic effects. Provided herein are compounds that meet such needs. Due to their pharmacology, such compounds may be useful in treating a broad range of addictions. Addictions to substances, for example, alcohol and drug addictions, and behavioural addictions, such as gambling disorders and compulsive sexual behavior may be ameliorated by administration of the compounds provided herein.

A. General Definitions and Terms

As used in this specification and the appended claims, the singular forms "a," "an," and "the" include plural referents unless the context clearly dictates otherwise. Thus, for example, reference to "an active agent" includes reference to a combination of one or more active agents, and reference to "an excipient" includes reference to a combination of one or more excipients. While the term "one or more" may be used, its absence (or its replacement by the singular) does not signify the singular only, but simply underscores the possibility of multiple agents or ingredients in particular embodiments.

The terms "comprising," "including," "such as," and "having" are intended to be inclusive and not exclusive (i.e., there may be other elements in addition to the recited elements). Thus, the term "including" as used herein means, and is used interchangeably with, the phrase "including but not limited to." The term "or" is used herein to mean, and is used interchangeably with, the term "and/or," unless context clearly indicates otherwise.

Unless otherwise indicated, all numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, "about" refers to plus or minus five percent (±5%) of the recited unit of measure. The term "substantially," where it is applied to modify a feature or limitation herein, will be read in the context of the invention and in light of the knowledge in the art to provide the appropriate certainty, e.g., by using a standard that is recognized in the art for measuring the meaning of "substantially" as a term of degree, or by ascertaining the scope as would one of skill in the art.

In some embodiments, the numerical parameters should be construed in light of the number of reported significant digits and by applying ordinary rounding techniques. Notwithstanding that the numerical ranges and parameters setting forth the broad scope of some embodiments are approximations, the numerical values set forth in the specific examples are reported as precisely as practicable. The numerical values presented in some embodiments of the invention may contain certain errors necessarily resulting from the standard deviation found in their respective testing measurements.

A comprehensive list of the abbreviations utilized by organic chemists of ordinary skill in the art appears in the first issue of each volume of the Journal of Organic Chemistry; this list is typically presented in a table entitled Standard List of Abbreviations; the current list as of the date of this filing is hereby incorporated by reference as if fully set forth herein.

Unless defined otherwise, all technical and scientific terms herein have the meaning as commonly understood by one having ordinary skill in the art to which this invention belongs, who as a shorthand may be referred to simply as "one of skill." Further definitions that may assist the reader in understanding the disclosed embodiments are as follows; however, it will be appreciated that such definitions are not intended to limit the scope of the invention, which shall be properly interpreted and understood by reference to the full specification (as well as any plain meaning known to one of skill in the relevant art) in view of the language used in the appended claims. The terminology used herein is for the purpose of describing particular embodiments only and is not intended to be limiting.

Generally, the nomenclature used and procedures performed herein are those known in fields relating to one or more aspects of the invention, such as biology, pharmacology, neuroscience, organic chemistry, synthetic chemistry, and/or medicinal chemistry, and are those that will be well known and commonly employed in such fields. Standard techniques and procedures will be those generally performed according to conventional methods in the art.

"Alkyl" will be understood to include straight or branched radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" can also be used. Preferably, an alkyl group comprises from 1 to 10 carbon atoms, more preferably from 1 to 6 carbon atoms, more preferably from 1 to 4 carbon atoms, and most preferably from 1 to 3 carbon atoms. For any alkyl, the alkyl may be optionally substituted at one or more positions by deuterium, halogen, alkyl, alkyl ester, hydroxy, alkoxy, carboxy, formyl, aryl, cycloalkyl, heterocycloalkyl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, —$OP(O)(OH)_2$, —OC(O)H, $OSO_2OH$, —$OC(O)NH_2$, and —$SONH_2$. As used herein, "Me" refers to methyl, "Et" refers to ethyl, "Pr" refers to propyl, "Pr" refers to isopropyl, "Bu" refers to butyl, and "Su" refers to tert-butyl or tertiary butyl.

"Alkanyl" refers to saturated branched, straight-chain, or cyclic alkyl radicals derived by the removal of one hydrogen atom from a single carbon atom of a parent alkane. Typical alkanyl groups include methanyl; ethanyl; propanyls such as propan-1-yl, propan-2-yl (isopropyl), and cyclopropan-1-yl; butanyls such as butan-1-yl, butan-2-yl (sec-butyl), 2-methyl-propan-1-yl (isobutyl), 2-methyl-propan-2-yl (t-butyl), and cyclobutan-1-yl; etc.

"Alkenyl" refers to an unsaturated branched, straight-chain, or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include ethenyl; propenyls such as prop-1-en-1-yl, prop-1-en-2-yl, prop-2-en-1-yl (allyl), prop-2-en-2-yl, cycloprop-1-en-1-yl, and cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2yl, buta-1,3-dien-1-yl, buta-1,3-dien-2-yl, cyclobut-1-en-1-yl, cyclobut-1-en-3-yl, and cyclobuta-1,3-dien-1-yl; and the like.

"Alkynyl" refers to an unsaturated branched, straight-chain, or cyclic alkyl radical having at least one carbon-carbon triple bond derived by the removal of one hydrogen atom from a single carbon atom of a parent alkyne. Typical alkynyl groups include ethynyl; propynyls such as prop-1-yn-1-yl, and prop-2-yn-1-yl; butynyls such as but-1-yn-1-yl, but-1-yn-3-yl, and but-3-yn-1-yl; and the like.

"Alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy.

"Substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR_a$, —$SR_a$, —OC(O)—$R_a$, —$N(R_a)_2$, —$C(O)R_a$, —$C(O)OR_a$, —$OC(O)N(R_a)_2$, —$C(O)N(R_a)_2$, —$N(R_a)C(O)OR_a$, —$N(R_a)C(O)R_a$, —$N(R_a)C(O)N(R_a)_2$, —$N(R_a)C(NR_a)N(R_a)_2$, —$N(R_a)S(O)_tR_a$ (where t is 1 or 2), —$S(O)_tOR_a$ (where t is 1 or 2), —$S(O)_tN(R_a)2$ (where t is 1 or 2), or —$PO_3(R_a)_2$, where each $R_a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Haloalkoxy" refers to an alkoxy group where some or all of the hydrogen atoms are substituted with halogen atoms. As for an alkyl group, haloalkoxy groups can have any suitable number of carbon atoms, such as C1-6. The alkoxy groups can be substituted with 1, 2, 3, or more halogens. When all the hydrogens are replaced with a halogen, for example by fluorine, the compounds are per substituted, for example, perfluorinated. Haloalkoxy includes, but is not limited to, trifluoromethoxy, 2,2,2, trifluoroethoxy, perfluoroethoxy, etc.

"Alkyl amine" refers to an alkyl group as defined within, having one or more amino groups. The amino groups can be primary, secondary or tertiary. The alkyl amine can be further substituted with a hydroxy group to form an amino-hydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The aryl component is as defined above. Examples of alkyl-aryl groups include, but are not limited to, benzyl and ethyl-benzene. Alkyl-aryl groups can be substituted or unsubstituted.

"Cycloalkyl" refers to a saturated or partially unsaturated, monocyclic, bicyclic, fused bicyclic or bridged polycyclic ring assembly containing from 3 to 12 ring atoms, or the number of atoms indicated. Cycloalkyl can include any number of carbons, such as 3 to 6 carbon atoms, 4 to 6 carbon atoms, 5 to 6 carbon atoms, 3 to 8 carbon atoms, 4 to 8 carbon atoms, 5 to 8 carbon atoms, 6 to 8 carbon atoms, 7 to 8 carbon atoms, 3 to 9 carbon atoms, 4 to 9 carbon atoms, 5 to 9 carbon atoms, 6 to 9 carbon atoms, 7 to 9 carbon atoms, 8 to 9 carbon atoms, 3 to 10 carbon atoms, 4 to 10 carbon atoms, 5 to 10 carbon atoms, 6 to 10 carbon atoms, 7 to 10 carbon atoms, 8 to 10 carbon atoms, 9 to 10 carbon atoms, 3 to 11 carbon atoms, 4 to 11 carbon atoms, 5 to 11 carbon atoms, 6 to 11 carbon atoms, 7 to 11 carbon atoms, 8 to 11 carbon atoms, 9 to 11 carbon atoms, 10 to 11 carbon atoms, 3 to 12 carbon atoms, 4 to 12 carbon atoms, 5 to 12 carbon atoms, 6 to 12 carbon atoms, 7 to 12 carbon atoms, 8 to 12 carbon atoms, 9 to 12 carbon atoms, 10 to 12 carbon atoms, and 11 to 12 carbon atoms. Saturated monocyclic cycloalkyl rings include, for example, cyclopropyl, cyclobutyl, cyclopentyl, cyclohexyl, and cyclooctyl. Bicyclic compounds include spirocyclic compounds, fused bicyclic compounds and bridged bicyclic compounds. Saturated bicyclic and polycyclic cycloalkyl rings include, for example, norbornane, bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Halogen" refers to fluorine, chlorine, bromine, and iodine. In some preferred embodiments, halogen will be chlorine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. In some instances, the term "perfluoro" can be used to define a compound or radical where all the hydrogens are replaced with fluorine. For example, perfluoromethyl refers to 1,1,1-trifluoromethyl.

"Heterocycloalkyl" refers to a cycloalkyl as defined above, having from 3 to 12 ring members and from 1 to 4 heteroatoms of N, O and S. Heterocycloalkyl includes bicyclic compounds which include a heteroatom. Bicyclic compounds includes spirocyclic compounds, fused bicyclic compounds, and bridged bicyclic compounds The heteroatoms can also be oxidized, such as, but not limited to, —S(O)— and —$S(O)_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent.

The heterocycloalkyl component is as defined above. Alkyl-heterocycloalkyl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Heteroaryl groups can include any number of ring atoms, such as, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heteroaryl component is as defined within. Alkyl-heteroaryl groups can be substituted or unsubstituted.

"Oxo" refers to =O.

B. Compounds

In some embodiments, the compounds described herein are characterized by Formula (I):

(I)

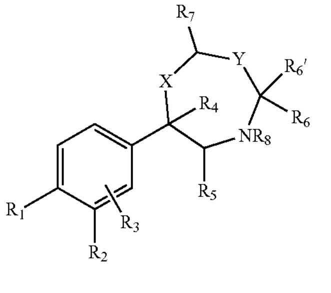

wherein $R_1$, $R_2$, $R_3$ and $R_4$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ substituted alkoxy, $C_{1-6}$ haloalkoxy, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, $C_{4-16}$ alkyl-heteroaryl, $—NO_2$, —CN, —C(O)$R_{9a}$, —C(O)O$R_{9a}$, —OC(O)$R_{9a}$, —OC(O)O$R_{9a}$, —N($R_{9a}R_{9b}$), —N($R_{9a}$)C(O)$R_{9b}$, —C(O)N($R_{9a}R_{9c}$), —N($R_{9a}$)C(O)O$R_{9b}$, —OC(O)N($R_{9a}R_{9b}$), —N($R_{9a}$)C(O)N($R_{9b}R_{9c}$), —C(O)C(O)N($R_{9a}R_{9b}$), —S($O_2$)$R_{9a}$, —S(O)$_2$N($R_{9a}R_{9b}$), or —$(CH_2)_l$—$CO_2R_{10}$, where l is an integer between 1 and 3 inclusive;

alternatively two of $R_1$, $R_2$ and $R_3$ can be combined with the atoms to which they are each attached to form a $C_{4-8}$ cycloalkyl, $C_{4-10}$ heterocycloalkyl, or $C_{6-12}$ aryl;

X is O, S, or $CR_{11}$;

$R_5$, $R_6$, $R_7$ and $R_{11}$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ substituted alkoxy, $C_{1-6}$ haloalkoxy, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, $C_{4-16}$ alkyl-heteroaryl, oxo, $—NO_2$, —CN, —C(O)$R_{9a}$, —C(O)O$R_{9a}$, —OC(O)$R_{9a}$, —OC(O)O$R_{9a}$, —N($R_{9a}R_{9b}$), —N($R_{9a}$)C(O)$R_{9b}$, —C(O)N($R_{9a}R_{9b}$), —N($R_{9a}$)C(O)O$R_{9b}$, —OC(O)N($R_{9a}R_{9b}$), —N($R_{9a}$)C(O)N($R_{9b}R_{9c}$), —C(O)C(O)N($R_{9a}R_{9b}$), —S($O_2$)$R_{9a}$, or —S(O)$_2$N($R_{9a}R_{9c}$);

$R_6$' is hydrogen, or $C_{1-3}$ alkyl;

$R_8$ is hydrogen, $C_{1-3}$ alkyl, $C_{3-6}$ cycloalkyl, or —$(CH_2)_1$—$CO_2R_{10}$;

$R_{9a}$, $R_{9b}$ and $R_{9c}$ are each independently hydrogen or $C_{1-6}$ alkyl;

$R_{10}$ is any of hydrogen; $C_{1-6}$ alkyl, $C_{4-8}$ cycloalkyl, $C_{6-12}$ aryl, $C_{7-18}$ alkyl-aryl; —$(CH_2)_m$Z$(CH_2)_m$$CH_3$, or $(CH_2)_m R^{cyc}$;

Z is, and in either orientation, —O—, —C≡C—, —NH—, —NHNH—, —ONH—, —OCNH—, —CONH, —CH($NH_2$)—, —OC(O)—, —S—, —S(O)—, $—SO_2—$, —CHF—, and $—CF_4$;

$R^{cyc}$ is an $C_{6-12}$ aryl, $C_{4-10}$ heterocycloalkyl, or $C_{5-10}$ heteroaryl;

each m is independently between 0 and 4 inclusive;

alternatively, two of $R_5$, $R_6$, $R_7$, and $R_{11}$ are combined with the atoms to which they are attached to form a $C_{4-8}$ cycloalkyl, $C_{4-10}$ heterocycloalkyl, or $C_{6-12}$ aryl; and Y is —$(CH_2)_n$, wherein n is 0 or 1;

or a pharmaceutically acceptable salt, hydrate, or solvate thereof (which will be understood to include all amorphous and polymorphic forms).

In some embodiments, for instance consisting of a single compound of Formula (I), or a composition consisting essentially of a single compound of Formula (I), the compound of Formula (I) will be as described above but wherein the compound is other than:

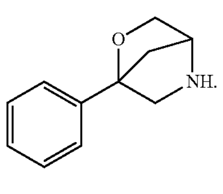 [SMILES: c1ccc(C23CNC(CO2)C3)cc1]

In another aspect, provided is a compound having the structure of Formula (A):

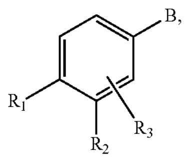

(A)

or a pharmaceutically acceptable salt, hydrate, or solvate thereof, wherein:

B is

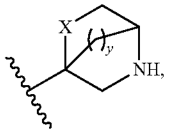

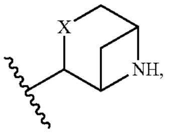

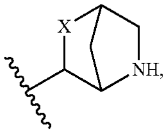

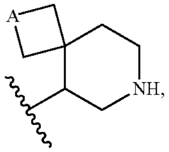

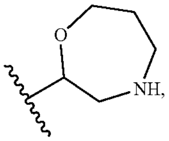

or

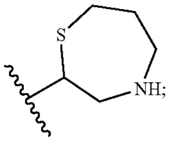

$R_1$, $R_2$, and $R_3$ are each independently hydrogen, —$CH_3$, —$OCH_3$, —$CF_3$, or halogen; or two of $R_1$, $R_2$ and $R_3$ are combined with the atoms to which they are each attached to form a $C_{4-8}$ cycloalkyl, $C_{4-10}$ heterocycloalkyl, or $C_{6-12}$ aryl;

X is O, S, —O—$CH_2$, —O—C(O)—, or y is 1 or 2; and

A is absent or —O—;

wherein at least one of $R_1$, $R_2$, and $R_3$ is not hydrogen; and when B is

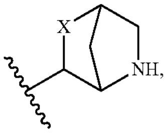

$R_1$ is not Br, and $R_3$ is not F; when B is

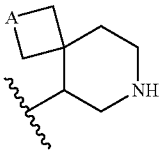

and A is —O—, none of $R_1$, $R_2$, and $R_3$ are halogen or methyl; and when B is

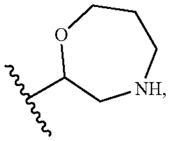 [SMILES: *C1CNCCCO1]

$R_1$ and $R_2$ are both Cl, and $R_3$ is hydrogen.

In some embodiments of Formula (A), B is

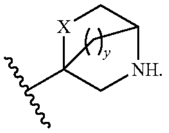

In embodiments, B is

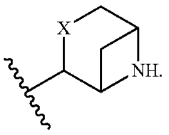

In embodiments, B is

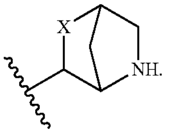

In embodiments, B is

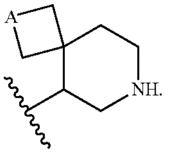

In embodiments, B is

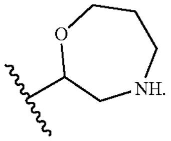 [SMILES: *C1CNCCCO1]

In embodiments, B is

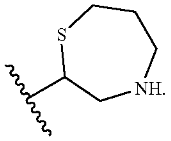

In some embodiments of Formula (A), $R_1$, $R_2$, and $R_3$ are each independently hydrogen, —$CH_3$, —$OCH_3$, —$CF_3$, or halogen; or two of $R_1$, $R_2$ and $R_3$ are combined with the atoms to which they are each attached to form a $C_{4-8}$ cycloalkyl, $C_{4-10}$ heterocycloalkyl, or $C_{6-12}$ aryl.

In some embodiments of Formula (A), $R_1$, $R_2$, and $R_3$ are each independently hydrogen, —$CH_3$, —$OCH_3$, —$CF_3$, or halogen. In embodiments, $R_1$ is hydrogen. In embodiments, $R_1$ is —$CH_3$. In embodiments, $R_1$ is —$OCH_3$. In embodiments, $R_1$ is —$CF_3$. In embodiments, $R_1$ is halogen (i.e., fluoro, chloro, bromo, iodo). In embodiments, $R_1$ is fluoro. In embodiments, $R_1$ is chloro. In embodiments, $R_1$ is bromo. In embodiments, $R_1$ is iodo. In embodiments, $R_2$ is hydrogen. In embodiments, $R_2$ is —$CH_3$. In embodiments, $R_2$ is —$OCH_3$. In embodiments, $R_2$ is —$CF_3$. In embodiments, $R_2$ is halogen (i.e., fluoro, chloro, bromo, iodo). In embodiments, $R_2$ is fluoro. In embodiments, $R_2$ is chloro. In embodiments, $R_2$ is bromo. In embodiments, $R_2$ is iodo. In embodiments, $R_3$ is hydrogen. In embodiments, $R_3$ is —$CH_3$. In embodiments, $R_3$ is —$OCH_3$. In embodiments, $R_3$ is —$CF_3$. In embodiments, $R_3$ is halogen (i.e., fluoro, chloro, bromo, iodo). In embodiments, $R_3$ is fluoro. In embodiments, $R_3$ is chloro. In embodiments, $R_3$ is bromo. In embodiments, $R_3$ is iodo. In embodiments, $R_1$ and $R_2$ are both chloro. In some preferred embodiments, $R_1$ and $R_2$ are both chloro, and $R_3$ is hydrogen. In embodiments, $R_1$ and $R_2$ are both methyl. In some preferred embodiments, $R_1$ and $R_2$ are both methyl, and $R_3$ is hydrogen.

In some embodiments of Formula (A), two of $R_1$, $R_2$ and $R_3$ are combined with the atoms to which they are each attached to form a $C_{4-8}$ cycloalkyl, $C_{4-10}$ heterocycloalkyl, or $C_{6-12}$ aryl. In embodiments, $R_1$ and $R_2$ are combined with the atoms to which they are each attached to form a $C_{4-8}$ cycloalkyl, $C_{4-10}$ heterocycloalkyl, or $C_{6-12}$ aryl. In embodiments, $R_1$ and $R_2$ are combined with the atoms to which they are each attached to form a $C_{4-8}$ cycloalkyl. In embodiments, $R_1$ and $R_2$ are combined with the atoms to which they are each attached to form a $C_{4-10}$ heterocycloalkyl. In embodiments, $R_1$ and $R_2$ are combined with the atoms to which they are each attached to form a methylenedioxy group. It will be understood that "a methylenedioxy group" refers to a moiety having the formula

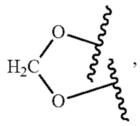, wherein the wavy lines indicate the points of connectivity to the remainder of the compound. In embodiments, $R_1$ and $R_2$ are combined with the atoms to which they are each attached to form a methylenedioxy group, and $R_3$ is hydrogen. In embodiments, $R_1$ and $R_2$ are combined with the atoms to which they are each attached to form a $C_{6-12}$ aryl. In embodiments, $R_2$ and $R_3$ are combined with the atoms to which they are each attached to form a $C_{4-8}$ cycloalkyl, $C_{4-10}$ heterocycloalkyl, or $C_{6-12}$ aryl. In embodiments, $R_2$ and $R_3$ are combined with the atoms to which they are each attached to form a $C_{4-8}$ cycloalkyl. In embodiments, $R_2$ and $R_3$ are combined with the atoms to which they are each attached to form a $C_{4-10}$ heterocycloalkyl. In embodiments, $R_2$ and $R_3$ are combined with the atoms to which they are each attached to form a methylenedioxy group. In embodiments, $R_2$ and $R_3$ are combined with the atoms to which they are each attached to form a $C_{6-12}$ aryl. In embodiments, $R_1$ and $R_3$ are combined with the atoms to which they are each attached to form a $C_{4-8}$ cycloalkyl, $C_{4-10}$ heterocycloalkyl, or $C_{6-12}$ aryl. In embodiments, $R_1$ and $R_3$ are combined with the atoms to which they are each attached to form a $C_{4-8}$ cycloalkyl. In embodiments, $R_1$ and $R_3$ are combined with the atoms to which they are each attached to form a $C_{4-10}$ heterocycloalkyl. In embodiments, $R_1$ and $R_3$ are combined with the atoms to which they are each attached to form a methylenedioxy group. In embodiments, $R_1$ and $R_3$ are combined with the atoms to which they are each attached to form a $C_{6-12}$ aryl.

In some embodiments of Formula (A) wherein B is

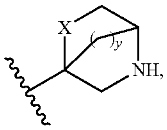, 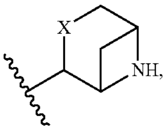, or 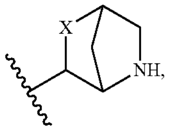,

X is O, S, —O—$CH_2$, —O—C(O)—, or —S—$CH_2$. In embodiments, X is O. In embodiments, X is S. In embodiments, —O—$CH_2$. In embodiments, X is —O—C(O)—. In embodiments, X is —S—$CH_2$. In embodiments, B is

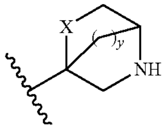

and X is O. In embodiments, B is

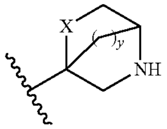

and X is S. In embodiments, B is

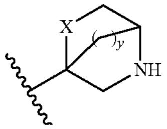

and X is —O—$CH_2$. In embodiments, B is

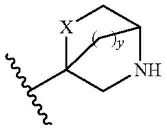

and X is —O—C(O)—. In embodiments, B is

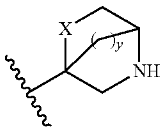

and X is —S—$CH_2$—. In embodiments, B is

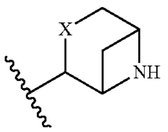

and X is O. In embodiments, B is

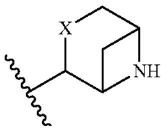

and X is S. In embodiments, B is

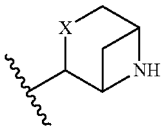

and X is —O—$CH_2$. In embodiments, B is

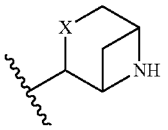

and X is —O—C(O)—. In embodiments, B is

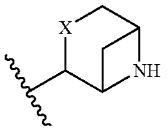

and X is —S—$CH_2$.

In embodiments, B is

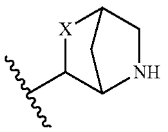

and X is O. In embodiments, B is

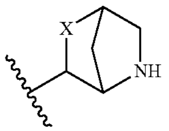

and X is S. In embodiments, B is

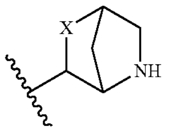

and X is —O—$CH_2$—. In embodiments, B is

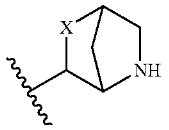

and X is —O—C(O)—. In embodiments, B is

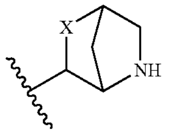

and X is —S—$CH_2$.

In some embodiments of Formula (A) wherein B is

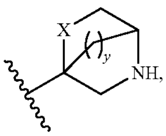, y is 1 or 2. In embodiments, B is

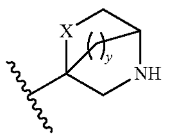

and y is 1. In embodiments, B is

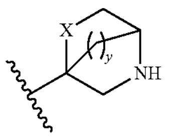

and y is 2.

In embodiments, B is

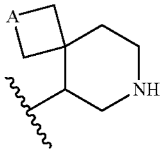

and A is absent or —O—. In embodiments, B is

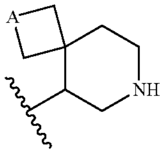

and A is absent. In embodiments, B is

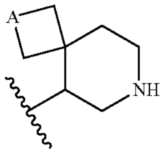

and A is —O—.

In some embodiments of Formula (A), at least one of $R_1$, $R_2$, and $R_3$ is not hydrogen. In embodiments, $R_1$ is not hydrogen. In embodiments, $R_2$ is not hydrogen. In embodiments, $R_3$ is not hydrogen. In embodiments, $R_1$ and $R_2$ are not hydrogen. In embodiments, $R_1$ and $R_3$ are not hydrogen. In embodiments, $R_2$ and $R_3$ are not hydrogen. In embodiments, $R_1$, $R_2$, and $R_3$ are each not hydrogen.

In embodiments of Formula (A) wherein B is

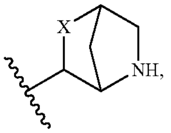

$R_1$ is not Br, and $R_3$ is not F. In embodiments, B is

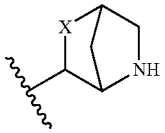

and $R_1$ is not Br. In embodiments, B is

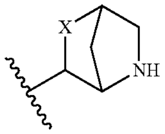

and $R_1$ is not F. In some embodiments of Formula (A) wherein B is

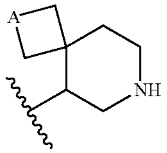

and A is —O—, none of $R_1$, $R_2$, and $R_3$ are halogen or methyl. In embodiments, B is

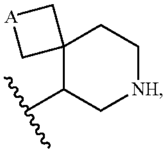

A is —O—, and $R_1$ is not halogen (i.e., $R_1$ is not fluoro, chloro, bromo, or iodo). In embodiments, B is

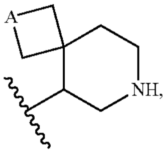

A is —O—, and $R_1$ is not methyl. In embodiments, B is,

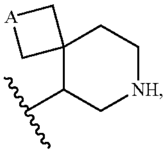

A is —O—, and $R_2$ is not halogen (i.e., $R_2$ is not fluoro, chloro, bromo, or iodo). In embodiments, B is

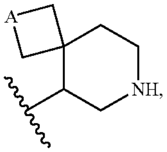

A is —O—, and $R_2$ is not methyl. In embodiments, B is

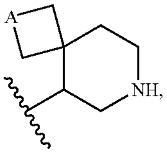

A is —O—, and $R_3$ is not halogen (i.e., $R_3$ is not fluoro, chloro, bromo, or iodo). In embodiments, B is

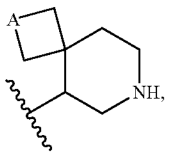

A is —O— and $R_3$ is not methyl. In some embodiments of Formula (A) wherein B is

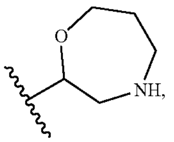 [SMILES: *C1CNCCCO1]

$R_1$ and $R_2$ are both Cl, and $R_3$ is hydrogen.

In another aspect, provided is a compound having the structure of Formula (1):

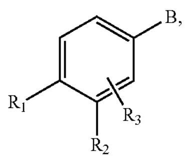

(1)

or a pharmaceutically acceptable salt, hydrate, or solvate thereof, wherein

B is

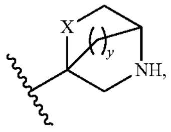 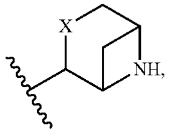 or 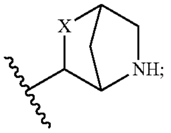

$R_1$, $R_2$, and $R_3$ are each independently hydrogen, $—CH_3$, $—OCH_3$, $—CF_3$, or halogen; or two of $R_1$, $R_2$ and $R_3$ can be combined with the atoms to which they are each attached to form a $C_{4-8}$ cycloalkyl, $C_{4-10}$ heterocycloalkyl, or $C_{6-12}$ aryl;

X is O, S, —O—$CH_2$, —O—C(O)—, or y is 1 or 2; and wherein at least one of $R_1$, $R_2$, and $R_3$ is not hydrogen.

In some embodiments of Formula (1), B is

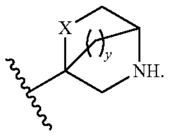

In embodiments, B is

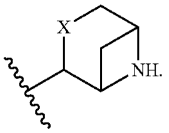

In embodiments, B is

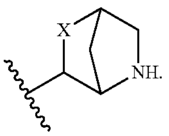

In some embodiments of Formula (1), $R_1$, $R_2$, and $R_3$ are each independently hydrogen, $—CH_3$, $—OCH_3$, $—CF_3$, or halogen; or two of $R_1$, $R_2$ and $R_3$ are combined with the atoms to which they are each attached to form a $C_{4-8}$ cycloalkyl, $C_{4-10}$ heterocycloalkyl, or $C_{6-12}$ aryl.

In some embodiments of Formula (1), $R_1$, $R_2$, and $R_3$ are each independently hydrogen, $—CH_3$, $—OCH_3$, $—CF_3$, or halogen. In embodiments, $R_1$ is hydrogen. In embodiments, $R_1$ is $—CH_3$. In embodiments, $R_1$ is $—OCH_3$. In embodiments, $R_1$ is $—CF_3$. In embodiments, $R_1$ is halogen (i.e., fluoro, chloro, bromo, iodo). In embodiments, $R_1$ is fluoro. In embodiments, $R_1$ is chloro. In embodiments, $R_1$ is bromo. In embodiments, $R_1$ is iodo. In embodiments, $R_2$ is hydrogen. In embodiments, $R_2$ is $—CH_3$. In embodiments, $R_2$ is $—OCH_3$. In embodiments, $R_2$ is $—CF_3$. In embodiments, $R_2$ is halogen (i.e., fluoro, chloro, bromo, iodo). In embodiments, $R_2$ is fluoro. In embodiments, $R_2$ is chloro. In embodiments, $R_2$ is bromo. In embodiments, $R_2$ is iodo. In embodiments, $R_3$ is hydrogen. In embodiments, $R_3$ is $—CH_3$. In embodiments, $R_3$ is $—OCH_3$. In embodiments, $R_3$ is $—CF_3$. In embodiments, $R_3$ is halogen (i.e., fluoro, chloro, bromo, iodo). In embodiments, $R_3$ is fluoro. In embodiments, $R_3$ is chloro. In embodiments, $R_3$ is bromo. In embodiments, $R_3$ is iodo. In embodiments, $R_1$ and $R_2$ are both chloro. In some preferred embodiments, $R_1$ and $R_2$ are both chloro, and $R_3$ is hydrogen. In embodiments, $R_1$ and $R_2$ are both methyl. In some preferred embodiments, $R_1$ and $R_2$ are both methyl, and $R_3$ is hydrogen.

In some embodiments of Formula (1), two of $R_1$, $R_2$ and $R_3$ are combined with the atoms to which they are each attached to form a $C_{4-8}$ cycloalkyl, $C_{4-10}$ heterocycloalkyl, or $C_{6-12}$ aryl. In embodiments, $R_1$ and $R_2$ are combined with the atoms to which they are each attached to form a $C_{4-8}$ cycloalkyl, $C_{4-10}$ heterocycloalkyl, or $C_{6-12}$ aryl. In embodiments, $R_1$ and $R_2$ are combined with the atoms to which they are each attached to form a $C_{4-8}$ cycloalkyl. In embodiments, $R_1$ and $R_2$ are combined with the atoms to which they are each attached to form a $C_{4-10}$ heterocycloalkyl. In embodiments, $R_1$ and $R_2$ are combined with the atoms to which they are each attached to form a methylenedioxy group. In embodiments, $R_1$ and $R_2$ are combined with the atoms to which they are each attached to form a methylenedioxy group, and $R_3$ is hydrogen. In embodiments, $R_1$ and $R_2$ are combined with the atoms to which they are each attached to form a $C_{6-12}$ aryl. In embodiments, $R_2$ and $R_3$ are combined with the atoms to which they are each attached to form a $C_{4-8}$ cycloalkyl, $C_{4-10}$ heterocycloalkyl, or $C_{6-12}$ aryl. In embodiments, $R_2$ and $R_3$ are combined with the atoms to which they are each attached to form a $C_{4-8}$ cycloalkyl. In embodiments, $R_2$ and $R_3$ are combined with the atoms to which they are each attached to form a $C_{4-10}$ heterocycloalkyl. In embodiments, $R_2$ and $R_3$ are combined with the atoms to which they are each attached to form a methylenedioxy group. In embodiments, $R_2$ and $R_3$ are combined with the atoms to which they are each attached to form a $C_{6-12}$ aryl. In embodiments, $R_1$ and $R_3$ are combined with the atoms to which they are each attached to form a $C_{4-8}$ cycloalkyl, $C_{4-10}$ heterocycloalkyl, or $C_{6-12}$ aryl. In embodiments, $R_1$ and $R_3$ are combined with the atoms to which they are each attached to form a $C_{4-8}$ cycloalkyl. In embodiments, $R_1$ and $R_3$ are combined with the atoms to which they are each attached to form a $C_{4-10}$ heterocycloalkyl. In embodiments, $R_1$ and $R_3$ are combined with the atoms to which they are each attached to form a methylendioxy group. In embodiments, $R_1$ and $R_3$ are combined with the atoms to which they are each attached to form a $C_{6-12}$ aryl.

In some embodiments of Formula (1), X is O, S, —O—$CH_2$, —O—C(O)—, or —S—$CH_2$. In embodiments, X is O. In embodiments, X is S. In embodiments, —O—$CH_2$. In embodiments, X is —O—C(O)—. In embodiments, X is —S—$CH_2$. In embodiments, B is

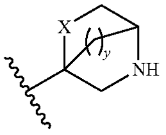

and X is O. In embodiments, B is

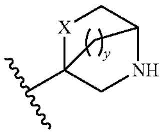

and X is S. In embodiments, B is

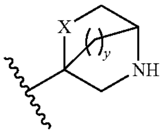

and X is —O—$CH_2$. In embodiments, B is

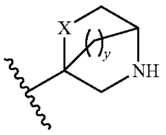

and X is —O—C(O)—. In embodiments, B is

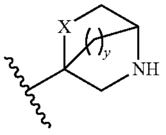

and X is —S—$CH_2$—. In embodiments, B is

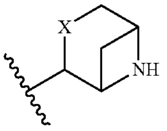

and X is O. In embodiments, B is

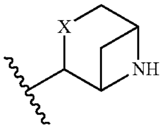

and X is S. In embodiments, B is

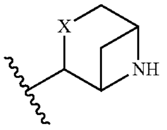

and X is —O—$CH_2$. In embodiments, B is

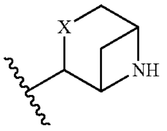

and X is —O—C(O)—. In embodiments, B is

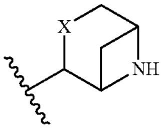

and X is —S—$CH_2$.

In embodiments, B is

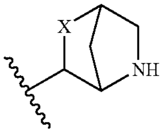

and X is O. In embodiments, B is

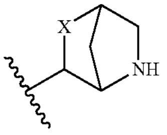

and X is S. In embodiments, B is

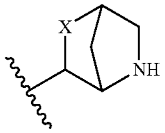

and X is —O—$CH_2$. In embodiments, B is

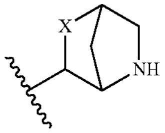

and X is —O—C(O)—. In embodiments, B is

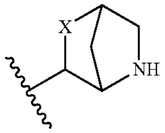

and X is —S—$CH_2$.

In some embodiments of Formula (1) wherein B is

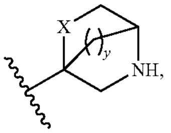

y is 1 or 2. In embodiments, B is

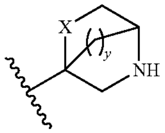

and y is 1. In embodiments, B is

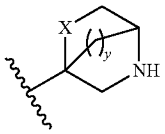

and y is 2.

In another aspect, provided is a compound having the structure of Formula (2):

(2)

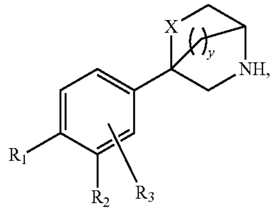

or a pharmaceutically acceptable salt, hydrate, or solvate thereof.

In some embodiments of Formula (2), X is O, S, —O—$CH_2$, —O—C(O)—, or —S—$CH_2$. In embodiments, X is O. In embodiments, X is S. In embodiments, —O—$CH_2$. In embodiments, X is —O—C(O)—. In embodiments, X is —S—$CH_2$.

In some embodiments of Formula (2), y is 1 or 2. In embodiments, y is 1. In embodiments, y is 2.

In some embodiments of Formula (2), $R_1$, $R_2$, and $R_3$ are each independently hydrogen, —$CH_3$, —$OCH_3$, —$CF_3$, or halogen; or two of $R_1$, $R_2$ and $R_3$ are combined with the atoms to which they are each attached to form a $C_{4-8}$ cycloalkyl, $C_{4-10}$ heterocycloalkyl, or $C_{6-12}$ aryl.

In some embodiments of Formula (2), $R_1$, $R_2$, and $R_3$ are each independently hydrogen, —$CH_3$, —$OCH_3$, —$CF_3$, or halogen. In embodiments, $R_1$ is hydrogen. In embodiments, $R_1$ is —$CH_3$. In embodiments, $R_1$ is —$OCH_3$. In embodiments, $R_1$ is —$CF_3$. In embodiments, $R_1$ is halogen (i.e., fluoro, chloro, bromo, iodo). In embodiments, $R_1$ is fluoro. In embodiments, $R_1$ is chloro. In embodiments, $R_1$ is bromo. In embodiments, $R_1$ is iodo. In embodiments, $R_2$ is hydrogen. In embodiments, $R_2$ is —$CH_3$. In embodiments, $R_2$ is —$OCH_3$. In embodiments, $R_2$ is —$CF_3$. In embodiments, $R_2$ is halogen (i.e., fluoro, chloro, bromo, iodo). In embodiments, $R_2$ is fluoro. In embodiments, $R_2$ is chloro. In embodiments, $R_2$ is bromo. In embodiments, $R_2$ is iodo. In embodiments, $R_3$ is hydrogen. In embodiments, $R_3$ is —$CH_3$. In embodiments, $R_3$ is —$OCH_3$. In embodiments, $R_3$ is —$CF_3$. In embodiments, $R_3$ is halogen (i.e., fluoro, chloro, bromo, iodo). In embodiments, $R_3$ is fluoro. In embodiments, $R_3$ is chloro. In embodiments, $R_3$ is bromo. In embodiments, $R_3$ is iodo. In embodiments, $R_1$ and $R_2$ are both chloro. In some preferred embodiments, $R_1$ and $R_2$ are both chloro, and $R_3$ is hydrogen. In embodiments, $R_1$ and $R_2$ are both methyl. In some preferred embodiments, $R_1$ and $R_2$ are both methyl, and $R_3$ is hydrogen.

In some embodiments of Formula (2), two of $R_1$, $R_2$ and $R_3$ are combined with the atoms to which they are each attached to form a $C_{4-8}$ cycloalkyl, $C_{4-10}$ heterocycloalkyl, or $C_{6-12}$ aryl. In embodiments, $R_1$ and $R_2$ are combined with the atoms to which they are each attached to form a $C_{4-8}$ cycloalkyl, $C_{4-10}$ heterocycloalkyl, or $C_{6-12}$ aryl. In embodiments, $R_1$ and $R_2$ are combined with the atoms to which they are each attached to form a $C_{4-8}$ cycloalkyl. In embodiments, $R_1$ and $R_2$ are combined with the atoms to which they are each attached to form a $C_{4-10}$ heterocycloalkyl. In embodiments, $R_1$ and $R_2$ are combined with the atoms to which they are each attached to form a methylenedioxy group. In embodiments, $R_1$ and $R_2$ are combined with the atoms to which they are each attached to form a methylenedioxy group, and $R_3$ is hydrogen. In embodiments, $R_1$ and $R_2$ are combined with the atoms to which they are each attached to form a $C_{6-12}$ aryl. In embodiments, $R_2$ and $R_3$ are combined with the atoms to which they are each attached to form a $C_{4-8}$ cycloalkyl, $C_{4-10}$ heterocycloalkyl, or $C_{6-12}$ aryl. In embodiments, $R_2$ and $R_3$ are combined with the atoms to which they are each attached to form a $C_{4-8}$ cycloalkyl. In embodiments, $R_2$ and $R_3$ are combined with the atoms to which they are each attached to form a $C_{4-10}$ heterocycloalkyl. In embodiments, $R_2$ and $R_3$ are combined with the atoms to which they are each attached to form a methylenedioxy group. In embodiments, $R_2$ and $R_3$ are combined with the atoms to which they are each attached to form a $C_{6-12}$ aryl. In embodiments, $R_1$ and $R_3$ are combined with the atoms to which they are each attached to form a $C_{4-8}$ cycloalkyl, $C_{4-10}$ heterocycloalkyl, or $C_{6-12}$ aryl. In embodiments, $R_1$ and $R_3$ are combined with the atoms to which they are each attached to form a $C_{4-8}$ cycloalkyl. In embodiments, $R_1$ and $R_3$ are combined with the atoms to which they are each attached to form a $C_{4-10}$ heterocycloalkyl. In embodiments, $R_1$ and $R_3$ are combined with the atoms to which they are each attached to form a methylendioxy group. In embodiments, $R_1$ and $R_3$ are combined with the atoms to which they are each attached to form a $C_{6-12}$ aryl.

In another aspect, provided is a compound having the structure of Formula (2A), (2A)

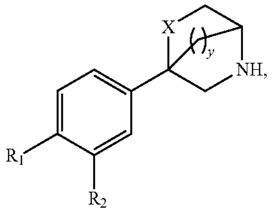

or a pharmaceutically acceptable salt, hydrate, or solvate thereof.

In some embodiments of Formula (2A), X is O, S, —O—$CH_2$, —O—C(O)—, or —S—$CH_2$. In embodiments, X is O. In embodiments, X is S. In embodiments, —O—$CH_2$. In embodiments, X is —O—C(O)—. In embodiments, X is —S—$CH_2$.

In some embodiments of Formula (2A), y is 1 or 2. In embodiments, y is 1. In embodiments, y is 2.

In some embodiments of Formula (2A), $R_1$ and $R_2$ are each independently hydrogen, —$CH_3$, —$OCH_3$, —$CF_3$, or halogen; or $R_1$ and $R_2$ are combined with the atoms to which they are each attached to form a $C_{4-8}$ cycloalkyl, $C_{4-10}$ heterocycloalkyl, or $C_{6-12}$ aryl.

In some embodiments of Formula (2A), $R_1$ and $R_2$ are each independently hydrogen, —$CH_3$, —$OCH_3$, —$CF_3$, or halogen. In embodiments, $R_1$ is hydrogen. In embodiments, $R_1$ is —$CH_3$. In embodiments, $R_1$ is —$OCH_3$. In embodiments, $R_1$ is —$CF_3$. In embodiments, $R_1$ is halogen (i.e., fluoro, chloro, bromo, iodo). In embodiments, $R_1$ is fluoro. In embodiments, $R_1$ is chloro. In embodiments, $R_1$ is bromo. In embodiments, $R_1$ is iodo. In embodiments, $R_2$ is hydrogen. In embodiments, $R_2$ is —$CH_3$. In embodiments, $R_2$ is —$OCH_3$. In embodiments, $R_2$ is —$CF_3$. In embodiments, $R_2$ is halogen (i.e., fluoro, chloro, bromo, iodo). In embodiments, $R_2$ is fluoro. In embodiments, $R_2$ is chloro. In embodiments, $R_2$ is bromo. In embodiments, $R_2$ is iodo. In embodiments, $R_1$ and $R_2$ are both chloro. In embodiments, $R_1$ and $R_2$ are both methyl.

In some embodiments of Formula (2A), $R_1$ and $R_2$ are combined with the atoms to which they are each attached to form a $C_{4-8}$ cycloalkyl, $C_{4-10}$ heterocycloalkyl, or $C_{6-12}$ aryl.

In embodiments, $R_1$ and $R_2$ are combined with the atoms to which they are each attached to form a $C_{4-8}$ cycloalkyl, $C_{4-10}$ heterocycloalkyl, or $C_{6-12}$ aryl. In embodiments, $R_1$ and $R_2$ are combined with the atoms to which they are each attached to form a $C_{4-8}$ cycloalkyl. In embodiments, $R_1$ and $R_2$ are combined with the atoms to which they are each attached to form a $C_{4-10}$ heterocycloalkyl. In embodiments, $R_1$ and $R_2$ are combined with the atoms to which they are each attached to form a methylenedioxy group. In embodiments, $R_1$ and $R_2$ are combined with the atoms to which they are each attached to form a $C_{6-12}$ aryl.

In another aspect, provided is a compound having the structure of Formula (II):

(II)

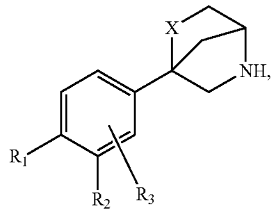

wherein $R_1$, $R_2$ and $R_3$ are independently hydrogen, —$CH_3$, —$OCH_3$, —$CF_3$, or halogen;

wherein, when $R_3$ is —Cl, $R_1$ and $R_2$ are both hydrogen;

alternatively $R_1$ and $R_2$ can be combined with the atoms to which they are each attached to form a $C_5$ heterocycloalkyl; and X is O or S;

or a pharmaceutically acceptable salt, hydrate, or solvate thereof (which will be understood to include all amorphous and polymorphic forms).

In a further aspect, provided is a compound having the structure of any of Formulas (III)—(XIII):

(III)

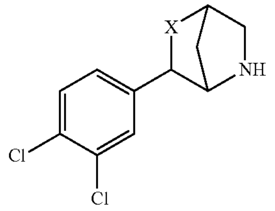

(IV)

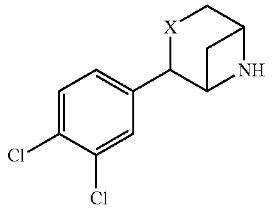

(V)

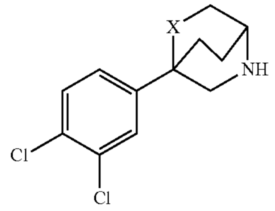

-continued (VI)

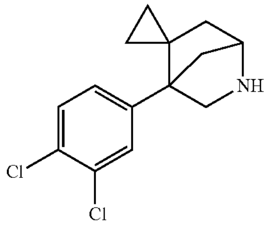

(VII)

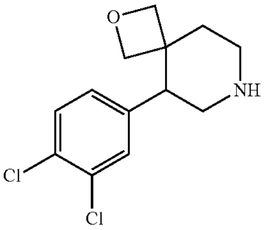

(VIII)

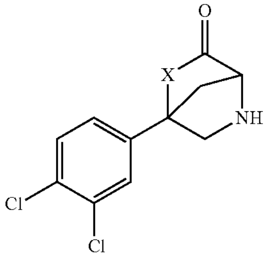

(IX)

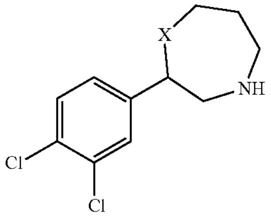

(X)

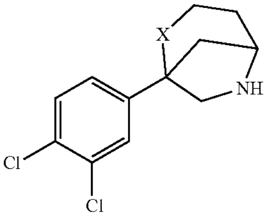

(XI)

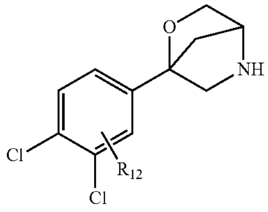

(XII)

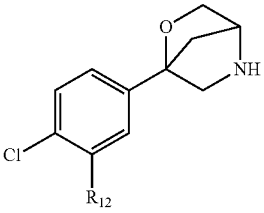

-continued (XIII)

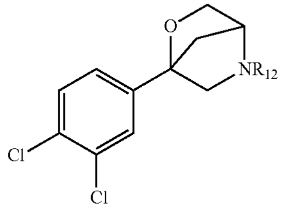

wherein any X is O or S;

and wherein $R_{12}$ is $-(CH_2)_1-CO_2R_{10}$, wherein Z is an integer between 1 and 3 inclusive;

wherein $R_{IO}$ is any of hydrogen; alkyl, cycloalkyl, aryl, or arylalkyl; $-(CH_2)_mZ(CH_2)_mCH_3$, or $-(CH_2)_mR^{cyc}$;

wherein Z is, and in either orientation, —O—, —C≡C—, —NH—, —NHNH—, —ONH—, —OCNH—, —CONH, $-CH(NH_2)-$, —OC(O)—, —S—, —S(O)—, $-SO_2-$, —CHF—, and $-CF_2-$;

wherein $R^{cyc}$ is an aryl, heterocycle, or heteroaryl; and wherein each m is independently between 0 and 4 inclusive;

or a pharmaceutically acceptable salt, hydrate, or solvate thereof (which will be understood to include all amorphous and polymorphic forms).

Non-limiting exemplary compounds described herein are below in TABLE 1, and such compounds may be referred to collectively and claimed collectively as the "compounds of Table 1" or "Table 1 compounds," or individually as "a compound of Table 1" or "a Table 1 compound" (and likewise for the compounds of any other Tables set forth herein):

TABLE 1

| Exemplary Embodiments of Formula (I) |
| --- |
| 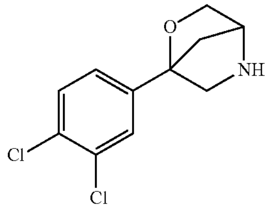 [SMILES: Clc1ccc(C23CNC(CO2)C3)cc1Cl] |
| 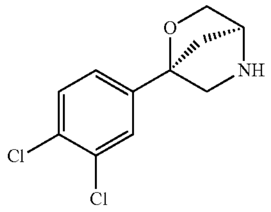 [SMILES: Clc1ccc([C@]23CN[C@H](CO2)C3)cc1Cl] |
| 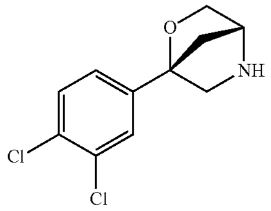 [SMILES: Clc1ccc([C@@]23CN[C@@H](CO2)C3)cc1Cl] |

TABLE 1-continued
| Exemplary Embodiments of Formula (I) |
| --- |
| 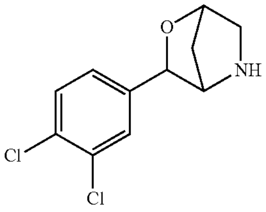 [SMILES: Clc1ccc(C2OC3CNC2C3)cc1Cl] |
| 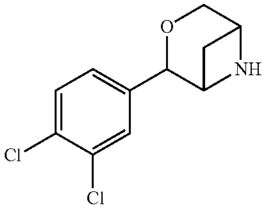 [SMILES: Clc1ccc(C2OCC3CC2N3)cc1Cl] |
| 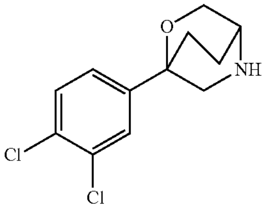 [SMILES: Clc1ccc(C23CCC(CO2)NC3)cc1Cl] |
| 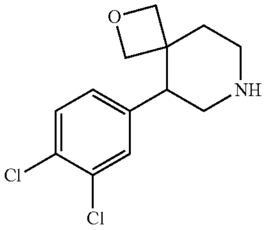 [SMILES: Clc1ccc(C2CNCCC23COC3)cc1Cl] |
| 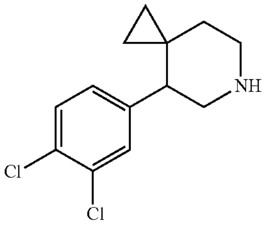 [SMILES: Clc1ccc(C2CNCCC23CC3)cc1Cl] |
| 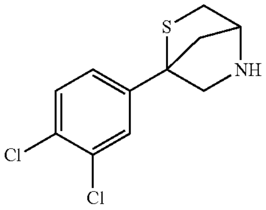 [SMILES: Clc1ccc(C23CNC(CS2)C3)cc1Cl] |
| 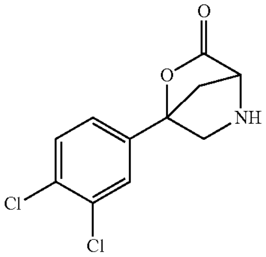 |
TABLE 1-continued
| Exemplary Embodiments of Formula (I) |
| --- |
| 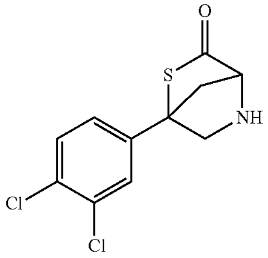 |
| 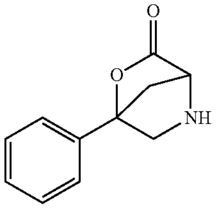 |
| 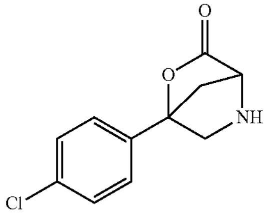 [SMILES: O=C1OC2(c3ccc(Cl)cc3)CNC1C2] |
| 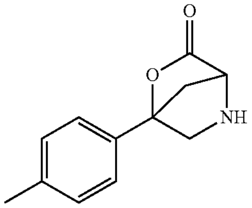 |
| 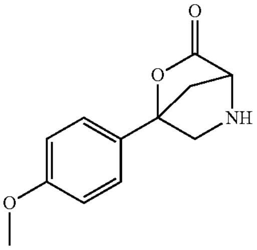 [SMILES: COc1ccc(C23CNC(C2)C(=O)O3)cc1] |
| 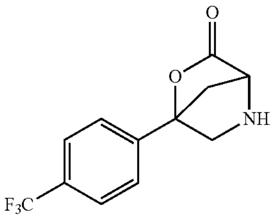 [SMILES: O=C1OC2(c3ccc(C(F)(F)F)cc3)CNC1C2] |

TABLE 1-continued
| Exemplary Embodiments of Formula (I) |
| --- |
| 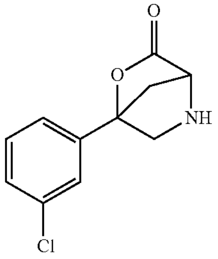 [SMILES: O=C1OC2(c3cccc(Cl)c3)CNC1C2] |
| 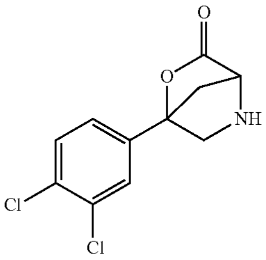 |
| 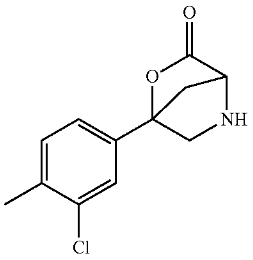 [SMILES: Cc1ccc(C23CNC(C2)C(=O)O3)cc1Cl] |
| 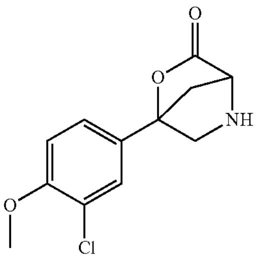 |
| 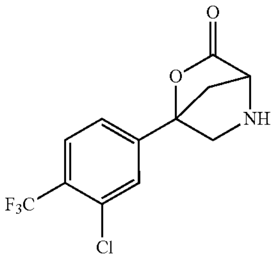 [SMILES: O=C1OC2(c3ccc(C(F)(F)F)c(Cl)c3)CNC1C2] |
| 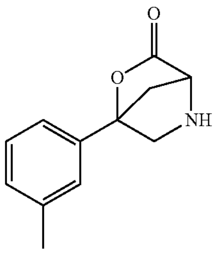 |
TABLE 1-continued
| Exemplary Embodiments of Formula (I) |
| --- |
| 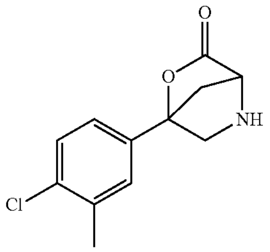 [SMILES: Cc1cc(C23CNC(C2)C(=O)O3)ccc1Cl] |
| 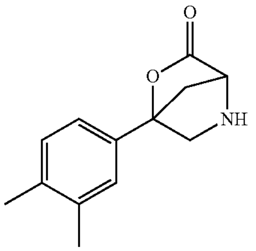 [SMILES: Cc1ccc(C23CNC(C2)C(=O)O3)cc1C] |
| 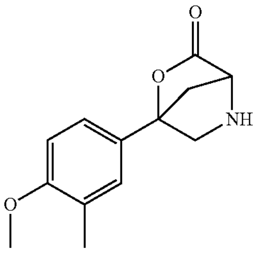 |
| 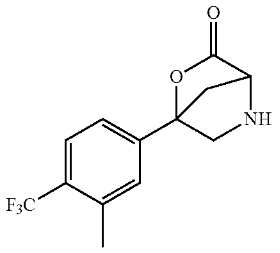 [SMILES: Cc1cc(C23CNC(C2)C(=O)O3)ccc1C(F)(F)F] |
| 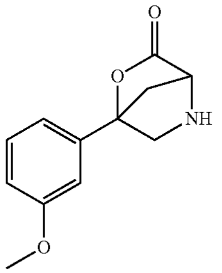 [SMILES: COc1cccc(C23CNC(C2)C(=O)O3)c1] |
| 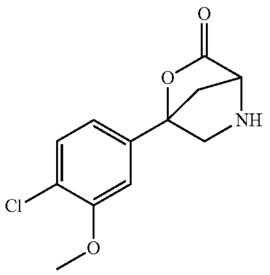 [SMILES: COc1cc(C23CNC(C2)C(=O)O3)ccc1Cl]

TABLE 1-continued
| Exemplary Embodiments of Formula (I) |
| --- |
| 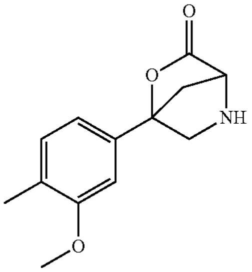 [SMILES: COc1cc(C23CNC(C2)C(=O)O3)ccc1C] |
| 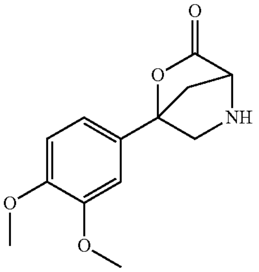 |
| 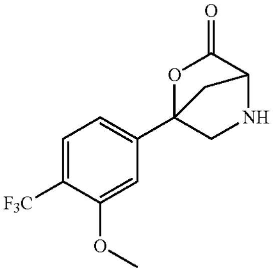 [SMILES: COc1cc(C23CNC(C2)C(=O)O3)ccc1C(F)(F)F] |
| 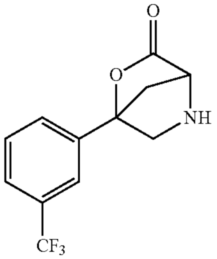 |
| 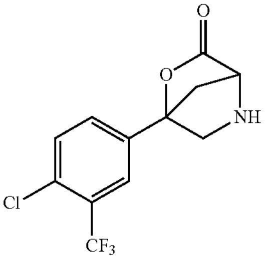 [SMILES: O=C1OC2(c3ccc(Cl)c(C(F)(F)F)c3)CNC1C2] |
TABLE 1-continued
| Exemplary Embodiments of Formula (I) |
| --- |
| 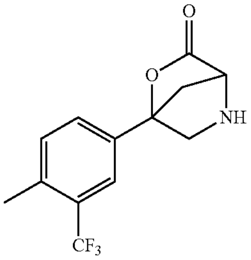 [SMILES: Cc1ccc(C23CNC(C2)C(=O)O3)cc1C(F)(F)F] |
| 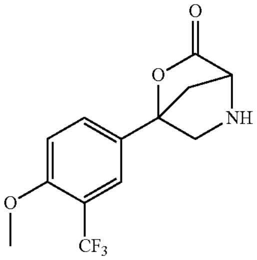 |
| 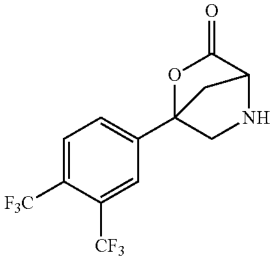 [SMILES: O=C1OC2(c3ccc(C(F)(F)F)c(C(F)(F)F)c3)CNC1C2] |
| 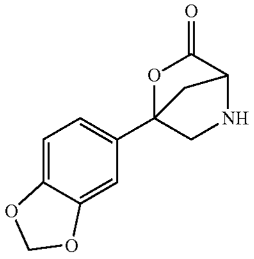 [SMILES: O=C1OC2(c3ccc4c(c3)OCO4)CNC1C2] |
| 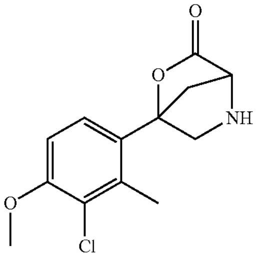 |
| 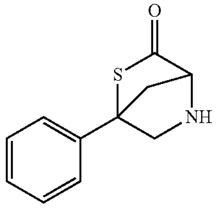 [SMILES: O=C1SC2(c3ccccc3)CNC1C2] |

TABLE 1-continued
Exemplary Embodiments of Formula (I)
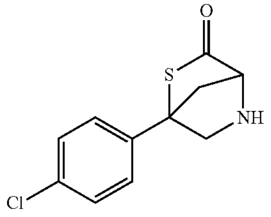 [SMILES: O=C1SC2(c3ccc(Cl)cc3)CNC1C2]
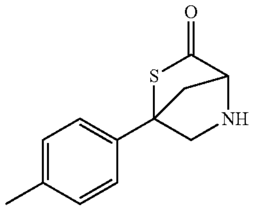
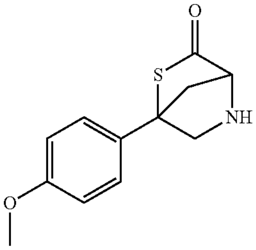
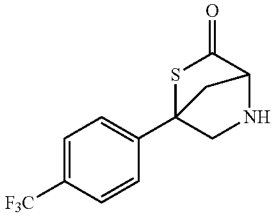
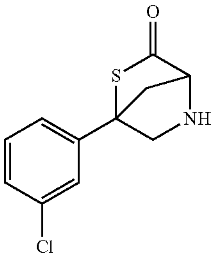 [SMILES: O=C1SC2(c3cccc(Cl)c3)CNC1C2]
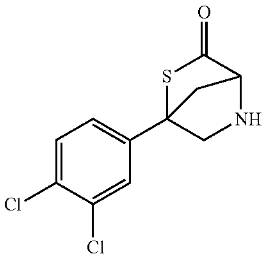 [SMILES: O=C1SC2(c3ccc(Cl)c(Cl)c3)CNC1C2]
TABLE 1-continued
Exemplary Embodiments of Formula (I)
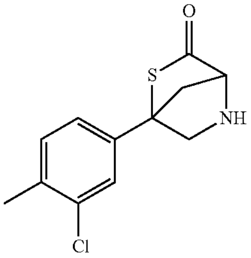
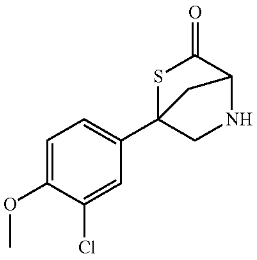 [SMILES: COc1ccc(C23CNC(C2)C(=O)S3)cc1Cl]
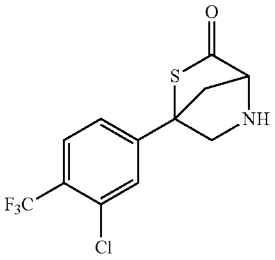
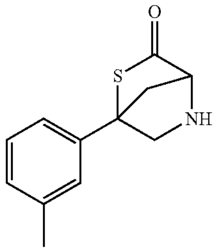
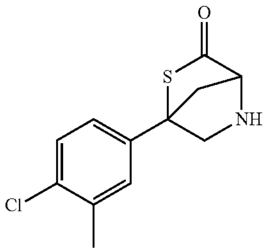 [SMILES: Cc1cc(C23CNC(C2)C(=O)S3)ccc1Cl]
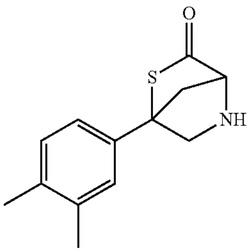 [SMILES: Cc1ccc(C23CNC(C2)C(=O)S3)cc1C]

TABLE 1-continued
| Exemplary Embodiments of Formula (I) |
|---|
| 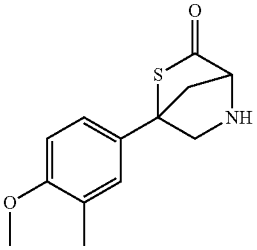 [SMILES: COc1ccc(C23CNC(C2)C(=O)S3)cc1C] |
| 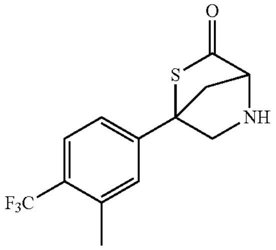 |
| 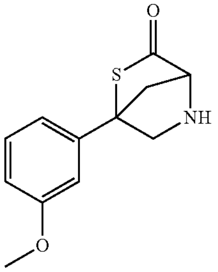 |
| 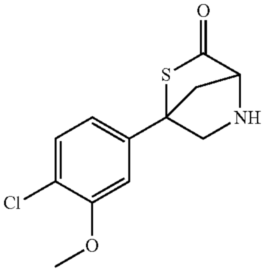 |
| 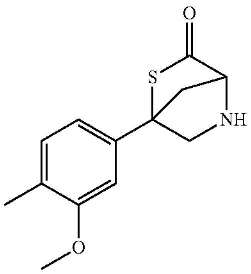 |
TABLE 1-continued
| Exemplary Embodiments of Formula (I) |
|---|
| 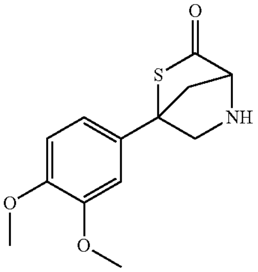 [SMILES: COc1ccc(C23CNC(C2)C(=O)S3)cc1OC] |
| 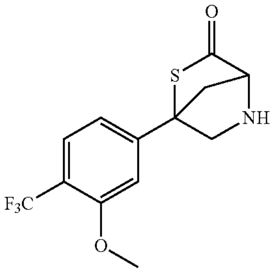 |
| 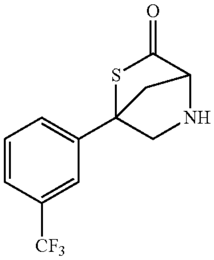 [SMILES: O=C1SC2(c3cccc(C(F)(F)F)c3)CNC1C2] |
| 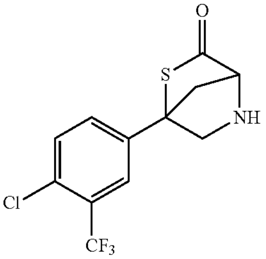 |
| 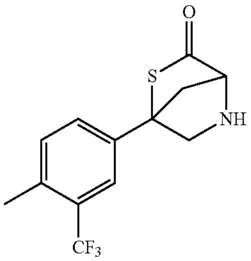 |

TABLE 1-continued
| Exemplary Embodiments of Formula (I) |
| --- |
| 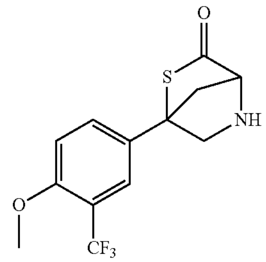 [SMILES: COc1ccc(C23CNC(C2)C(=O)S3)cc1C(F)(F)F] |
| 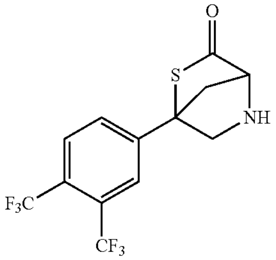 |
| 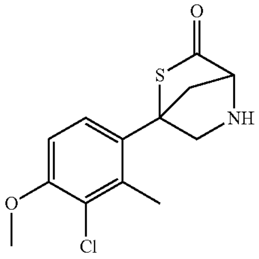 [SMILES: COc1ccc(C23CNC(C2)C(=O)S3)c(C)c1Cl] |
| 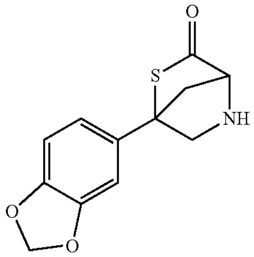 |
| 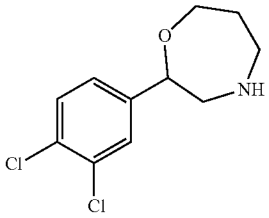 [SMILES: Clc1ccc(C2CNCCCO2)cc1Cl] |
| 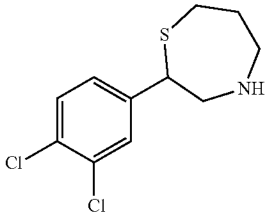 [SMILES: Clc1ccc(C2CNCCCS2)cc1Cl] |
TABLE 1-continued
| Exemplary Embodiments of Formula (I) |
| --- |
| 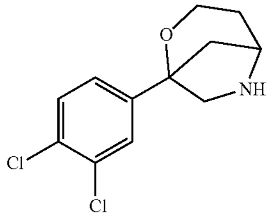 [SMILES: Clc1ccc(C23CNC(CCO2)C3)cc1Cl] |
| 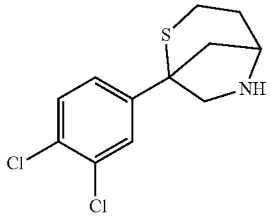 [SMILES: Clc1ccc(C23CNC(CCS2)C3)cc1Cl] |
| 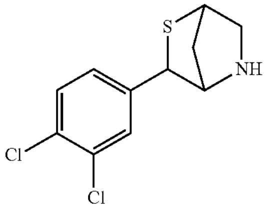 [SMILES: Clc1ccc(C2SC3CNC2C3)cc1Cl] |
| 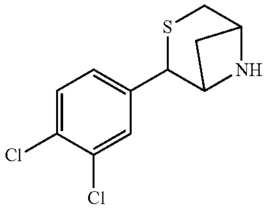 [SMILES: Clc1ccc(C2SCC3CC2N3)cc1Cl] |
| 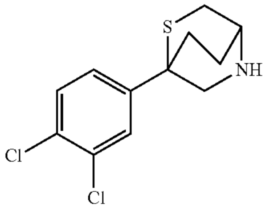 [SMILES: Clc1ccc(C23CCC(CS2)NC3)cc1Cl] |
| 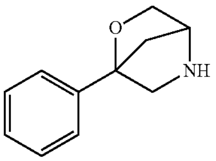 [SMILES: c1ccc(C23CNC(CO2)C3)cc1] |
| 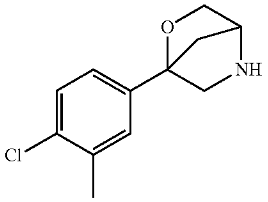 |

TABLE 1-continued
| Exemplary Embodiments of Formula (I) |
| --- |
| 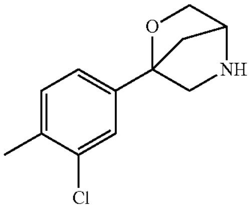 |
| 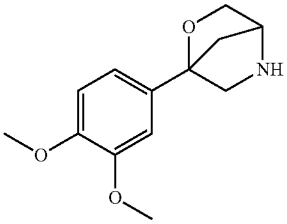 [SMILES: COc1ccc(C23CNC(CO2)C3)cc1OC] |
| 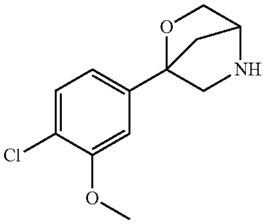 [SMILES: COc1cc(C23CNC(CO2)C3)ccc1Cl] |
| 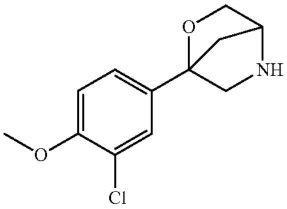 [SMILES: COc1ccc(C23CNC(CO2)C3)cc1Cl] |
| 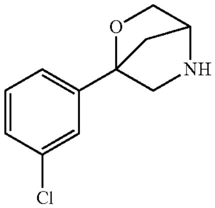 [SMILES: Clc1cccc(C23CNC(CO2)C3)c1] |
| 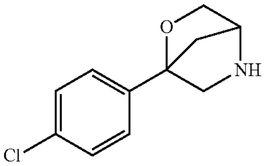 [SMILES: Clc1ccc(C23CNC(CO2)C3)cc1] |
| 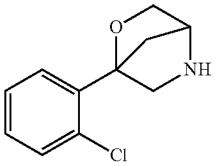 [SMILES: Clc1ccccc1C12CNC(CO1)C2] |
TABLE 1-continued
| Exemplary Embodiments of Formula (I) |
| --- |
| 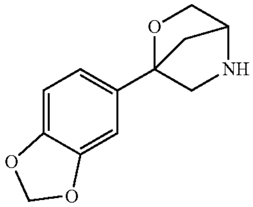 [SMILES: c1cc2c(cc1C13CNC(CO1)C3)OCO2] |
| 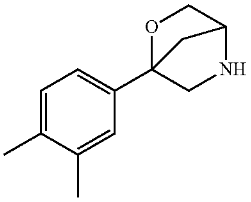 |
| 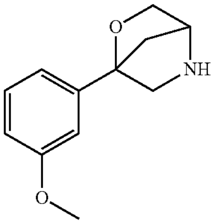 |
| 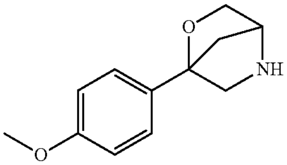 |
| 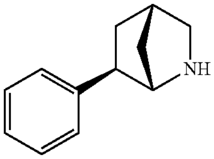 [SMILES: c1ccc([C@H]2C[C@@H]3CN[C@H]2C3)cc1] |
| 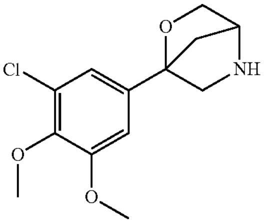 [SMILES: COc1cc(C23CNC(CO2)C3)cc(Cl)c1OC] |
| 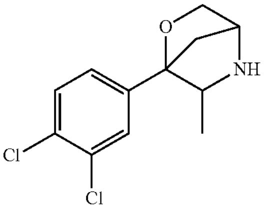 [SMILES: CC1NC2COC1(c1ccc(Cl)c(Cl)c1)C2] |

TABLE 1-continued
| Exemplary Embodiments of Formula (I) |
| --- |
| 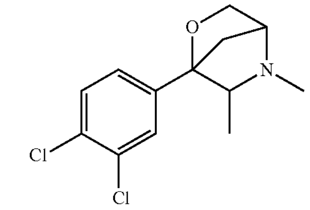 [SMILES: CC1N(C)C2COC1(c1ccc(Cl)c(Cl)c1)C2] |
| 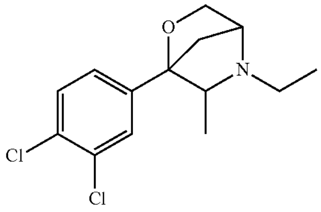 [SMILES: CCN1C2COC(c3ccc(Cl)c(Cl)c3)(C2)C1C] |
| 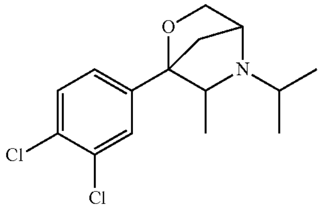 [SMILES: CC(C)N1C2COC(c3ccc(Cl)c(Cl)c3)(C2)C1C] |
| 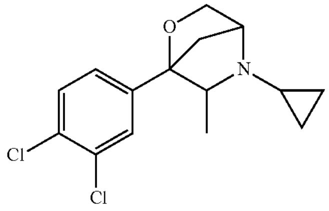 [SMILES: CC1N(C2CC2)C2COC1(c1ccc(Cl)c(Cl)c1)C2] |
| 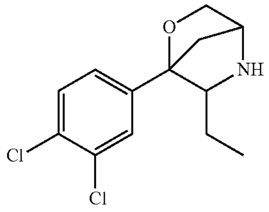 [SMILES: CCC1NC2COC1(c1ccc(Cl)c(Cl)c1)C2] |
| 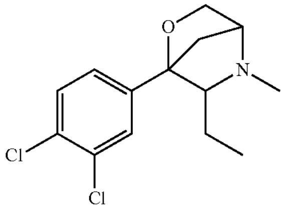 [SMILES: CCC1N(C)C2COC1(c1ccc(Cl)c(Cl)c1)C2] |
| 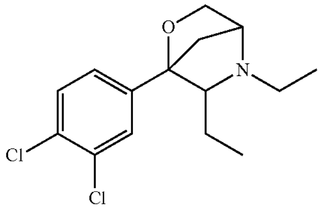 [SMILES: CCC1N(CC)C2COC1(c1ccc(Cl)c(Cl)c1)C2] |
TABLE 1-continued
| Exemplary Embodiments of Formula (I) |
| --- |
| 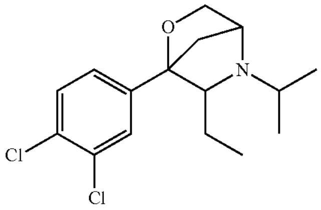 [SMILES: CCC1N(C(C)C)C2COC1(c1ccc(Cl)c(Cl)c1)C2] |
| 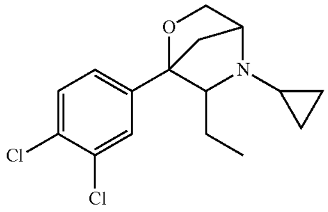 [SMILES: CCC1N(C2CC2)C2COC1(c1ccc(Cl)c(Cl)c1)C2] |
| 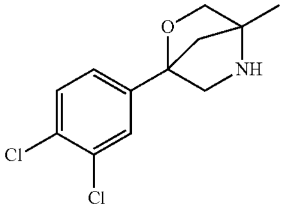 [SMILES: CC12COC(c3ccc(Cl)c(Cl)c3)(CN1)C2] |
| 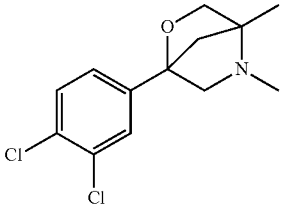 [SMILES: CN1CC2(c3ccc(Cl)c(Cl)c3)CC1(C)CO2] |
| 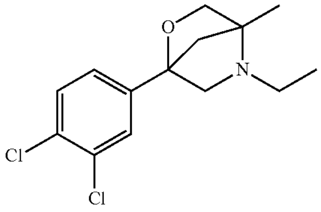 [SMILES: CCN1CC2(c3ccc(Cl)c(Cl)c3)CC1(C)CO2] |
| 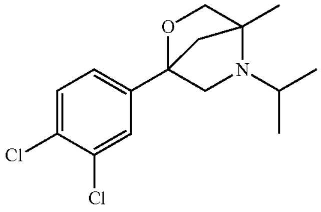 [SMILES: CC(C)N1CC2(c3ccc(Cl)c(Cl)c3)CC1(C)CO2] |
| 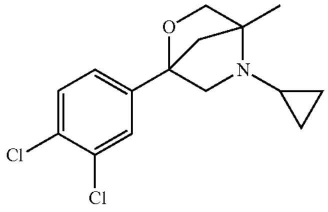 [SMILES: CC12COC(c3ccc(Cl)c(Cl)c3)(CN1C1CC1)C2] |

TABLE 1-continued
Exemplary Embodiments of Formula (I)
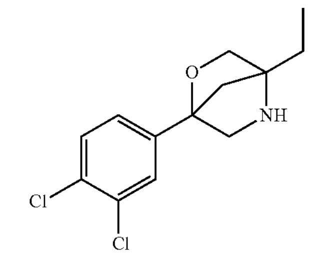 [SMILES: CCC12COC(c3ccc(Cl)c(Cl)c3)(CN1)C2]
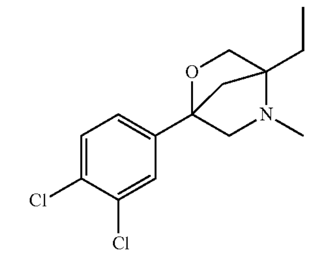 [SMILES: CCC12COC(c3ccc(Cl)c(Cl)c3)(CN1C)C2]
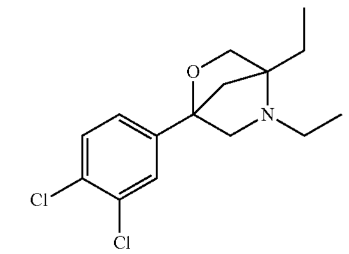 [SMILES: CCN1CC2(c3ccc(Cl)c(Cl)c3)CC1(CC)CO2]
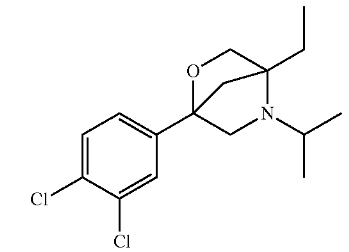 [SMILES: CCC12COC(c3ccc(Cl)c(Cl)c3)(CN1C(C)C)C2]
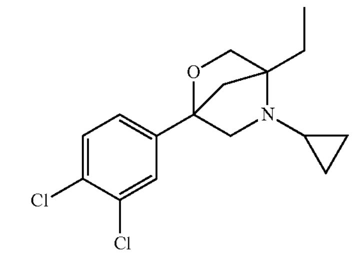 [SMILES: CCC12COC(c3ccc(Cl)c(Cl)c3)(CN1C1CC1)C2]
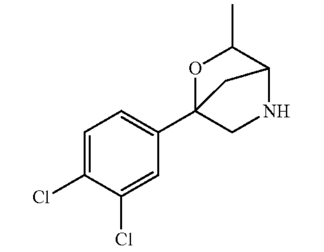 [SMILES: CC1OC2(c3ccc(Cl)c(Cl)c3)CNC1C2]
TABLE 1-continued
Exemplary Embodiments of Formula (I)
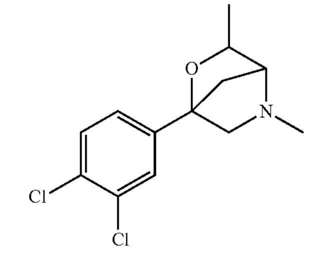 [SMILES: CC1OC2(c3ccc(Cl)c(Cl)c3)CC1N(C)C2]
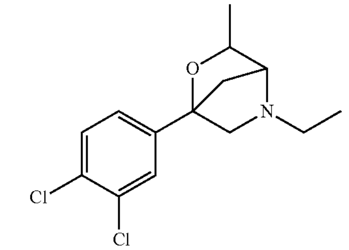 [SMILES: CCN1CC2(c3ccc(Cl)c(Cl)c3)CC1C(C)O2]
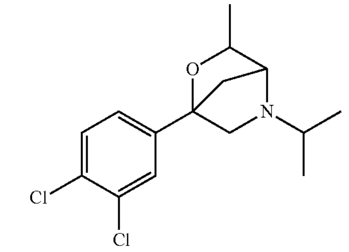 [SMILES: CC1OC2(c3ccc(Cl)c(Cl)c3)CC1N(C(C)C)C2]
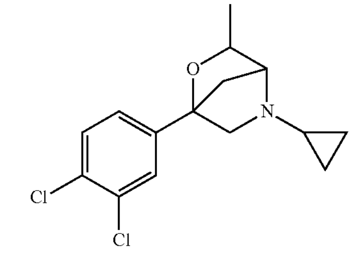 [SMILES: CC1OC2(c3ccc(Cl)c(Cl)c3)CC1N(C1CC1)C2]
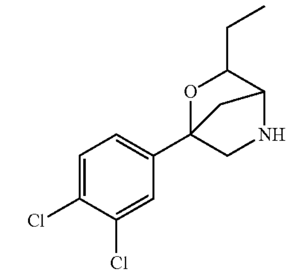 [SMILES: CCC1OC2(c3ccc(Cl)c(Cl)c3)CNC1C2]
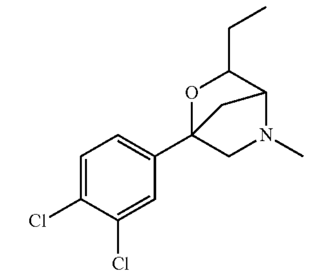 [SMILES: CCC1OC2(c3ccc(Cl)c(Cl)c3)CC1N(C)C2]

TABLE 1-continued
Exemplary Embodiments of Formula (I)
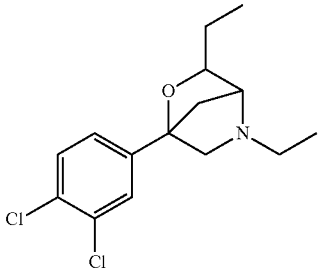 [SMILES: CCC1OC2(c3ccc(Cl)c(Cl)c3)CC1N(CC)C2]
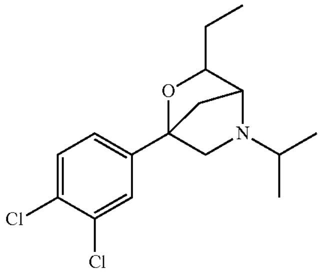 [SMILES: CCC1OC2(c3ccc(Cl)c(Cl)c3)CC1N(C(C)C)C2]
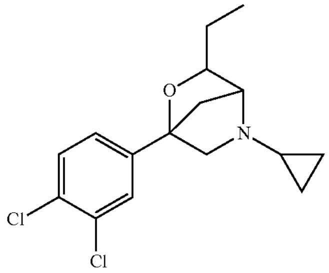 [SMILES: CCC1OC2(c3ccc(Cl)c(Cl)c3)CC1N(C1CC1)C2]
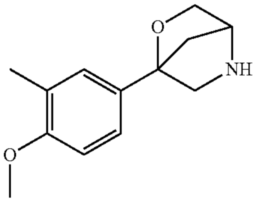 [SMILES: COc1ccc(C23CNC(CO2)C3)cc1C]
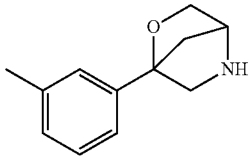
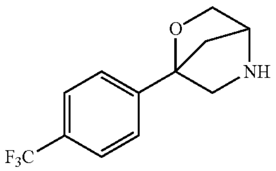
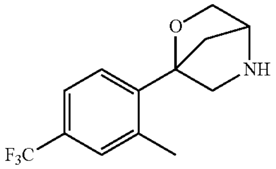 [SMILES: Cc1cc(C(F)(F)F)ccc1C12CNC(CO1)C2]
TABLE 1-continued
Exemplary Embodiments of Formula (I)
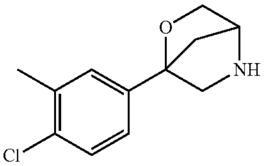
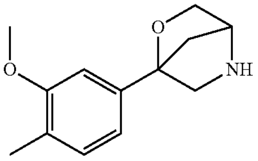 [SMILES: COc1cc(C23CNC(CO2)C3)ccc1C]
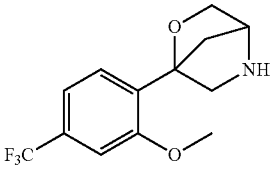 [SMILES: COc1cc(C(F)(F)F)ccc1C12CNC(CO1)C2]
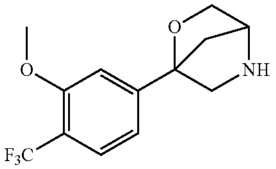 [SMILES: COc1cc(C23CNC(CO2)C3)ccc1C(F)(F)F]
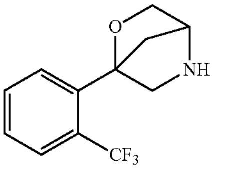 [SMILES: FC(F)(F)c1ccccc1C12CNC(CO1)C2]
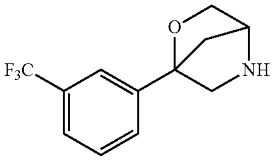 [SMILES: FC(F)(F)c1cccc(C23CNC(CO2)C3)c1]
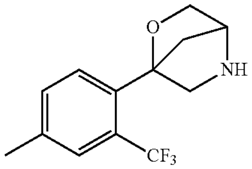 [SMILES: Cc1ccc(C23CNC(CO2)C3)c(C(F)(F)F)c1]
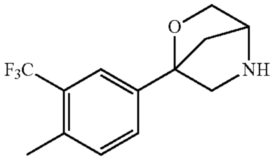 [SMILES: Cc1ccc(C23CNC(CO2)C3)cc1C(F)(F)F]

TABLE 1-continued
| Exemplary Embodiments of Formula (I) |
|---|
| 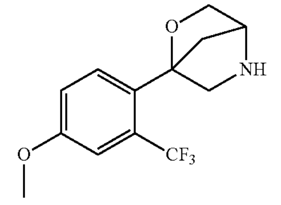 [SMILES: COc1ccc(C23CNC(CO2)C3)c(C(F)(F)F)c1] |
| 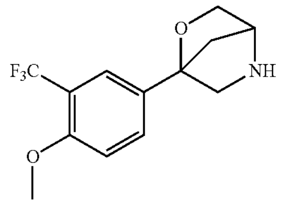 [SMILES: COc1ccc(C23CNC(CO2)C3)cc1C(F)(F)F] |
| 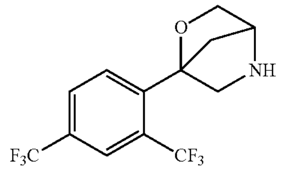 [SMILES: FC(F)(F)c1ccc(C23CNC(CO2)C3)c(C(F)(F)F)c1] |
| 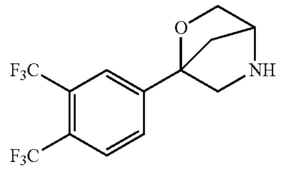 |
| 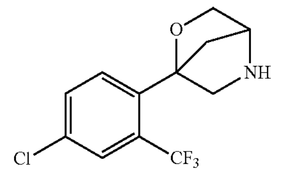 [SMILES: FC(F)(F)c1cc(Cl)ccc1C12CNC(CO1)C2] |
| 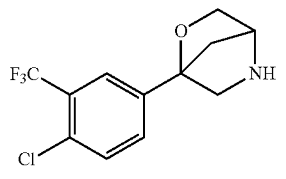 [SMILES: FC(F)(F)c1cc(C23CNC(CO2)C3)ccc1Cl] |
| 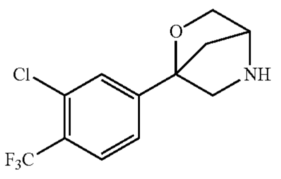 [SMILES: FC(F)(F)c1ccc(C23CNC(CO2)C3)cc1Cl] |
| 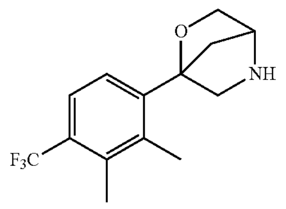 [SMILES: Cc1c(C(F)(F)F)ccc(C23CNC(CO2)C3)c1C] |
TABLE 1-continued
| Exemplary Embodiments of Formula (I) |
|---|
| 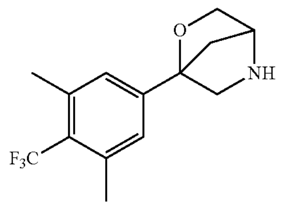 [SMILES: Cc1cc(C23CNC(CO2)C3)cc(C)c1C(F)(F)F] |
| 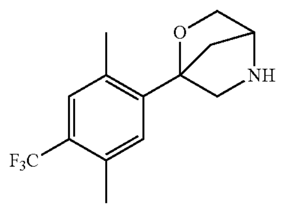 [SMILES: Cc1cc(C23CNC(CO2)C3)c(C)cc1C(F)(F)F] |
| 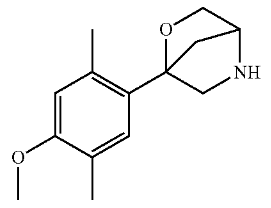 [SMILES: COc1cc(C)c(C23CNC(CO2)C3)cc1C] |
| 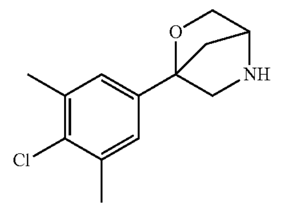 [SMILES: Cc1cc(C23CNC(CO2)C3)cc(C)c1Cl] |
| 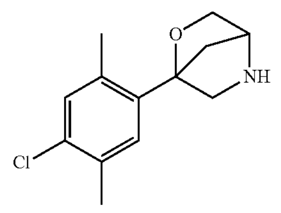 [SMILES: Cc1cc(C23CNC(CO2)C3)c(C)cc1Cl] |
| 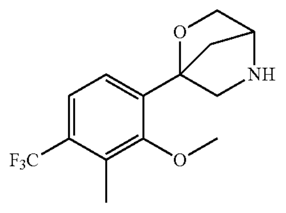 [SMILES: COc1c(C23CNC(CO2)C3)ccc(C(F)(F)F)c1C] |
| 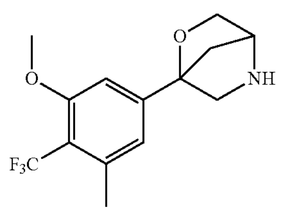 [SMILES: COc1cc(C23CNC(CO2)C3)cc(C)c1C(F)(F)F] |

TABLE 1-continued
| Exemplary Embodiments of Formula (I) |
|---|
| 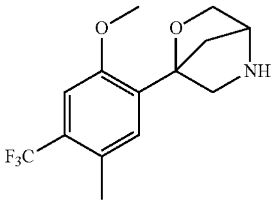 [SMILES: COc1cc(C(F)(F)F)c(C)cc1C12CNC(CO1)C2] |
| 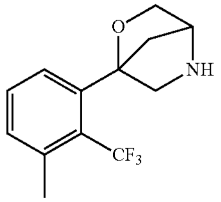 [SMILES: Cc1cccc(C23CNC(CO2)C3)c1C(F)(F)F] |
| 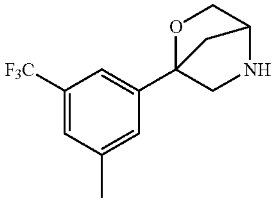 [SMILES: Cc1cc(C(F)(F)F)cc(C23CNC(CO2)C3)c1] |
| 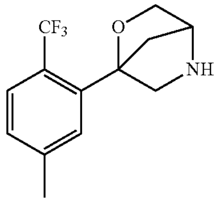 [SMILES: Cc1ccc(C(F)(F)F)c(C23CNC(CO2)C3)c1] |
| 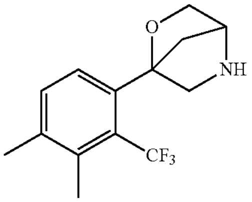 [SMILES: Cc1ccc(C23CNC(CO2)C3)c(C(F)(F)F)c1C] |
| 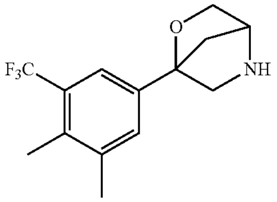 [SMILES: Cc1cc(C23CNC(CO2)C3)cc(C(F)(F)F)c1C] |
| 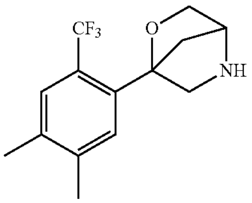 [SMILES: Cc1cc(C(F)(F)F)c(C23CNC(CO2)C3)cc1C] |
TABLE 1-continued
| Exemplary Embodiments of Formula (I) |
|---|
| 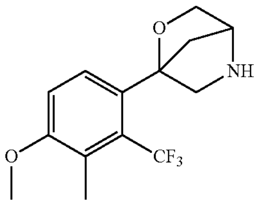 [SMILES: COc1ccc(C23CNC(CO2)C3)c(C(F)(F)F)c1C] |
| 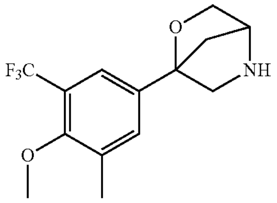 [SMILES: COc1c(C)cc(C23CNC(CO2)C3)cc1C(F)(F)F] |
| 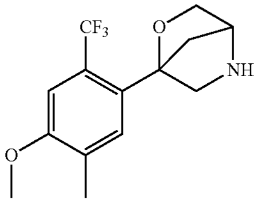 [SMILES: COc1cc(C(F)(F)F)c(C23CNC(CO2)C3)cc1C] |
| 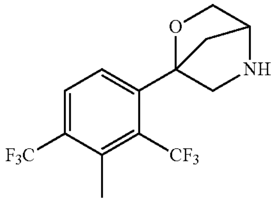 [SMILES: Cc1c(C(F)(F)F)ccc(C23CNC(CO2)C3)c1C(F)(F)F] |
| 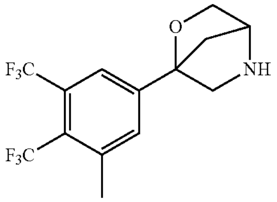 [SMILES: Cc1cc(C23CNC(CO2)C3)cc(C(F)(F)F)c1C(F)(F)F] |
| 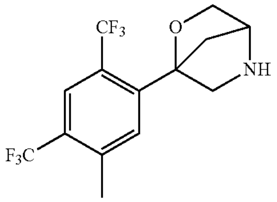 [SMILES: Cc1cc(C23CNC(CO2)C3)c(C(F)(F)F)cc1C(F)(F)F] |
| 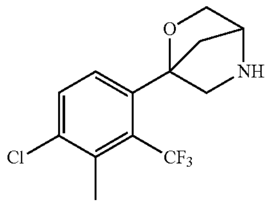 [SMILES: Cc1c(Cl)ccc(C23CNC(CO2)C3)c1C(F)(F)F] |

TABLE 1-continued
| Exemplary Embodiments of Formula (I) |
|---|
| 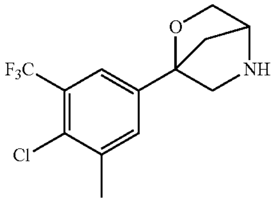 [SMILES: Cc1cc(C23CNC(CO2)C3)cc(C(F)(F)F)c1Cl] |
| 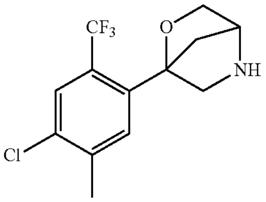 [SMILES: Cc1cc(C23CNC(CO2)C3)c(C(F)(F)F)cc1Cl] |
| 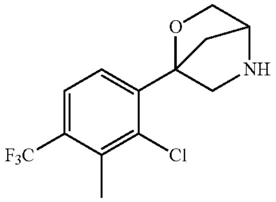 [SMILES: Cc1c(C(F)(F)F)ccc(C23CNC(CO2)C3)c1Cl] |
| 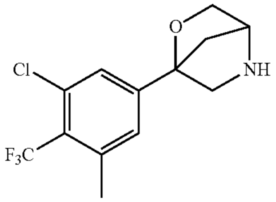 [SMILES: Cc1cc(C23CNC(CO2)C3)cc(Cl)c1C(F)(F)F] |
| 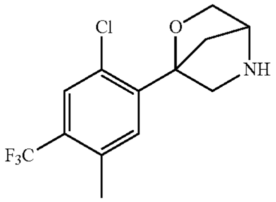 [SMILES: Cc1cc(C23CNC(CO2)C3)c(Cl)cc1C(F)(F)F] |
| 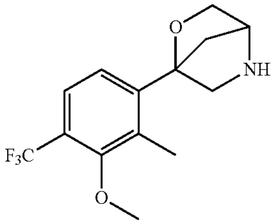 [SMILES: COc1c(C(F)(F)F)ccc(C23CNC(CO2)C3)c1C] |
| 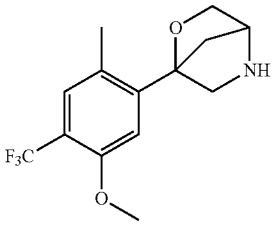 [SMILES: COc1cc(C23CNC(CO2)C3)c(C)cc1C(F)(F)F] |
TABLE 1-continued
| Exemplary Embodiments of Formula (I) |
|---|
| 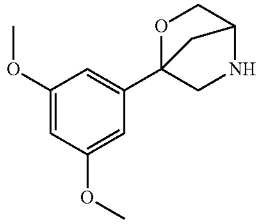 [SMILES: COc1cc(OC)cc(C23CNC(CO2)C3)c1] |
| 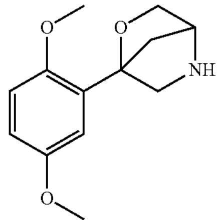 [SMILES: COc1ccc(OC)c(C23CNC(CO2)C3)c1] |
| 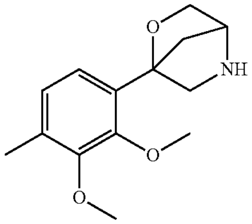 [SMILES: COc1c(C)ccc(C23CNC(CO2)C3)c1OC] |
| 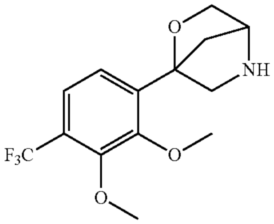 [SMILES: COc1c(C(F)(F)F)ccc(C23CNC(CO2)C3)c1OC] |
| 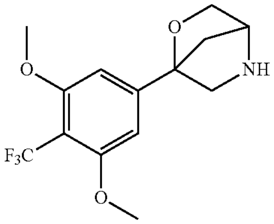 [SMILES: COc1cc(C23CNC(CO2)C3)cc(OC)c1C(F)(F)F] |
| 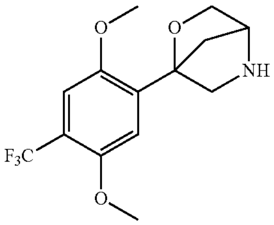 [SMILES: COc1cc(C23CNC(CO2)C3)c(OC)cc1C(F)(F)F] |

TABLE 1-continued
| Exemplary Embodiments of Formula (I) |
| --- |
| 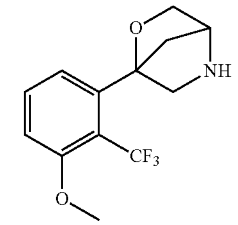 [SMILES: COc1cccc(C23CNC(CO2)C3)c1C(F)(F)F] |
| 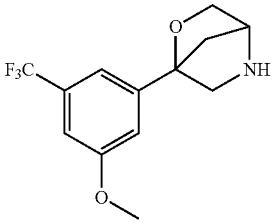 [SMILES: COc1cc(C(F)(F)F)cc(C23CNC(CO2)C3)c1] |
| 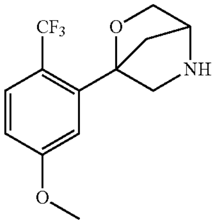 [SMILES: COc1ccc(C(F)(F)F)c(C23CNC(CO2)C3)c1] |
| 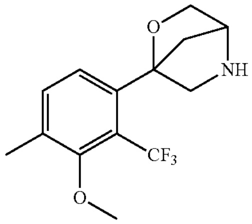 [SMILES: COc1c(C)ccc(C23CNC(CO2)C3)c1C(F)(F)F] |
| 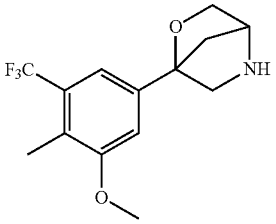 [SMILES: COc1cc(C23CNC(CO2)C3)cc(C(F)(F)F)c1C] |
| 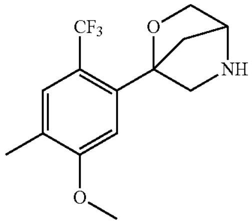 [SMILES: COc1cc(C23CNC(CO2)C3)c(C(F)(F)F)cc1C] |
TABLE 1-continued
| Exemplary Embodiments of Formula (I) |
| --- |
| 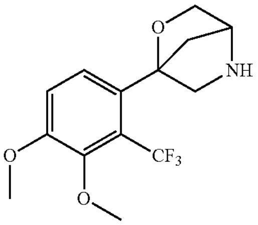 [SMILES: COc1ccc(C23CNC(CO2)C3)c(C(F)(F)F)c1OC] |
| 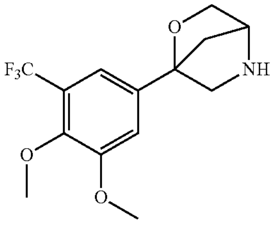 [SMILES: COc1cc(C23CNC(CO2)C3)cc(C(F)(F)F)c1OC] |
| 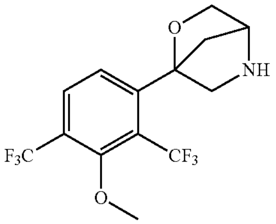 [SMILES: COc1c(C(F)(F)F)ccc(C23CNC(CO2)C3)c1C(F)(F)F] |
| 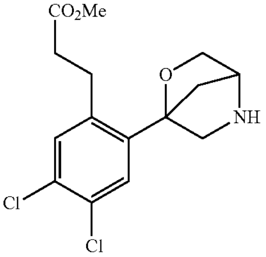 [SMILES: COC(=O)CCc1cc(Cl)c(Cl)cc1C12CNC(CO1)C2] |
| 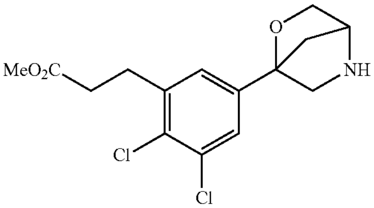 |
| 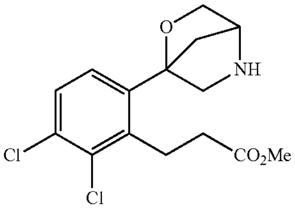 [SMILES: COC(=O)CCc1c(C23CNC(CO2)C3)ccc(Cl)c1Cl] |

TABLE 1-continued
| Exemplary Embodiments of Formula (I) |
|---|
| 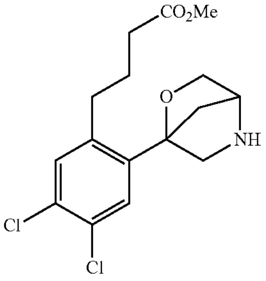 |
| 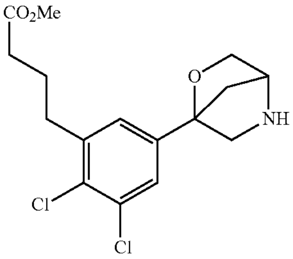 [SMILES: COC(=O)CCCc1cc(C23CNC(CO2)C3)cc(Cl)c1Cl] |
| 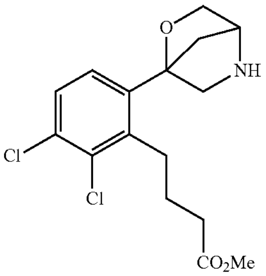 [SMILES: COC(=O)CCCc1c(C23CNC(CO2)C3)ccc(Cl)c1Cl] |
| 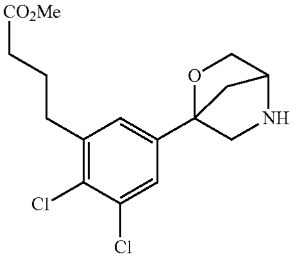 [SMILES: COC(=O)CCCc1cc(C23CNC(CO2)C3)cc(Cl)c1Cl] |
| 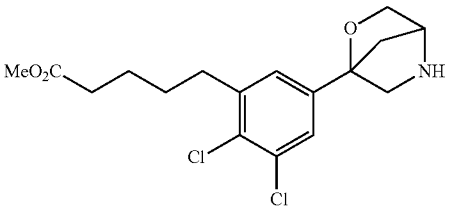 |
| 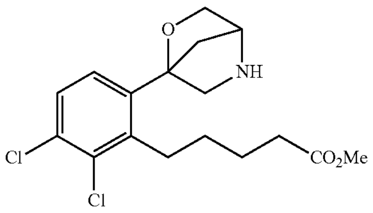 [SMILES: COC(=O)CCCCc1c(C23CNC(CO2)C3)ccc(Cl)c1Cl] |
| 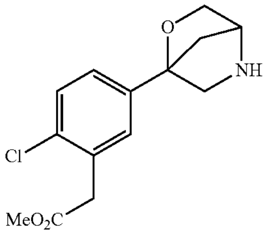 [SMILES: COC(=O)Cc1cc(C23CNC(CO2)C3)ccc1Cl] |
| 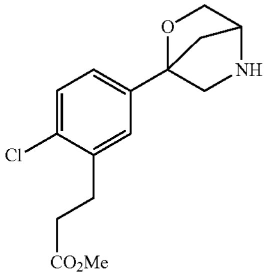 [SMILES: COC(=O)CCc1cc(C23CNC(CO2)C3)ccc1Cl] |
| 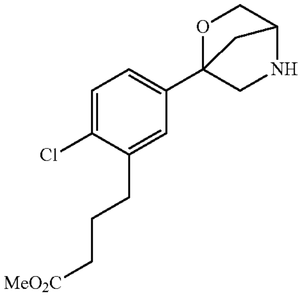 [SMILES: COC(=O)CCCc1cc(C23CNC(CO2)C3)ccc1Cl] |
| 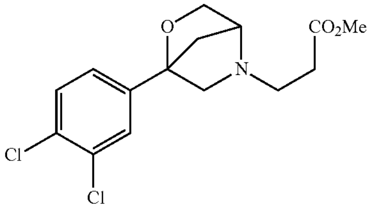 [SMILES: COC(=O)CCN1CC2(c3ccc(Cl)c(Cl)c3)CC1CO2] |
| 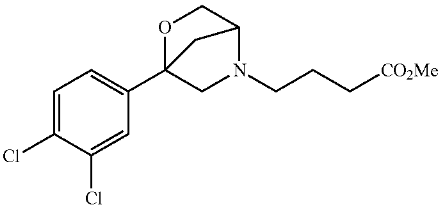 [SMILES: COC(=O)CCCN1CC2(c3ccc(Cl)c(Cl)c3)CC1CO2] |
| 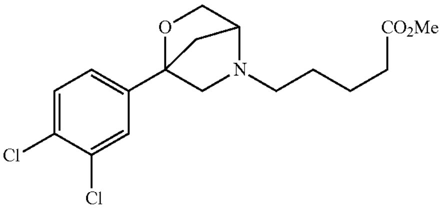 [SMILES: COC(=O)CCCCN1CC2(c3ccc(Cl)c(Cl)c3)CC1CO2] |

TABLE 1-continued
| Exemplary Embodiments of Formula (I) |
| --- |
| 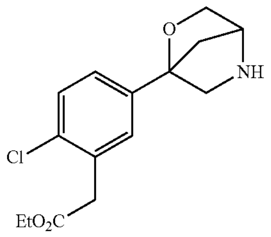 |
| 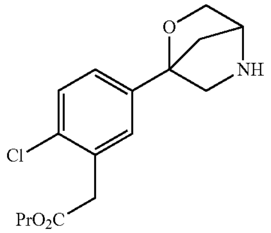 |
| 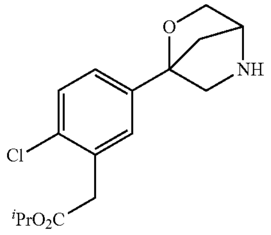 |
| 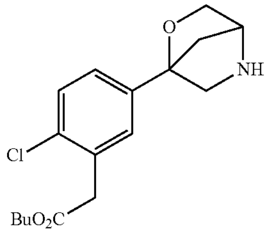 |
| 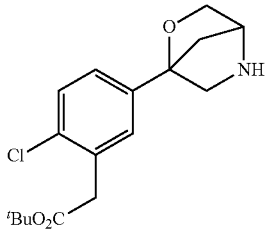 |
| 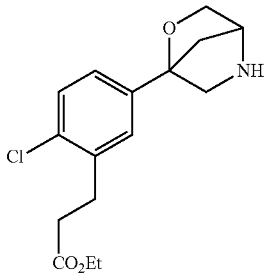 [SMILES: CCOC(=O)CCc1cc(C23CNC(CO2)C3)ccc1Cl] |
TABLE 1-continued
| Exemplary Embodiments of Formula (I) |
| --- |
| 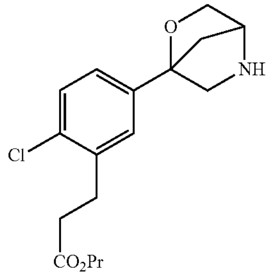 |
| 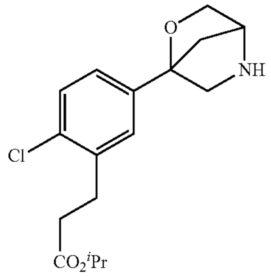 |
| 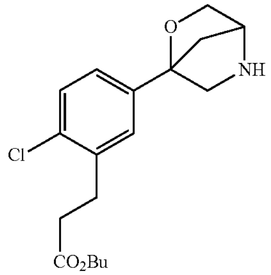 |
| 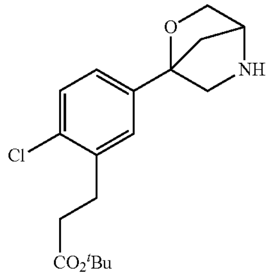 |
| 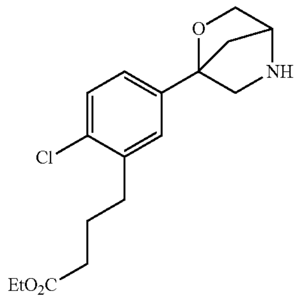 [SMILES: CCOC(=O)CCCc1cc(C23CNC(CO2)C3)ccc1Cl] |

TABLE 1-continued
Exemplary Embodiments of Formula (I)
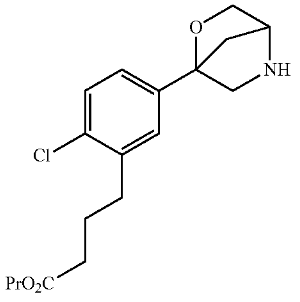
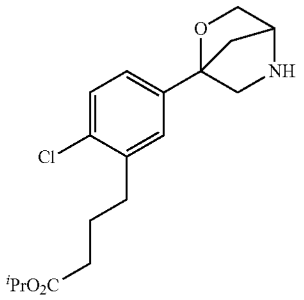
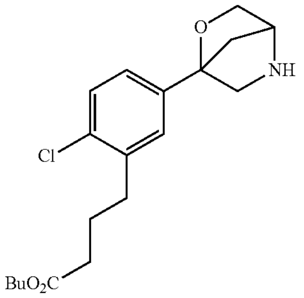
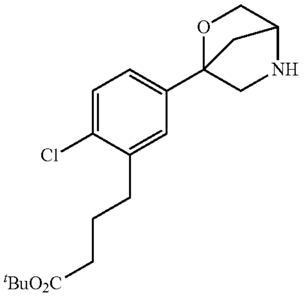
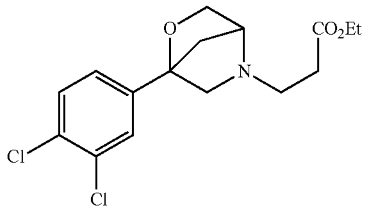
TABLE 1-continued
Exemplary Embodiments of Formula (I)
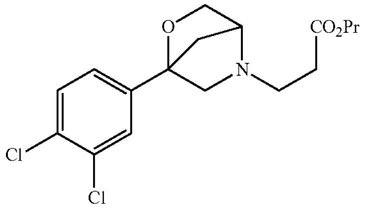 [SMILES: CCOC(=O)CCN1CC2(c3ccc(Cl)c(Cl)c3)CC1CO2]
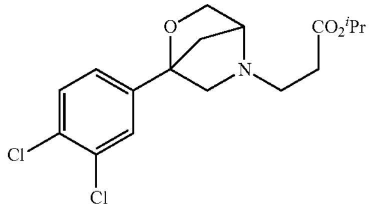
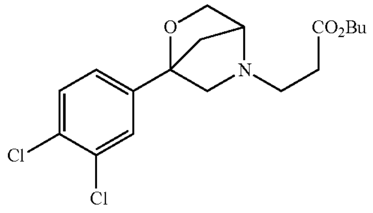
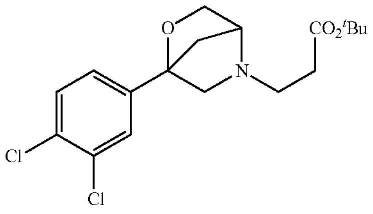
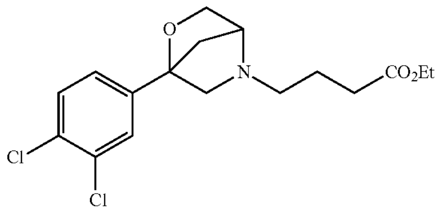
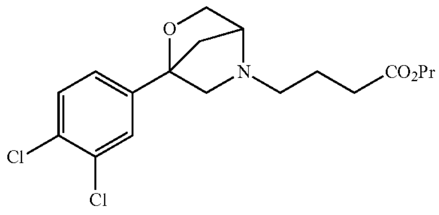
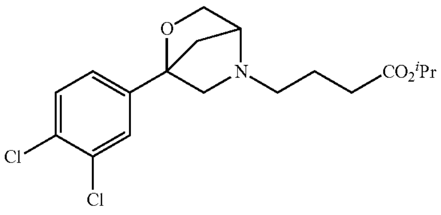

TABLE 1-continued
| Exemplary Embodiments of Formula (I) |
| --- |
| 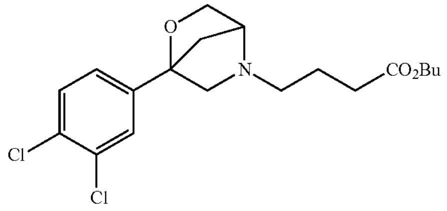 |
| 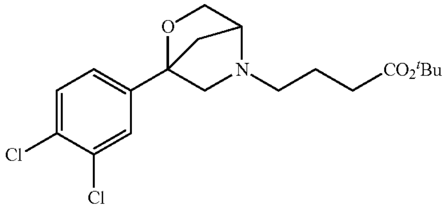 |
| 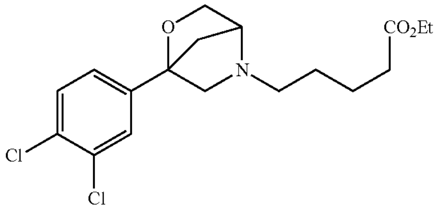 [SMILES: CCOC(=O)CCCCN1CC2(c3ccc(Cl)c(Cl)c3)CC1CO2] |
| 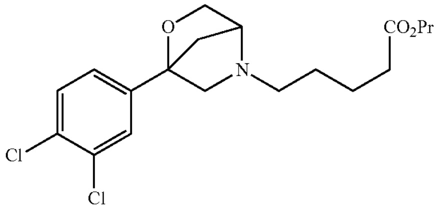 |
| 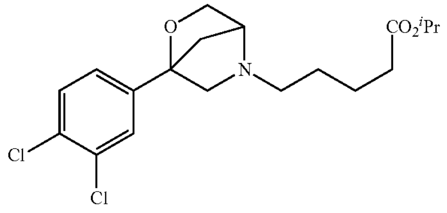 |
| 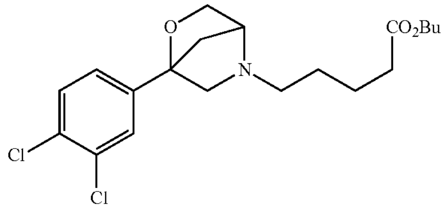 |
| 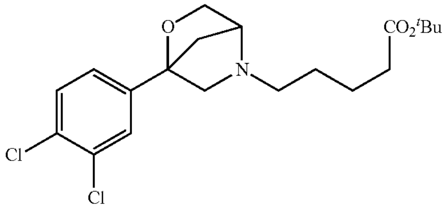 |
TABLE 1-continued
| Exemplary Embodiments of Formula (I) |
| --- |
| 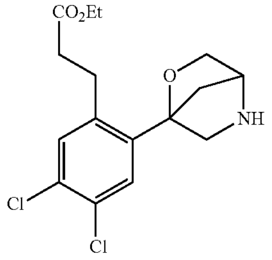 |
| 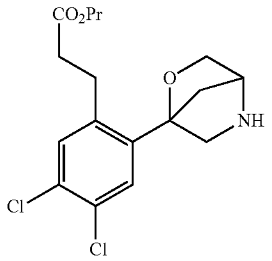 |
| 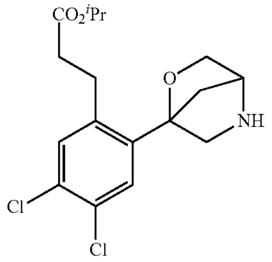 |
| 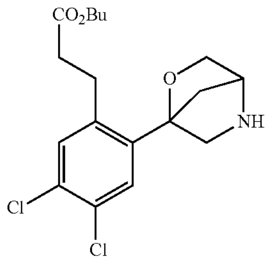 |
| 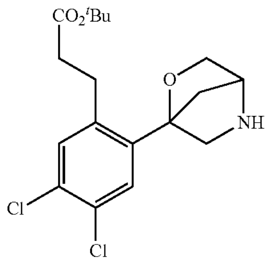 [SMILES: CC(C)(C)OC(=O)CCc1cc(Cl)c(Cl)cc1C12CNC(CO1)C2] |
| 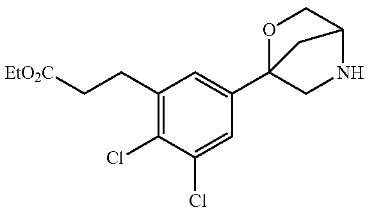 |

TABLE 1-continued
| Exemplary Embodiments of Formula (I) |
|---|
| 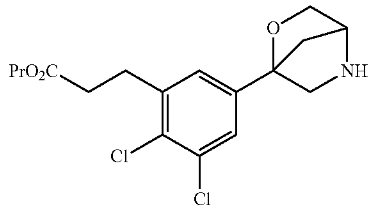 |
| 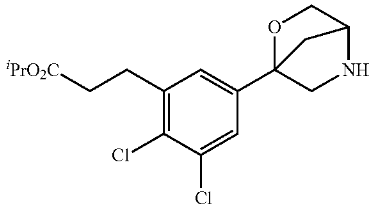 |
| 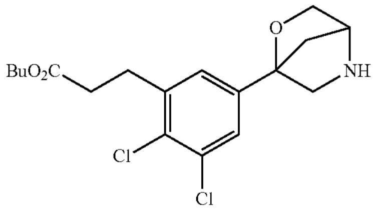 |
| 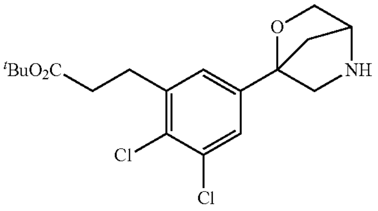 |
| 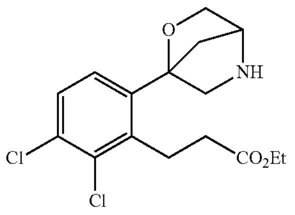 [SMILES: CCOC(=O)CCc1c(C23CNC(CO2)C3)ccc(Cl)c1Cl] |
| 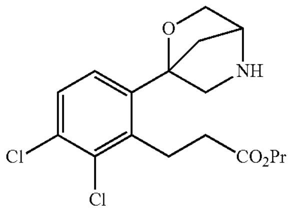 |
| 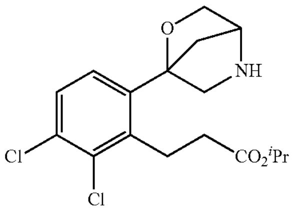 |
| 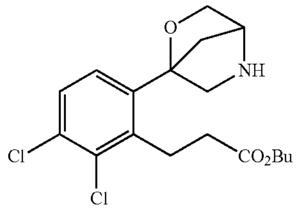 |
| 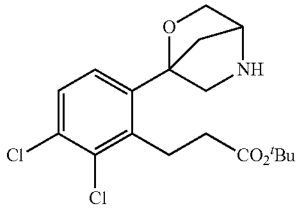 [SMILES: CC(C)(C)OC(=O)CCc1c(C23CNC(CO2)C3)ccc(Cl)c1Cl] |
| 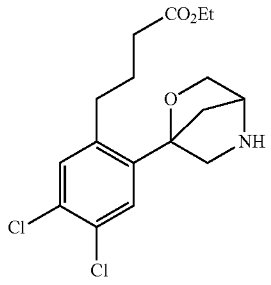 [SMILES: CCOC(=O)CCCc1cc(Cl)c(Cl)cc1C12CNC(CO1)C2] |
| 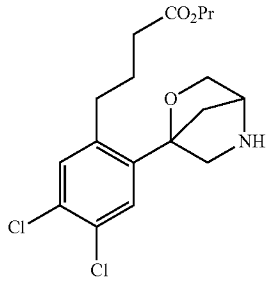 |
| 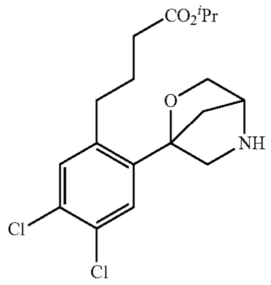 |
| 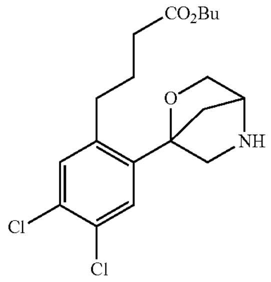 |

TABLE 1-continued
| Exemplary Embodiments of Formula (I) |
| --- |
| 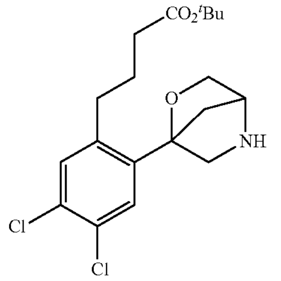 [SMILES: CC(C)(C)OC(=O)CCCc1cc(Cl)c(Cl)cc1C12CNC(CO1)C2] |
| 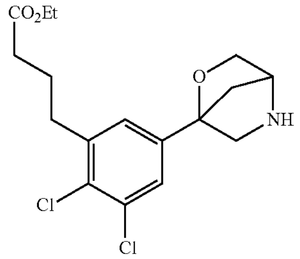 [SMILES: CCOC(=O)CCCc1cc(C23CNC(CO2)C3)cc(Cl)c1Cl] |
| 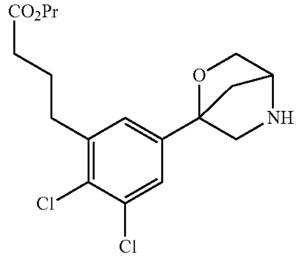 |
| 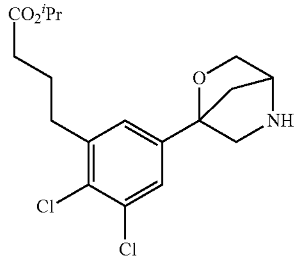 |
| 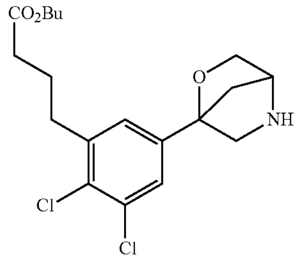 |
TABLE 1-continued
| Exemplary Embodiments of Formula (I) |
| --- |
| 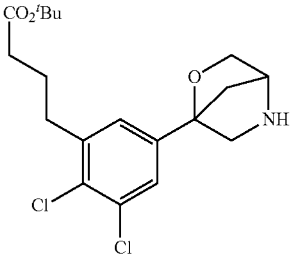 [SMILES: CC(C)(C)OC(=O)CCCc1cc(C23CNC(CO2)C3)cc(Cl)c1Cl] |
| 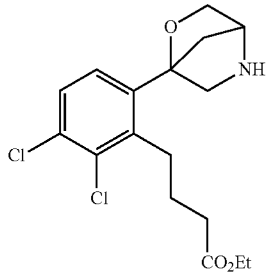 [SMILES: CCOC(=O)CCCc1c(C23CNC(CO2)C3)ccc(Cl)c1Cl] |
| 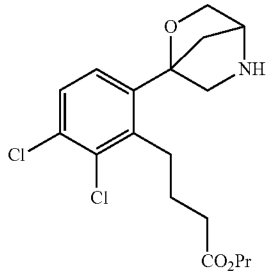 |
| 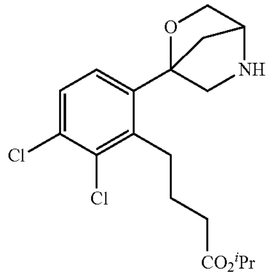 |
| 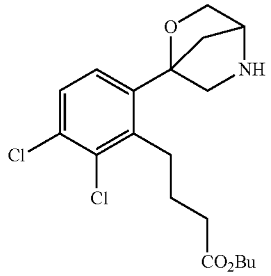 |

TABLE 1-continued
| Exemplary Embodiments of Formula (I) |
| --- |
| 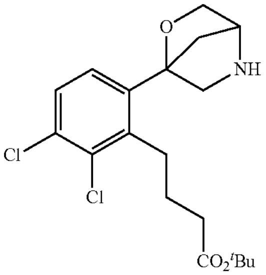 [SMILES: CC(C)(C)OC(=O)CCCc1c(C23CNC(CO2)C3)ccc(Cl)c1Cl] |
| 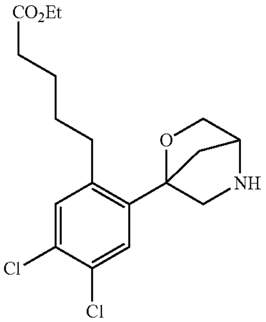 [SMILES: CCOC(=O)CCCCc1cc(Cl)c(Cl)cc1C12CNC(CO1)C2] |
| 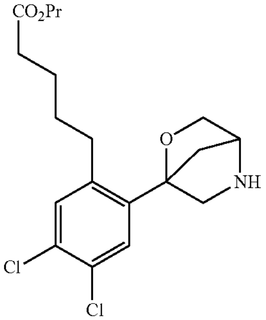 |
| 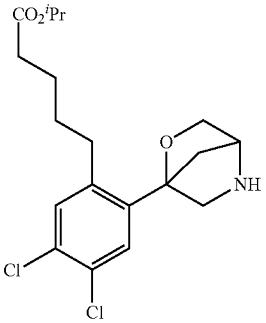 |
| 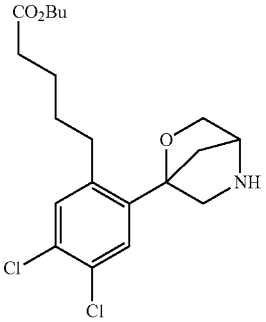 |
TABLE 1-continued
| Exemplary Embodiments of Formula (I) |
| --- |
| 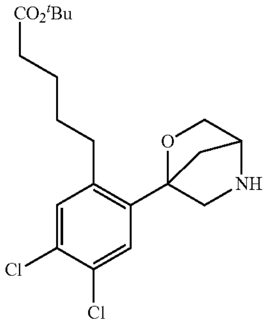 [SMILES: CC(C)(C)OC(=O)CCCCc1cc(Cl)c(Cl)cc1C12CNC(CO1)C2] |
| 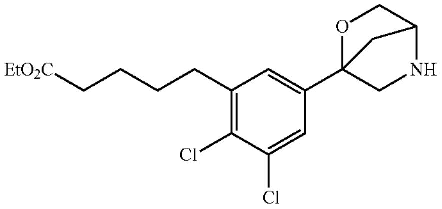 |
| 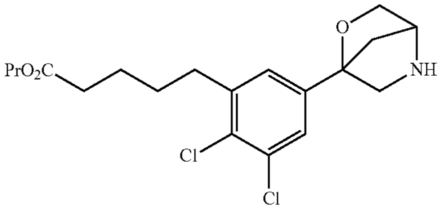 |
| 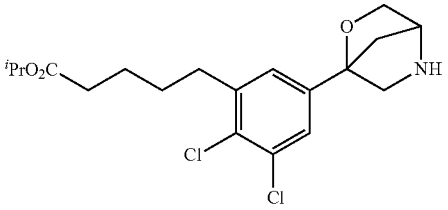 |
| 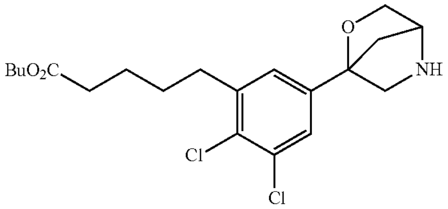 |
| 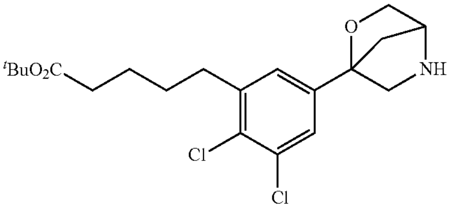 |

TABLE 1-continued

| Exemplary Embodiments of Formula (I) |
| --- |
| 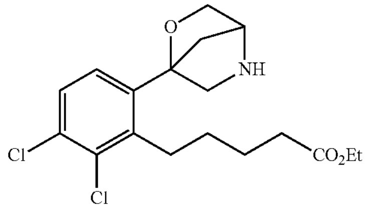 [SMILES: CCOC(=O)CCCCc1c(C23CNC(CO2)C3)ccc(Cl)c1Cl] |
| 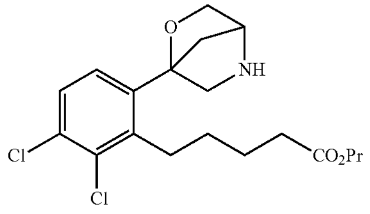 |
| 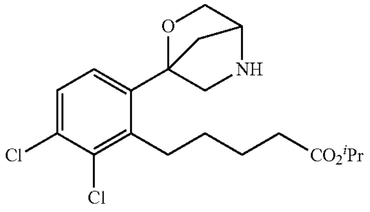 |
| 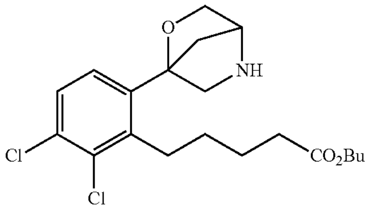 |
| 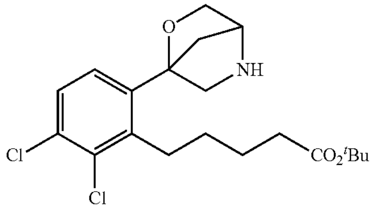 |

In some embodiments, the compounds are:

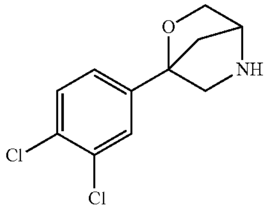

APV2415224 (“522A”)

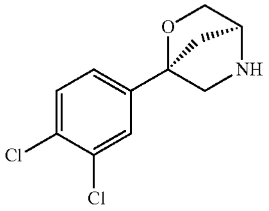

APV243516A (Enl; “516A”)

-continued

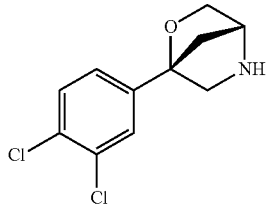

APV243518A (En2; “518A”)

In some embodiments, the compounds are:

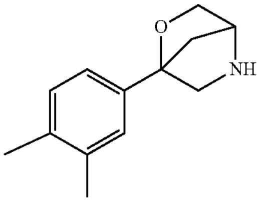

APV245514A (“514A”)

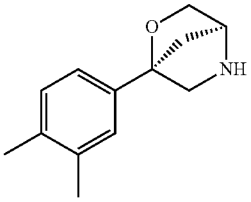

APV245514A
Enantiomer A

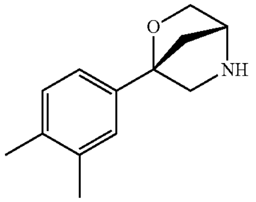

APV245514A
Entantiomer B

In some embodiments, the compounds are:

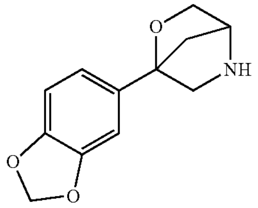

APV245562A (“514A”)

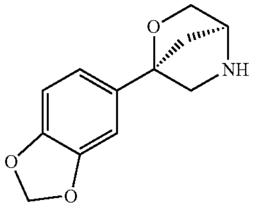

APV245562A
Enantiomer A

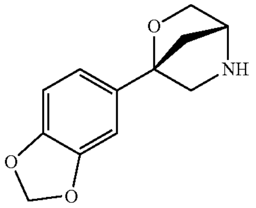

APV245562A
Entantiomer B

In some embodiments, provided herein is a compound, or a pharmaceutically acceptable salt thereof, having a structure of Formula II:

(II)

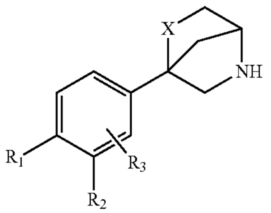

wherein $R_1$, $R_2$ and $R_3$ are independently hydrogen, $—CH_3$, $—OCH_3$, $—CF_3$, or halogen;

wherein, when $R_3$ is —Cl, $R_1$ and $R_2$ are both hydrogen;

alternatively $R_1$ and $R_2$ can be combined with the atoms to which they are each attached to form a $C_5$ heterocycloalkyl; and X is O or S;

or a pharmaceutically acceptable salt, hydrate, or solvate thereof (which will be understood to include all amorphous and polymorphic forms).

In some embodiments, for instance embodiments consisting of a single compound of Formula (II), or a composition consisting essentially of a single compound of Formula (II), the compound of Formula (II) will be as described above, but wherein the compound is other than:

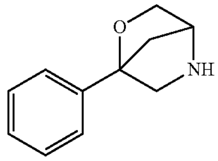 [SMILES: c1ccc(C23CNC(CO2)C3)cc1]

In some embodiments, provided herein is a compound, or a pharmaceutically acceptable salt thereof, having a structure of Formula III:

(III)

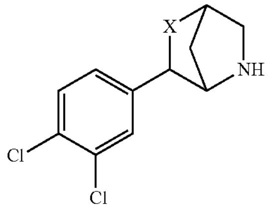

wherein X is O or S;

or a pharmaceutically acceptable salt, hydrate, or solvate thereof (which will be understood to include all amorphous and polymorphic forms).

In some embodiments, provided herein is a compound, or a pharmaceutically acceptable salt thereof, having a structure of Formula IV:

(IV)

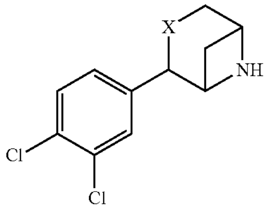

wherein X is O or S;

or a pharmaceutically acceptable salt, hydrate, or solvate thereof (which will be understood to include all amorphous and polymorphic forms).

In some embodiments, provided herein is a compound, or a pharmaceutically acceptable salt thereof, having a structure of Formula V:

(V)

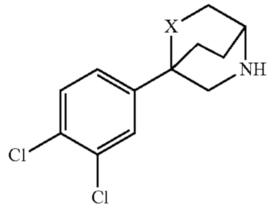

wherein X is O or S;

or a pharmaceutically acceptable salt, hydrate, or solvate thereof (which will be understood to include all amorphous and polymorphic forms).

In some embodiments, provided herein is a compound, or a pharmaceutically acceptable salt thereof, having a structure of Formula VI:

(VI)

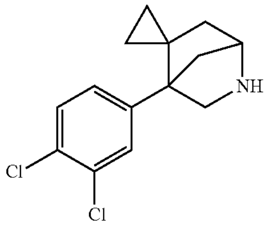

or a pharmaceutically acceptable salt, hydrate, or solvate thereof (which will be understood to include all amorphous and polymorphic forms).

In some embodiments, provided herein is a compound, or a pharmaceutically acceptable salt thereof, having a structure of Formula VII:

(VII)

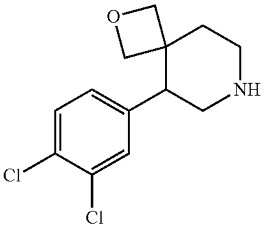

or a pharmaceutically acceptable salt, hydrate, or solvate thereof (which will be understood to include all amorphous and polymorphic forms).

In some embodiments, provided herein is a compound, or a pharmaceutically acceptable salt thereof, having a structure of Formula VIII:

(VIII)

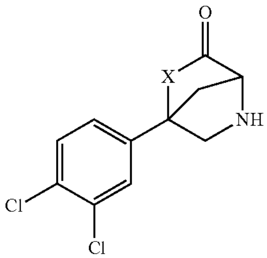

wherein X is O or S;

or a pharmaceutically acceptable salt, hydrate, or solvate thereof (which will be understood to include all amorphous and polymorphic forms).

In some embodiments, provided herein is a compound, or a pharmaceutically acceptable salt thereof, having a structure of Formula IX:

(IX)

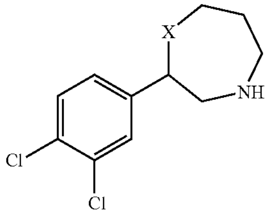

wherein X is O or S;

or a pharmaceutically acceptable salt, hydrate, or solvate thereof (which will be understood to include all amorphous and polymorphic forms).

In some embodiments, provided herein is a compound, or a pharmaceutically acceptable salt thereof, having a structure of Formula X:

(X)

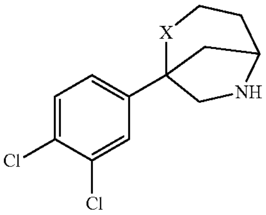

wherein X is O or S;

or a pharmaceutically acceptable salt, hydrate, or solvate thereof (which will be understood to include all amorphous and polymorphic forms).

In some embodiments, provided herein is a compound, or a pharmaceutically acceptable salt thereof, having a structure of Formula XI:

(XI)

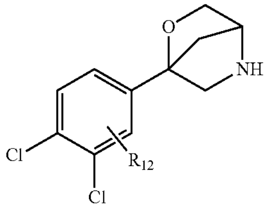

wherein $R_{12}$ is $-(CH_2)_1-CO_2R_{10}$, where I is an integer between 1 and 3 inclusive; $R_{10}$ is any of hydrogen; alkyl, cycloalkyl, aryl, or arylalkyl; $-(CH_2)_mZ(CH_2)_mCH_3$; or $(CH_2)_mR^{cyc}$;

Z is, and in either orientation, —O—, —C≡C—, —NH—, —NHNH—, —ONH—, —OCNH—, —CONH, $-CH(NH_2)-$, —OC(O)—, —S—, —S(O)—, $-SO_2-$, —CHF—, and $-CF_A$;

$R^{cyc}$ is an aryl, heterocycle, or heteroaryl; and each m is independently between 0 and 4 inclusive;

or a pharmaceutically acceptable salt, hydrate, or solvate thereof (which will be understood to include all amorphous and polymorphic forms).

Non-limiting exemplary compounds described herein of Formula (XI) include:

TABLE 2

| Exemplary Embodiments of Formula (XI) |
| --- |
| 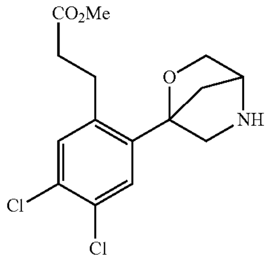 [SMILES: COC(=O)CCc1cc(Cl)c(Cl)cc1C12CNC(CO1)C2] |

TABLE 2-continued

| Exemplary Embodiments of Formula (XI) |
| --- |
| 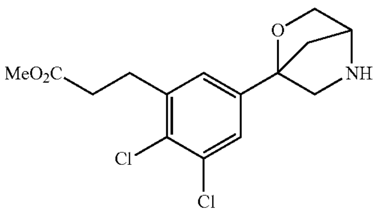 |
| 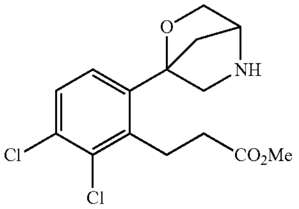 [SMILES: COC(=O)CCc1c(C23CNC(CO2)C3)ccc(Cl)c1Cl] |
| 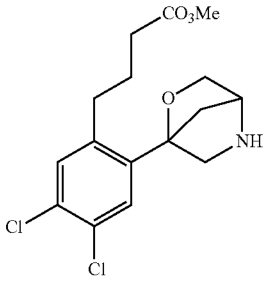 |
| 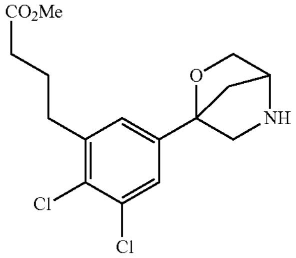 |
| 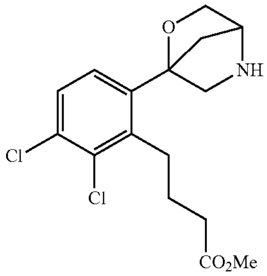 |
| 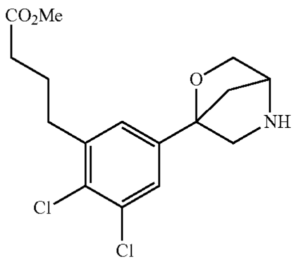 |

TABLE 2-continued

| Exemplary Embodiments of Formula (XI) |
| --- |
| 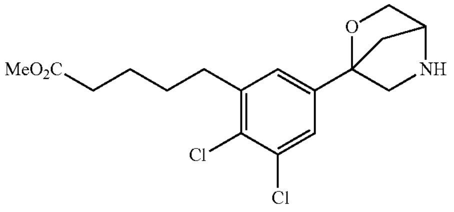 |
| 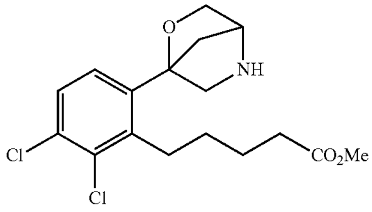 [SMILES: COC(=O)CCCCc1c(C23CNC(CO2)C3)ccc(Cl)c1Cl] |

In some embodiments, provided herein is a compound, or a pharmaceutically acceptable salt thereof, having a structure of Formula XII:

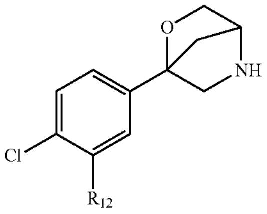

(XII)

wherein $R_{12}$ is $-(CH_2)_l-CO_2R_{10}$, where I is an integer between 1 and 3 inclusive; $R_{10}$ is any of hydrogen; alkyl, cycloalkyl, aryl, or arylalkyl; $-(CH_2)_m Z(CH_2)_mCH_3$; or $-(CH_2)_mR^{cyc}$;

Z is, and in either orientation, —O—, —C≡C—, —NH—, —NHNH—, —ONH—, —OCNH—, —CONH, $-CH(NH_2)-$, —OC(O)—, —S—, —S(O)—, $-SO_2-$, —CHF—, and $-CF_2-$;

$R^{cyc}$ is an aryl, heterocycle, or heteroaryl; and each m is independently between 0 and 4 inclusive;

or a pharmaceutically acceptable salt, hydrate, or solvate thereof (which will be understood to include all amorphous and polymorphic forms).

Non-limiting exemplary compounds described herein of Formula (XII) include:

TABLE 3

| Exemplary Embodiments of Formula (XII) |
| --- |
| 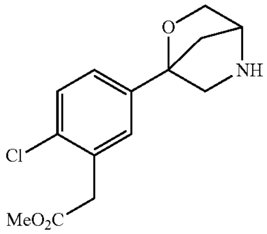 [SMILES: COC(=O)Cc1cc(C23CNC(CO2)C3)ccc1Cl] |

TABLE 3-continued

| Exemplary Embodiments of Formula (XII) |
| --- |
| 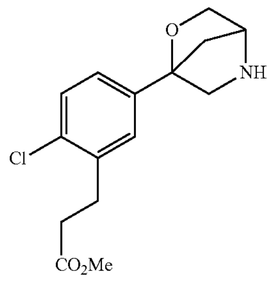 [SMILES: COC(=O)CCc1cc(C23CNC(CO2)C3)ccc1Cl] |
| 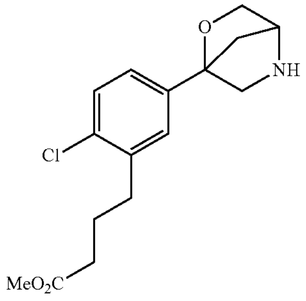 |

In some embodiments, provided herein is a compound, or a pharmaceutically acceptable salt thereof, having a structure of Formula XIII:

(XIII)

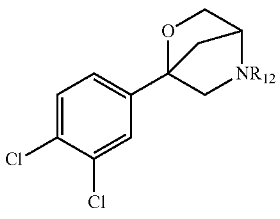

wherein $R_{12}$ is $—(CH_2)_l—CO_2R_{10}$, where I is an integer between 1 and 3 inclusive;

$R_{10}$ is any of hydrogen; alkyl, cycloalkyl, aryl, or arylalkyl; $—(CH_2)_mZ(CH_2)_mCH_3$; or $(CH_2)_mR^{cyc}$;

Z is, and in either orientation, —O—, —C≡C—, —NH—, —NHNH—, —ONH—, —OCNH—, —CONH, $—CH(NH_2)—$, —OC(O)—, —S—, —S(O)—, $—SO_2—$, —CHF—, and $—CF_2—$;

$R^{cyc}$ is an aryl, heterocycle, or heteroaryl;

each m is independently between 0 and 4 inclusive;

or a pharmaceutically acceptable salt, hydrate, or solvate thereof (which will be understood to include all amorphous and polymorphic forms).

Non-limiting exemplary compounds described herein of Formula (XIII) include:

TABLE 4

| Exemplary Embodiments of Formula (XIII) |
| --- |
| 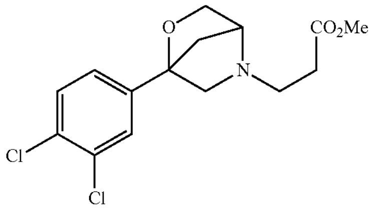 [SMILES: COC(=O)CCN1CC2(c3ccc(Cl)c(Cl)c3)CC1CO2] |
| 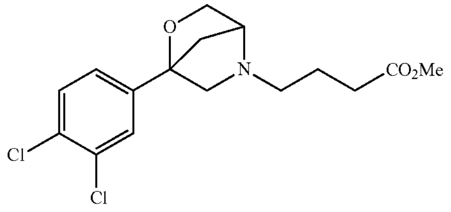 [SMILES: COC(=O)CCCN1CC2(c3ccc(Cl)c(Cl)c3)CC1CO2] |
| 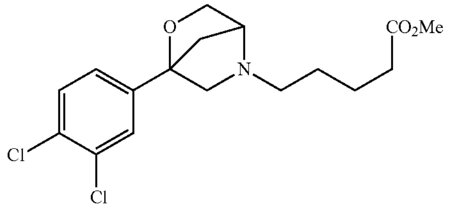 [SMILES: COC(=O)CCCCN1CC2(c3ccc(Cl)c(Cl)c3)CC1CO2] |

The compounds described herein may contain one or more asymmetric centers and give rise to enantiomers, diastereomers, and other stereoisomeric forms. Each chiral center may be defined, in terms of absolute stereochemistry, as (R)- or (S)—. The invention includes all such possible isomers, as well as mixtures thereof, including racemic and optically pure forms.

Optically active (R)- and (S)—, (−)- and (+)-, or (D)- and (L)-isomers may be prepared using chiral synthons or chiral reagents, or resolved using conventional techniques. Various methods are known in the art for preparing optically active forms and determining activity.

In some embodiments are disclosed pharmaceutical compositions in which the compound is present as a pure or substantially pure individual enantiomer, or an enantiomerically enriched mixture having an optical purity of between 0-25%, between 25-50%, between 50-75%, between 75-90%, between 90-95%, or at least 95% enantiomeric excess.

When the compounds described herein contain olefinic double bonds or other centers of geometric asymmetry, and unless specified otherwise, it is intended that the compounds include both E and Z geometric isomers. Likewise, tautomeric forms are included.

The invention also includes compounds with at least one desired isotopic substitution of an atom, at an amount above the natural abundance of the isotope, i.e., isotopically enriched. Isotopes are atoms having the same atomic number but different mass numbers, i.e., the same number of protons but a different number of neutrons. Examples of isotopes that can be incorporated into compounds described herein include isotopes of hydrogen, carbon, nitrogen, oxygen, and chlorine such as $^{2}H$, $^{3}H$, $^{11}C$, $^{13}C$, $^{14}C$, $^{15}N$, $^{17}O$, $^{18}O$, and $^{36}Cl$ respectively. In one non-limiting embodiment, isotopically labeled compounds can be used in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and pro-soft drugs thereof can generally be prepared by carrying out the procedures disclosed in the schemes or in the examples and preparations described below by substituting a readily available isotopically labeled reagent for a non-isotopically labeled reagent.

By way of example and without limitation, isotopes of hydrogen including deuterium ($^2H$) and tritium ($^3H$) may be used anywhere in described structures that achieves the desired result. Alternatively or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is at least 60, 70, 80, 90, 95, or 99% or more enriched in an isotope at any location of interest. In one non-limiting embodiment, deuterium is 90, 95, or 99% enriched at a desired location.

The term "isotopically-labeled" analog refers to an analog that is a "deuterated analog," a "$^{13}C$-labeled analog" or a "deuterated/$^{13}C$-labeled analog." "Deuterated analog" means a disclosed compound, whereby a H-isotope, i.e., hydrogen/protium ($^1H$), is substituted by a H-isotope, i.e., deuterium ($^2H$). Deuterium substitution can be partial or complete. Partial deuterium substitution means at least one hydrogen is substituted by at least one deuterium. In certain embodiments, the isotope is at least 60, 70, 80, 90, 95, or 99% or more enriched in an isotope at any location of interest. In embodiments it is deuterium that is 90, 95, or 99% enriched at a desired location. Unless indicated to the contrary, deuteration is at least 80% at the selected location. Deuteration can occur at any replaceable hydrogen that provides the desired results.

The individual compounds of the compositions of the invention will be understood to also encompass pharmaceutically acceptable salts of such compounds. The term "pharmaceutically acceptable salt" refers to salts prepared from pharmaceutically acceptable non-toxic acids or bases, which may be synthesized by conventional chemical methods. Generally, such salts are prepared by reacting the free acid or base forms of these agents with a stoichiometric amount of the appropriate base or acid in water or in an organic solvent, or in a mixture of the two; generally, nonaqueous media (e.g., ether, ethyl acetate, ethanol, isopropanol, or acetonitrile) are preferred. For therapeutic use, salts of the compounds are those wherein the counter-ion is pharmaceutically acceptable. Exemplary salts include 2-hydroxyethanesulfonate, 2-naphthalenesulfonate, 2-napsylate, 3-hydroxy-2-naphthoate, 3-phenylpropionate, 4-acetamidobenzoate, acefyllinate, acetate, aceturate, adipate, alginate, aminosalicylate, ammonium, amsonate, ascorbate, aspartate, benzenesulfonate, benzoate, besylate, bicarbonate, bisulfate, bitartrate, borate, butyrate, calcium edetate, calcium, camphocarbonate, camphorate, camphorsulfonate, camsylate, carbonate, cholate, citrate, clavulariate, cyclopentanepropionate, cypionate, d-aspartate, d-camsylate, d-lactate, decanoate, dichloroacetate, digluconate, dodecylsulfate, edentate, edetate, edisylate, estolate, esylate, ethanesulfonate, ethyl sulfate, fumarate, furate, fusidate, galactarate (mucate), galacturonate, gallate, gentisate, gluceptate, glucoheptanoate, gluconate, glucuronate, glutamate, glutarate, glycerophosphate, glycolate, glycollylarsanilate, hemisulfate, heptanoate (enanthate), heptanoate, hexafluorophosphate, hexanoate, hexylresorcinate, hippurate, hybenzate, hydrabamine, hydrobromide, hydrobromide/bromide, hydrochloride, hydroiodide, hydroxide, hydroxybenzoate, hydroxynaphthoate, iodide, isethionate, isothionate, 1-aspartate, 1-camsylate, 1-lactate, lactate, lactobionate, laurate, laurylsulphonate, lithium, magnesium, malate, maleate, malonate, mandelate, meso-tartrate, mesylate, methanesulfonate, methylbromide, methylnitrate, methylsulfate, mucate, myristate, N-methylglucamine ammonium salt, napadisilate, naphthylate, napsylate, nicotinate, nitrate, octanoate, oleate, orotate, oxalate, p-toluenesulfonate, palmitate, pamoate, pantothenate, pectinate, persulfate, phenylpropionate, phosphate, phosphateldiphosphate, picrate, pivalate, polygalacturonate, potassium, propionate, pyrophosphate, saccharate, salicylate, salicylsulfate, sodium, stearate, subacetate, succinate, sulfate, sulfosaliculate, sulfosalicylate, suramate, tannate, tartrate, teoclate, terephthalate, thiocyanate, thiosalicylate, tosylate, tribrophenate, triethiodide, undecanoate, undecylenate, valerate, valproate, xinafoate, zinc and the like. (See Berge et al., "Pharmaceutical Salts," J. Pharm. Sci., 1977; 66:1-19.)

In some embodiments, the compounds provided herein provide a rapid onset of therapeutic effect. In embodiments, the compounds provided herein provide a short-term duration of action. In embodiments, the compounds provided herein provide rapid onset of therapeutic effect and a short-term duration of action. As used herein, "fast-acting" is used to describe a compound that produces a therapeutic effect more rapidly than a comparator. As used herein, "short-acting" is used to describe a compound that exhibits a shorter duration of action relative to a comparator. In embodiments, rapid onset of action and/or short duration of action is determined from subjective and/or objective measures of drug effects. In embodiments, the fast-acting and/or the short-acting compounds described herein provide entactogenic effects with a magnitude or intensity that is comparable to a known entactogen, such as MDMA, or enhanced. Non-limiting examples of determining the magnitude or intensity of an entactogenic experience include measuring blood plasma levels of various monoamines and collecting or rating subjective and/or observer reports of drug effects. Various measures of the entactogenic experience include the evaluating responses to stimuli, for example, as in the Multifaceted Empathy Test or the Face Emotion Recognition Test, and assessing responses to psychometric evaluations, for example, using the Psychometric Evaluation of the Altered States of Consciousness Rating Scale (OAV) (Studerus et al., PloS one, 2010; 5(8), e12412; Hysek et al., Social Cognitive and Affective Neuroscience, 2014; 9(11):1645-1652).

In some embodiments, identifying compounds with rapid onset and/or abbreviated drug action involves comparing pharmacokinetic parameters, for example, between a parent compound and a derivative of the same, modified as described herein. Exemplary pharmacokinetic parameters, such as a relatively short half-life ($T_{1/2}$), increased rate of clearance (Cl), reduced time to peak concentration ($T_{max}$), and decreased area under the curve (AUC), may be representative of rapid onset and/or short-term duration of action.

In some embodiments, a fast-acting and/or a short-acting compound as described herein exhibits a half-life ($t_{1/2}$) that is reduced by at least about 5%, at least about 10%, at least about 15%, at least about 20%, at least about 25%, at least about 30%, at least about 35%, at least about 50%, at least about 75%, or at least about 100% relative to a comparator. In embodiments, a fast-acting and/or a short-acting compound as described herein exhibits a clearance rate that is at least 5%, at least 10%, at least 15%, at least 20%, at least 25%, at least 30%, at least 35%, at least 50%, at least 75%, or at least 100% faster than a comparator. In some embodiments, a comparator comprises the parent compound of a fast-acting and/or a short-acting derivative, for example, an ester provided herein. In some embodiments a comparator comprises a known entactogen, for example, MDMA.

In some embodiments, a fast-acting and/or short-acting compound reaches peak concentration ($t_{max}$) at least about 5%, at least about 10%, at least about 15%, at least about 20%, at least about 25%, at least about 30%, at least about 35%, at least about 50%, at least about 75%, or at least about 100% faster than a comparator. In some embodiments, the AUC of a fast-acting and/or short-acting compound is at least about 5%, at least about 10%, at least about 15%, at least about 20%, at least about 25%, at least about 30%, at least about 35%, at least about 50%, at least about 75%, or at least about 100% less than a comparator. In some embodiments, a comparator comprises the parent compound of a fast-acting and/or a short-acting derivative, for example, an ester provided herein. In some embodiments a comparator comprises a known entactogen, for example, MDMA Introduction of esters has been described in the pursuit of providing rapid onset anesthetics with a short duration, for example, midazolam and ketamine derivatives. Some have exhibited unpredictable effects on receptor binding and potency relative to the parent compound (Pacofsky et al., Bioorg. Med. Chem. Lett., 2002; 12:3219-22; Dimitrov et al., Molecules, 2020; 25(12):2950). In some embodiments, the introduced ester does not prevent a compound provided herein from interacting with, such as binding to, a target, for example, a receptor or a transporter. In some embodiments, the acid metabolite of ester degradation displays a lower binding affinity to a target, exhibits reduced efficacy, or is less potent than the ester-containing compound. In some embodiments, the bulk of the introduced ester group may modify the duration of action, for example, the half-life, of a compound provided herein. In some embodiments, increasing the bulk of the introduced ester may extend a compound's duration of action, for example, increase the half-life. An exemplary non-limiting series of increasing ester bulk is provided: $CO_2$Methyl< $CO_2$Ethyl<$CO_2$Propyl<$CO_2$Butyl<$CO_2$Pentyl< $CO_2$Hexyl<$CO_2$Heptyl<$CO_2$Octyl.

In some embodiments, rapid onset and/or short-acting properties are provided by introducing an ester into a structure as provided herein, such as a morpholine scaffold. In some embodiments, an internal ester may be introduced to provide a fast-acting derivative. In some embodiments, an internal ester may be introduced to provide a short-acting derivative. In some embodiments, an external ester may be introduced to provide a fast-acting derivative. In some embodiments, an external ester may be introduced to provide a short-acting derivative.

In some embodiments, biologically active pharmaceutical esters described herein may be "soft drugs." Soft drugs exert therapeutic effects, for example, by interacting with a target receptor or site of action, prior to rapid metabolic conversion into a biologically inactive metabolite. In addition to considering efficacy, an aim of soft drug design is to leverage moieties that will yield inactive and/or non-toxic compounds after metabolism, such as a predictable one-step metabolic conversion (Buchwald & Bodor, Pharmazie. 2014 June; 69(6):403-13). Quick metabolism of soft drugs yields various effects, including minimizing duration of action, eliminating exposure to toxic metabolites, and reducing any possible drug-drug interactions. For example, various esters of ketamine have exhibited diverse effects on potency, duration of action, and psychomimetic effects of the drug (Jose et al., Bioorg. Med. Chem., 2013; 21(17):5098-106; Harvey et al., Anesthesia & Analgesia, 2015; 121(4):925-33; Dimitrov et al., Bioorg. Med. Chem., 2019; 27(7):1226-1231). Provided that CYP450 enzymes, the major metabolizers, are subject to saturation and inhibition, fast metabolism may be facilitated by directing metabolism to hydrolytic enzymes, for example, by incorporating a metabolically sensitive "soft spot," such as an ester (Buchwald, Expert Opin Drug Metab Toxicol. 2020 August; 16(8):645-650).

Several strategies exist for preparing soft drugs. Some major approaches described herein pertain to soft analogs, active metabolite-based soft drugs, inactive metabolite-based soft drugs, controlled release endogenous agents or natural soft drugs, and activated soft compounds. Soft analogs are close structural analogs of a known or lead compound wherein metabolically sensitive moieties have been introduced to modify inactivation and/or excretion properties. The active metabolite approach leverages the biotransformation of a compound. Selecting an active species of biotransformation that exerts a desired pharmacological effect and undergoes a predictable and singular conversion into an inactive metabolite is one example of this approach. In contrast, the inactive metabolite approach relies on chemically modifying an inactive form of a compound to produce a pharmacologically active compound. A predictable one-step metabolic conversion would then restore the initial inactive compound and eliminate exposure to any toxic intermediates. Endogenous biologically active agents that are efficiently metabolized can be described as natural soft drugs. A pro-soft drug approach can be adopted to modify the metabolism and duration of action of such compounds, for example, when metabolism of a desired compound is so rapid that it interferes with or precludes a desired pharmacological effect. Activated soft compounds result from incorporating a moiety with known pharmacological activity into a non-toxic compound. After exerting therapeutic activity, activated soft compounds are metabolized into their original non-toxic state (Bhardwaj et al., Saudi Pharm. J., 2014; 22(4):290-302).

Esterases, hydrolases that split ester bonds, are ubiquitously distributed throughout the body, and can facilitate metabolism in the plasma, gut, liver, and other tissues (Williams, Man. Clin Pharmacokinet, 1985; 10, 392-403). Hydrolytic degradation can inactivate an ester, for example, by introducing a change in charge and/or shape that diminishes the metabolite's binding affinity for the original target (Buchwald, Expert Opin Drug Metab Toxicol. 2020 August; 16(8):645-650). However, like CYP enzymes, genetic polymorphisms of esterases exist, and the enzymes are subject to induction, inhibition, and altered activity resulting from liver disease (Laizure et al. Pharmacotherapy. 2013 February; 33(2):210-22). Additionally, the activity of esterases can be unpredictable. The activity of such enzymes varies across tissues and between individuals, and is influenced by a variety of factors, including age (Di, Current Drug Metabolism, 2019; 20(2): 91-102).

In some embodiments, the compounds provided herein are quickly metabolized. In some embodiments, aspects of the metabolism of the compounds provided herein, such as the rate of metabolism, can be modified by adjusting the size and bulk of the R group in an ester ($CO_2R$). In some embodiments, the compounds provided herein are rapidly inactivated and/or eliminated, such as in and from the body of a subject. In some embodiments, rapid inactivation and/or elimination of the compounds provided herein facilitates a short duration of action. In some embodiments, hydrolysis of esters of the compounds provided herein facilitates a predictable duration of action. In some embodiments, hydrolysis of esters of the compounds provided herein facilitates a short duration of action. In embodiments, the compounds provided herein exhibit a reduced duration of action relative to a comparator compound, such as MDMA.

Pro-soft drugs, which require metabolic transformation for conversion into an active soft drug, have been described (Mukker et al., J Pharm Sci. 2016 September; 105(9):2509-2514). Prodrugs are differentiated from soft drugs in that they must undergo metabolic conversion to become biologically active, whereas metabolism of soft drugs, which are delivered as active agents, promotes inactivation and excretion. Incorporation of an ester moiety is an approach in preparing prodrugs (Rautio et al., Nat Rev Drug Discov. 2008; 7, 255-270). Examples of prodrugs using ester or phosphoramidate as biologically labile or cleavable (protecting) groups are disclosed in U.S. Pat. Nos. 6,875,751, 7,585,851, and 7,964,580.

In some embodiments, the compounds provided herein are not converted, such as metabolized, into pharmacologically active metabolites. In some embodiments, the compounds provided herein are not converted, such as metabolized, into toxic metabolites, such as metabolites associated with side effects. In some embodiments, the compounds provided herein are not associated with side effects, such as following administration to a subject. In some embodiments, the compounds provided herein do not cause side effects, such as following administration to a subject.

Prodrugs of the active agents also will be appreciated to be within the scope of the invention. The term "prodrug" refers to a precursor of a biologically active pharmaceutical agent. Prodrugs undergo a chemical or a metabolic conversion to become a biologically active pharmaceutical agent. A prodrug can be converted ex vivo to the biologically active pharmaceutical agent by chemical transformative processes. In vivo, a prodrug is converted to the biologically active pharmaceutical agent by the action of a metabolic process, an enzymatic process or a degradative process that removes the prodrug moiety, such as a glycoside or acetyl group, to form the biologically active pharmaceutical agent. Other examples include addition of hydroxyl groups (Tsujikawa et al. 2011. Xenobiotica, 41(7), 578-584; Yamamoto et al. 1984. Xenobiotica, 14(11), 867-875), acyloxyalkoxycarbonyl derivatives, amino acids, or peptides (Vig et al. 2013. Advanced Drug Delivery Reviews, 65(10), 1370-1385), which are generally added to the amine, and can be removed within the body by chemical reactions or enzymes, but other prodrugs and precursors, at the amine and other sites, should be understood to be within the scope of the invention (Simplicio, Clancy, & Gilmer. 2008. Molecules, 13(3), 519-547; Shah, Chauhan, Chauhan, & Mishra (Eds.). 2020. Recent Advancement in Prodrugs. CRC Press).

Types of prodrugs contemplated to be within the scope and spirit of the invention therefore include compounds that are transformed in various organs or locations in the body (e.g., liver, kidney, G.I., lung, tissue) to release the active compound. For example, liver prodrugs will include active compounds conjugated with a polymer or chemical moiety that is not released until acted upon by liver cytochrome enzymes; CYP metabolism includes dealkylation, dehydrogenation, reduction, hydrolysis, oxidation, and the breakdown of aromatic rings. Kidney prodrugs will include active compounds conjugated to L-gamma-glutamyl or N-acetyl-L-gamma glutamic moieties so that they are metabolized by gamma-glutamyl transpeptidase before they are bioactive; alternatively, they may be conjugated to alkylglucoside moieties to create glycosylation-based prodrugs. Digestive or G.I. prodrugs will include those where an active compound is, e.g., formulated into microspheres or nanospheres that do not degrade until the spheres are subjected to an acidic pH; formulated with an amide that will resist biochemical degradation until colonic pH is achieved; or conjugated with a linear polysaccharide such as pectin that will delay activation until the combination reaches the bacteria in the colon. Besides these exemplary prodrug forms, many others will be known to those of ordinary skill.

Typical examples of prodrugs also include compounds with biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound as described herein. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

In the case of solid compositions, it is understood that the compounds used in the methods of the invention may exist in different forms. For example, the compounds may exist in stable and metastable crystalline forms, isotropic and amorphous forms, milled forms and nano-particulate forms, all of which are intended to be within the scope of the present invention. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravimetric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

The compounds described herein now generally described will be more readily understood by reference to the following description and examples, which are included for the purposes of illustration of certain aspects of the embodiments of the invention. The following is not intended to limit the invention, as one of skill in the art would recognize from the teachings and examples herein that other techniques and methods can satisfy the claims and be employed without departing from the scope of the invention. Indeed, while this invention has been particularly shown and described with reference to certain exemplary embodiments, it will be understood by those skilled in the art that various changes in form and details may be made without departing from the scope or spirit of the invention encompassed by the appended claims.

C. Pharmaceutical Compositions and Methods of Administration

Provided are compositions, such as pharmaceutical compositions and formulations, and methods of administering the same. As referred to herein, "compositions" and "formulations" may be used interchangeably. In some embodiments, the individual compounds described herein are administered as part of a pharmaceutical composition or formulation, e.g., as the drug substance or active pharmaceutical ingredient ("API"). "Pharmaceutical compositions" are compositions comprising disclosed compound(s) together in an amount (for example, in a unit dosage form) with a pharmaceutically acceptable carrier, diluent, or excipient. It should be understood that some embodiments do not have a single carrier, diluent, or excipient alone, but include multiple carriers, diluents, and/or excipients. Compositions can be prepared by standard pharmaceutical formulation techniques such as disclosed in Remington: The Science and Practice of Pharmacy (2005) 21th ed., Mack Publishing Co., Easton, Pa.; The Merck Index (1996) 12th ed., Merck Publishing Group, Whitehouse, N.J.; Pharm. Principles of Solid Dosage Forms (1993), Technomic Publishing Co., Inc., Lancaster, Pa.; and Ansel and Stoklosa, Pharm. Calculations (2001) 11th ed., Lippincott Williams & Wilkins, Baltimore, Md.; and Poznansky et al. Drug Delivery Systems (1980), R. L. Juliano, ed., Oxford, N.Y, pp. 253-315).

"Pharmaceutically acceptable" as used in connection with one or more ingredients means that the ingredients are generally safe and, within the scope of sound medical judgment, suitable for use in contact with the cells of humans and other animals without undue toxicity, irritation, allergic response, or complication, and commensurate with a reasonable risk/benefit ratio.

In some embodiments, pure or substantially pure individual compounds described herein are administered as part of a pharmaceutical composition or formulation. The terms "pure" or "substantially pure," as used herein, refer to material that is substantially or essentially free from components that normally accompany the material when the material is synthesized, manufactured, or otherwise produced. A "pure" or "substantially pure" preparation of a compound is accordingly defined as a preparation having a chromatographic purity (of the desired compound) of greater than 90%, more preferably greater than 95%, more preferably greater than 96%, more preferably greater than 97%, more preferably greater than 98%, more preferably greater than 99%, more preferably greater than 99.5%, and most preferably greater than 99.9%, as determined by area normalization of an HPLC profile or other similar detection method. Preferably the pure or substantially pure compound used in the invention is substantially free of any other active compounds which are not intended to be administered to a subject. In this context, "substantially free" refers to the fact that no active compound(s), other than the active compound intended to be administered to a subject, are detectable by HPLC or another similar detection method, or are below a desired threshold of detection such as defined above.

a. Compositions, Dosage Forms, and Methods for Preparing the Same

In some embodiments, a compound described herein can be formulated into any suitable dosage form, including aqueous oral dispersions, aqueous oral suspensions, solid dosage forms including oral solid dosage forms, aerosols, controlled release formulations, fast melt formulations, effervescent formulations, self-emulsifying dispersions, solid solutions, liposomal dispersions, lyophilized formulations, tablets, capsules, pills, powders, delayed-release formulations, immediate-release formulations, modified release formulations, extended-release formulations, pulsatile release formulations, multi particulate formulations, and mixed immediate release and controlled release formulations. Generally speaking, one will desire to administer an amount of the active agent of the invention that is effective to achieve a plasma level commensurate with the concentrations found to be effective in vivo for a period of time effective to elicit the desired therapeutic effect(s).

In embodiments, compositions comprising a compound provided herein are formulated in a unit dosage form. The term "unit dosage form" refers to a physically discrete unit suited as unitary dosages for the subject to be treated, each unit containing a predetermined quantity of active material calculated to produce the desired therapeutic effect(s), in association with a suitable pharmaceutical carrier, diluent, or excipient. Unit dosage forms are often used for ease of administration and uniformity of dosage. Unit dosage forms can contain a single or individual dose or unit, a sub-dose, or an appropriate fraction thereof (e.g., one half a "full" dose), of the pharmaceutical composition administered. Unit dosage forms include capsules, troches, cachets, lozenges, tablets, ampules and vials, which may include a composition in a freeze-dried or lyophilized state; a sterile liquid carrier, for example, can be added prior to administration or delivery in vivo. Unit dosage forms also include ampules and vials with liquid compositions disposed therein. Unit dosage forms further include compounds for transdermal administration, such as "patches" that contact the epidermis of a subject for an extended or brief period of time.

In embodiments, compositions comprising a compound provided herein are formulated in a pharmaceutically acceptable oral dosage form, including oral solid dosage forms and oral liquid dosage forms. In some embodiments, the compositions are formulated as a pharmaceutically acceptable oral solid dosage form. Oral solid dosage forms may include but are not limited to, lozenges, troches, tablets, capsules, caplets, powders, pellets, multiparticulates, beads, spheres, and/or any combinations thereof. Oral solid dosage forms may be formulated as immediate release, controlled release, sustained release, extended release, or modified release formulations.

In some embodiments, the solid dosage provided herein, such as oral solid dosage forms, may be in the form of a tablet (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including a fast-melt tablet. In some embodiments, pharmaceutical formulations described herein may be administered as a single capsule or in multiple capsule dosage form. In some embodiments, the pharmaceutical formulation is administered in two, three, four, or more capsules or tablets.

In some embodiments, solid dosage forms comprise pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof. In embodiments, solid dosage forms comprise one or more pharmaceutically acceptable additives such as a compatible carrier, complexing agent, ionic dispersion modulator, disintegrating agent, surfactant, lubricant, colorant, moistening agent, plasticizer, stabilizer, wetting agent, anti-foaming agent, alone or in combination, as well as supplementary active agent(s). In some embodiments, supplementary active agents include preservatives, antioxidants, antimicrobial agents including biocides and biostats such as antibacterial, antiviral and antifungal agents.

In some aspects, provided herein are methods for preparing a composition, such as a pharmaceutical composition comprising a compound described herein. In some embodiments, a pharmaceutical composition, as provided herein, comprises one or more excipients, such as a pharmaceutically acceptable excipient. Non-limiting examples of excipients include fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof.

In some embodiments, the pharmaceutical composition may be an immediate release formulation, wherein a therapeutically effective amount of the pharmaceutical composition is administered to the subject in a way that facilitates rapid release. Immediate-release formulations may be prepared by combining a superdisintegrant such as croscarmellose sodium and different grades of microcrystalline cellulose in different ratios. In some embodiments, to aid disintegration, sodium starch glycolate may be added.

In embodiments, tablets provided herein are prepared by methods well known in the art. Various methods for the preparation of the immediate release, modified release, controlled release, and extended-release dosage forms (e.g., as matrix tablets having one or more modified, controlled, or extended-release layers) and the vehicles therein are well known in the art. In embodiments, a tablet may be made by compression or molding. In embodiments, compressed tablets may be prepared by compressing, in a suitable machine, an active ingredient in a free-flowing form such as a powder or granules, optionally mixed with a binder, lubricant, inert diluent, preservative, surface-active or dispersing agent. In embodiments, molded tablets may be produced by molding, in a suitable apparatus, a mixture of powdered compound moistened with an inert liquid diluent. In some embodiments, the tablets may optionally be coated or scored and may be formulated so as to provide a slow or controlled release of the active ingredient therein. Generally recognized compendia of methods include Remington 2020 and Sheth et al. 1980.

In embodiments, solid dosage forms are prepared by mixing the active agents of the invention with one or more pharmaceutical excipients to form a "bulk blend" composition. In some embodiments, the bulk blend composition is homogeneous, i.e., the active agents are dispersed evenly throughout so that the bulk blend may be readily subdivided into equally effective unit dosage forms, such as tablets, pills, and capsules. In embodiments, the individual unit dosages may also comprise film coatings, which disintegrate upon oral ingestion or upon contact with diluents. In embodiments, these formulations are manufactured by conventional pharmaceutical techniques. Conventional pharmaceutical techniques for preparation of solid dosage forms include, but are not limited to, the following methods, which may be used alone or in combination: (1) dry mixing, (2) direct compression, (3) milling, (4) dry or non-aqueous granulation, (5) wet granulation, or (6) fusion (see, e.g., Lachman et al. 1986). Other methods include spray drying, pan coating, melt granulation, granulation, fluidized bed spray drying or coating (e.g., Wurster coating), tangential coating, top spraying, tableting, and extruding.

In some embodiments, a composition comprising a compound as provided herein can be formulated to achieve a specific release profile. In some embodiments, oral solid dosage forms may be prepared as immediate release formulations, or as modified release formulations, such as controlled release, extended release, sustained release, or delayed release.

In some embodiments of modified release formulations, the plasma half-life compared to the plasma half-life of an immediate release formulation is greater by at least 5%, at least 10%, at least 15%, at least 20%, at least 25%, at least 30%, at least 35%, at least 50%, at least 75%, at least 100%, or values in between. In some embodiments of modified release formulations, the formulations are designed to result in a comparable area under the curve, or $AUC_{0\_24}$, and a similar safety and efficacy profile, but having a delayed time to maximum concentration ($t_{max}$) of at least 5%, at least 10%, at least 15%, at least 20%, at least 25%, at least 30%, at least 35%, at least 50%, at least 75%, at least 100%, or values in between, as would be appreciated by one of skill. In some preferred embodiments, a formulation is designed to be a product with a specific time course based on an optimum "therapeutic window," such as less than about 30 minutes, about 30 minutes, about 45 minutes, about 60 minutes, about 90 minutes, about 2 hours, about 3 hours, about 4 hours, about 5 hours, about 6 hours, about 7 hours, about 8 hours, and greater than 8 hours, including lengths of time in between.

In some embodiments, a provided pharmaceutical composition comprises compounds which have been modified to be fast-acting and/or exhibit a short duration of action, as described herein. In some embodiments, a pharmaceutical composition provided herein may facilitate a fast acting, (rapid onset), of therapeutic activity. In some embodiments, a fast-acting pharmaceutical composition provided herein may be short-acting, e.g., provide a relatively abbreviated duration of action. In some embodiments, the duration of action comprises the duration of perceptible and pharmacological effects. Formulations and routes of administration that facilitate rapid absorption and rapid onset are known in the art. Rapid onset may be achieved, for example, by parenteral administration or nasal administration.

In some embodiments, a provided pharmaceutical composition comprises a fast-acting compound as provided herein. In some embodiments, a provided pharmaceutical composition comprises a short-acting compound as provided herein. In some embodiments, a provided pharmaceutical composition comprises a fast-acting and a short-acting compound as provided herein. In some embodiments, the formulation facilitates rapid onset of therapeutic action, for example, a fast-acting formulation.

In some embodiments, a provided pharmaceutical composition comprises a short-acting compound as described herein that exhibits a half-life ($t_{1/2}$) that is reduced by at least about 5%, at least about 10%, at least about 15%, at least about 20%, at least about 25%, at least about 30%, at least about 35%, at least about 50%, at least about 75%, or at least about 100% relative to a comparator. In some embodiments, a fast-acting formulation reaches peak concentration ($t_{max}$) at least about 5%, at least about 10%, at least about 15%, at least about 20%, at least about 25%, at least about 30%, at least about 35%, at least about 50%, at least about 75%, or at least about 100% faster than a comparator. In some embodiments, a comparator comprises the parent compound of a fast-acting and/or a short-acting derivative, for example, an ester provided herein. In some embodiments a comparator comprises a known entactogen, for example, MDMA. In some embodiments, the fast-acting formulation exhibits a short duration of action.

In some embodiments, a provided pharmaceutical composition comprises a short-acting compound as described herein that exhibits a clearance rate that is at least 5%, at least 10%, at least 15%, at least 20%, at least 25%, at least 30%, at least 35%, at least 50%, at least 75%, or at least 100% faster than a comparator. In some embodiments, the AUC of a pharmaceutical composition comprising a short-acting compound is at least about 5%, at least about 10%, at least about 15%, at least about 20%, at least about 25%, at least about 30%, at least about 35%, at least about 50%, at least about 75%, or at least about 100% less than a comparator. In some embodiments, a comparator comprises the parent compound of a fast-acting and/or a short-acting derivative, for example, an ester provided herein. In some embodiments a comparator comprises a known entactogen, for example, MDMA. In some embodiments, the short-acting composition has a rapid onset of therapeutic action.

In some embodiments, oral solid dosage forms are formulated as a delayed release dosage form by utilizing an enteric coating to affect release in the small intestine of the gastrointestinal tract. An enteric-coated oral dosage form may be a compressed or molded or extruded tablet/mold (coated or uncoated) containing granules, powder, pellets, beads or particles of the active ingredient and/or other composition components, which are themselves coated or uncoated. The enteric-coated oral dosage form may also be a capsule (coated or uncoated) containing pellets, beads or granules of the solid carrier or the composition, which are themselves coated or uncoated. In some embodiments, enteric coatings may be used to prepare other controlled release dosage forms, including but not limited to extended release and pulsatile release dosage forms. Pulsatile release dosage forms may be formulated using techniques known in the art, such as those described in U.S. Pat. Nos. 5,011,692, 5,017,381, 5,229,135, and 5,840,329. Other suitable dosage forms are described in U.S. Pat. Nos. 4,871,549, 5,260,068, 5,260,069, 5,508,040, 5,567,441 and 5,837,284.

In some embodiments, the controlled release dosage form is a pulsatile release solid oral dosage form comprising at least two groups of particles, each containing active agents of the invention. In some embodiments, the first group of particles, upon ingestion by a subject, provides a substantially immediate dose of the active agents of the invention, and may either be uncoated, or comprise a coating and/or sealant. In some embodiments, using such means, a single unit dosage form can provide both a first and a second dosage amount in the single form (i.e., a first dosage amount in an immediate release form, and a second dosage amount in a delayed release form). In some embodiments, gastroretentive sustained release tablets are formulated by using a combination of hydrophilic polymer (e.g., hydroxypropyl methylcellulose), together with at least one swelling agent (e.g., crospovidone, sodium starch glycolate, and croscarmellose sodium), and an effervescent substance (e.g., sodium bicarbonate). Using known methods, gastroretentive tablets can be formulated to prolong the gastric emptying time and extend the mean residence time (MRT) in the stomach for optimal drug release and absorption (see, e.g., Arza et al., AAPS PharmSci Tech, 2009; 10, 220-226). In some embodiments, coatings for providing a controlled, delayed, or extended release may be applied to the compositions of the invention or to a core containing the compositions, and may comprise a pharmaceutically acceptable ingredient in an amount sufficient to provide a delayed release from, for example, about 1 hour to about 7 hours following ingestion before release of the active agents. In some embodiments, suitable coatings include one or more differentially degradable coatings including pH-sensitive coatings (enteric coatings), or non-enteric coatings having variable thickness to provide differential release of the active agents. Many other types of modified release systems will be known to those of skill in the art. Non-limiting examples of additional delivery systems include both polymer- and non-polymer-based systems, silastic systems, peptide-based systems, wax coatings, bioerodible dosage forms, and compressed tablets using conventional binders (see, e.g., Liberman et al., Pharmaceutical Dosage Forms, 2 Ed., v.1, 209-214, 1990; Singh et al., Encyclopedia of Pharm. Technology, 2nd Ed., 751-753, 2002; U.S. Pat. Nos. 4,327,725; 4,624,848; 4,968,509; 5,461,140; 5,456,923; 5,516,527; 5,622,721; 5,686,105; 5,700,410; 5,977,175; 6,465,014; and 6,932,983).

In some embodiments, a composition comprising a compound provided herein is formulated as a pharmaceutically acceptable oral liquid dosage form. Non-limiting examples of oral liquid dosage forms include tinctures, drops, emulsions, syrups, elixirs, suspensions, and solutions, and the like. In some embodiments, oral liquid dosage forms may be formulated with any pharmaceutically acceptable excipient known to those of skill for the preparation of liquid dosage forms, and with solvents, diluents, carriers, excipients, and the like, chosen as appropriate to the solubility and other properties of the active agents and other ingredients. Non-limiting examples of solvents include, e.g., water, glycerin, simple syrup, alcohol, medium chain triglycerides (MCT), and combinations thereof.

In some embodiments, oral liquid dosage forms may be monophasic or biphasic, the former being a substantially homogenous solution dissolved in water or non-aqueous solvent, while the latter refers to oral liquid dosage forms in which the active ingredients do not fully dissolve in common solvents. In some embodiments, over time, the solid particles (i.e., the active agents) within the oral liquid dosage form may form a precipitate at the bottom of the containerrequiring vigorous shaking to redisperse the active ingredients. Non-limiting examples of monophasic liquid forms include syrups, linctuses, spirits/essences, elixirs, and fluid extracts. Non-limiting examples of biphasic liquid forms include oral suspensions, oral emulsions, and mixtures.

Liquid dosage forms for oral administration may be prepared as liquid suspensions or solutions using a sterile liquid, such as but not limited to, an oil, water, an alcohol, combinations of pharmaceutically suitable surfactants, suspending agents, and emulsifying agents. In some embodiments, liquid formulations also may be prepared as single dose or multi-dose beverages. In some embodiments, suspensions may include oils. Such oils include but are not limited to peanut oil, sesame oil, cottonseed oil, corn oil, and olive oil. Suitable oils also include carrier oils such as MCT and long chain triglyceride (LCT) oils. In some embodiments, as suspension preparation may also contain esters of fatty acids such as ethyl oleate, isopropyl myristate, fatty acid glycerides, and acetylated fatty acid glycerides. In some embodiments, suspension formulations may include alcohols, such as ethanol, isopropyl alcohol, hexadecyl alcohol; glycerol, and propylene glycol. In some embodiments, ethers, such as polyethylene glycol; petroleum hydrocarbons, such as mineral oil and petrolatum; and water may also be used in suspension formulations. In some embodiments, a suspension can thus include an aqueous liquid or a non-aqueous liquid, an oil-in-water liquid emulsion, or a water-in-oil emulsion.

Dosage forms for oral administration may be aqueous suspensions such as aqueous oral dispersions, emulsions, solutions, and syrups (see, e.g., Singh et al., Encyclopedia of Pharm. Technology, 2nd Ed., 751-753, 2002). In addition to the active agents, the liquid dosage forms may comprise additives, such as one or more (a) disintegrating agents, (b) dispersing agents, (c) wetting agents, (d) preservatives, (e) viscosity enhancing agents, (f) sweetening agents, and/or (g) flavoring agents. In addition to the additives above, the liquid formulations of the invention, in some embodiments, may also comprise inert diluents commonly used in the art such as water or other solvents, solubilizing agents, emulsifiers, flavoring agents, and/or sweeteners. In some embodiments, co-solvents and adjuvants also may be added to a formulation.

In some embodiments, effervescent powders containing the compositions of the invention may be prepared. In some embodiments, effervescent salts are used to disperse medicines in water for oral administration. In some embodiments, effervescent salts also may be packaged as single dose or multi-dose drink mixes, alone or in combination with other ingredients, such as vitamins or electrolytes. In some embodiments, effervescent salts are granules or coarse powders containing a medicinal agent in a dry mixture, usually composed of sodium bicarbonate and sodium carbonate, citric acid, and/or tartaric acid. In some embodiments, when salts of the invention are added to water, the acids and the base react to liberate carbon dioxide gas, thereby causing "effervescence." In some embodiments, any acid-base combination that results in the liberation of carbon dioxide may be used, as long as the ingredients are suitable for pharmaceutical use, and result in a pH of about 6.0 or higher.

In some embodiments, the compositions of the invention are formulated in a pharmaceutically acceptable transdermal application, and delivered transdermally. Generally speaking, transdermal delivery involves contacting the formulations of the invention with a subject's skin under conditions effective for the active agent(s) to penetrate the skin and cause an effect. Non-limiting examples of transdermal formulations include ointments, creams, suspensions, lotions, pastes, gels, sprays, foams, oils, and the like, and any combination thereof.

An exemplary transdermal delivery form is a transdermal "patch" which contains the pharmaceutical compositions. Transdermal patches may be used to provide continuous or discontinuous infusion of the compounds described herein in controlled amounts. Such patches may be constructed for continuous, gradual, pulsatile, or on demand delivery of pharmaceutical agents. In some embodiments, a patch will be a medicated adhesive patch, i.e., a patch impregnated with a composition of the invention for application onto the skin. In some embodiments, a patch may be a single-layer or multi-layer drug-in-adhesive patch, wherein the one or more adhesive layers also contain the active agents. In some embodiments, a patch also may be a "matrix" (or "monolithic") patch, wherein the adhesive layer surrounds and overlays the drug layer (wherein a solution or suspension of the active agents is in a semisolid matrix). In some embodiments, a "reservoir" patch may also be used, comprising a drug layer, typically as a solution or suspension of the active agents in a liquid compartment (i.e., the reservoir), separate from an adhesive layer. In some embodiments, a patch also may be part of a delivery system, for instance used with an electronic device communicatively coupled to the mobile device of a user, and coupled with a mobile application (e.g., to control the delivery rate from the reservoir, and optionally to provide information about delivery back to the application or user). Various transdermal patch technologies may be accordingly utilized.

In some embodiments, the compositions of the invention may also be prepared as formulations designed for subcutaneous, intravenous, intra-arterial, intraperitoneal, intraosseous, intramuscular, intrathecal, or intracerebroventricular, injection. In some embodiments, injection formulations may be prepared by dissolving, suspending, or emulsifying the active agent(s) in an aqueous or nonaqueous solvent, non-limiting examples of which include oils, such as vegetable oil, synthetic aliphatic acid glycerides, and esters of higher aliphatic acids or propylene glycol; and may also contain additives such as solubilizers, stabilizers, and suspending, preserving, wetting, emulsifying, dispensing, and isotonic agents.

In some embodiments, the compositions of the invention are formulated in a pharmaceutically acceptable nanostructured formulation, such as a nanoemulsion, a nanocapsule, a nanoparticle conjugate, or a nano-encapsulated oral or nasal spray. In some embodiments, preparations of the compositions of the invention as certain nanostructured formulations may be prepared by reference to the general knowledge of the art (see, e.g., Jaiswal et al., 3 Biotech, 5(2):123-127, 2015). The prefix "nano" as used in the terms describing various embodiments of a nanostructured formulation denotes a size range in the nanometer ("nm") scale. Accordingly, sizes of such nanoparticle delivery vehicles include those in the range of about 1 to about 100 nm, about 100 to about 200 nm, about 200 to about 400 nm, about 400 to about 600 nm, about 600 to about 800 nm, and about 800 to about 1000 nm, as well as "microparticles" in the range of about 1000 to about 2000 nm (1-2 micrometer ("μm") scale). Particles of certain sizes may be particularly advantageous depending on the method of administration, as will be immediately appreciated by one of skill (e.g., for oral liquid emulsion versus for transdermal or topical application). In some embodiments, lipid-based nanoparticles (LBNPs) such as liposomes, solid lipid nanoparticles (SLN), or nanostructured lipid carriers (NLC) are used.

In some embodiments, the active ingredients, such as the compounds described herein, are mixed with an excipient, diluted by an excipient, or enclosed within, encapsulated by, or attached to a carrier in the manufacture of a composition, such as a pharmaceutical composition. In some embodiments, the excipient serves as a diluent, it can be a solid, semi-solid, or liquid material, which acts as a vehicle, carrier, or medium for the active ingredient. In some embodiments, the compositions can be in the form of, e.g., tablets, pills, lozenges, sachets, cachets, elixirs, suspensions, emulsions, solutions, syrups, aerosols (as a solid or in a liquid medium), ointments, soft or hard gelatin capsules, suppositories, sterile injectable solutions, and sterile packaged powders. In some embodiments, it may be necessary to mill the active agent to provide the appropriate particle size prior to combining with the other ingredients. In some embodiments, if an active agent is substantially insoluble, it ordinarily is milled to a particle size of less than about 200 mesh. Different embodiments include immediate, delayed, extended, and controlled release forms. Many other variations are possible and known to those skilled in the art.

It should be readily appreciated that the compositions of the invention are not limited to combinations of a single compound, or (when formulated as a pharmaceutical composition) limited to a single carrier, diluent, and/or excipient alone, but may also include combinations of multiple compounds (including additional active compounds), and/or multiple carriers, diluents, and excipients. Pharmaceutical compositions of this invention thus may comprise a compound of the disclosure together with one or more other active agents (or their derivatives and analogs) in combination, together with one or more pharmaceutically-acceptable carriers, diluents, and/or excipients, and additionally with one or more other active compounds.

In some embodiments, a formulation of the invention will be prepared so as to increase an existing therapeutic effect, provide an additional therapeutic effect, increase a desired property such as stability or shelf-life, decrease an unwanted effect or property, alter a property in a desirable way (such as pharmacokinetics or pharmacodynamics), modulate a desired system or pathway (e.g., a neurotransmitter system), or provide synergistic effects.

"Therapeutic effects" that may be increased or added in embodiments of the invention include, but are not limited to, antioxidant, anti-inflammatory, analgesic, antineuropathic, antinociceptive, antimigraine, anxiolytic, antidepressant, antipsychotic, anti-PTSD, dissociative, immunostimulant, anti-cancer, antiemetic, orexigenic, antiulcer, antihistamine, antihypertensive, anticonvulsant, antiepileptic, bronchodilator, neuroprotective, entheogenic, entactogenic or empathogenic, psychedelic, sedative, and stimulant effects.

"Synergistic effects" will include increases in potency, bioactivity, bioaccessibility, bioavailability, or therapeutic effect, that are greater than the additive contributions of the components acting alone. Numerous methods known to those of skill in the art exist to determine whether there is synergy as to a particular effect, i.e., whether, when two or more components are mixed together, the effect is greater than the sum of the effects of the individual components when applied alone, thereby producing "1+1>2." One such method is the isobologram analysis (or contour method) (see Huang et al., Front. Pharmacol., 10:1222, 2019).

The goal of increasing an existing therapeutic effect, providing an additional therapeutic effect, increasing a desired property such as stability or shelf-life, decreasing an unwanted effect or property, altering a property in a desirable way (such as pharmacokinetics or pharmacodynamics), modulating a desired system or pathway (e.g, a neurotransmitter system), or otherwise inducing synergy, in some embodiments is achieved by the inclusion of an additional active compound.

Such additional active compounds may be selected from the group including amino acids, antioxidants, anti-inflammatory agents, analgesics, antineuropathic and antinociceptive agents, antimigraine agents, anxiolytics, antidepressants, antipsychotics, anti-PT SD agents, cannabinoids, dissociatives, immunostimulants, anti-cancer agents, antiemetics, orexigenics, antiulcer agents, antihistamines, antihypertensives, anticonvulsants, antiepileptics, bronchodilators, neuroprotectants, entheogens, entactogens and empathogens, psychedelics, monoamine oxidase inhibitors, tryptamines, terpenes, phenethylamines, sedatives, stimulants, and vitamins. These ingredients may be in ion, free-base, or salt form, and may be isomers, prodrugs, derivatives (preferably physiologically functional derivatives), or analogs.

For any of the compounds described herein, substitution of the compound by its ion, free base, salt form, polymorph, hydrate or solvate form, co-crystal, or an isomer or enantiomerically enriched mixture, shall be understood to provide merely an alternative embodiment still within the scope of the invention (with modifications to the formulation and dosage amounts made according to the teachings herein and ordinary skill, if necessary or desired). Further, compositions within the scope of the invention should be understood to be open-ended and may include additional active or inactive compounds and ingredients.

In some preferred embodiments, disclosed compounds, or pharmaceutically acceptable salts, hydrates, solvates, or pro-soft drugs thereof, are produced and tested in compliance with current Good Manufacturing Practice ("GMP" or "cGMP") requirements.

The type of formulation employed for the administration of the compounds employed in the methods of the invention generally may be dictated by the compound(s) employed, the type of pharmacokinetic profile desired from the route of administration and the compound(s), and the state of the patient. It will be readily appreciated that any of the above embodiments and classes of embodiments can be combined to form additional embodiments.

b. Route of Administration

A "route of administration" is the path by which the compound or composition is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract).

In some aspects, provided are compositions comprising a compound described herein, such as pharmaceutical compositions, that are suitable for administration by a variety of routes. Non-limiting examples of routes of administration include enteral administration, such as oral, sublingual, buccal, and rectal administration; parenteral administration, including bolus injection or continuous infusion, intravenous, intra-arterial, intraperitoneal, intraosseous, intramuscular, intrathecal, intracerebroventricular, vaginal, ocular, nasal, cutaneous, topical, otic, ocular, transdermal, and subcutaneous administration.

In some embodiments, as appreciated by one of skill in the art, the compounds employed in the methods of the invention are effectively administered as oral solid and oral liquid dosage forms; sublingually or buccally; as injections, including intravenous, intra-arterial, intraperitoneal, intraosseous, intramuscular, intrathecal, and intracerebroventricular; rectally, vaginally, ocularly, nasally, cutaneously, topically, optically, transdermally, and subcutaneously.

c. Methods of Administration

In some aspects, provided are methods of administration or methods of administering a compound described herein. As used herein, the terms "subject," "user," "patient," and "individual" are used interchangeably, and refer to any mammal, preferably a human. Such terms will be understood to include one who has an indication for which a compound, composition, or method described herein may be efficacious, or who otherwise may benefit by the invention. In general, all of the compounds, compositions, and methods of the invention will be appreciated to work for all individuals, although individual variation is to be expected, and will be understood.

The invention provides methods for using therapeutically effective amounts of the pharmaceutical compositions of the invention in a mammal, and preferably a human. Such methods include those for treating a CNS disorder and for improving mental health and functioning, including in a healthy individual.

Administration of pharmaceutical compositions in an "effective amount," a "therapeutically effective amount," a "therapeutically effective dose," or a "pharmacologically effective amount," refers to an amount of an active agent that is sufficient to provide the desired therapeutic effect, for example, relieving to some extent one or more of the symptoms of the disease or condition being treated. The result can be reduction and/or alleviation of the signs, symptoms, or causes of a disease or disorder, or any other desired alteration of a biological system. The term "therapeutically effective amount" includes, for example, a prophylactically effective amount.

An "effective amount" of a compound disclosed herein is an amount effective to achieve a desired pharmacologic effect or meaningful therapeutic improvement. It is understood that "an effective amount" or "a therapeutically effective amount" can vary from subject to subject due to variation in metabolism of a compound, such as a compound described herein, of age, weight, general condition of the subject, the condition being treated, the severity of the condition being treated, and the judgment of the prescribing physician. The effective amount will vary depending upon the subject and the disease condition being treated or health benefit sought, the weight and age of the subject, the severity of the disease condition or degree of health benefit sought, the manner of administration, and the like, all of which can readily be determined by one of skill. Additionally, pharmacogenomic (the effect of genotype on the pharmacokinetic, pharmacodynamic or efficacy profile of a therapeutic) information about a particular patient may affect dosage used.

As used herein, "therapeutic effect" or "therapeutic efficacy" means the responses(s) in a mammal, and preferably a human, after treatment that is judged to be desirable and beneficial. Hence, depending on the disorder to be treated, or improvement in physiological or psychological functioning sought, and depending on the particular constituent(s) in the compositions of the invention under consideration, those responses shall differ, but would be readily understood by those of skill. For example, in some embodiments, "therapeutic effect" may refer to an effect caused by the pharmaceutical composition of the invention, or its use in a method of the invention, such as the treatment of a CNS disorder.

"Therapeutically effective dose" refers to the dose necessary to elicit a desired result within a patient undergoing treatment. A therapeutically effective dose therefore may, in some embodiments, refer to a dose of the pharmaceutical composition or therapeutic combination necessary to deliver measurable patient-specific biologic effects in the treatment or prevention of a condition or disorder. A "therapeutically effective dose" may be used interchangeably with a "therapeutically effective amount" or an "effective amount."

d. Dosing

It will be readily appreciated that dosages may vary depending upon whether the treatment is therapeutic or prophylactic, the onset, progression, severity, frequency, duration, probability of or susceptibility of the symptom to which treatment is directed, clinical endpoint desired, previous, simultaneous or subsequent treatments, general health, age, gender, and race of the subject, bioavailability, potential adverse systemic, regional or local side effects, the presence of other disorders or diseases in the subject, and other factors that will be appreciated by the skilled artisan (e.g., medical or familial history).

In some embodiments, the pharmaceutical composition of the invention comprises the compounds described herein (e.g., a compound of Formula (A), Formula (1), Formula (2), or Formulas (I)—(XIII)), in an amount so that a single dose is (whether or not such dose is present in a unit dosage form), about 1 mg or less (including a dose of about 0.5 mg or less, about 0.25 mg or less, about 0.1 mg or less, about 0.05 mg or less, about 0.005 mg or less, about 0.001 mg or less, and about 0.0005 mg or less), or at least about 1 mg or more, including 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, and 200 mg, as well as amounts within these ranges. In some embodiments, a single dose may be greater than 200 mg, including 225 mg, 250 mg, or greater than 250 mg.

In some embodiments, the pharmaceutical composition of the invention comprises the compounds described herein (e.g., a compound of Formula (A), Formula (1), Formula (2), or Formulas (I)—(XIII)) in an amount so that a single dose is (whether or not such dose is present in a unit dosage form), when administered to a patient, about 1 mg/kg or less (including a dose of about 0.5 mg/kg or less, about 0.25 mg/kg or less, about 0.1 mg/kg or less, about 0.05 mg/kg or less, about 0.005 mg/kg or less, about 0.001 mg/kg or less, and about 0.0005 mg/kg or less), or at least about 1 mg/kg or more, including 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, as well as amounts within these ranges. In some embodiments, a single dose may be greater than 5.0 mg/kg, including 7.5 mg/kg, 10.0 mg/kg, or greater than 10 mg/kg.

In some embodiments, a patient will be administered a therapeutically effective dose of the pharmaceutical composition of the invention on a regular or "chronic" basis, wherein the patient is administered the pharmaceutical composition of the invention daily, several times per day (at least one, at least two, at least three, at least four, or greater than four times per day); on a set, repeating schedule, wherein the patient is administered a therapeutically effective dose of the pharmaceutical composition of the invention every other day, every three days, every four days, every five days, every six days, every seven days, or more than every seven days; or, in some embodiments, a varying schedule comprised of a plurality of days "on" (wherein the therapeutically effective dose of the pharmaceutical composition of the invention is administered), and a plurality of days "off" (wherein no administration occurs), such as one day on two days off, two days on three days off, three days on four days off, or other such schedules as would be apparent to those of skill (cf., e.g., the Stamets or Fadimen microdosing protocols).

In some embodiments, the dosage administered to, or taken by a patient in need thereof, is a "macrodose" (whether or not so named), wherein the dose is a sufficient amount to cause at least one perceptible subjective effect within a patient, and preferably the full range of subjective effects desired through administration of the drug (e.g., empathogenic or entactogenic effects), or a desired subset thereof, as chosen through ordinary skill. In some embodiments, such perceptible subjective effects are those characteristic of, or substantially characteristic of, or sharing at least one or more subjective qualities of, an entactogen.

In some embodiments, the dosage administered to, or taken by a patient in thereof, is a "microdose" (whether or not so named), wherein the dose is not perceptible by the patient to which it is administered. In some embodiments, a microdose may be 0.001 to 0.25 of a macro-dose, such as but not limited to 0.003, 0.005, 0.007, 0.009, 0.01, 0.03, 0.05, 0.07, 0.09, 0.1, 0.2, and 0.25 of a macrodose (wherein the list is inclusive, and modified by the term "about"). In some embodiments, a microdose is between about 0.001 mg and about 50 mg, including 0.001 mg, 0.005 mg, 0.01 mg, 0.05 mg, 0.1 mg, 0.5 mg, 1 mg, 1 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg and values in between, wherein each value is modified by the term "about."

It will be understood that, in some embodiments, the dose actually administered will be determined by a physician, in light of the relevant circumstances, the method of delivery, (i.e., methods that are systemic and that are not subject to first pass effect will require less of a dose than those which are metabolized prior to entering the bloodstream); the age of the patient, the weight of the patient, whether the patient has any comorbidities (i.e., any other medical conditions simultaneously present within a patient), other medications the patient is taking (routinely or presently), and any patient-specific aspects that could affect the way in which the pharmaceutical composition interacts with the patient, such as variations in metabolism, variations in patient response, etc., and therefore any dosage ranges disclosed herein are not intended to limit the scope of the invention. In some instances, dosage levels below the lower limit of a disclosed range may be more than adequate, while in other cases doses above a range may be employed without causing any harmful side effects, provided for instance that such larger doses also may be divided into several smaller doses for administration, either taken together or separately.

In such embodiments, the pharmaceutical compositions may be administered and dosed in accordance with good medical practice, taking into account the method and scheduling of administration, prior and concomitant medications and medical supplements, the clinical condition of the individual patient and the severity of the underlying disease, the patient's age, sex, body weight, and other such factors relevant to medical practitioners, and knowledge of the particular compound(s) used. Dosage levels, including starting and maintenance dosages if different, thus may differ from patient to patient, for individual patients across time, and for different pharmaceutical compositions and formulations, but shall be able to be determined with ordinary skill. Determination of appropriate dosing shall include not only the determination of single dosage amounts, but also the determination of the number and timing of doses, and the time(s) of day or time(s) during a psychotherapeutic session preferable for their administration.

In some embodiments, a patient may be on a dosing schedule as described above, but may administer the dose to themselves. In such embodiments, the pharmaceutical composition of the invention may be prescribed to a patient in need thereof, wherein the patient obtains a therapeutically effective dose from a pharmacy or healthcare provider.

Dose amount, frequency or duration may be increased or reduced, as indicated by the clinical outcome desired, status of the pathology or symptom, any adverse side effects of the treatment or therapy, or concomitant medications. The skilled artisan with the teaching of this disclosure in hand will appreciate the factors that may influence the dosage, frequency, and timing required to provide an amount sufficient or effective for providing a therapeutic effect or benefit, and to do so depending on the type of therapeutic effect desired, as well as to avoid or minimize adverse effects.

In other embodiments, appropriate dosages to achieve a therapeutic effect, including the upper and lower bounds of any dose ranges, can be determined by an individual, including an individual who is not a clinician, by reference to available public information and knowledge, and reference to subjective considerations regarding desired outcomes and effects.

e. Pharmaceutical Kits

In some embodiments, especially where a formulation is prepared in single unit dosage form, suggested dosage amounts shall be known by reference to the format of the preparation itself. In other embodiments, suggested dosage amounts may be known by reference to the means of administration or by reference to the packaging and labeling, package insert(s), marketing materials, training materials, or other information and knowledge available to those of skill or the public. Another aspect of this disclosure therefore provides pharmaceutical kits containing a pharmaceutical composition or formulation of the invention, suggested administration guidelines or prescribing information therefor, and a suitable container. Individual unit dosage forms can be included in multi-dose kits or containers. Pharmaceutical formulations also can be packaged in single or multiple unit dosage forms for uniformity of dosage and ease of administration. Accordingly, another aspect of this disclosure provides pharmaceutical kits containing a pharmaceutical composition or formulation of the invention, suggested administration guidelines or prescribing information therefore, and a suitable container. Individual unit dosage forms can be included in multi-dose kits or containers. Pharmaceutical formulations also can be packaged in single or multiple unit dosage forms for uniformity of dosage and ease of administration.

D. Methods of Treatment

In some aspects, provided herein are methods of treatment comprising administration of a compound described herein. In some embodiments, provided are methods for use in treating a disease or condition in a subject. In some embodiments, the compounds described herein are used to treat CNS disorders, mental conditions or mental health disorders, neurodegenerative conditions, and behavioral addictions.

As used herein, the terms “treating” or “treatment” include preventing or delaying the appearance of clinical symptoms of a disease or condition developing within a subject afflicted with, or predisposed to, the disease or condition but who does not yet experience or display clinical or subclinical symptoms of the disease or condition; inhibiting the disease or condition, i.e., arresting or reducing the development of the disease or condition, or at least one clinical or subclinical symptom thereof, and relieving the disease or condition, i.e., causing regression of the disease or condition or at least one of its clinical or subclinical symptoms.

In some embodiments, a therapeutically effective amount of the pharmaceutical composition of the invention is administered to a subject in need thereof. As it relates to the invention, “effective,” “an effective amount,” “effective dose,” “sufficient amount,” “sufficient dose,” “therapeutically effective,” “a therapeutically effective amount,” “a therapeutically effective dose,” “therapeutically sufficient amount,” “therapeutically sufficient dose,” or “a pharmacologically effective amount” refer to an amount of an active agent that is sufficient to provide the desired therapeutic effect. An effective amount will vary depending upon the subject and the disease condition being treated or health benefit sought, the weight and age of the subject, the severity of the disease condition or degree of health benefit sought, the manner of administration, and the like, all of which will be readily determined by one of skill.

As used herein, “therapeutic effect” or “therapeutic efficacy” means the responses(s) in a mammal, and preferably a human, after treatment that is judged to be desirable and beneficial. Hence, depending on the disorder to be treated, or improvement in physiological or psychological functioning sought, and depending on the particular constituent(s) in the compositions of the invention under consideration, those responses shall differ, but would be readily understood by those of skill. In preferred embodiments, the mammal is a human.

Measures of therapeutic effect include outcome measures (primary or secondary), endpoints, effect measures, and measures of effect within clinical or medical practice or research which can be used to assess an effect (positive and/or negative) of an intervention or treatment, whether patient-reported (e.g., questionnaires); based on other patient data (e.g., patient monitoring); gathered through laboratory tests such as from blood or urine; through medical examination by a doctor or other medical professional, or by digital means, such as by using electronic tools such as online tools, smartphones, wireless devices, biosensors, or health apps.

In some embodiments, the compounds described herein are administered (to the patient alone, with another patient as in couples therapy, or as part of group therapy) in the presence of one or more therapists in a therapeutic setting to facilitate psychotherapy. Numerous such treatment paradigms have been described in the art, using terms such as psychedelic-assisted psychotherapy or drug-assisted therapy (see, e.g., Sessa et al., BMJ Case Reports, 2019; 12:e230109). Drug-assisted therapy, broadly, includes a range of related approaches that involve at least one session where the patient ingests a psychoactive compound or substance and is monitored, supported, and/or otherwise engaged by one or more trained mental health professionals while under the effects of said substance (see, e.g., Schenberg, Front. Pharmacol., 2018; 9). In some embodiments, two therapists are present and/or oversee administration of a compound or composition as described herein. In some embodiments, the two therapists are a dyadic therapist team.

In various embodiments, a patient may be administered a compound or composition and be monitored, a patient may be administered a compound or composition and receive psychological support, and a patient may be administered a compound or composition and receive psychotherapy, and such may take place for example with a psychiatrist, medical doctor, clinical psychologist, or other trained clinician, as well as with a “guide” or non-clinical practitioner. “Therapist” herein therefore may refer to any person who treats a patient using the compositions and methods of the invention, whether that person is a care provider, a psychiatrist, clinical psychologist, clinical therapist, psychotherapist, or other trained counselor, facilitator, or guide, and who may or may not be a trained counselor. Generally, therapists are certified in the use of the treatment manual for the drug-assisted therapy or psychotherapy administered (and familiar with any applicable requirements in a Risk Evaluation and Mitigation Strategies (REMS) or its equivalents), and will have completed or have the intent to complete the appropriate training in delivering one or more forms of drug-assisted therapy or psychotherapy.

Protocols have been developed for the standardization of procedures which emphasize a high degree of care (see, e.g., Johnson, Richards, & Griffiths, Journal of Psychopharmacology, 2008; 22(6), 603-620), such as the therapeutic approach used by MAPS to treat patients with PTSD using MDMA (e.g., as described in Mithoefer, A Manual for MDMA-Assisted Psychotherapy in the Treatment of Posttraumatic Stress Disorder, 2017). Other forms of MDMA-assisted or psychedelic-assisted psychotherapy which may be applied as part of methods of drug-assisted psychotherapy herein, will be known to those in the field and are disclosed, for example, in Grof (2008) *LSD Psychotherapy* (Ben Lomond, CA: Multidisciplinary Association for Psychedelic Studies); Passie (2012) *Healing with Entactogens: Therapist and Patient Perspectives on MDMA-Assisted Group Psychotherapy* (Ben Lomond, CA: Multidisciplinary Association for Psychedelic Studies); Johnson, Richards, & Griffiths, Journal of Psychopharmacology, 2008; 22(6), 603-620); Sessa & Fischer (2015, *Underground MDMA-, LSD- and 2-CB-assisted individual and group psychotherapy in Zurich*: Outcomes, implications and commentary. *Drug Science, Policy and Law,* 2, 2050324515578080); Schmid, Gasser, Oehen, & Liechti (2020. Acute subjective effects in LSD- and MDMA-assisted psychotherapy. *Journal of psychopharmacology,* 0269881120959604); Greer & Tolbert (1998. A method of conducting therapeutic sessions with MDMA. *Journal of psychoactive drugs,* 30(4), 371-379); Mithoefer et al. A Manual for MDMA-Assisted Therapy in the Treatment of PTSD (2017); Mithoefer (2013. MDMA-assisted psychotherapy: How different is it from other psychotherapy. *Manifesting minds: A review of psychedelics in science, medicine, sex, and spirituality,* 125). see also U.S. Pat. App. No. 2020/0360311A1, generally discussing drug-assisted psychotherapy practices, which can be applied with MDMA.

In some embodiments, the compounds described herein are administered to a subject along with the provision of therapy or the use of one or more therapeutic techniques. Non-limiting examples of therapy or therapeutic techniques include breathing exercises, mindfulness, acceptance and commitment therapy (ACT), psychoanalytic therapy, cognitive behavioral therapy, and other similar practices. In such embodiments, the compounds described herein may be administered to a patient in a controlled environment wherein the patient is monitored (e.g., a treatment room, such as but not limited to a traditional practitioner's office; an inviting space, wherein temperature, lighting, scent, music, the display of symbolic items, and/or other aspects of "setting" are tailored to the patient undergoing the dosing session, etc.), or may be prescribed to a patient with instructions to self-administer at a place of the patient's choosing.

In some embodiments, the compounds described herein are used to treat CNS disorders, including mental conditions and mental health disorders, psychiatric and neuropsychiatric disorders, and neurodegenerative conditions. In some embodiments, such disorders and conditions will be related to, or affected by, one or more monoamine neurotransmitter systems, such as the serotonin, dopamine, and/or norepinephrine systems. Non-limiting examples of disorders and conditions that may be treated by the compounds and compositions disclosed herein include CNS disorders, which broadly includes mental health conditions, such as but not limited to post-traumatic stress disorder (PTSD), adjustment disorder, affective disorder, depression, atypical depression, postpartum depression, catatonic depression, a depressive disorder due to a medical condition, premenstrual dysphoric disorder, seasonal affective disorder, dysthymia, anxiety, phobia disorders, binge disorders, body dysmorphic disorder, alcohol or drug abuse or dependence disorders, substance-related disorders, substance use disorders, alcohol use disorder, substance-induced mood disorder, a mood disorder related to another health condition, disruptive behavior disorders, eating disorders, impulse control disorders, obsessive compulsive disorder (OCD), attention deficit hyperactivity disorder (ADHD), personality disorders, attachment disorders, and dissociative disorders; neurodegenerative conditions, such as but not limited to Alzheimer's disease, ataxia, Huntington's disease, Parkinson's disease, motor neuron disease, multiple system atrophy, progressive supranuclear palsy, migraines, cluster headaches, short-lasting unilateral neuralgiform headaches, fibromyalgia, traumatic brain injury, and mild-traumatic brain injury; and behavioral addictions, including but not limited to gambling disorder, compulsive sexual behavior, sexual addiction, gaming addiction, shopping addiction, internet addiction, kleptomania, pyromania, compulsive buying, pornography addiction, binge eating disorder, internet gaming addiction, exercise addiction or overtraining syndrome, love addiction, work addiction or workaholism, and technological addictions.

E. Mental Health Conditions

"Mental health conditions," broadly, refers to a disease condition that generally involves negative changes in emotion, mood, thinking, or behavior. Examples of mental health disorders include, but are not limited to, post-traumatic stress disorder (PTSD), adjustment disorder, affective disorder, depression, atypical depression, postpartum depression, catatonic depression, a depressive disorder due to a medical condition, premenstrual dysphoric disorder, seasonal affective disorder, dysthymia, anxiety, phobia disorders, binge disorders, body dysmorphic disorder, alcohol or drug abuse or dependence disorders, substance-related disorders, substance use disorders, alcohol use disorder, substance-induced mood disorder, a mood disorder related to another health condition, disruptive behavior disorders, eating disorders, impulse control disorders, obsessive compulsive disorder (OCD), attention deficit hyperactivity disorder (ADHD), personality disorders, attachment disorders, and dissociative disorders. Broadly, mental health disorders include those characterized by the DSM-5, Merck Manual, or other such diagnostic resources known to those of skill.

A variety of methods for screening or assessing a subject for a mental health disorder exist. In some embodiments, a diagnosis of a mental health disorder is facilitated with use of the Diagnostic and Statistical Manual of Mental Disorders, such as the DSM-5. In some embodiments, diagnosis of a mental health disorder is facilitated with use of self-reported or observer-report surveys or questionnaires. Non-limiting examples of such questionnaires include the Patient Health Questionnaire 9 (PHQ-9), the Generalized Anxiety Disorder 7 (GAD-7), PTSD Checklist for DSM-5 (PCL-5), The Alcohol Use Disorders Identification Test (AUDIT), Binge Eating Scale (BES), Obsessive-Compulsive Inventory (OCI), the Personality Disorders Questionnaire (PDQ-IV), Dissociative Experiences Scale (DES), Drug Use Questionnaire (DAST-20), The Mood Disorder Questionnaire (MDQ), and other similar questionnaires. In some embodiments, alternative questionnaires, such as the Clinical Global Impression—Improvement scale (CGI-I), may be used to assess improvement of a subject's mental health state, such as by comparing baseline responses to responses after a treatment intervention. In some embodiments, any of the diagnostic manuals and assessments described, and other similar tools, may be used to confirm a reduction in symptoms, a reduction in symptom severity, or elimination of symptoms and/or a previous diagnosis.

In some embodiments, the compounds described herein are useful in treating a patient diagnosed with at least one mental health condition. In some embodiments, a patient diagnosed with at least one mental health condition is prescribed a therapeutically effective amount of the compounds described herein. In some embodiments, the compounds described herein are prescribed to a patient diagnosed with at least one mental health condition in a pharmaceutical composition comprising an effective amount of the compounds described herein, as well as a pharmaceutically acceptable carrier, diluent, or excipient. In some embodiments, a patient diagnosed with at least one mental health condition obtains the compounds described herein without a prescription. In some embodiments, a patient diagnosed with at least one mental health condition is administered an effective amount of the compounds described herein by a clinician. In some embodiments, a patient diagnosed with at least one mental health condition self-administers the compounds described herein. In some embodiments, a patient diagnosed with at least one mental health condition is supervised by a health professional while self-administering the compounds described herein while, in other embodiments, the patient is not supervised by a health professional while self-administering the compounds described herein. In some embodiments, a patient diagnosed with at least one mental health condition is administered, either by the patient or a third-party, an effective amount of the compounds described herein as part of a psychotherapy regimen. In some embodiments, a patient diagnosed with at least one mental health condition is administered, either by the patient or a third-party, an effective amount of the compounds described herein not part of a psychotherapy regimen.

In some embodiments, the compounds described herein are efficacious in reducing at least one symptom of a mental health condition within a patient diagnosed with the same. As would be apparent to one of skill, symptoms for each mental health condition will be different, however, through medical monitoring (such as monitoring of objective measurements, as described herein), patient reporting (such as, but not limited to through journaling), completion of questionnaires, etc., one will be able to objectively determine if a symptom has reduced in its frequency and/or magnitude.

In some embodiments, the patient is diagnosed with substance use disorder. In some embodiments, a patient diagnosed with substance use disorder is prescribed or receives without a prescription, a therapeutically effective dose of the compounds described herein, wherein the dose is administered by the patient, or a third party, and is administered in combination, or without, psychotherapy. In some embodiments, administration by a patient or a third party of a therapeutically effective dose of the compounds described herein will lessen the frequency or severity of at least one symptom of a substance use disorder, non-limiting examples of which include decreasing the frequency with which the individual takes a substance, decreasing the urge the individual has of taking a substance, decreasing the duration of a substance use session, or decreasing the likelihood of relapse.

In some embodiments, the substance use disorder is characterized by use of one or more of marijuana, alcohol, tobacco, cocaine, amphetamines and methamphetamine; opiates and opioids, such as heroin, fentanyl, and prescription opioids; other prescription drugs; and broad classes of substances such as dissociatives, stimulants, depressants, narcotics, and inhalants.

In some embodiments, the patient is diagnosed with alcohol use disorder. In some embodiments, a patient diagnosed with alcohol use disorder is prescribed or receives without a prescription, a therapeutically effective dose of the compounds described herein, wherein the dose is administered by the patient, or a third party, and is administered in combination, or without, psychotherapy. In some embodiments, administration by a patient or a third party of a therapeutically effective dose of the compounds described herein will lessen the frequency or severity of at least one symptom of alcohol use disorder, non-limiting examples of which include decreasing the frequency with which the individual consumes alcohol (i.e., increasing sobriety), decreasing the urge the individual has of consuming alcohol, decreasing the duration of an alcohol use session (i.e., decreasing the amount of drinks consumed in an alcohol use session), or increasing the time between drinks of alcohol, whether that be during an alcohol use session, or between alcohol use sessions.

F. Neurodegenerative Conditions

Neurodegenerative conditions encompass a wide range of disorders that result from progressive damage to cells and nervous system connections essential for at least one of mobility, coordination, strength, sensation, and cognition. Symptoms of neurodegenerative diseases include any of reductions in mobility and balance, abnormal movements, difficulty swallowing, abnormal bladder and bowel movement function, wide variations in blood pressure, difficulty sleeping, difficulty breathing, abnormal heart function, reduced memory and cognitive abilities, alterations in mood, and changes to speech (Peter O'Donnell Jr. Brain Institute, UT Southwestern Medical Center, Neurodegenerative Disorders, 2022).

As mentioned, neurodegenerative conditions include, but are not limited to, Alzheimer's disease, ataxia, Huntington's disease, Parkinson's disease, motor neuron disease, multiple system atrophy, progressive supranuclear palsy, migraines, cluster headaches, short-lasting unilateral neuralgiform headaches, fibromyalgia, traumatic brain injury, and mild-traumatic brain injury.

In some embodiments, the compounds described herein are useful in treating a patient diagnosed with at least one neurodegenerative condition. In some embodiments, a patient diagnosed with at least one neurodegenerative condition is prescribed a therapeutically effective amount of the compounds described herein. In some embodiments, the compounds described herein are prescribed to a patient diagnosed with at least one neurodegenerative condition in a pharmaceutical composition comprising an effective amount of the compounds described herein, as well as a pharmaceutically acceptable carrier, diluent, or excipient. In some embodiments, a patient diagnosed with at least one neurodegenerative condition obtains the compounds described herein without a prescription. In some embodiments, a patient diagnosed with at least one neurodegenerative condition is administered an effective amount of the compounds described herein by a clinician. In some embodiments, a patient diagnosed with at least one neurodegenerative condition self-administers the compounds described herein. In some embodiments, a patient diagnosed with at least one neurodegenerative condition is supervised by a health professional while self-administering the compounds described herein while, in other embodiments, the patient is not supervised by a health professional while self-administering the compounds described herein. In some embodiments, a patient diagnosed with at least one neurodegenerative condition is administered, either by the patient or a third-party, an effective amount of the compounds described herein as part of a psychotherapy regimen. In some embodiments, a patient diagnosed with at least one neurodegenerative condition is administered, either by the patient or a third-party, an effective amount of the compounds described herein not part of a psychotherapy regimen.

In some embodiments, the compounds described herein are efficacious in reducing at least one symptom of a neurodegenerative condition within a patient diagnosed with the same. As would be apparent to one of skill, symptoms for each neurodegenerative condition will be different, however, through medical monitoring (such as monitoring of objective measurements, as described herein), patient reporting (such as, but not limited to through journaling), completion of questionnaires, etc., one will be able to objectively determine if a symptom has reduced in its frequency and/or magnitude.

G. Behavioral Addictions

The concept of "addiction" traditionally indicated the use of and dependence on psychotropic substances. Presently, however, "addiction" has expanded to additionally describe a heterogeneous group of syndromes known as behavioral addictions (Konkoly et al., BMC Psychiatry, 2015; 15:4). Addiction, in and of itself, is not a unitary construct, but rather incorporates a number of features such as, but not limited to, repetitive engagement in behaviors that are rewarding (at least initially), the loss of control (increasing engagement over time), persistence despite detrimental consequences, and physical dependence (evidenced by withdrawal symptoms when intake of the substance diminishes) (Chamberlain et al., Neuropsychopharmacol. 2016; 26(5): 841-855). Behavioral addictions include, as examples, gambling disorder, compulsive sexual behavior, sexual addiction, gaming addiction, shopping addiction, internet addiction, kleptomania, pyromania, compulsive buying, pornography addiction, binge eating disorder, internet gaming addiction, exercise addiction or overtraining syndrome, love addiction, work addiction or workaholism, and technological addictions.

Certain psychiatric disorders characterized by maladaptive, repetitive behaviors share some at least surface similarities with substance addiction and are referred to as behavioral addictions. This perspective has influenced the Diagnostic and Statistical Manual of Mental Disorders, Fifth Edition (DSM-5) to create a new class of disorder, "Substance Related and Addictive Disorders." At present, there is insufficient evidence to support the categorisation of many behavioral addictions within the substance related and addictive disorders class of the DSM-5, and a need to establish diagnostic criteria in order to classify these behaviors as behavioral disorders (Pinna et al., J. of Psychopathology, 2015; 21(4), 380-9). Gambling disorder, however, has been recognized as an addictive disorder in the DSM-5 and has established diagnostic criteria.

Behavioral addictions, broadly, are characterized by an intense desire to repeat an action that is pleasurable, or perceived to improve well-being, or capable of alleviating some personal distress, despite the awareness that such an action may have negative consequences. Substance use disorders generally involve an aspect of impulsivity at their outset, and subsequent substance related changes can then produce organic disruption in the prefrontal cortex that further reduces control over behavior (e.g., Goldstein & Volkow, Nat. Rev. Neurosci., 2011; 12(11): 652-69). In contrast, behavioral addictions, whilst also characterized by a loss of control of behavior, often exhibit greater compulsive than impulsive features. Compulsivity, a habitual response in the absence of reward, is key to behavioral addictions—but research has found it difficult to treat.

Behavioral addictions not only affect the individual, but carry detrimental social, cultural, and economic consequences. There also is extensive evidence for overlapping comorbidity amongst behavioral addictions themselves, and for the co-occurrence of substance use disorders (SUDs) and behavioral addictions. For example, problem gambling has been found to co-occur with Internet addiction and AUD (Tozzi et al., Swiss Medical Weekly, 2013; 143(w13768), 1-6).

In some embodiments, the compounds described herein are useful in treating a patient diagnosed with at least one behavioral addiction. In some embodiments, a patient diagnosed with at least one behavioral addiction is prescribed a therapeutically effective amount of the compounds described herein. In some embodiments, the compounds described herein are prescribed to a patient diagnosed with at least one behavioral addiction in a pharmaceutical composition comprising an effective amount of the compounds described herein, as well as a pharmaceutically acceptable carrier, diluent, or excipient. In some embodiments, a patient diagnosed with at least one behavioral addiction obtains the compounds described herein without a prescription. In some embodiments, a patient diagnosed with at least one behavioral addiction is administered an effective amount of the compounds described herein by a clinician. In some embodiments, a patient diagnosed with at least one behavioral addiction self-administers the compounds described herein. In some embodiments, a patient diagnosed with at least one behavioral addiction is supervised by a health professional while self-administering the compounds described herein while, in other embodiments, the patient is not supervised by a health professional while self-administering the compounds described herein. In some embodiments, a patient diagnosed with at least one behavioral addiction is administered, either by the patient or a third-party, an effective amount of the compounds described herein as part of a psychotherapy regimen. In some embodiments, a patient diagnosed with at least one behavioral addiction is administered, either by the patient or a third-party, an effective amount of the compounds described herein not part of a psychotherapy regimen.

In some embodiments, the compounds described herein are efficacious in reducing at least one symptom of a behavioral addiction within a patient diagnosed with the same. As would be apparent to one of skill, symptoms for each behavioral addiction will be different, however, through medical monitoring (such as monitoring of objective measurements, as described herein), patient reporting (such as, but not limited to through journaling), completion of questionnaires, etc., one will be able to objectively determine if a symptom has reduced in its frequency and/or magnitude.

In some embodiments, the patient is diagnosed with gambling disorder. Gambling disorder (APA, Washington D.C.: American Psychiatric Association, 2013), refers to addictive disorder in which individuals present with a cluster of symptoms of varying severity that cause psychological and psychical harms and social dysfunction due to their gambling practices. In some embodiments, a patient diagnosed with gambling disorder is prescribed or receives without a prescription, a therapeutically effective dose of the compounds described herein, wherein the dose is administered by the patient, or a third party, and is administered in combination, or without, psychotherapy. In some embodiments, administration by a patient or a third party of a therapeutically effective dose of the compounds described herein will lessen the frequency or severity of at least one symptom of gambling disorder, non-limiting examples of which include decreasing the frequency with which the individual gambles, decreasing the urge the individual has of gambling, or increasing the ability of the person to quit gambling once the person begins gambling (i.e., lessens the duration of a gambling session).

H. Synthesis of Select Compounds Described Herein a. General Experimental Details

$^1$H-NMR spectra were performed on a Varian MR-400 spectrometer operating at 400 MHZ (proton frequency), equipped with: a self-shielded Z-gradient coil 5 mm 1H/nX broadband probe head for reverse detection, deuterium digital lock channel unit, quadrature digital detection unit with transmitter offset frequency shift, or on AgilentVNMRS-500 or on a Bruker Avance 400 spectrometers. Chemical shifts are reported as b values in ppm relative to trimethylsilane (TMS) as an internal standard. Coupling constants (J values) are given in hertz (Hz) and multiplicities are reported using the following abbreviation (s=singlet, d=doublet, t=triplet, q=quartet, m=multiplet, br=broad, nd=not determined).

b. LC/UV/MS Analytical Methods

The purity of all compounds screened in the biological assays was estimated by LC/UV/MS analysis and was found to be ≥95%. LC/MS retention times were estimated to be affected by an experimental error of ±0.5 min. The following methods were used: Method a, LC instrument: UPLC/MS (ES+/ES−) Acquity™ system coupled a QDA massspectrometer; Column: Acquity UPLC CSH C18 column (50×2.1 mm i.d. 1.7 μm particle size); Column Temperature (° C.): 40.0; Mobile phases: 0.1% v/v solution of HCOOH in water (A), 0.1% v/v solution of HCOOH in Acetonitrile (B); Flow (ml/min): 1; Stop Time (mins): 2.0; Gradient: 3-99.9% B over 1.50 min; UV detection range: 210 nm to 350 nm, Acquisition rate: Hz=40; Ionization mode: alternate Positive/Negative Electrospray (ES+/ES−); San range: 100 to 1000 amu. Method b, LC instrument: UPLC/MS (ES+/ES−) Acquity system coupled a ZQ mass spectrometer; Column: Acquity UPLC CSH C18 column (50×2.1 mm i.d. 1.7 μm particle size); Column Temperature (° C.): 40.0; Mobile phases: 0.1% v/v solution of HCOOH in water (A), 0.1% v/v solution of HCOOH in Acetonitrile (B); Flow (ml/min): 1; Stop Time (mins): 2.0; Gradient: 3-99.9% B over 1.50 min; UV detection range: 210 nm to 350 nm, Acquisition rate: Hz=40; Ionization mode: alternate Positive/Negative Electrospray (ES+/ES−); San range: 100 to 1000 amu.

c. Analytical Chiral Chromatography for Chiral Compounds

The enantiomeric excess of chiral compounds were determined by chiral HPLC analysis on a HPLC Agilent 1100 equipped with 6-position switching valve, DAD, and CD detectors. The following method was used: Method 1: Column: Chiralpak IC (25×0.46 cm), 5 μm; Mobile phase: (n-Hexane/Ethanol) 60/40 v/v %; Flow rate: 1.0 mL/min; DAD: 220 nm.

I. Abbreviations

| | |
|---|---|
| cHex = cyclohexane; | $KHSO_4$ = potassium bisulfate; |
| DCM = dichloromethane; | LC-MS = liquid chromatography/mass spectrometry; |
| DMSO = dimethyl sulfoxide; | MeOH = methyl alcohol; |
| EtOAc = ethyl acetate; | $NaHCO_3$ = sodium bicarbonate; |
| EtOH = ethanol; | $Na_2SO_4$ = sodium sulfate; |
| FA = formic acid; | NMR = nuclear magnetic resonance; |
| FC = flash chromatography; | r.t. = room temperature; |
| Fmoc = 9-Fluorenylmethoxycarbonyl; | THF = tetrahydrofuran; |
| h = hour; | UPLC = ultra-performance liquid chromatography. |
| HPLC = high pressure liquid chromatography; | |

In some embodiments, disclosed compounds, including compounds of Formula (I), Formula (A), Formula (1), Formula (2), and others disclosed herein, are synthesized following the reaction scheme provided below. Although the scheme below depicts the synthesis of APV241522A ("522A"), APV243516A ("516A"), and APV243518A ("518A"), the same synthesis may be used for producing other compounds of the disclosure, such as APV245514A ("514A") and APV245562A ("562A")

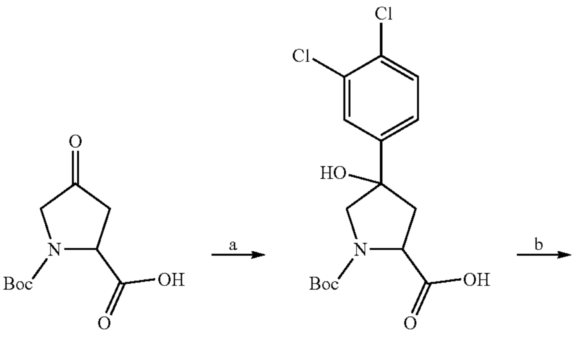

(1) (2)

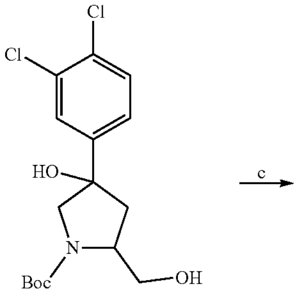

(3)

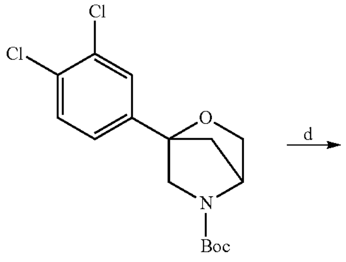

(4)

-continued

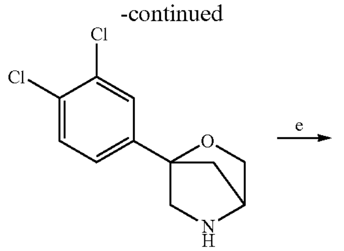

APV241522A

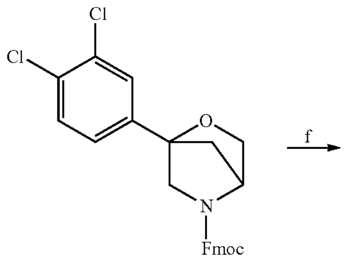

(5)

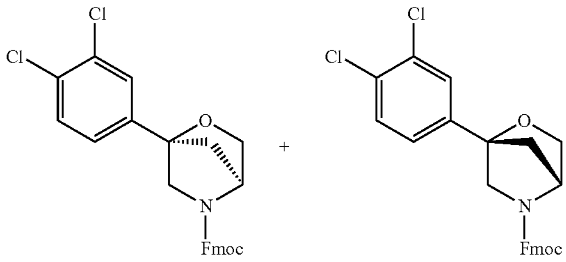

(6) (7)

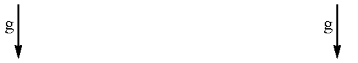

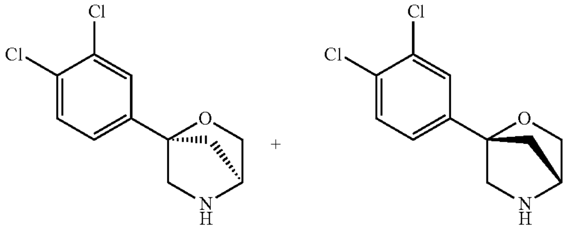

APV243516A APV243518A a) 3,4-dichlorophenylmagnesium bromide, THF, 0° C.; b) Borane-THF complex, THF, 60° C., 5 h; c) TsCl, pyridine, r.t., 24 h; then NaH, THF, r.t., 5 d; d) TFA, DCM, r.t., 1 h; e) carbonochloridic acid 9H-fluoren-9-yl methyl ester, TEA, DCM, r.t., 2 h; f) chiral purification; g) piperidine, MeOH, r.t., 30 min.

1-(tert-butoxycarbonyl)-4-(3,4-dichlorophenyl)-4-hydroxypyrrolidine-2-carboxylic acid (2)

(2)

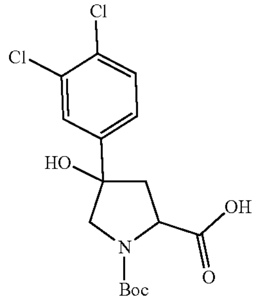

To a solution of bromo-(3,4-dichlorophenyl)magnesium (6.98 mL, 3.49 mmol) 0.5 M in 2-Me-THF a solution of 1-(tert-butoxycarbonyl)-4-oxopyrrolidine-2-carboxylic acid (1) (0.200 g, 0.870 mmol) in 2-Me-THF (1.7 mL) was added at 0° C. The reaction was stirred at the same temperature for 2 h. After this time, a saturated aqueous solution of $NaHCO_3$ was added and the reaction was washed with DCM. The aqueous phase was acidified with a 5% solution of $KHSO_4$ and extracted with AcOEt. The organic phase was washed with brine, dried over $Na_2SO_4$, filtered and concentrated under vacuum. The residue was purified by FC on C18 (from $H_2O/CH_3CN$ 95:5+0.1% of FA to $H_2O/CH_3CN$ 5:95+0.1% of FA) affording 1-(tert-butoxycarbonyl)-4-(3,4-dichlorophenyl)-4-hydroxypyrrolidine-2-carboxylic acid (2) (0.035 g, 0.093 mmol, 10.66% yield). UPLC-MS: 1.12, 374.3 $[M-H]^-$, method a. $^1H$ NMR (400 MHz, DMSO-$d_6$) δ ppm 12.38 (bs, 1H), 7.71 (d, J=2.2 Hz, 1H), 7.61 (d, J=8.4 Hz, 1H), 7.41-7.51 (m, 1H), 5.72 (bs, 1H), 4.26-4.37 (m, 1H), 3.52-3.66 (m, 2H), 2.60-2.70 (m, 1H), 2.16-2.27 (m, 1H), 1.40 (s, 9H).

tert-butyl 4-(3,4-dichlorophenyl)-4-hydroxy-2-(hydroxymethyl)pyrrolidine-1-carboxylate (3)

(3)

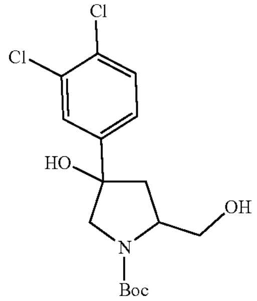

A solution of 1-(tert-butoxycarbonyl)-4-(3,4-dichlorophenyl)-4-hydroxy-pyrrolidine-2-carboxylic acid (2) (0.400 g, 1.063 mmol) was cooled to 0° C. and boron;oxolane (3.39 mL, 3.39 mmol) 1M in THE was added. The reaction was stirred to reflux for 4h. MeOH was added (5 mL) and the reaction was stirred at r.t. for 1h. After this time the reaction was concentrated under vacuum and the residue was purified by FC on C18 (from $H_2O/CH_3CN$ 95:5+0.1% of FA to $H_2O/CH_3CN$ 3:7+0.1% of FA) affording tert-butyl 4-(3,4- dichlorophenyl)-4-hydroxy-2-(hydroxymethyl)pyrrolidine-1-carboxylate (3) (0.188 g, 0.519 mmol, 48.8% yield). UPLC-MS: 1.05, 362.09 [M+H]+, method b. $^1$H NMR (400 MHz, DMSO-$d_6$) δ ppm 7.69-7.75 (m, 1H), 7.57-7.63 (m, 1H), 7.44-7.53 (m, 1H), 5.97-6.11 (m, 1H), 5.02-5.28 (m, 1H), 3.79-3.97 (m, 1H), 3.68-3.79 (m, 1H), 3.52-3.66 (m, 2H), 3.39-3.49 (m, 1H), 2.36-2.46 (m, 1H), 2.07-2.24 (m, 1H), 1.35-1.46 (m, 9H).

tert-butyl 1-(3,4-dichlorophenyl)-2-oxa-5-azabicyclo [2.2.1]heptane-5-carboxylate (4)

(4)

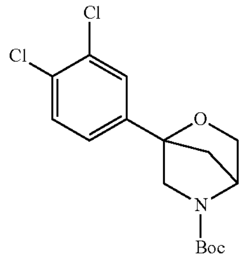

To a solution of tert-butyl 4-(3,4-dichlorophenyl)-4-hydroxy-2-(hydroxymethyl)-pyrrolidine-1-carboxylate (3) (0.188 g, 0.520 mmol) in Pyridine (2 mL) 4-methylbenzenesulfonyl chloride (0.129 g, 0.670 mmol) was added and the reaction was stirred over the weekend. After this time other 0.3 eq of Tos-Cl were added and the reaction was stirred at r.t. for an additional 4h. A 10% solution of citric acid was added and the reaction was extracted with DCM 3 times. The combined organic fractions were passed through a phase separator and concentrated under vacuum. The residue was dissolved in THE (4 mL) and cooled to 0° C. After 10 minutes sodium hydride (0.031 g, 0.780 mmol) was added and the reaction stirred at r.t. overnight. Water was added and the reaction was extracted with AcOEt. The combined organic fractions were washed with brine, dried over $Na_2SO_4$, filtered and concentrated under vacuum. The residue was purified by FC on $C_{18}$ (from $H_2O/CH_3CN$ 95:5+0.1% of FA to $H_2O/CH_3CN$ 20:80+0.1% of FA) affording tert-butyl 1-(3,4-dichlorophenyl)-2-oxa-5-azabicyclo[2.2.1]-heptane-5-carboxylate (4) (0.080 g, 0.232 mmol, 44.78% yield). UPLC-MS: 1.22, 344.05 $[M+H]^+$, method b. $^1$H NMR (400 MHz, DMSO-$d_6$) δ ppm 7.76 (d, J=2.1 Hz, 1H), 7.65 (d, J=8.3 Hz, 1H), 7.51 (dd, J=8.4, 2.1 Hz, 1H), 4.37-4.56 (m, 1H), 3.91-3.98 (m, 1H), 3.82-3.91 (m, 1H), 3.57 (t, J=8.6, 8.6 Hz, 1H), 3.40 (t, J=8.6, 8.6 Hz, 1H), 2.35 (t, J=9.5, 9.5 Hz, 1H), 1.92-1.98 (m, 1H), 1.36-1.49 (m, 9H).

Example 12: 1-(3,4-dichlorophenyl)-2-oxa-5-azabicyclo[2.2.1]heptane (APV241522A)

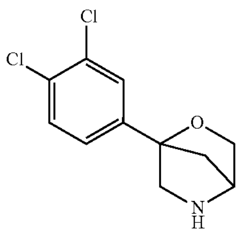

APV241522A

To a solution of tert-butyl tert-butyl 1-(3,4-dichlorophenyl)-2-oxa-5-azabicyclo-[2.2.1]heptane-5-carboxylate (4) (0.523 g, 1.52 mmol) in DCM (15 mL) Trifluoroacetic acid (0.58 mL, 7.6 mmol) was added and the reaction was stirred at r.t. for 3 h. The reaction was concentrated under vacuum and the residue was purified by SCX first washing with MeOH and then eluting with 1M $NH_3$ in MeOH. Basic fractions were collected and evaporated. The residue was purified by FC on silica gel (from DCM to DCM/MeOH 9:1) to afford 1-(3,4-dichlorophenyl)-2-oxa-5-azabicyclo[2.2.1] heptane (APV241522A) (0.260 g, 1.065 mmol, 70.1% yield). UPLC-MS: 0.58 min, 244.22 $[M+H]^+$, method a. $^1$H NMR (400 MHz, Methanol-$d_4$) δ ppm 7.65 (d, J=2.1 Hz, 1H), 7.51 (d, J=8.4 Hz, 1H), 7.40 (dd, J=8.4, 2.1 Hz, 1H), 3.89-4.07 (m, 2H), 3.81 (s, 1H), 3.04-3.16 (m, 2H), 2.17 (ddd, J=9.8, 2.5, 0.8 Hz, 1H), 1.89-2.01 (m, 1H).

(9H-fluoren-9-yl)methyl 1-(3,4-dichlorophenyl)-2-oxa-5-azabicyclo[2.2.1]heptane-5-carboxylate (5)

(5)

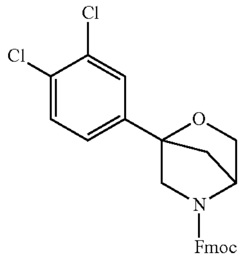

To a mixture of 1-(3,4-dichlorophenyl)-2-oxa-5-azabicyclo[2.2.1]heptane (APV241522A) (0.040 g, 0.160 mmol) and carbonochloridic acid 9H-fluoren-9-ylmethyl ester (0.047 g, 0.180 mmol) in DCM (3 mL), triethylamine (0.03 mL, 0.250 mmol) was added. The reaction was stirred at r.t. for 2 h and then it was concentrated under vacuum. The residue was purified by FC on silica (from cHex to cHex/AcOEt 8:2) affording (9H-fluoren-9-yl)methyl 1-(3,4-dichloro-phenyl)-2-oxa-5-azabicyclo[2.2.1]heptane-5-carboxylate (5) (0.070 g, 0.150 mmol, 91.61% yield). UPLC-MS: 1.50 min, 466.39 $[M+H]^+$, method a. $^1$H NMR (400 MHz, Methanol-$d_4$) δ ppm 7.83 (t, J=7.7 Hz, 2H), 7.59-7.72 (m, 3H), 7.55 (t, J=9.8 Hz, 1H), 7.27-7.47 (m, 5H), 4.60 (d, J=9.5 Hz, 2H), 4.31 (d, J=19.5 Hz, 1H), 3.79-4.01 (m, 2H), 3.55-3.67 (m, 1H), 3.39-3.46 (m, 1H), 3.21-3.28 (m, 1H), 2.15-2.29 (m, 1H), 1.94-2.01 (m, 1H).

(9H-fluoren-9-yl)methyl (1R,4S)-1-(3,4-dichlorophenyl)-2-oxa-5-azabicyclo[2.2.1]-heptane-5-carboxylate (6) and (9H-fluoren-9-yl)methyl (1S,4R)-1-(3,4-dichlorophenyl)-2-oxa-5-azabicyclo[2.2.1] heptane-5-carboxylate (7)

(6)

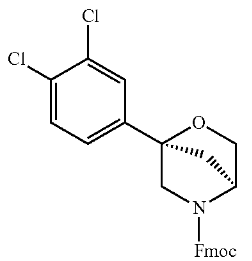

-continued (7)

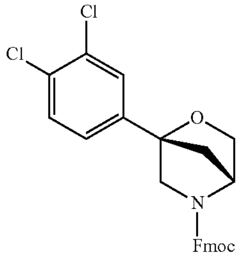

The racemic mixture (9H-fluoren-9-yl)methyl 1-(3,4-dichlorophenyl)-2-oxa-5-azabicyclo[2.2.1]heptane-5-carboxylate (5) (0.070 g, 0.150 mmol) was dissolved in 8 mL of DCM/(EtOH/MeOH 1/1) 1/1 v/v/v and submitted to chiral resolution by Chiral preparative chromatography. Conditions: Column: Chiralpak IC (25×2.0 cm), 5 μm; Mobile phase: n-Hexane/Ethanol 60/40% v/v; Flow rate: 18 ml/min; DAD detection: 220 nm; Loop: 1250 μL; Injection: 10.5 mg (each injection). The fractions containing the first eluted enantiomer were evaporated to dryness to afford (9H-fluoren-9-yl)methyl (1R,4 S)—1-(3,4-dichlorophenyl)-2-oxa-5-azabicyclo-[2.2.1]heptane-5-carboxylate (6) (0.030 g, 0.064 mmol, 39.26% yield). Chiral HPLC: 5.4 min, e.e.>99%, method 1. UPLC-MS: 1.50 min, 466.39 $[M+H]^+$, method a. $^1H$ NMR (400 MHz, Methanol-$d_4$) δ ppm 7.83 (t, J=7.7 Hz, 2H), 7.59-7.72 (m, 3H), 7.55 (t, J=9.8 Hz, 1H), 7.27-7.47 (m, 5H), 4.60 (d, J=9.5 Hz, 2H), 4.31 (d, J=19.5 Hz, 1H), 3.79-4.01 (m, 2H), 3.55-3.67 (m, 1H), 3.39-3.46 (m, 1H), 3.21-3.28 (m, 1H), 2.15-2.29 (m, 1H), 1.94-2.01 (m, 1H). The fractions containing the second eluted enantiomer were evaporated to dryness to afford (9H-fluoren-9-yl)methyl (1 S,4R)—1-(3,4-dichlorophenyl)-2-oxa-5-azabicyclo[2.2.1]heptane-5-carboxylate (7) (0.034 g, 0.073 mmol, 44.49% yield). Chiral HPLC: 9.4 min, e.e.>99%, method 1. UPLC-MS: 1.50 min, 466.39 $[M+H]^+$, method a. $^1H$ NMR (400 MHz, Methanol-$d_4$) δ ppm 7.83 (t, J=7.7 Hz, 2H), 7.59-7.72 (m, 3H), 7.55 (t, J=9.8 Hz, 1H), 7.27-7.47 (m, 5H), 4.60 (d, J=9.5 Hz, 2H), 4.31 (d, J=19.5 Hz, 1H), 3.79-4.01 (m, 2H), 3.55-3.67 (m, 1H), 3.39-3.46 (m, 1H), 3.21-3.28 (m, 1H), 2.15-2.29 (m, 1H), 1.94-2.01 (m, 1H). The stereochemistry of the isomers was assigned arbitrarily to be (9H-fluoren-9-yl)methyl (1R,4S)-1-(3,4-dichlorophenyl)-2-oxa-5-azabicyclo[2.2.1]heptane-5-carboxylate (6) as first eluting isomer and (9H-fluoren-9-yl)methyl (1 S,4R)—1-(3,4-dichlorophenyl)-2-oxa-5-azabicyclo-[2.2.1]heptane-5-carboxylate (7) as second eluting isomer.

Example 13: (1R,4S)-1-(3,4-dichlorophenyl)-2-oxa-5-azabicyclo[2.2.1]heptane (APV243516A; En)

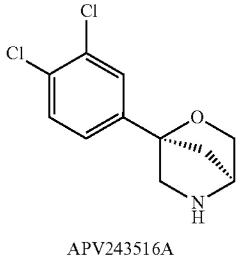 [SMILES: Clc1ccc([C@]23CN[C@H](CO2)C3)cc1Cl]

APV243516A

To a solution of (9H-fluoren-9-yl)methyl (1R,4S)-1-(3,4-dichlorophenyl)-2-oxa-5-azabicyclo[2.2.1]heptane-5-carboxylate (6) (0.030 g, 0.060 mmol) in Methanol (5 mL) piperidine (1.0 mL, 10.12 mmol) was added and the reaction was stirred at r.t. for 30 minutes. The reaction was concentrated under vacuum and the residue was purified by SCX first washing with MeOH and then eluting with 1M $NH_3$ in MeOH. Basic fractions were collected and evaporated. The residue was purified by FC on silica gel (from DCM to DCM/MeOH 9:1) affording (1R,4S)-1-(3,4-dichlorophenyl)-2-oxa-5-azabicyclo[2.2.1]heptane (APV243516A) (0.010 g, 0.043 mmol, 69.71% yield). UPLC-MS: 0.57 min, 246.22 $[M+H]^+$, method a. $^1H$ NMR (400 MHz, Methanol-$d_4$) δ ppm 7.67 (d, J=2.0 Hz, 1H), 7.53 (d, J=8.4 Hz, 1H), 7.42 (dd, J=8.4, 2.1 Hz, 1H), 3.97-4.09 (m, 2H), 3.83 (d, J=2.4 Hz, 1H), 3.09-3.20 (m, 2H), 2.19 (ddd, J=9.9, 2.3, 0.9 Hz, 1H), 1.98 (dt, J=10.0, 1.1 Hz, 1H).

Example 14: (1S,4R)-1-(3,4-dichlorophenyl)-2-oxa-5-azabicyclo[2.2.1]heptane (APV243518A; En2)

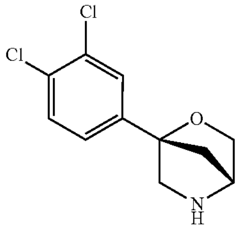

APV243518A

To a solution of (9H-fluoren-9-yl)methyl (1 S,4R)—1-(3,4-dichlorophenyl)-2-oxa-5-azabicyclo[2.2.1]heptane-5-carboxylate (7) (0.034 g, 0.070 mmol) in Methanol (5 mL) piperidine (1.13 mL, 11.47 mmol) was added and the reaction was stirred at r.t. for 30 minutes. The reaction was concentrated under vacuum and the residue was purified by SCX first washing with MeOH and then eluting with 1M $NH_3$ in MeOH. Basic fractions were collected and evaporated. The residue was purified by FC on silica gel (from DCM to DCM/MeOH 9:1) affording (1 S,4R)—1-(3,4-dichlorophenyl)-2-oxa-5-azabicyclo[2.2.1]heptane (APV243518A) (0.003 g, 0.051 mmol, 73.93% yield). UPLC-MS: 0.57 min, 244.22 $[M+H]^+$, method a. $^1H$ NMR (400 MHz, Methanol-$d_4$) δ ppm 7.67 (d, J=2.0 Hz, 1H), 7.53 (d, J=8.4 Hz, 1H), 7.42 (dd, J=8.4, 2.1 Hz, 1H), 3.97-4.09 (m, 2H), 3.83 (d, J=2.4 Hz, 1H), 3.09-3.20 (m, 2H), 2.19 (ddd, J=9.9, 2.3, 0.9 Hz, 1H), 1.98 (dt, J=10.0, 1.1 Hz, 1H).

In some embodiments, the compounds of Formula (VIII) are synthesized following the reaction scheme provided below

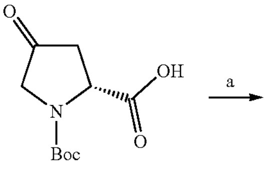

(8)

-continued

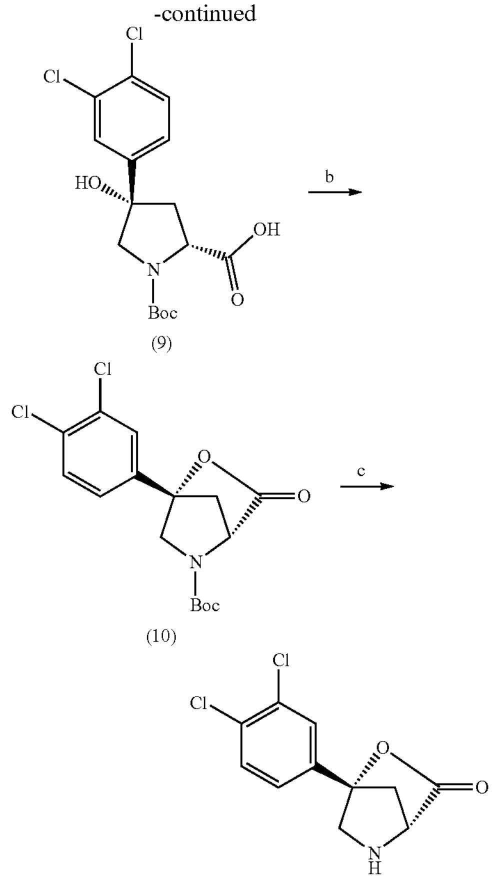

(9)
(10)
(11)

a) 3,4-dichlorophenylmagnesium bromide, THF; b) BOP, $Et_3N$, DMF; c) TFA, DCM, r.t., 1 h.

Although exemplary synthesis methods are described above for certain specific compounds, methods for synthesis of these and other compounds described herein and any necessary starting materials are also either described in the art or will be readily apparent to the skilled artisan in view of general references well-known in the art (see, e.g., Green et al., "Protective Groups in Organic Chemistry," (Wiley, 2nd ed. 1991); Harrison et al., "Compendium of Synthetic Organic Methods," Vols. 1-8 (John Wiley and Sons, 1971-1996); Beilstein Handbook of Organic Chemistry," Beilstein Institute of Organic Chemistry, Frankfurt, Germany; Feiser et al, "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995) and may be used to synthesize the compounds described herein.

The following examples are included for illustrative purposes only and are not intended to limit the scope of the invention. The compounds described herein were tested in multiple assays as now described.

Example 15: Functional Dopamine Active Transporter (DAT) and Serotonin Active Transporter (SERI) Uptake Assay in Recombinant hDAT-CHO Cells, and Dopamine and Serotonin Release Assay in Rat Synaptosomes Purpose: The goal of the study described in this Example was to determine the inhibitory activity of tested compounds on DAT and SERT function, as well as the effects of the compounds described herein on dopamine and serotonin release.

Overview: Eighty-eight compounds were tested in SERT (serotonin transporter) and DAT (dopamine transporter) uptake assays (completed as scintillation proximity assays, or SPAs, in a recombinant CHO cell line). Fifty-two compounds were tested in release assays for 5-HT and DA release in rat synaptosomes. Fifteen compounds were surprisingly shown to have a SERT release $pEC_{50}$ higher than the SERT uptake inhibition.

Methods and Procedure-Uptake: The potency of the compounds described herein for inhibiting DAT function was measured using an uptake assay in a recombinant CHO cell line stably expressing human DAT (hDAT-CHO). Potency was measured in terms of $pIC_{50}$ by testing for inhibition of $[^3H]$-dopamine uptake in hDAT-CHO cells in a 384-well format scintillation proximity assay (SPA).

Briefly, on experiment days, hDAT-CHO cells were detached using Versene and added at a density of approximately 300,000 cells/mL to the SPA Mixture, which contains the following components in Assay Buffer (20 mM HEPES, 145 mM NaCl, 5 mM KCl, 2 mM $CaCl_2$, 1 mM $MgCl_2$, 5.5 mM glucose, 0.01% Pluronic F127, pH 7.3): 0.75 mg/mL SPA Imaging beads (RPNQ0001, PerkinElmer), 10 μM pargyline and 80 nM of $[^3H]$-dopamine (NET673, PerkinElmer). The SPA Mixture was added 20 μL/well to 384 well plates containing 0.1 μL/well of test compound in neat DMSO (11 points of 1:5 serial dilution, 0.5% DMSO final) or 0.1 μL of DMSO (total uptake) or 0.1 μL of the standard inhibitor indatraline (at 1 μM final concentration, as non-specific uptake). Plates were sealed with a Top-seal A and read using a Microbeta counter (PerkinElmer) after 45 minutes of incubation at room temperature.

In addition, hSERT-CHO cells were detached using Versene and added at a density of 150,000 cells/mL to the SPA Mixture, which contains the following components in the Assay Buffer described above: 0.5 mg/mL SPA Imaging beads (RPNQ0001, PerkinElmer), 10 μM pargyline and 35 nM of $[^3H]$-serotonin (NET498, PerkinElmer). The SPA Mixture was added 20 μL/well to 384 well plates containing 0.1 μL/well of test compound in neat DMSO (11 points of 1:5 serial dilution, 0.5% DMSO final), 0.1 μL of DMSO (total uptake), or 0.1 μL of the standard inhibitor indatraline (1 μM, nonspecific uptake). Plates were sealed with a Top-seal A and read using a Microbeta counter (PerkinElmer) after 120 minutes of incubation at room temperature.

For both tests, the raw experimental data (cpm) were elaborated for the determination of $pIC_{50}/IC_{50}$ values as % inhibition of specific uptake. Concentration-response curves of MDMA, MDDMA, citalopram and GBR-12909 were used as internal standards in all experiments, and the signal window was monitored in each plate performing Z' calculations, as described in Zhang et al., J. Biomol. Screen., 1999; 4: 67-73.

Methods and Procedure—Release: The potency of the disclosed compounds for stimulating dopamine (DA) release was measured by an endpoint release filtration assay in a 96-well format using rat synaptosomes, essentially as described by Sandtner et al., Mol. Pharmacol., 2016; 89(1): 165-75, and Baumann et al., Neuropsychopharmacol., 2013; 38:552-562, with some variations.

One male rat was sacrificed and striatum/cortex regions were dissected over ice. The striatum portions were weighed and put in a glass tube for homogenization, containing ice-cold 0.32 M sucrose (dilution 1:24 w/v), while the frontal cortex tissue was diluted in ice-cold 0.32 M sucrose, 1:20 w/v. Tissues were homogenized and centrifuged for 10 mins at 1000×g. The two supernatants from striatum and cortex (crude synaptosomes) were retained on ice until use.

Test compounds were then serially diluted 1:4 in neat DMSO as concentration-response curves (CRC) of 11 points. To each well of a 2-mL 96 deep-well plate (Whatman UNIPLATE 96 well) were added: 2 μL of CRC of test compounds or 2 μL of DMSO (no-release condition) or 2 μL of MDMA 10 mM solution (final 50 μM, for maximal release), followed by 200 μL/well of complete Krebs-phosphate buffer (126 mM NaCl, 2.4 mM KCl, 0.83 mM $CaCl_2$, 0.8 mM $MgCl_2$, 0.5 mM $KH_2PO_4$, 0.5 mM $Na_2SO_4$, 11.1 mM Glucose, 0.05 mM pargyline, 1 mg/mL ascorbic acid, freshly added, pH 7.4), containing 1 μM reserpine to block vesicular uptake of substrate. Desipramine (100 nM) and citalopram (100 nM) were also added to the release assay buffer in order to inhibit NET and SERT uptake, respectively. The final compound dilution, then, was 1:200 in 0.5% DMSO.

$^3$H-Dopamine was added to the tube containing the crude striatal synaptosomes preparation, diluted 1:20 (v/v) in complete Krebs-phosphate buffer, and was incubated at RT and gently mixed for 60 minutes. Then, 200 μL/well of $^3$H-DA loaded synaptosomes were dispensed to the compound plate (final 400 μL/well) and the release reaction proceeded for an additional 15 minutes at RT. The release was terminated by vacuum filtration and washing three times with 1 mL of saline solution (NaCl 0.9%) at RT. The retained radioactivity was counted in a scintillation counter after the addition of 50 μL/well Microscint-20.

The raw data (cpm) from residual radioactivity onto the filter were elaborated for the determination of $pEC_{50}/EC_{50}$ values. Specifically, the compound effect was expressed as the percent of maximal release obtained with 50 μM MDMA (100% release) in comparison to vehicle (0.5% DMSO, 0% release). Both MDMA and D-amphetamine in CRC were used as internal controls in each release experiment. In each plate, for both 0% and 100% of release, the signal window is monitored performing Z' calculations using raw data of four replicates.

Serotonin release was calculated in an identical fashion, except that 5 nM $^3$H-serotonin was added to crude cortex synaptosomes preparation diluted 1:13 (v/v) in complete Krebs-phosphate buffer containing 1 μM Reserpine, 100 nM GBR12909 and 100 nM nomifensine—to block vesicular, DAT, and NET uptake, respectively. Synaptosomes were then loaded with $^3$H-5HT for 60 minutes at RT. After dispensing loaded synaptosomes onto a compound plate (200 μL/well), the release reaction proceeded for an additional 15 minutes. Stop by filtration, counting, and data elaboration were performed as described for DA release.

Results and Significance: Inhibitory activity on DAT and SERT was determined for the compounds described herein and compared to MDMA. Additionally, the ability of the compounds to stimulate release of dopamine and serotonin was assessed. The results of exemplary compounds APV241522A ("522A"), APV243516A ("516A"), and APV243518A ("518A"), APV245562A ("562A"), and APV245514A ("514A") are shown in Table 5.

TABLE 5

DAT and SERT uptake and release data for certain disclosed compounds.

| Compound | 522A | 516A | 518A | 562A | 514A |
|---|---|---|---|---|---|
| SERT uptake pIC50 | 7.25 | 7.33 | 7.09 | 5.81 | 6.52 |
| SERT release pEC50 | 7.72 | 7.74 | 7.77 | 6.79 | 7.33 |
| DAT update pIC50 | 7.20 | 7.14 | 7.05 | 5.15 | 4.77 |
| DAT release pEC50 | 7.21 | 5.96 | 7.48 | 5.66 | 4.71 |

The results of exemplary compound APV241522A ("522A") and reference compound MDMA are expressed as either pIC50 or pEC50, as shown in FIG. 1. pIC50 and pEC50 are defined as the negative logarithm of the IC50 or EC50; larger values indicate greater potency.

The results illustrate the relatively greater potency of the exemplary compound in blocking DAT and SERT function, which are implicated in the reuptake of dopamine and serotonin, respectively. Broadly, compounds that inhibit DAT and SERT may reduce DAT-mediated dopamine trafficking and SERT-mediated serotonin trafficking, respectively, and prolong the effects of dopamine/serotonin activity. Additionally, the results demonstrate the enhanced potency of the exemplary compound for stimulating dopamine and serotonin release relative to MDMA.

Example 16: Measurement of Intracellular Calcium Response in CHO Cells Expressing the Human 5-$HT_{2A}$ Receptor Purpose: The aim of the study was to assess the 5-$HT_{2A}$ selectivity of the compounds described herein. Selectivity was assessed in agonist and antagonist modes.

Methods and Procedure: Selectivity for the 5-$HT_{2A}$ receptor was assessed by measuring $[Ca^{2+}]_i$ in a CHO recombinant cell line stably expressing the human 5-$HT_{2A}$ receptor, using Fluorometric Imaging Plate Reader (FLIPR TETRA, Molecular Devices).

The day before the experiment, CHO cells were seeded into clear-bottom 384-well plates at a density of 10,000 cells per well, in F-12K Medium (ThermoFisher #21127) supplemented with 10% dialyzed fetal bovine serum, and grown overnight at 37° C., 5% $CO_2$.

On the day of the experiment, the medium was replaced with assay buffer (20 mM HEPES, 145 mM NaCl, 5 mM KCl, 5.5 mM glucose, 1 mM $MgCl_2$, 2 mM $CaCl_2$ and 2.5 mM probenecid, pH 7.4) containing the cytoplasmic $Ca^{2+}$ indicator Fluo-4 AM at 2 μM and 0.02% Pluronic F-127. After an incubation of 45-60 minutes at 37° C., 0% $CO_2$, cells were washed by Microplate Washer (BIOTEK) 384 with assay buffer, and the plate was transferred in the FLIPR TETRA. Then, intracellular fluorescence was measured in real time by FLIPR TETRA (excitation wavelength at 470-495 nm, emission wavelength at 515-575 nm), using a dual addition protocol.

In the first addition, test compounds (11 points of 1:4 serial dilution, 0.5% DMSO final) were added to the cell plate to evaluate their effect on intracellular calcium levels. In the event of a response, the signal was elaborated for the determination of $pEC_{50}/EC_{50}$ values. After 10 minutes of incubation, a second addition of a submaximal concentration of serotonin ($EC_{80}$) was performed. Inhibition of 5-HT response vs. vehicle effect (0.5% DMSO) was elaborated for the determination of $pIC_{50}/IC_{50}$ values. Concentration-response curves (CRC) of serotonin and LSD were used as internal controls in the agonist format, full agonist and partial agonist, respectively. A CRC of ketanserin was used as the internal antagonist control. The activity of MDMA was also assessed and used as a reference.

Results and Significance: The 5-$HT_{2A}$ selectivity of test compounds were calculated and compared to MDMA. The agonist selectivity of the exemplary compound APV241522A ("522A") was 4.3, while the antagonist selectivity was 5.4 (represented as $pEC_{50}$). Regarding MDMA, both the agonist and antagonist selectivities were less than 4.3 (measured as $pEC_{50}$). Thus, 522A exhibited greater potency than MDMA in both agonist and antagonist modes. For reference, the mean $pEC_{50}$ values of full 5-$HT_{2A}$ receptor agonist serotonin and partial agonist LSD were 8.38 and 7.77, respectively. The mean $pEC_{50}$ value of 5-$HT_{2A}$ receptor antagonist ketanserin was 5.52. Broadly, a comparison of 5-$HT_{2A}$ selectivity across different compounds may be used to provide insight into the agonistic and antagonistic effects of such compounds.

Example 17: In Vivo Analysis of Monoamines in Rat Brains Following Intraperitoneal Administration of Exemplary Compound 522A Purpose: The aim of the study was to assess the effect of intraperitoneal (IP) administration of compounds described herein, including exemplary compound APV241522A ("522A"), on extracellular dopamine (DA), serotonin (5-HT), and noradrenaline (NE) levels over time in the nucleus accumbens (NAcc).

Methods and Procedure: This study was conducted in compliance with previously described procedures to assure data integrity, adherence to GLP regulations, and standard preclinical study and surgery procedures. The in vivo microdialysis technique was applied to measure the over-time variations of DA, 5-HT, and NE extracellular (EC) concentrations in conscious, freely-moving Sprague Dawley rats. Levels of the neurotransmitters in microdialysis samples were determined using LC-MS/MS analysis. The experiment was also conducted with MDMA, which was used for comparative purposes.

As it relates to cannula implantation, the rats were anesthetized with isoflurane 4% in oxygen (2-2.5 L/min), then the isoflurane concentration 2-2.5% was maintained via a nose cone adapted to the stereotaxic apparatus. The rats were treated with meloxicam (0.2 mg/kg, subcutaneously, sc; Meloxidolor) and amoxicilline (150 mg/kg, sc, Betamox LA). The skull was then shaved and disinfected. Rats were then placed in a stereotaxic apparatus for small animals. One vertical guide cannula was inserted through a 1 mm hole drilled on the exposed skull. Coordinates—with respect to bregma—to target specific brain areas, followed indications from stereotaxic atlas of the rat brain. Specifically a guide cannula (MAB 4.12.IC, Agn Tho's AB, Lidingo, Sweden) was inserted in the NAcc (anteroposterior+1.6; lateral −1.6; dorsoventral −6.0). The guide cannula was then secured with dental cement and 2-4 screws. At the end of the surgery the animal was isolated in a single cage during recovery, for a period of at least one week, during which animal health conditions were checked twice daily and the weight recorded twice a week. Animals continued to be housed singly throughout the experiment. One day before the experiment the cannula stylet was removed and a microdialysis probe with a dialyzing length of 2 mm (MAB 4.12.2 Cu, Agn Tho's AB, Lidingo, Sweden) was inserted. Probes can be re-used 2 times for 2 experimental sessions after appropriate cleaning with fresh milliQ water.

Post-surgery, the rats were maintained in a heating chamber prior to waking up in order to avoid hypothermia that could be caused by anaesthesia. 5 mL of physiologic solution was subcutaneously administered immediately after surgery, and once/day for 2-3 days, if signs of dehydration are noticed. Meloxicam (Meloxidolor) 0.2 mg/kg was again administered subcutaneously the day after surgery as well as after 48h after surgery together with Amoxicilline Long Acting (Betamox LA) 150 mg/kg. Health status and body weight was checked every day during the first week.

The animals were treated with test compounds described herein, MDMA, or their vehicle (saline) according to a Latin square design over 5 separate experimental days (one day/week). The treatments were administered in a volume of 1 mL/kg intraperitoneally.

On the day of the experiment, each animal was taken into the laboratory in its home cage. Inlet tubing of the probe was attached to a dual quartz-lined two channel liquid swivel mounted on a low mass spring counterbalance arm which, in turn, was connected to a gas-tight syringe on a microinfusion pump. Artificial cerebrospinal fluid (aCSF; containing KCl 2.5 mM, NaCl 125 mM, $CaCl_2$) 1.3 mM, MgCl 2 1.18 mM, Na2HPO4 2 mM, pH 7.4) was perfused through the probe (Univentor 864 Syringe Pump, Agn Tho's, Sweden) at a steady flow rate of 1 μL/min. An equilibration period of about two hours of perfusion was allowed before collecting samples. Following the equilibration period, 4 basal samples were collected for each experimental animal followed by further 10 post-treatment samples. Samples were collected every 20 minutes (up to 3 hours and 20 minutes post-treatment) by means of a refrigerated auto-sampler (Univentor 820 Microsampler, Agn tho's, Sweden) maintained at +8° C. At the end of all experimental sessions, 2 μL of 0.1% methylene blue solution was injected through the microdialysis probe, animals were euthanized, and their brains removed to confirm the correct probe-position.

The concentrations of DA, 5-HT and NE in CSF samples were determined using an optimized method based on LC-MS/MS analysis. Study samples were spiked with appropriate Internal Standard (IS) to improve the precision of the assay.

Liquid chromatography separations were performed using Agilent HP1100 system (Agilent Technologies) equipped with a binary pump, a column oven and a PAL CTC Autosampler. The LC system was coupled with an API4000 Triple Quadrupole System (ABSciex) equipped with a TIS ion source. Analyst software 1.6.2 (ABSciex) was used to control the instruments.

Figure 2:
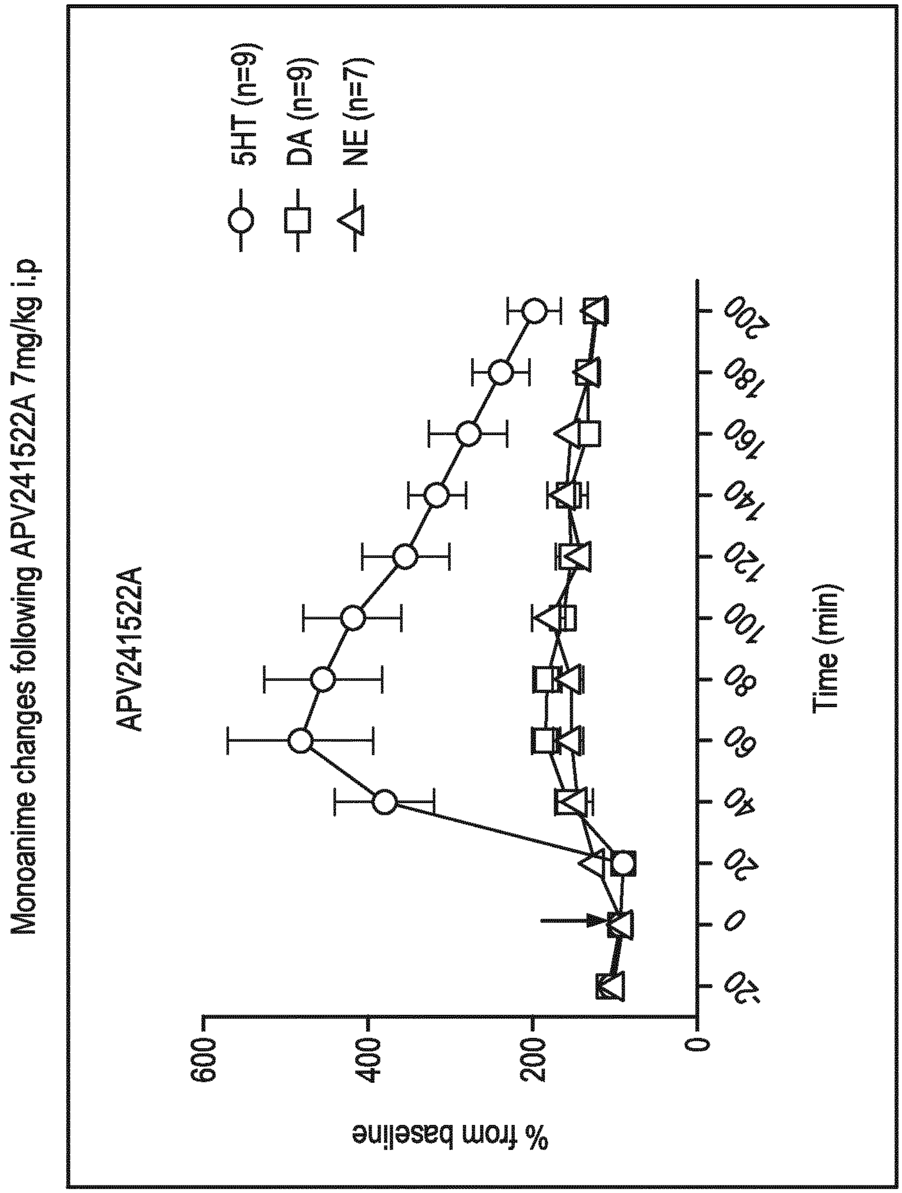
FIG. 2 depicts the effects of test compound APV241522A on extracellular concentrations of serotonin (5-HT), dopamine (DA), and norepinephrine (NE) in the rat brain.

Results and Significance: The results of the study illustrate the effects of test compound APV241522A ("522A") and reference compound MDMA on extracellular concentrations of 5-HT, DA, and NE in the rat brain. The effects of 522A on monoamine levels are illustrated in FIG. 2 and Table 6. At 20 minutes post-administration of 522A, serotonin and dopamine reached a two-fold increase (100%) of basal levels, while norepinephrine was measured at 130% of basal levels. At the final time-point, 200 minutes, serotonin was 200% of basal levels, and dopamine and norepinephrine were each 125% of basal levels.

TABLE 6

Serotonin (5HT), dopamine (DA), and norepinephrine (NE) levels post-administration of 522A, relative to baseline levels (100%).

| Time post-administration | 5HT | DA | NE |
|---|---|---|---|
| 20 min | 100% | 100% | 130% |
| 40 min | 380% | 160% | 150% |

TABLE 6-continued

| Serotonin (5HT), dopamine (DA), and norepinephrine (NE) levels post-administration of 522A, relative to baseline levels (100%). | | | |
|---|---|---|---|
| Time post-administration | 5HT | DA | NE |
| 60 min | 480% | 185% | 160% |
| 200 min | 200% | 125% | 125% |

Figure 3:
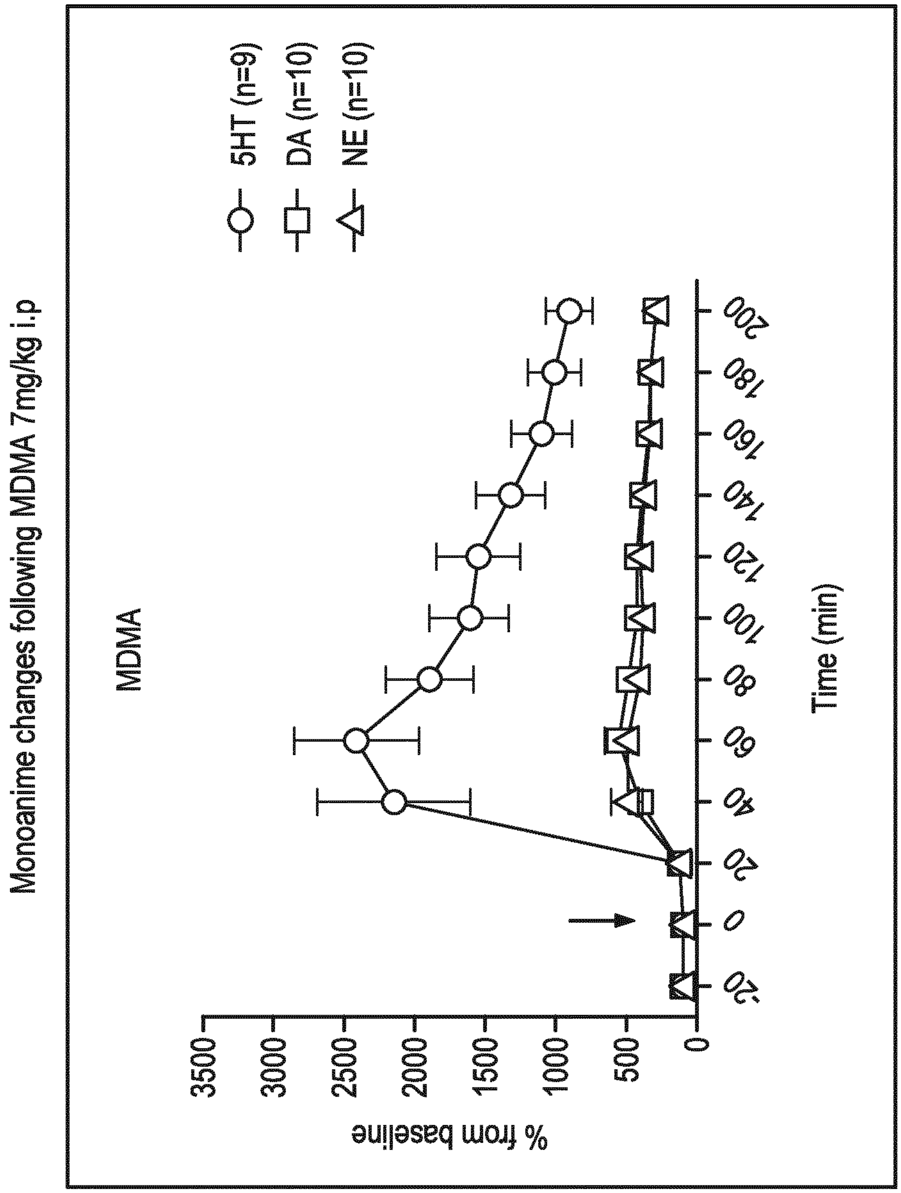
FIG. 3 depicts the effects of reference compound MDMA on extracellular concentrations of serotonin (5-HT), dopamine (DA), and norepinephrine (NE) in the rat brain.

Changes in monoamine levels in response to MDMA are shown in FIG. 3 and Table 7. Like 522A, peak monoamine levels were detected at 60 minutes: serotonin was 2,420% of basal levels, dopamine was 560% of basal levels, and norepinephrine was 500% of basal levels.

TABLE 7

| Serotonin (5HT), dopamine (DA), and norepinephrine (NE) levels post-administration of MDMA, relative to baseline levels (100%). | | | |
|---|---|---|---|
| Time post-administration | 5HT | DA | NE |
| 20 min | 130% | 120% | 120% |
| 40 min | 2150% | 400% | 500% |
| 60 min | 2420% | 560% | 500% |
| 200 min | 900% | 300% | 300% |

For each compound, peak levels of each neurotransmitter, as determined from baseline, were detected at the 60 minute time-point. Comparatively, greater increases in extracellular 5-HT, DA, and NE were detected in the MDMA-treated group. At peak levels (60 min), normalized 5-HT MDMA levels were five times that of 522A. Peak normalized levels of DA and NE in the MDMA group were about three times that measured in the 522A group. Together, these results demonstrate in vivo modulation of monoamine transmitters by exemplary compound 522A.

Example 18: A Pharmacokinetic Study of Intravenous and Oral Administration of Exemplary Compound 522A in Rats Purpose: The objective of this study was to assess the pharmacokinetics, including penetration into the brain, of compounds described herein, such as exemplary compound APV241522A ("522A"), in rats following intravenous (IV) and oral administration.

Methods and Procedure: The study was conducted in agreement with procedures to assure data integrity and GLP principles. Three experimental groups, as outlined below, were included in the study:

Group 1: Exemplary compound 522A was administered via the IV route to three rats at a target dose level of 0.5 mg/kg. Blood and brain samples were collected at 2h after IV administration.

Group 2: Exemplary compound 522A was administered via the IV route to three rats (brain penetration group) at a target dose level of 0.5 mg/kg. Blood and brain samples were collected at 2h after IV administration.

Group 3: Exemplary compound 522A was orally administered to three rats at a target dose level of 1 mg/kg. Blood samples were collected up to 24h after oral administration.

All test formulations were prepared on the day of administration prior to dosing, stored at room temperature, and used as soon as possible. Formulations were prepared and administered by volume for both IV and oral dosing. Actual body weights were determined on the day of dose administration, and the dose volumes were adjusted to the weight of the animal at the time of dose administration.

Blood was collected into K3 EDTA tubes at each of the following time points post-administration:

Group 1 (ITS): 0.083, 0.33, 1, 2, 4, 6, 8, and 24 hours after dosing

Group 2 (ITS): 2 hours after dosing for terminal brain analysis

Group 3 (Oral): 0.250, 0.5, 1, 2, 4, 6, 8, and 24 hours after dosing

All blood samples were thoroughly but gently mixed following collection and then placed on wet ice. Within 0.5 h of collection, blood was centrifuged (3000 g for 10 minutes at approximately 4° C.). Within 0.5 hours, 20 µL of each plasma sample was transferred into micronic tubes containing 80 µL of 0.1N Hepes buffer (pH 7.0-7.5). Residual plasma was transferred in micronic tubes as a second aliquot.

Brain specimens were diluted with 4 volumes of 0. IN Hepes buffer and homogenized using the Precellys system. Blood and brain samples were assayed using an optimized method based on protein precipitation with acetonitrile followed by HPLC/MS-MS analysis. Given the unknown stability of analytes in blood and brain, Calibration standards (CS) and Quality control samples (QC) were prepared in blood and brain samples on the day of dosing and stored together with study samples. It is assumed this procedure accounted for any possible analyte degradation.

Study samples, CS, QC, and blanks were spiked with an internal standard (IS), to improve the precision of the assay. Study samples were analyzed together with CS, QC and blank samples (including double blanks). From the calibration curve, the linear range of the analytical method was determined and the lower/upper limits of quantitation were specified.

The results of blood and brain specimens were subjected to non-compartmental pharmacokinetic analysis using Phoenix WinNonlin 6.3, with the following parameters reported: Calculated concentration of test items in the corresponding formulation (expressed as mg/mL), dose levels (expressed as mg/kg) for each compound, actual collection times (expressed as hh: mM), blood concentrations (expressed as ng/ml) for each compound, brain concentrations (expressed as ng/g) for each compound, PK parameters (iv: $C_{max}$, AUC, CLp, Vss, $t_{1/2}$, if applicable; oral (po): Cmax, $t_{max}$, AUC, F %, Fa %, Eh, AUC BB ratio, if applicable) for each compound, and abnormal clinical signs and relevant findings, if any.

Figure 4:
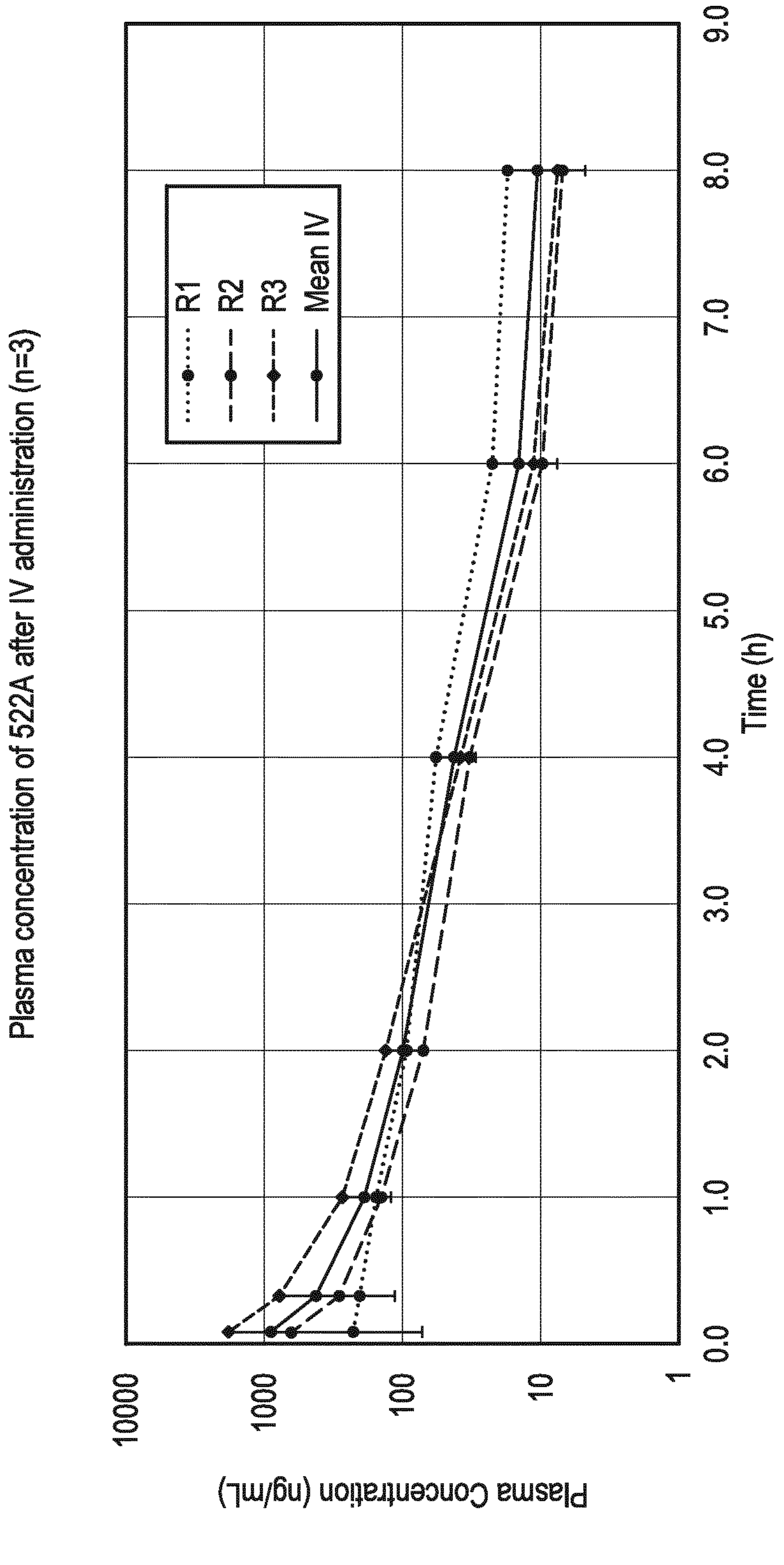
FIG. 4 depicts the plasma concentration of exemplary compound APV241522A ("522A") following IV administration in a rat in vivo assay.
Figure 5:
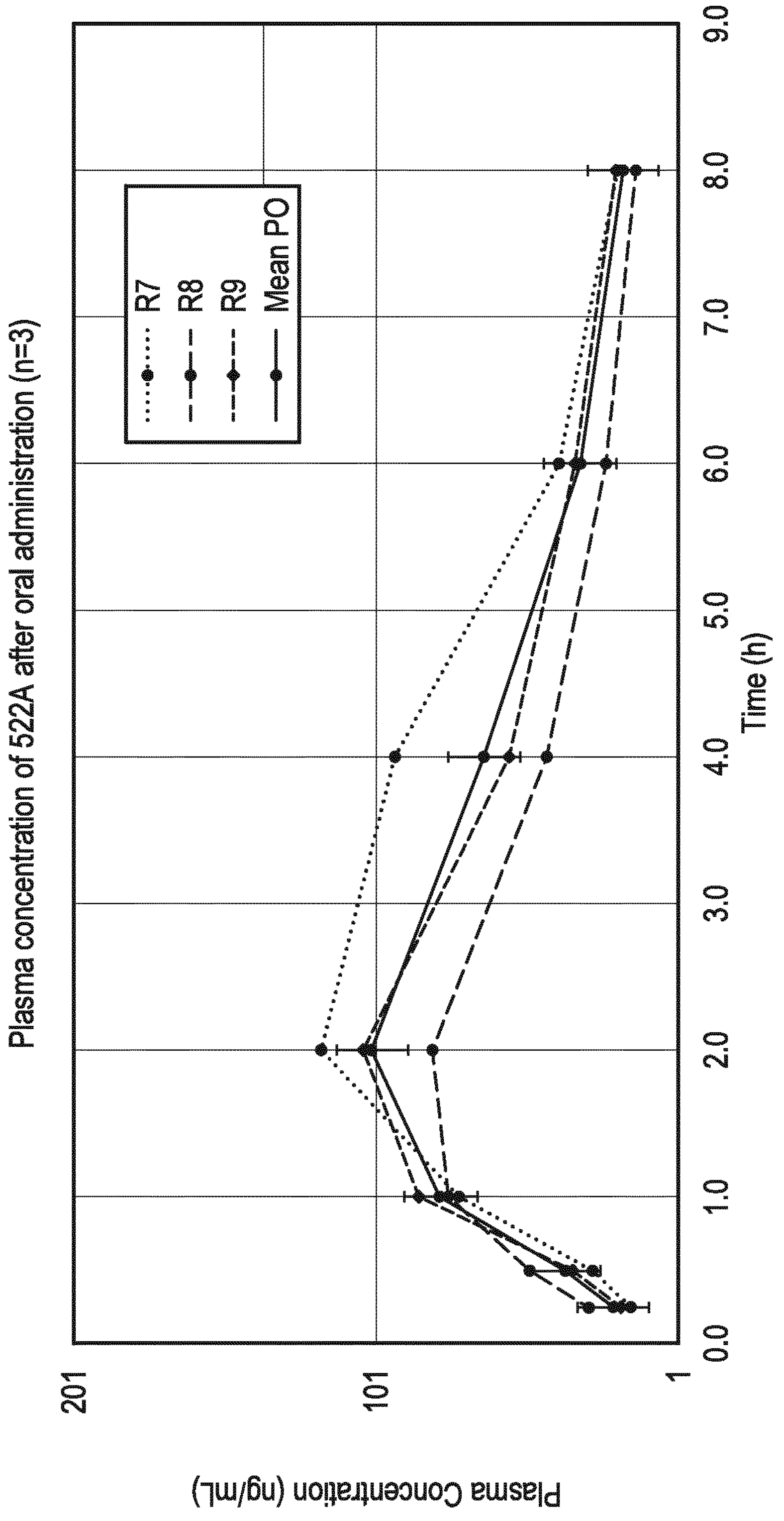
FIG. 5 depicts the plasma concentration of exemplary compound APV241522A ("522A") following oral administration in a rat in vivo assay.
Figure 6:
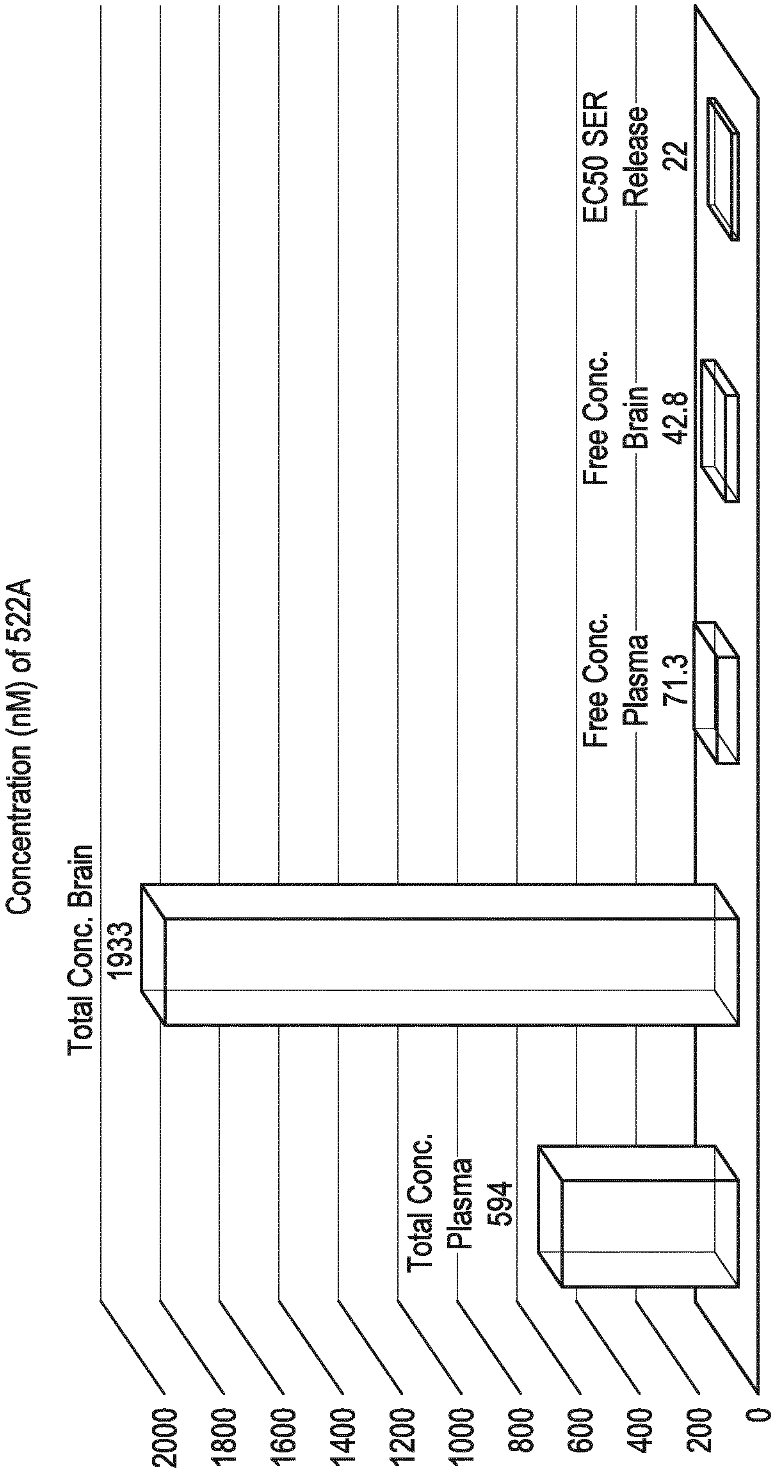
FIG. 6 depicts the concentrations of exemplary compound APV241522A ("522A") in brain and plasma samples measured two hours after IV administration in a rat in vivo assay.

Results and Significance: The pharmacokinetic properties of test compounds were determined. The pharmacokinetic properties of exemplary compound 522A are shown in Table 8 and FIG. 4 (IV administration), FIG. 5 (oral administration), and FIG. 6.

TABLE 8

| IV pharmacokinetic properties of test compound 522A in vivo. In Vivo Rat PK - IV Administration of Exemplary Compound 522A | |
|---|---|
| $C_{max}$ (ng/mL) | 1890 |
| $T_{max}$ (h) | 0.08 |
| $C_{last}$ (ng/mL) | 9.32 |
| $T_{last}$ (h) | 8 |
| $AUC_{last}$ (h*ng/mL) | 1460 |
| $AUC_{inf}$ (h*ng/mL) | 1480 |

TABLE 8-continued

| IV pharmacokinetic properties of test compound 522A in vivo. In Vivo Rat PK - IV Administration of Exemplary Compound 522A | |
|---|---|
| Clearance (mL/min/kg) | 5.71 |
| $T_{1/2}$ (h) | 1.36 |
| $V_{ss}$ (L/kg) | 0.411 |

The comparative pharmacokinetics of IV and oral administration of exemplary compound 522A is shown in Table 9 below:

TABLE 9

IV and oral pharmacokinetic properties of test compound 522A in vivo. In Vivo Rat PK - IV and Oral (PO) Administration of Exemplary Compound 522A

| | IV | PO |
|---|---|---|
| $C_{max}$ (ng/mL) | 878 | 102 |
| $T_{max}$ (h) | 0.08 | 2 |
| $C_{last}$ (ng/mL) | 10.6 | 19.3 |
| $T_{last}$ (h) | 8 | 8 |
| $AUC_{last}$ (h*ng/mL) | 772 | 442 |
| $AUC_{inf}$ (h*ng/mL) | 799 | 509 |
| Clearance (mL/min/kg) | 11.6 | |
| $T_{1/2}$ (h) | 1.65 | 2.42 |
| $V_{ss}$ (L/kg) | 1.48 | |
| Bioavailability (%) | | 30.8 |

Regarding brain penetration, the concentrations of test compounds in brain and plasma samples were measured two hours after IV administration. For exemplary compound 522A, total plasma concentration was 594 nM, total concentration in the brain was 1933 nM, free concentration in plasma was 71.3 nM, and free concentration in the brain was 42.8 nM. Additionally, the $EC_{50}$ of 522A to influence SER release was determined to be 22 nM. The mean brain-to-plasma ratio for 522A was calculated at 4.96, and the determined concentration ratio of unbound drug in brain to blood (kp, uu) was 0.77. Together, the results are consistent with oral bioavailability and penetration of the exemplary compound into the brain.

Example 19: Solubility Assessment of Compounds in PBS (pH 7.4)

Purpose: The main objective of this study is to evaluate the solubility of compounds described herein using an HPLC-UV-based method.

Methods and Procedure: This study was designed in compliance with previously described procedures to assure data integrity and adherence to GLP principles. Control compounds included ibuprofen as a reference for high solubility and progesterone as a reference for low solubility. Stock solutions of compounds described herein (20 mM) were prepared in DMSO, on the same day of the experiment when feasible.

These solutions were compared with an external standard solution of known concentration via HPLC-UV To prepare the standard, 4 μL from a 20 mM compound stock solution was added to DMSO in a vial/well, and mixed with shaking at room temperature for 10 minutes. The standard buffer used for the assessment was PBS buffer (pH 7.4), but alternative buffers may also be used, such as biologically relevant Fluids, including Simulated Gastric fluid (SGF) at pH 1.2, Fasted State Simulated Intestinal Fluid (FaSSIF) at pH 6.5, and Fed State Simulated Intestinal Fluid (FeSSIF) at pH 5.0.

An isotonic phosphate buffer (iPBS) was prepared by dissolving a phosphate buffered saline tab (Sigma-Aldrich P4417-50Tab) in 200 mL deionized water, the final composition of the solution being 10 mM PBS, 2.7 mM kCl, and 137 mM NaCl, yielding a final pH of 7.4 at 25° C.

Samples were prepared by dispensing 8 μL from a 20 mM compound stock solution in DMSO in a vial/well in duplicate, adding 392 μL of buffer in each vial/well, and mixed by shaking at room temperature for 120 minutes. The final compound concentration was approximately 400 μM, while the final concentration of DMSO was about 2%. The solutions were then filtered prior to analysis.

Concentrations were determined by comparing UV absorbance of the test solution and of the known standard solution following HPLC separation using a generic fast gradient method employing a DAD detector and UV detection at 230 and 254 nm. Concerning the HPLC Mobile phase, Phase A was a 50 mM ammonium acetate aqueous solution (pH adjusted to 7.4 with ammonia), and Phase B was acetonitrile. For data analysis, chromatographic peaks were automatically integrated, and the parameters were optimized to enable consistent integration of all chromatograms in the entire analytical run. The solubility of each compound was expressed as the ratio of compound amount in the sample test solution to the amount of compound in the standard solution, calculated from the equation "solubility of sample=peak area of sample/peak area of standard×concentration of standard."

Results and Significance: The solubility of the compounds described herein was determined and compared to reference compound MDMA. A solubility of 383.6 μM was determined for exemplary compound 522A in PBS pH 7.4. For comparison, the solubility of MDMA was determined to be 386 μM. Solubility is a key physicochemical property of a new chemical entity that can be further evaluated in a pharmacological context, such as when considering absorption. Exemplary compounds described herein were classified as highly-soluble compounds.

Example 20: Evaluation of Lipophilicity by Determining the Chromatographic Hydrophobicity Index (CHI)

Purpose: The aim of this study is to evaluate the lipophilicity of compounds using an HPLC-UV-based method.

Methods and Procedure: The methods employed herein comply with previously described procedures to assure data integrity and adherence to GLP regulations. Briefly, a CHI value was determined by comparing the retention time of a test compound to a linear curve based on a set of calibration compounds with known CHI values. The resultant CHI value can be further converted to a CHI Log D value using an established linear regression equation.

Reference compounds with known CHI values, including theophylline, phenyltetrazole, benzymidazole, colchicine, phenyltheophylline, acetophenone, indole, propiophenone, butyrophenone, valerophenone, were used to create a calibration line. Test compounds (10 mM) were prepared in DMSO on the same day of the experiment, when feasible. For sample preparation, 10 μL of test solution was diluted with 190 μL of a solution of Ammonium Acetate solution (50 mM) and Acetonitrile (1:1) pH7.4, which was then mixed via shaking at room temperature for 10 minutes. Test solutions were compared with the reference compounds via HPLC-UV, as described in Example 19. The gradient was calibrated by determining the retention time of each reference compound on a reverse phase LC system at a pH of 7.4.

The relationship of CHI with retention time is "CHI=Atr+B," wherein A and B are the constants of a linear plot of CHI against their gradient retention times, and tr is retention time.

The test compounds were analyzed on the same system as the test mix. The equation generated from the calibration line for the reference compounds was then used to determine the unknown CHI value for the test compound. From the CHI value, the Log D was extrapolated according to the following equation, as described in Valko et al, 2001: Log D=0.0525×CHI pH7.4-1.467. Log D represents the log of the partitioning of a chemical compound between the lipid and aqueous phases.

Results and Significance: The lipophilicity of the compounds described herein were determined and compared to MDMA. CHI Log D values for certain test compounds are shown below in Table 10.

TABLE 10

CHI LogD values for exemplary compounds and reference compound (MDMA).

| Compound | MDMA | 522A | 516A | 518A | 562A | 514A |
|---|---|---|---|---|---|---|
| Chi LogD | 0.29 | 0.75 | 0.75 | 0.75 | 0.10 | 0.84 |

A higher Log D value indicates a more lipophilic compound. The calculated Log D values of exemplary compounds 522A, 516A, and 518A were each 1.15, while the Log D of MDMA was 0.29, indicating greater lipophilicity of 522A.

Broadly, lipophilicity represents the affinity of a molecule for a lipophilic environment. Differences in lipophilicity may affect the comparative absorption, distribution, metabolism, and excretion of compounds.

Example 21: In Vitro Clearance Study in Rat and Human Liver Microsomes

Purpose: The objective of the study is to evaluate the in vitro metabolic stability and hepatic clearance of compounds described herein in liver microsomes of rat and human origin.

Methods and Procedure: The general procedure involves incubating test compounds with liver microsomes and subsequently detecting the compounds to determine intrinsic clearance. Clearance was estimated from the rate of depletion k (min−1), the volume of the incubation V (mL), and the amount of microsomal proteins in the incubation M (mg). Intrinsic clearance is defined by the following equation: $Cl_{int}$ k*V/M.

Values for $CL_{int}$ are expressed as μL/min/mg protein. Verapamil and dextromethorphan were used as positive controls for CYP3A4 and CYP2D6 isoforms, respectively, to confirm metabolic activity.

TABLE 11

Stock and working solutions used in this Example

| Test Item | Stock Solution in DMSO | Working Solution (stock solution diluted in MeOH) |
|---|---|---|
| APV241522A ("522A") | 10 mM | 50 μM |
| APV243516A ("516A") | | |
| APV243518A ("518A") | | |
| APV245562A ("562A") | | |
| APV245514A ("514A") | | |
| Positive Controls | | |
| Verapamil | 10 mM | 50 μM |
| Dextromethorphan | 10 mM | 50 μM |

Positive control and compounds for testing were dissolved in an appropriate solvent to obtain a 10 mM stock solution, which was diluted to achieve a final working solution, as detailed in the above table. Stock solutions were usually prepared at 10 mM DMSO, whereas working solutions were made by adding 5 μL 10 mM DMSO+995 μL MeOH. However, this concentration can be varied, e.g., when the test item is not soluble in the selected solvent.

Prior to experimentation, frozen liver microsomes were thawed in a water bath at 37° C. and kept on ice until use. The microsomes were then diluted with 50 mM potassium phosphate buffer pH 7.4 to a protein concentration of 0.56 mg/mL. To prepare test and control items in final incubation conditions, 5 μL of test compound and positive control working solutions were added to 445 μL of microsomes incubation mixture at 0.56 mg/mL and 50 μL of regenerating system.

As it relates to the automated incubation procedure for microsomes incubation, the following procedure was followed:

1. 150 μL of quenching solution (ACN containing an appropriate Internal Standard, i.e. Rolipram and Diclofenac for positive and negative ion mode, respectively) was manually dispensed or dispensed by using the Hamilton system in each well of 96 deep well 1 mL plates.
2. 800-1000 μL-aliquots of NADPH regenerating system were pre-warmed at 37° C. for 5 minutes.
3. 5 μL of 50 μM test items and control were added to 445 μL of the 0.56 mg/mL microsomes solution, and the incubation mixture was pre-warmed in a 96 deep well 2 mL plate (incubation plate) at 37° C. for 5 minutes.
4. The incubation reactions were initiated by adding 50 μL of pre-warmed NADPH regenerating system to the incubation mixtures.
5. 50 μL-aliquots were sampled from incubation mixtures at: 0, 3, 10, 15, 30, and 45 minutes.
6. Samples were centrifuged at 3,000 rpm for 10 minutes and further diluted in order to optimize the analytical condition prior to the LC MS/MS or Rapid Fire-MS/MS analysis.
7. Incubations of test items were run in duplicate (n=2) with a single positive control (n=1).
8. For sample analysis, an LC-MS/MS system was used to monitor the test samples/control to internal standard peak area ratios as representative of the test or control item's concentration. Data from test item incubation was processed to give mean values where applicable. Metabolic stability was calculated from the ratio of peak area of the remaining test or control item with internal standard versus time.
9. Peak areas for test and control items were integrated using Integrator Software from Agilent or Analyst or MultiQuant Software from AB Sciex™ and were exported to XLFit or Morphit (The Edge), which were designed to calculate in vitro metabolic stability parameters. The integrated peak areas of the test and control items at the selected time points were divided by the respective peak areas of the IS, and the percent of parent remaining was calculated by normalizing the peak area ratio of parent to IS at 0 min. Observed rate constant ($k_{obs}$) for parent degradation was calculated by determining the slope of the line of the graph of the natural log of percentage parent remaining versus time of incubation. This was scaled for the protein in the incubation relative to that in the liver.

Results and Significance: Intrinsic clearance (μL/min/mg protein) was determined for test compounds described herein and MDMA, as shown in Table 12.

TABLE 12

Intrinsic clearances (μL/min/mg protein) of test compounds and reference compound (MDMA).

| Compound | Intrinsic clearance (μL/min/mg protein) rat | Intrinsic clearance (μL/min/mg protein) human |
|---|---|---|
| MDMA | 171 | 30 |
| 522A | 83 | 10 |
| 516A | 167 | 31 |
| 518A | 268 | 40 |
| 562A | 16 | 12 |
| 514A | 136 | 12 |

Generally, compounds with higher intrinsic clearance are likely to be cleared rapidly in vivo, thereby minimizing their duration of action. In contrast, metabolically stable molecules with low clearance may exhibit a relatively prolonged duration of action.

Example 22: In Vitro Evaluation of Membrane Permeability and Interactions with P-Glycoprotein (P-Gp) in MDCKII MDR1 Cells Purpose: In this study, compounds are screened to assess their rate of transport across a cell membrane, i.e., apparent permeability ($P_{app}$). Evaluations were also made to determine whether the compounds act as substrates for P-glycoprotein (P-gp), an efflux transporter.

Methods and Procedure: This study was conducted in compliance with previously described procedures to assure data integrity and adherence to GLP regulations. The experiments described herein were designed to evaluate the apparent permeability ($P_{app}$) of test compounds at pH 7.4. Additionally, the MDCKII-MDR1 cell line (Madin-Darby Canine Kidney clone II cell line heterologously expressing the human P-glycoprotein transporter) and mock cell line MDCKII were used to determine whether a compound acted as a P-gp substrate, in the absence and in the presence of the potent P-gp inhibitor. Test control items (digoxin, metoprolol, and atenolol) and control P-gp inhibitor (GF120918) stock solution were prepared in DMSO. Bidirectional assays (Apical to Basolateral [AB] and Basolateral to Apical [BA]) were run, in both the absence and presence of P-gp inhibitor GF120918 in MDCKII-MDR1 and mock cell line MDCKII, using as transport buffer HBSSH at a pH of 7.4 (n=3).

Compounds were tested at a single concentration (i.e. at 3 or 10 μM) at one time point (i.e. 60 min). Alternative concentrations or time-points may also be investigated. As reference compounds, digoxin (P-gp substrate), atenolol (low permeable compound) and metoprolol (high permeable compound) were included at a single concentration (e.g., 10 or 25 μM) and at single time point (e.g., 60 min). Digoxin transport was evaluated in two directions (apical-to-basolateral [AB] and basolateral-to-apical [BA]) in the absence and presence of GF120918 or in mock cells, MDCKII (n=3). Atenolol and metoprolol were only tested in the AB direction in absence of GF120918 or in mock cells, MDCKII (n=3). The integrity of the cell monolayer was evaluated after the permeability experiment using the paracellular permeability marker Lucifer yellow (LY) in the apical to basolateral direction in each well.

MDCKII or MDCKII-MDRI cells cultivated using DMEM (high glucose, GlutaMAX™ supplemented with pyruvate, 10% FBS HI and Pen/Strep) and seeded onto microporous PET (Polyethylene Terephthalate) membranes in HTS 96-Multiwell Insert plates at density of ~175,000-245,000 cells/cm$^2$ (25000-35000 cells/well; 50 μL/well) in DMEM medium and incubated for 3-4 days at 37° C.-5% $CO_2$. Medium was changed a day before the experiment.

Stock solutions of test items were prepared in DMSO at a concentration of 5 or 10 mM and stored at −20° C. until use. The potent P-gp inhibitor, GF120918 (stock solution 10 mM) and the reference controls digoxin, atenolol, metoprolol (stock solutions 3 or 10 mM) were prepared in DMSO and stored at −20° C. until use.

Donor working solutions of test items and reference controls will be prepared at a concentration of 10 or 25 μM, diluting the stock solutions in HBSSH. Receiver working solutions contained transport buffer only. All working solutions were prepared such that the final concentration of DMSO was <1% (v/v). A donor working solution containing LY was also prepared in transport buffer at 100 M.

MDCKII and MDCKII-MDR1 cells were preincubated (37° C., 15 to 30 minutes) in receiver working solutions containing transport buffer on apical (A) and basolateral (B) sides. Following pre-incubation, test items and control items (digoxin) transport were measured in two directions (apical to basolateral [AB]) and basolateral to apical [BA]), and these directions were performed in triplicate sets of wells, in both the absence and presence of 10 M GF120918 or mock MDCKII cells. For [AB] directional transport, 75 μL of donor working solution was added to the A (apical) compartment and 235 μL of receiver working solution was added to the B (basolateral) compartment. For [BA] directional transport, 235 μL donor working solution with test items or reference controls was added to the B compartment and 75 μL receiver working solution was added to the A compartment. Transport of permeability reference controls, atenolol and metoprolol, were measured in one direction (apical to basolateral [AB]) (n=3).

The cells were incubated (at 37° C., with shaking) for 60 minutes. Samples were removed from donor solutions and transport buffer (blank samples) for t=0 samples (Co) and at the end of the incubation period, from the receptor site (basolateral compartment for A→B direction and apical compartment for B→A direction) and from donor side ($C_0$ fin). Samples were extracted by protein precipitation with acetonitrile containing rolipram (for positive ion mode) or diclofenac (for negative ion mode) as generic internal standard compounds and centrifuged for 10 minutes at 3,000 rpm.

Additionally, to evaluate the integrity of the cell monolayer, LY permeability was measured in one direction, A→B, at the end of incubation. Residual solutions in the apical compartment were gently removed, and 75 μL of donor working solution containing LY at 100 μM was then added to the A compartment and 235 μL of receiver working solution to the B compartment. The cells were incubated (at 37° C.) for 60 minutes.

100 μL from each sample receiver well, 100 μL/well of donor solution containing 100 μM LY and 100 μL/well of Transport buffer were transferred to a 96-well clear bottom black plate. Fluorescence was measured using a fluorescence plate reader, such as the Tecan Spectrafluor plus, at Ex=485 nm, Em=535 nm.

The samples themselves were analyzed using a LC MS/MS system via discrete or cassette analysis to monitor the test item or positive control to internal standard peak area ratios as representative of the test or control item's concentrations. The rate of transport (Papp) of test items and digoxin were determined in the apical to basolateral ([AB]) and basolateral to apical ([BA]) directions in the absence and presence of GF120918, where feasible. The rate of transport (Papp) of metoprolol and atenolol will be determined in the apical to basolateral ([AB]) direction in the absence of GF120918 or mock MDCKII cells.

The efflux ratio of test items and of digoxin in the absence and presence of GF120918 or in mock MDCKII cells was then calculated. Comparing the efflux ratios generated in the presence and absence of GF120918 or in mock MDCKII cells indicated whether test items were P-gp substrates. A test item was considered to be a P-gp substrate when the efflux ratio in the absence of inhibitor was >2 and if the ratio was significantly reduced in the presence of inhibitor or in mock MDCKII cells.

Mass balance as a percentage (%) was calculated using the following equation:

$$\%\,\text{Recovery} = 100\times(CD\,(t)+CR\,(t))/C_0$$

Where CD(t) is the measured concentration in the donor well at time t (expressed as IS ratio), CR(t) is the measured concentration in the receiver well at time t (expressed as IS ratio), $C_0$ is the initial concentration in the donor solution (expressed as IS ratio). The amount of compound associated with the cells or plastic was not determined.

The percentage of cell integrity was calculated using the following equation:

$$\%\,\text{Integrity} = 100\times\left[1 - RFUbasolateral/RFUapical\right]$$

LY RFU values were normalized by background mean values. Wells were considered fully acceptable if the % Integrity was >98%, acceptable with caution for values included between 98% and 95%, and not acceptable for values <95%.

Results and Significance: The relative permeability of compounds described herein, and whether they act as P-gp substrates, was assessed according to the methods described herein. Results for exemplary compounds 522A and 518A are shown in Tables 13 and 14 below. For reference, the permeability of MDMA was calculated at 140 nm/sec, indicating high permeability. The B/A ratio in MDCKII-MDR1 cells of MDMA was 1.5, indicating the compound is not a P-gp substrate. Similarly, 522A and 518A were found to demonstrate high permeability and were not determined to be a substrate for P-gp.

TABLE 13

Permeability and P-gp substrate classification of 522A, 516A, and 518A:

| Assay | 522A | 516A | 518A |
|---|---|---|---|
| $P_{app}$ AB in MDCKII cells (nm/sec) | 94.48 | 157.67 | 173.36 |
| Permeability Classification | HP | HP | HP |
| B/A ratio in MDCKII-MDR1 cells | 0.83 | 0.73 | 0.70 |
| Substrate Classification | pGP-NO | pGP-NO | pGP-NO |

TABLE 14

Permeability and P-gp substrate classification of 562A and 514A:

| Assay | 562A | 514A |
|---|---|---|
| $P_{app}$ AB in MDCKII cells (nm/sec) | 261 | 244 |
| Permeability Classification | HP | HP |
| B/A ratio in MDCKII-MDR1 cells | 0.72 | 0.81 |
| Substrate Classification | pGP-NO | pGP-NO |

Measures of permeability are widely used to understand the absorption of a compound into cells. P-gp is an efflux transporter found in different tissues in the body, such as the brain and liver. P-gp influences drug transport in various ways. Thus, permeability and P-gp substrate screening provide insight into the movement of a compound, such as in a biological system.

Example 23: In Vitro Assessment of Inhibitory Activity on CYP450 Isoforms

Purpose: The study objective was to investigate the potential inhibitory effect of the disclosed compounds on CYP450 enzymes, which mediate variability in drug pharmacokinetics and, consequently, responses to treatment. CYP450 enzyme isoforms CYP1A2, $CYP2C_8$, CYP2B6, $CYP2C_9$, CYP2C19, CYP2D6, and CYP3A4 were examined in this study.

Methods and Procedure: The study was performed in agreement with previously described procedures to assure data integrity and adherence to GLP standards. Briefly, recombinant human CYP450 isoenzymes were used to metabolize pro-fluorescent probe substrates to fluorescent products. $IC_{50}$ values determined from the effect of test compounds on the metabolism of these probe substrates were then used to determine inhibitory potency against CYP450 isoforms.

TABLE 15

Chemical reagents used in this Example.

| Component | Supplier/Cat. Number | Storage |
|---|---|---|
| Trizma | Sigma T2663 | Store at RT |
| EDTA | Sigma E6635 | Store at RT |
| Sodium Bicarbonate | Sigma S5761 | Store at RT |
| Potassium Phosphate monobasic solution | Sigma P8709 | Store at 4° C. |
| Potassium Phosphate dibasic solution | Sigma P8584 | Store at 4° C. |
| NAPD monosodium salt | Sigma N3886 | Store at −20° C. |
| Glucose-6-phosphate disodium salt hydrate | Sigma G7250 | Store at −20° C. |
| Glucose-6-phosphate dehydrogenase | Sigma G6378 | Store at −20° C. |
| Miconazole | Sigma M3512 | Store at RT |
| DMSO | Sigma 527963 | Store at RT |

TABLE 16

| Substrates used in this Example. | | |
|---|---|---|
| Component | Supplier/Cat. Number | MW |
| Ethoxyresorufin (ER) | Sigma E3763 | 249.249 |
| 7-Methoxy-4-trifluoromethylcoumarin-3-acetic acid (FCA) | SB-355907 | 302.203 |
| 3-Butyryl-7-methoxycoumarin (BMC) | SB-363399 | 249.241 |
| 4-Methylaminomethyl-7-methoxycoumarin (MMMC) | SB-285033 | 219.239 |
| 7-Benzyloxyquinoline (7-BQ) | Sigma B5182 | 235.288 |
| Vivid DBOMF substrate | Life Technologies P2974 | 572.6 |
| Vivid BOMCC substrate | Life Technologies P2974 | 307.3 |

The test system was based on a three-step procedure with a "mix and read" format, where PGP-432,TI reaction and reading were performed at 37° C. The assays described herein measure in vitro inhibitory effects ($pIC_{50}$) of compounds on the human P450 isoforms (1A2, 2B6, 2C8, 2C9, 2C19, 2D6, 3A4) expressed in recombinant microsomes. Pro-fluorescent probe substrates were metabolized to fluorescent products by the enzymes. Fluorescence was measured in kinetic mode (1 read/minutes for 10 minutes), and the fluorescence rate was calculated. Data were normalized to controls: DMSO represents 0% effect (i.e., no inhibition), while 10 μM of the CYP inhibitor miconazole demonstrates 100% effect (i.e., complete inhibition).

Inhibition of the fluorescent signal resulting from P450 activation indicated inhibitory activity and facilitated calculation of the compound $pIC_{50}$. A quality check was included in each compound plate, wherein the signal window was monitored by performing Z' calculations (Z'≥0.2), and the antagonist potency of internal standards was within the $pIC_{50}$±2SD range. Concentration response curves (CRCs) of compounds were run on two different test occasions (n=2) by preparing serial dilutions from the dame compound stock solution.

TABLE 17

| Stock solutions used in this Example | | |
|---|---|---|
| Solutions | Components | Guidelines |
| Assay buffer | 100 mM Trizma HCl + 0.5 mM EDTA | Store 4° C., shelf life: 3 months |
| Vivid Assay Buffer | Potassium Phosphate Buffer 100 mM, pH 8.0 | Store 4° C., shelf life: 3 months |
| Cofactor buffer | 2% (w/v) sodium bicarbonate | Store 4° C., shelf life: 3 months |
| Cofactor | 7.8 mg glucose-6-phosphate, 1.7 mg NADP, 6 Units glucose-6-phosphate dehydrogenase/mL of 2% sodium bicarbonate | Prepare fresh each time on the day of the experiment |
| Vivid Regeneration System | 333 mM Glucose-6-phosphate, 30 U/ml Glucose-6-phosphate dehydrogenase in Vivid Assay Buffer | Store at −80° C. |
| NADP | 10 mM in Vivid Assay Buffer | Store at −80° C. |
| 1A2 Substrate | 50 μM ER | Dissolve 12 μg/ml in acetonitrile |
| 2C9 Substrate | 12.5 mM FCA | Dissolve 3.67 mg/mL in acetonitrile |
| 2C19 Substrate | 2.5 mM BMC | Dissolve 0.615 mg/mL in DMSO |
| 2D6 Substrate | 2.5 mM MMMC | Dissolve 0.547 mg/mL in methanol |
| 3A4 Substrate | 2.5 mM 7-BQ | Dissolve 0.588 mg/mL in acetonitrile |

To prepare the compound plate, test compounds serial dilutions 1 to 3 were performed from a 10 mM stock solution in DMSO by Biomek FX to generate 10 point CRC with the highest concentrations in columns 3 and 13.

100% DMSO was placed in columns 1 and 2 and used for assay low controls. CYP inhibitor (10 mM miconazole solution in DMSO) was placed in columns 23 and 24 and served as an assay high controls. 1 μL copy plates were then stamped into V-bottom drug plates at a concentration that is 200 fold the final assay concentration. The copy plates were diluted prior to the experiment with assay buffer to reach 4 times the final assay concentration (2% w/v DMSO).

A reference compound (e.g., miconazole) was included in each compound plate in row A, column 3 and 13. The reference compound was diluted and stamped together with test compounds. The final concentrations of the 10 point CRCs of test compounds in the assay plate were 5.00E-05; 1.67E-05; 5.56E-06; 1.85E-06; 6.17E-07; 2.06E-07; 6.86E-08; 2.29E-08; 7.62E-09 and 2.54E-09, respectively. All solutions were prepared immediately before the assay.

As for assay plate preparation, microsomes and substrate were mixed together according to Table 18 below.

TABLE 18

| Composition of assay buffer, microsomes, and substrates of this Example. | | | | | |
|---|---|---|---|---|---|
| Mix | 1A2/ ER | 2C9/ FCA | 2C19/ BMC | 2D6/ MMMC | 3A4HR/ 7BQ |
| Assay buffer (mL) | 14 | 14 | 14 | 14 | 14 |
| Microsomes (μL) (0.1 mg/mL protein) | 330 | 330 | 330 | 330 | 330 |
| Substrate (μL) | 224 | 90 | 90 | 90 | 224 |

Microsomes were added to the buffer prior to the substrate addition. The solution was carefully mixed without vortexing. 30 μL/well of the mixture was then transferred to the assay plate (384-well black plate) using a 16-channel pipette. For each P450 isoform, a separate plate was prepared and labeled with a barcode. For fluorescence measurement, 10 μL/well of the test compounds were transferred from the compound plate to the assay plate using Biomek FX and the appropriate protocol. The assay plate was then incubated at 37° C. for 10 minutes on a shaker to allow for the interaction between compounds and enzymes.

10 μL/well of the cofactor was then added to the assay plate using the Multidrop before placing the assay plate in the plate reader EnVision to measure fluorescence. The overall final DMSO concentration for the assay was 0.5%. Plates were read every minute for 10 minutes, according to a P450 isoform specific protocol, as shown in the table below:

| Assay | 1A2/ ER | 2C9/ FCA | 2C19/ BMC | 2D6/ MMMC | 3A4HR/ 7BQ |
|---|---|---|---|---|---|
| Excitation | 535 | 405 | 405 | 405 | 405 |
| Emission | 590 | 515 | 515 | 515 | 535 |
| Mirror | 50/50 | 505 FITC | 505 FITC | 505 FITC | 505 FITC |

CYP3A4 and CYP2C8 were assayed using the Vivid CYP3A4 Baculosomes, CYP2C8 Baculosomes and Vivid DBOMF Substrate (Life Technologies, cat. P2377, PV6138 and P2974 respectively), while 2B6 is tested by Vivid CYP2B6 Baculosomes and Vivid BOMCC Substrate (Life Technologies, cat. P3028 and P2975). Test compounds were prepared as specified above.

Preparation of the assay plate was by preparing pre-mix by diluting P450 Baculosomes Plus Reagent and Vivid Regeneration System in 1× Vivid CYP450 Reaction Buffer (Potassium Phosphate Buffer, 100 mM, pH 8.0). Briefly, 8 μL/ml of P450 Baculosomes Plus Reagent and 16 μL/ml of Vivid Regeneration System were added to achieve appropriate final concentrations, then mixed by inversion. 30 μL of pre-mix was dispensed into each well of black, 384-well plate.

Next, 10 μL/well from the compound plate was added and incubated for 10 minutes at 37° C. on a plate shaker, while a mixture of Vivid Substrate and Vivid NADP+ in Vivid CYP450 Reaction Buffer was prepared. The reaction was initiated by adding 10 μL/well of the Vivid Substrate and NADP+ mixture, before transferring the plate into the fluorescent plate reader (immediately, within 2 minutes), and fluorescence was monitored every minute for 10 minutes according to the specific protocol. Regarding data analysis, the inhibition effect is expressed as a percentage. Normalization was based on the inhibition rate in the presence of 10 μM miconazole (100% effect=C2) and inhibition rate in presence of 0.5% DMSO (0% effect=C1), according to the following formula: $Y=100\times[(data-C1)/(C2-C1)]$. Curve fitting and $pIC_{50}$ estimations are carried out using a four-parameter logistic model in Morphit.

Results and Significance: The inhibitory effects, represented as $IC_{50}$, of exemplary compound APV241522A ("522A") and MDMA are presented in Table 19 below.

TABLE 19

| CYP450 inhibitory activity of compound 522A and reference compound MDMA. | | |
|---|---|---|
| CYP450 Isoform | CYP450 Inhibition of 522A ($IC_{50}$ in μM) | CYP450 Inhibition of MDMA ($IC_{50}$ in μM) |
| CYP1A2 | >50 | 50 |
| CYP2B6 | 40.96 | 50 |
| CYP2C19 | >50 | 50 |
| CYP2C8 | >50 | 50 |
| CYP2C9 | >50 | 50 |
| CYP2D6 | 2.87 | 1.6 |
| CYP3A4 (7BQ) | >50 | 50 |
| CYP3A4 (DBOMF) | >50 | 50 |

MDMA was a more potent inhibitor of the tested CYP enzymes than 522A, except at CYP2B6. Inhibitors of CYP450 isoforms interfere with or reduce an enzyme's metabolic activity. Some drugs are metabolized by only one CYP enzyme, while others may be metabolized by many. In some cases, CYP450 inhibition can lead to drug-drug interactions, wherein the pharmacokinetics of a co-administered drug are altered.

Example 24: In Vitro Determination of Plasma Protein Binding and Tissue Protein Binding Using an Equilibrium Dialysis Assay Purpose: This study is designed to determine the plasma protein binding of test compounds in rat and human specimens, including blood, brain, and lung samples.

Methods and Procedure: This study was performed in agreement with the previously described procedures to assure data integrity and adherence to GLP standards. Plasma protein binding and blood tissue binding of test items (0.5 μM) was determined using biological samples from male Sprague Dawley (SD) rats and humans. Clozapine was used as a control compound for plasma protein binding and blood and brain tissue binding, as it exhibits extensive binding to plasma proteins (~97%). Dexamethasone was used as a control for lung tissue binding. Various biological samples were spiked with test compounds according to the methods that follow.

Preparation of plasma or blood samples: An appropriate amount of test compound was dissolved in DMSO to yield a 10 mM solution. Further dilutions, to obtain 50 μM working solutions (WS), were then prepared using 50% acetonitrile in Milli-Q water. These 100×WS were used to spike plasma or blood to obtain a final concentration of 0.5 μM. From this initial spiking solution, control samples (n=3), referred to as T=0, were immediately extracted and used to calculate the recovery of the test item.

Preparation of brain homogenate samples: Test items were dissolved in DMSO (or an appropriate solvent) to give a 10 mM solution. Further dilutions, to obtain 166.7 μM working solutions (WS), were then prepared using 50% acetonitrile in Milli Q water. These 100×WS were used to spike the brain homogenate to obtain a final concentration of 5 μM. From this initial spiking solution, control samples (n=3) referred to as T=0, were immediately extracted by protein precipitation.

Preparation of lung homogenate samples: Test compounds were dissolved in DMSO (or an appropriate solvent) to give a 10 mM solution. Further dilutions, to obtain 71 μM working solutions (WS), were then prepared using 50% acetonitrile in MilliQ water. 71 μM WS was used to spike the lung homogenate to obtain a final concentration of 5 μM. From this initial spiking solution control samples (n=3), named T=0, were immediately extracted and used to calculate the recovery of the test item.

Preparation of tissue homogenate samples: Test compounds were dissolved in DMSO (or an appropriate solvent) to give a 10 mM solution. Further dilutions, to obtain working solutions (WS), were then prepared using 50% acetonitrile in MilliQ water. WS were used to spike the tissue homogenate to obtain a final concentration of 5 μM in neat tissue. From this initial spiking, solution control samples (n=3), named T=0, were immediately extracted and used to calculate the recovery of the test item.

An equilibrium dialysis method was performed to determine protein binding in the various biological samples described herein. Materials were prepared and methods were in accordance with the following procedures.

Membranes were prepared for use in the equilibrium dialysis experiment, by soaking in deionized water for at least 60 minutes. After this period, 20% of pure ethanol was added, and the membranes were left in this solution for at least 20 minutes. The membranes were then rinsed in Milli-Q water prior to use. To initiate the experiment, 150 μL of test item-free buffer (isotonic phosphate buffer for plasma and blood, artificial CSF buffer for brain or HBSS buffer for lung) was dispensed on one half-well of a 96-well dialyzer apparatus (HTDialysis LLC), and 150 μL of spiked matrix (plasma, blood, brain or lung) was loaded on the other half-well. Alternative volumes may be used according to the operating instructions of HTDialysis.

The artificial cerebral spinal fluid (CSF) buffer was prepared as follows, NaCl 3.652 g, KCl 93.2 mg, $MgCl_2$ 119.96 mg, $CaCl_2$ 92.61 mg, $Na_2HPO_4*H_2O$ 268.0 mg. These were dissolved in 0.5 L of MilliQ water, and the pH was adjusted to a pH of 7.4 with $H_3PO_4$.

Dialysis buffer was prepared by dissolving $Na_2HPO_4$ 8.69 g, $KH_2PO_4$ 1.90 g, and NaCl 4.11 g in 1 L of MilliQ water, and adjusting the pH to 7.4 with $H_3PO_4$. At the end of the equilibration period (device is sealed and incubated under shaking for 5 hours at 37° C.), 50 μL of dialysed matrix will be added to 50 μL of corresponding test item free dialysed buffer, and vice versa for buffer, such that the volume of buffer to matrix will be the same. Samples were extracted by protein precipitation with 300 μL of acetonitrile containing rolipram (for positive ionization mode) or diclofenac (for negative ionization mode) as internal standard and centrifuged for 10 minutes at 2800 rpm. Supernatants were collected (100 μL), diluted with 18% ACN in Milli Q water (200 μL). Samples were then injected onto an HPLC MS/MS or UPLC MS/MS system. In order to control the integrity of the membrane after the dialysis process, the presence of protein was assessed in the buffer compartment. 5 μL of dialysed buffer will be added with 250 μL of Bio-Rad protein assay reagent (Bio-Rad) diluted 1:5 with Milli-Q water. A change in color from brown to a brilliant blue indicates protein contamination. Contaminated samples were excluded from all calculations.

Samples were analyzed in a LC-MS/MS system using an analytical method to monitor the compound to internal standard peak area ratios as representative of the compound concentrations. Alternatively, samples were analyzed by RapidFire.

Protein binding in plasma, blood, brain, and lung tissue samples were determined with the following formula: Afu=Buffer/x, wherein "x" may be plasma, blood, brain, or lung, and "Afu" is the apparent fraction unbound, and the other variables refer to the analyte/internal standard ratio determined in their specific compartment (buffer, plasma, blood, brain homogenate, and lung homogenate);

$$fucr = \frac{\frac{1}{D}}{\left[\left(\frac{1}{Afu} - 1\right) + \frac{1}{D}\right]},$$

wherein fucr is the fraction unbound corrected, D is the matrix dilution factor (D=1 for plasma, 2 for blood, 3 for brain, 7 for lung). % Binding=1−fucr)×100 and % Unbound=100−% Bound.

Each test item and control compound (clozapine or dexamethasone) was processed in triplicate, and the average and standard deviation (SD) were calculated. If the SD was greater than 20%, the median (with range) was calculated. For result validation, the percent binding values for clozapine and dexamethasone must have been within Ave±2SD (where Ave is calculated from historical data). Recovery was determined by comparing the sum of area ratio (analyte/internal standard) determined in buffer and plasma, blood, brain, or lung compartments with area ratio of the T=0 samples, a recovery value will obtained, as described in the following formula: Recovery=[(Buffer+Matrix)/T=0]×100, wherein "Buffer" is the analyte/internal standard ratio determined in buffer compartment, "Matrix" is the analyte/internal standard ratio determined in plasma, blood, brain, or lung compartment, and T=0 are the control samples.

As it relates to recovery specifically, a recovery of >200 or <50 indicates that the experimental data is not valid; 50≤recovery<80 or 120<recovery≤200 indicates that the experimental data should be met with caution, and 80≤recovery≤120 indicate the data is valid.

Results and Significance: Protein binding, as represented by the fraction unbound (%), of exemplary compounds 522A and 518A in plasma and brain samples is shown in Table 20 below. For reference, the unbound fraction of MDMA was found to be >50% in both rat and human plasma samples, and its unbound fraction in brain tissue binding (BTB) experiments in rats was nearly 40%. Accordingly, 522A and 518A displayed greater protein binding than MDMA.

TABLE 20

Unbound fraction of compounds 522A, 518A, and 562A in biological samples.

| Specimen | Fraction Unbound (%) 522A | Fraction Unbound (%) 518A | Fraction Unbound (%) 562A |
|---|---|---|---|
| Human Plasma | 2.1 | 1.43 | 2.30 |
| Rat Plasma | 12 | 10.55 | >50 |
| BTB (rat) | 2.2 | 1.27 | >50 |

Broadly, the affinity of a compound to bind to plasma proteins and tissue influences its pharmacological efficacy. Generally, the free (unbound) form of a drug is available to reach a target site and exert pharmacological activity. In some examples, the extent of plasma protein binding may affect the volume of distribution, half-life, and clearance of a compound.

Example 25: Synthesis of Short-Acting Derivatives

In one method of creating a shorter-acting derivative based on the morpholine scaffold of the disclosed compounds, an ester is functionally added into the structure as illustrated below:

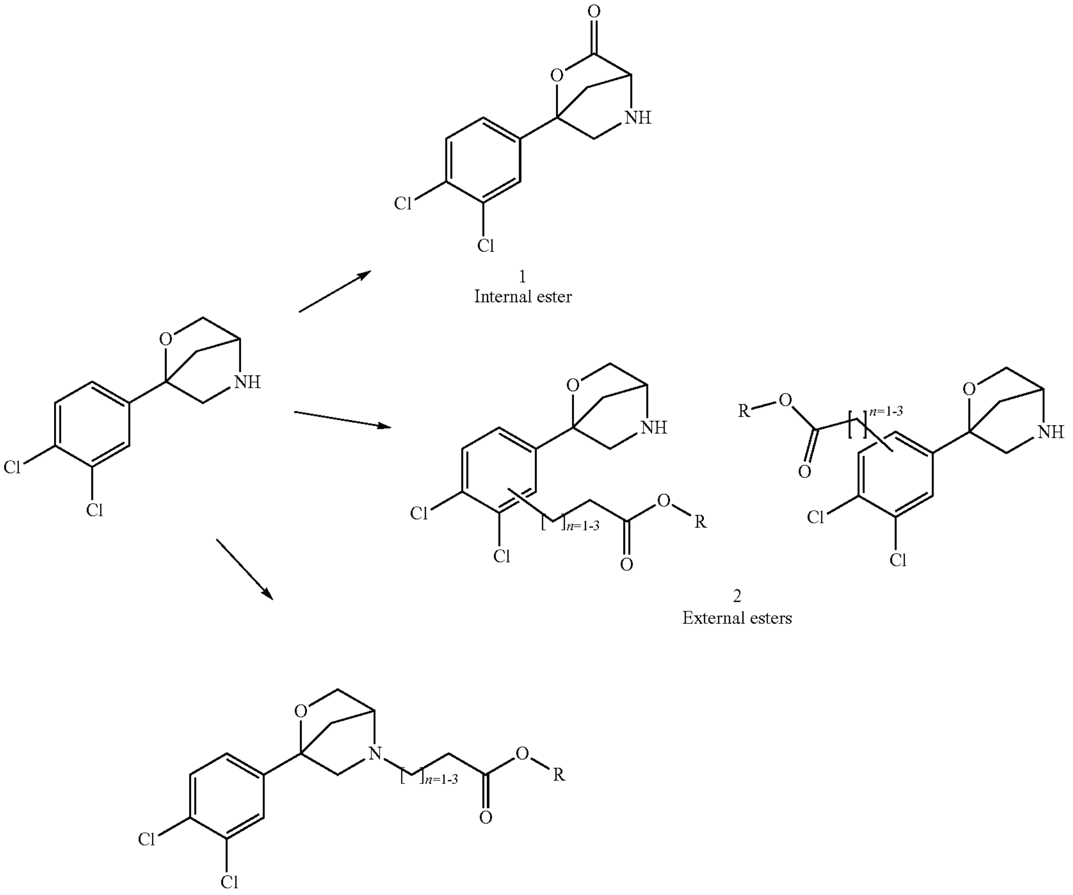

1
Internal ester

2
External esters

3

Example 26: Determining Short-Acting Compounds

To determine whether a compound described herein is modified in a way to make it a shorter-acting compound, rats are infused with the compounds described herein, as well as a compound based on at least one of the compounds described herein, that is modified as described herein to make it a shorter-acting compound. The resulting compound may then be assessed by determining the loss of righting reflex (LORR) and the return of righting reflex (RORR).

To do so, a study design is followed that is similar to that of McCarren, Moore, and Kelz, with some modifications. Specifically, 24 clear open-top acrylic chambers with a total volume of 1000 mL mounted on a rack sitting inside a 37° C. water bath are each individually filled with an adult rat. Each rat is connected to an intravenous continuous infusion system. The rats are first injected with a serum to ensure each has adequate hydration and concentration of electrolytes.

Once each rat is at equilibrium, the serum will be replaced with an equivalent serum containing a concentration of 0.1% of the compounds described herein. After 30 seconds of the rats being administered this dose, the rats will each be placed on their back by a practitioner. The righting reflex (RR) will be considered intact only if the rat is able to restore all of its paws to the floor of the chamber within two minutes. The dosage is then increased by about 0.05% every 15 minutes until the LORR (measured in mg/kg) is met. Once the LORR is met, the rats will no longer be administered a dose of the compounds described herein. The resultant time it takes for the rat to right itself after the delivery ceases will be the RORR.

The rats are then given a washout period of 7 days prior to the second phase of the experiment, wherein the procedure as listed above is repeated with a compound described herein modified to be a shorter-acting compound.

A relatively shorter RORR time is representative of abbreviated drug action, consistent with the activity of a short-acting compound. In some examples, the short-acting compounds provided herein result in a reduced RORR time in comparison to a parent compound, or a known entactogen, for example, MDMA. The LORR of the short-acting compound may be less than, comparable to, or higher than the LORR dose of a parent compound or known entactogen.

Example 27: Comparative Pharmacokinetics and Identification of Short Acting Compounds An in vivo study is conducted to determine the PK of a compound modified to act as a short acting compound. Briefly, effective or exploratory doses of a parent compound and a modified compound, such as an esterified derivative of the parent compound, are administered to one or more test groups in a pharmacokinetic (PK) study. The results of the study are compared to determine the relative duration of action of the modified compound, e.g., by comparing half-life ($t_{1/2}$). The PK parameters of the parent and modified compounds may also be compared to a known entactogen, such as MDMA, which may be evaluated in a concurrent PK study.

In one illustrative example, an effective dose of a parent or a modified compound is administered via tail vein injection to jugular vein cannulated rats. A vehicle control group is also included. Samples are taken from the cannula at desired time points, for example, 0.25, 0.5, 0.75, 1, 1.5, 2, 3, 4, 6, 8, and 10 hours post injection. Note that other subjects, routes of administration, and sampling techniques, among other aspects, may also be evaluated in accordance with a similar protocol, as described herein and in the art (de la Torre et al., British Journal of Clinical Pharmacology, 2000; 49(2), 104-109; Korfmacher et al., Journal of Pharmacological and Toxicological Methods, 2015; 76, 7-14; Ortuno et al. J. Chromatogr. B., 1999; 723:221-232).

Samples are analyzed, e.g., in accordance with methods described in EXAMPLE 18. PK parameters, for example, $T_{max}$ (min), $C_{max}$ (ng/mL), $AUC_{0-t}$ (ng*min/mL), Vd (mL/kg), Cl (mL/min/kg), and $T_{1/2}$ (min) may be determined with use of Phoenix WinNonlin 6.3.

The resultant PK parameters will indicate whether a modified compound, such as an esterified derivative, is short-acting relative to a parent compound and/or a known entactogen. Additionally, the resultant PK parameters will indicate whether a modified compound is fast-acting relative to a parent compound and/or a known entactogen. In some examples, a short-acting compound is identified by determining a relatively abbreviated course of action, for example, a reduced half-life ($T_{1/2}$). In some examples, a short-acting compound is identified by determining an increased rate of clearance (Cl). In some examples, a short-acting compound is identified by determining reduced time to peak levels ($T_{max}$). In some examples, a short-acting compound is identified by determining a reduced area under the curve (AUC). In some examples, one or more such parameters may be evaluated to determine whether a compound is fast-acting and/or exhibits a short duration of action.

Example 28: Human Trials

The compounds described herein are administered to human volunteers by administration means including oral solid form, such as capsule or tablet, inhaled form, and injected form, such as IM, IV, or subcutaneous administration, at a dosage selected following initial safety studies performed according to ordinary procedures therefor, for example a dosage of 15 mg, 25 mg, 50 mg, 100 mg, 125 mg, or 150 mg. Blood samples are collected at 20, 40, 60, and 200 minutes post-administration. The samples are analyzed by LCMS. The subjective effects are also measured by standardized questionnaires or assessments known to those of skill, such as the Subjective Drug Effects Questionnaire (Katz et al., J Abnormal Psych., 1968; 73(1), 1-14); the Brief Fear of Negative Evaluation-revised (BFNE) (Carleton et al., 2006, Depression and Anxiety, 23(5), 297-303; Leary, 1983, Personality and Social Psychology bulletin, 9(3), 371-375), the Authenticity Inventory (Kernis & Goldman. 2006. Advances in experimental social psychology, 38, 283-357) as modified by Baggott et al (Journal of Psychopharmacology 2016, 30.4: 378-87), the Abnormal Mental States questionnaire, first published in 1998 by Adolf Dittrich, which includes three dimensions, including "Oceanic Boundlessness (OSE)," "Dread of Ego Dissolution (AIA)," and Visionary Restructuralization (VUS)," Positive and Negative Symptom Schedule-X (PANAS-X), Brief Fear of Negative Evaluation (BFNE), Visual Analog Scale Items (VAS), and Trustworthy Face Task (TFT), and such other questionnaires or assessments as will be known to those of skill. The questionnaires will illustrate that patients perceive feelings associated with subjective entactogenic effects, the intensity of which is correlated with blood levels of the compounds described herein (e.g., by measuring sera concentrations using enzyme-linked immunosorbent assay or other methods known in the art). Regarding said blood levels, samples obtained at 20, 40, 60, and 200 minutes post-administration will illustrate higher levels of target monoamines than present at baseline, indicating the compounds described herein act as at least one of a monoamine uptake inhibitor and a monoamine releasing agent in human patients, when administered using the disclosed methods.

Example 29: Use in an Exemplary Psychedelic-Assisted Therapy Treatment

The compounds described herein are prescribed in a therapeutically effective amount to a patient suffering with at least one CNS disorder in a therapist-supervised dosing session, the at least one CNS disorder including mental health conditions, such as but not limited to post-traumatic stress disorder (PTSD), adjustment disorder, affective disorder, depression, atypical depression, postpartum depression, catatonic depression, a depressive disorder due to a medical condition, premenstrual dysphoric disorder, seasonal affective disorder, dysthymia, anxiety, phobia disorders, binge disorders, body dysmorphic disorder, alcohol or drug abuse or dependence disorders, substance-related disorders, substance use disorders, alcohol use disorder, substance-induced mood disorder, a mood disorder related to another health condition, disruptive behavior disorders, eating disorders, impulse control disorders, obsessive compulsive disorder (OCD), attention deficit hyperactivity disorder (ADHD), personality disorders, attachment disorders, and dissociative disorders; neurodegenerative conditions, such as but not limited to Alzheimer's disease, ataxia, Huntington's disease, Parkinson's disease, motor neuron disease, multiple system atrophy, progressive supranuclear palsy, migraines, cluster headaches, short-lasting unilateral neuralgiform headaches, fibromyalgia, traumatic brain injury, and mild-traumatic brain injury; and behavioral addictions, including but not limited to gambling disorder, compulsive sexual behavior, sexual addiction, gaming addiction, shopping addiction, internet addiction, kleptomania, pyromania, compulsive buying, pornography addiction, binge eating disorder, internet gaming addiction, exercise addiction or overtraining syndrome, love addiction, work addiction or workaholism, and technological addictions.

Prior to the administration, the patient may be evaluated to determine whether the therapist-supervised dosing session is appropriate for the patient. The evaluation may include completing questionnaires, obtaining objective health measurements from the patient, including but not limited to weight, body temperature, heart rate (HR), respiratory rate, blood oxygenation, blood pressure (BP) and its variables, including, but not limited to: systolic (SBP), diastolic (DBP), mean arterial (MAP), and pulse (PP); continuous non-invasive beat-by-beat blood pressure (CNIBP); measurements from an electrocardiogram (ECG), including, but not limited to, RR interval or its variability, QT interval or its variability, heart rate variability (HRV) (or measured by devices other than an ECG); hemodynamic response (HR), and levels of glucose, cortisol, serotonin, dopamine, cholesterol; electroencephalography (EEG) measures such as quantitative EEG (qEEG); electrocochleogram (ECochG), electromyography (EMG), electrooculography (EOG), magnetoencephalography (MEG); electrocorticography (ECoG); magnetic resonance imaging (MRI); functional MRI (fMR1); computed tomography (CT); positron emission tomography (PET); nuclear magnetic resonance (NMR) spectroscopy or magnetic resonance spectroscopy (MSR); single-photon emission computed tomography (SPECT); near infrared spectroscopy (NIRS); event-related optical signal (EROS); computed axial tomography; diffuse optical imaging (DOI); cranial ultrasound; or functional ultrasound imaging (fUS) (together, "EEG measures"); brain derived neurotrophic factor (BDNF); genetic markers including relating to CYP enzymes or drug metabolism; genetic variation in mGluR5 or FKBP5; and assessing the patient for "biomarkers" that may indicate a patient will have a sub-optimal response to psychedelic treatment, including those that may indicate poor metabolism of a psychedelic drug, such as but not limited to the CYP2D6 and CYP2B6 genes; those that may impact the response to serotonin, such as but not limited to the HTR2A gene; genes that may pose a mental health risk, such as but not limited to the C4A, NRG1, and DISC1 genes; and physiological fluctuations that may indicate a patient will not perceive the full psychedelic experience, including but not limited to having a higher diversity of executive network nodes (i.e., less efficient network segregation), and having a lesser rostral anterior cingulate (rACC) thickness; and numerous more, as will be readily appreciated by those of skill. If the objective measurements obtained from the patient are within established safety standards known to those of skill, the patient may proceed with the dosing session.

Dosing is performed in a quiet setting with the patient resting comfortably in an inclined, unrestrained position, and is supervised by at least one, but preferably two or more therapists, as part of a therapist team. The patient's eyes will be covered, and music played, to create a calming atmosphere. A therapeutically effective dose of the compounds described herein is then administered. While under the effects of the compounds described herein, the subject is encouraged to remain in a resting position, and to focus inwardly. Once the effects of the compounds described herein have ceased (e.g., after a duration of time where the therapy team is confident that the subject will cease to have significant subjective effectives, or that the subject otherwise will cease to have subjective effects above the threshold that, for example, may interfere with remaining daily activities or driving home), and/or the patient confirms subjective effects have ceased the patient is permitted to stand and move around. In some embodiments, e.g., for certain relatively short-acting compounds of the invention, when compared, e.g., to MDMA, this may be after about an hour, about 90 minutes, about two hours, about 150 minutes, or after about three hours. After the duration of drug effects, and the period of free movement and further acclimatization, the patient is discharged. The following day (i.e., roughly 24 hours after the initial dosing session) the patient meets again with the therapy team or with a single therapist from the team or another, and undergoes a psychotherapy session that recounts the experience ("integration"). The patient also may participate in activities that constitute integration on his or her own, e.g., by using a software app, or may interact with a therapist via telemedicine or via a pre-recorded session, which also may be interactive.

Example 30: Use as a Medication

The compounds described herein are prescribed in a therapeutically effective amount to a patient suffering with at least one CNS disorder in a therapist-supervised dosing session, the at least one CNS disorder including mental health conditions, such as but not limited to post-traumatic stress disorder (PTSD), adjustment disorder, affective disorder, depression, atypical depression, postpartum depression, catatonic depression, a depressive disorder due to a medical condition, premenstrual dysphoric disorder, seasonal affective disorder, dysthymia, anxiety, phobia disorders, binge disorders, body dysmorphic disorder, alcohol or drug abuse or dependence disorders, substance-related disorders, substance use disorders, alcohol use disorder, substance-induced mood disorder, a mood disorder related to another health condition, disruptive behavior disorders, eating disorders, impulse control disorders, obsessive compulsive disorder (OCD), attention deficit hyperactivity disorder (ADHD), personality disorders, attachment disorders, and dissociative disorders; neurodegenerative conditions, such as but not limited to Alzheimer's disease, ataxia, Huntington's disease, Parkinson's disease, motor neuron disease, multiple system atrophy, progressive supranuclear palsy, migraines, cluster headaches, short-lasting unilateral neuralgiform headaches, fibromyalgia, traumatic brain injury, and mild-traumatic brain injury; and behavioral addictions, including but not limited to gambling disorder, compulsive sexual behavior, sexual addiction, gaming addiction, shopping addiction, internet addiction, kleptomania, pyromania, compulsive buying, pornography addiction, binge eating disorder, internet gaming addiction, exercise addiction or overtraining syndrome, love addiction, work addiction or workaholism, and technological addictions.

Prior to prescribing the medication, the patient also may be evaluated to determine whether such is appropriate for the patient. The evaluation may include completing questionnaires, obtaining objective health measurements from the patient, including but not limited to weight, body temperature, heart rate, respiratory rate, blood oxygenation, BP and its variables, including, but not limited to: SBP, SBP, MAP, and PP; CNIBP; ECG measurements, including RR interval or its variability, QT interval or its variability, HRV (including measured by devices other than an ECG); hemodynamic response, and levels of glucose, cortisol, serotonin, dopamine, cholesterol; EEG measures; BDNF; genetic markers including relating to CYP enzymes or drug metabolism; genetic variation in mGluR5 or FKBP5, or other biomarkers. If the objective measurements obtained from the patient are within established safety standards known to those of skill, the patient may be prescribed the medication containing the compounds described herein, wherein the prescribed dose is appropriate for the age and weight of the patient, taking into consideration other factors known to those of skill, including but not limited to comorbidities, current medications (if any), and metabolic variations among patient populations.

To confirm a reduction in symptoms, a reduction in symptom severity, or elimination of symptoms and/or a previous diagnosis, one or more diagnostic or clinical tools is used, such as the DSM-5, one or more self-reported or observer-report surveys or questionnaires, and any one or more of the Patient Health Questionnaire 9 (PHQ-9), the Hamilton Depression Rating Scale (HAM-D); the Generalized Anxiety Disorder 7 (GAD-7), PTSD Checklist for DSM-5 (PCL-5), The Alcohol Use Disorders Identification Test (AUDIT), Binge Eating Scale (BES), Obsessive-Compulsive Inventory (OCI), the Personality Disorders Questionnaire (PDQ-IV), Dissociative Experiences Scale (DES), Drug Use Questionnaire (DAST-20), the Mood Disorder Questionnaire (MDQ), and one or more other similar questionnaires, which will be chosen based on the condition or disorder to be treated, as known to those of skill. By comparing baseline responses to responses after a treatment intervention, the compound or composition of the invention is shown to be effective in the methods disclosed herein.

Example 31: Self-Administration of the Pharmaceutical Compositions of the Invention A patient who is prescribed the pharmaceutical compositions of the invention may administer the compounds described herein to themselves. To do so, the patient may obtain the pharmaceutical composition from a doctor, pharmacist, nurse practitioner, psychiatrist, or other such health professional capable of prescribing medication, and then may self-administer the medication in a location of their choice—wherein the location may be a calming, intimate, safe clinical setting; or a non-clinical setting meeting the same criteria, such as but not limited to the patient's house, or any other location wherein the patient feels comfortable. After the patient self-administers the pharmaceutical composition of the invention, they may stay in a comfortable area, and focus inwardly. The patient may then record their thoughts and feelings in a journal, so that they are able to discuss the thoughts and feelings with a health professional at a later date.

In other embodiments, by contrast, a disclosed compound is taken as a take-home medication on a chronic basis, such as daily, more than once daily, or on a regular and recurring basis, such as every other day, certain days per week, and the like, as appreciated by one of skill.

Example 32: Study Comparing the Compounds Described Herein to MDMA

A study is devised to compare the compounds described herein to MDMA, including the effectiveness of treating at least one CNS disorder, wherein CNS disorder broadly includes mental health conditions, such as but not limited to post-traumatic stress disorder (PTSD), adjustment disorder, affective disorder, depression, atypical depression, postpartum depression, catatonic depression, a depressive disorder due to a medical condition, premenstrual dysphoric disorder, seasonal affective disorder, dysthymia, anxiety, phobia disorders, binge disorders, body dysmorphic disorder, alcohol or drug abuse or dependence disorders, substance-related disorders, substance use disorders, alcohol use disorder, substance-induced mood disorder, a mood disorder related to another health condition, disruptive behavior disorders, eating disorders, impulse control disorders, obsessive compulsive disorder (OCD), attention deficit hyperactivity disorder (ADHD), personality disorders, attachment disorders, and dissociative disorders; neurodegenerative conditions, such as but not limited to Alzheimer's disease, ataxia, Huntington's disease, Parkinson's disease, motor neuron disease, multiple system atrophy, progressive supranuclear palsy, migraines, cluster headaches, short-lasting unilateral neuralgiform headaches, fibromyalgia, traumatic brain injury, and mild-traumatic brain injury; and behavioral addictions, including but not limited to gambling disorder, compulsive sexual behavior, sexual addiction, gaming addiction, shopping addiction, internet addiction, kleptomania, pyromania, compulsive buying, pornography addiction, binge eating disorder, internet gaming addiction, exercise addiction or overtraining syndrome, love addiction, work addiction or workaholism, and technological addictions; as well as the frequency/severity of adverse reactions (such as those known in the art to be associated with MDMA administration).

In this exemplary study, 30 participants (15 male, 15 female), diagnosed with at least one CNS disorder are each administered either the compounds described herein (10 people, 5 male 5 female), MDMA (10 people, 5 male 5 female), or a placebo (10 people, 5 male 5 female), on three separate occasions over the course of 3 weeks. Prior to the experiment, the participants will undergo a "wash-out" period of 10 days, wherein the individuals will cease all medication that may interact with the compounds tested within the study, as would be apparent to one of skill.

During dosing sessions, individuals are monitored by a health professional and connected to equipment monitoring at least one objective measurement, as disclosed herein. At the end of each dosing session, individuals will record their experiences with the dosing (e.g., the emotions elicited by the compound, any fears, anxieties, etc., experienced; how they felt physiologically, e.g., if they experienced nausea, headache, noticeable increase in heart rate, etc.).

This information, in combination with the data obtained through monitoring of at least one objective measurement, will be compiled and compared between the three groups. It will be determined that the compounds described herein are at least as effective in treating CNS disorders as MDMA, while the patients will report—and it will be objectively illustrated via the at least one objective measurement(s) obtained—that the compounds described herein will have less adverse side effects than MDMA.

The foregoing description, for purposes of explanation, uses specific nomenclature to provide a thorough understanding of the invention. However, it will be apparent to one skilled in the art that specific details are not required in order to practice the invention. Thus, the foregoing description of specific embodiments of the invention is presented for purposes of illustration and description. It is not intended to be exhaustive or to limit the invention to the precise compositions, formulations, methods, or the like disclosed; many modifications and variations are possible in view of the above teachings. The embodiments were chosen and described in order to best explain the principles of the invention and its practical applications, through the elucidation of specific examples, and to thereby enable others skilled in the art to best utilize the invention and various embodiments with various modifications as are suited to the particular use contemplated, when such uses are beyond the specific examples disclosed. Accordingly, the scope of the invention shall be defined solely by the following claims and their equivalents.

The invention claimed is:

1. A compound having the structure of Formula (2):

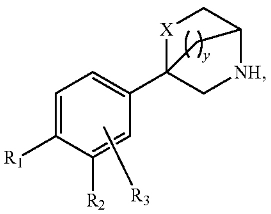

(2)

or a pharmaceutically acceptable salt, hydrate, or solvate thereof, wherein:

$R_1$, $R_2$, and $R_3$ are each independently hydrogen, —$CH_3$, —$OCH_3$, —$CF_3$, or halogen; or two of $R_1$, $R_2$ and $R_3$ are combined with the atoms to which they are each attached to form a $C_{1-8}$ cycloalkyl, $C_{1-10}$ heterocycloalkyl, or $C_{6-12}$ aryl;

X is O, S, —O—$CH_2$—, —O—C(O)—, or —S—$CH_2$—;

y is 1 or 2; and wherein at least one of $R_1$, $R_2$, and $R_3$ is not hydrogen.

2. The compound of claim 1, wherein X is O.

3. The compound of claim 1, wherein X is S.

4. The compound of claim 1, wherein X is —O—$CH_2$—.

5. The compound of claim 1, wherein X is —O—C(O)—.

6. The compound of claim 1, wherein X is —S—$CH_2$—.

7. The compound of claim 1, wherein y is 1.

8. The compound of claim 1, wherein y is 2.

9. The compound of claim 1, wherein $R_1$ is Cl.

10. The compound of claim 1, wherein $R_2$ is Cl.

11. The compound of claim 1, wherein $R_1$ and $R_2$ are both Cl.

12. The compound of claim 1, wherein $R_1$ and $R_2$ are both methyl.

13. The compound of claim 1, wherein $R_1$ and $R_2$ are taken together to form a methylenedioxy group.

14. The compound of claim 1, selected from the group consisting of:

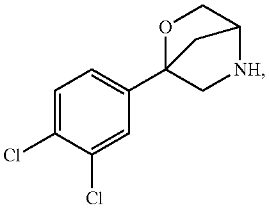

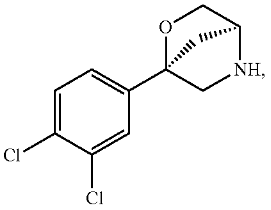

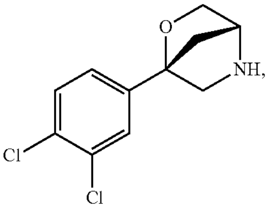

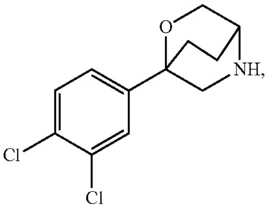

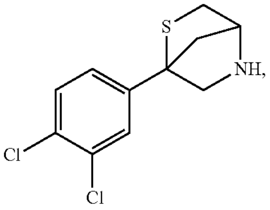

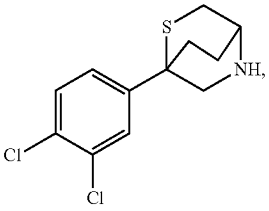

-continued

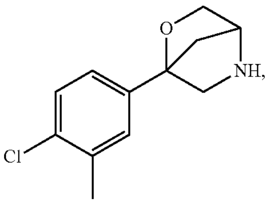

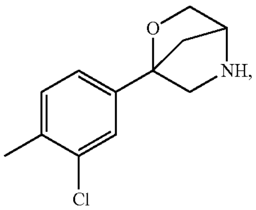

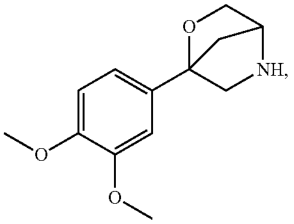

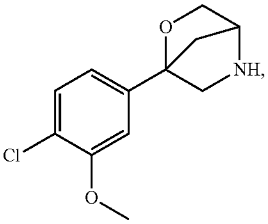

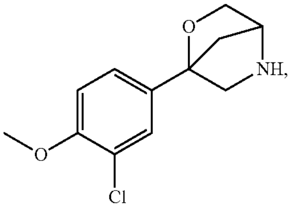

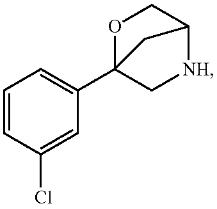

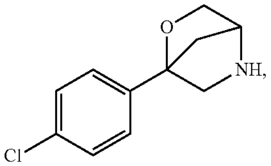

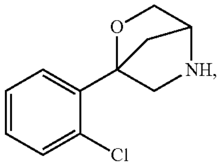

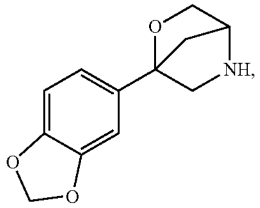

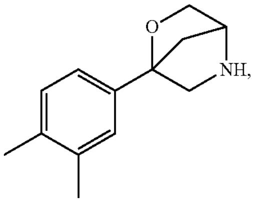

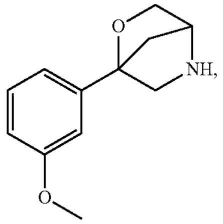

and

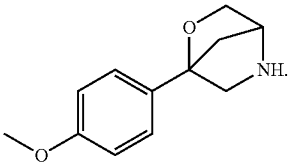

15. The compound of claim 1, wherein the compound is

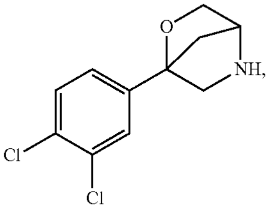

-continued

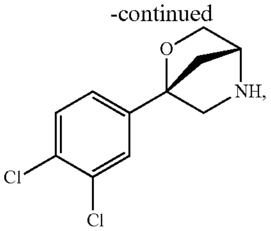, or

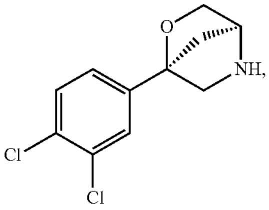,

16. The compound of claim 1, wherein the compound is

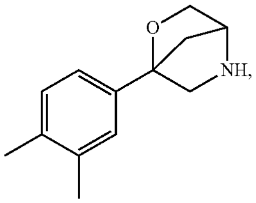,

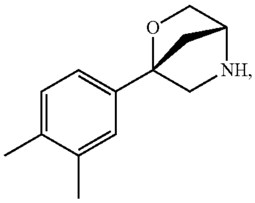, or

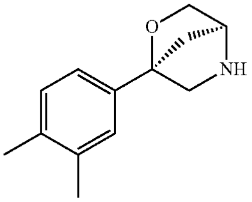

17. The compound of claim 1, wherein the compound is

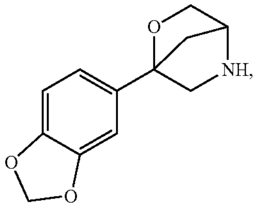,

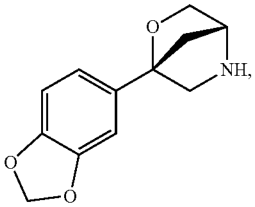, or

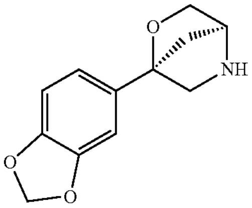

18. A pharmaceutical composition comprising a therapeutically effective amount of a compound of claim 1 for use in treating a substance use disorder, a behavioral addiction, or a mental health disorder, and a pharmaceutically acceptable carrier, diluent, or excipient.

19. A method of treating a medical condition in a mammal in need of such treatment, the method comprising administering the compound of claim 1.

20. The method of claim 19, wherein the medical condition is a substance use disorder, a behavioral addiction, or a mental health disorder.

* * * * *